United States Patent
Miller et al.

(10) Patent No.: US 12,180,529 B2
(45) Date of Patent: Dec. 31, 2024

(54) SUGAR TRANSPORTER-MODIFIED YEAST STRAINS AND METHODS FOR BIOPRODUCT PRODUCTION

(71) Applicant: CARGILL, INCORPORATED, Wayzata, MN (US)

(72) Inventors: Christopher K. Miller, Andover, MN (US); Ana Negrete-Raymond, Chanhassen, MN (US); Brian J. Rush, Minneapolis, MN (US); Amit Vas, Minneapolis, MN (US); Jon Veldhouse, Plymouth, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 1963 days.

(21) Appl. No.: 16/062,771

(22) PCT Filed: Dec. 16, 2016

(86) PCT No.: PCT/US2016/067314
§ 371 (c)(1),
(2) Date: Jun. 15, 2018

(87) PCT Pub. No.: WO2017/106739
PCT Pub. Date: Jun. 22, 2017

(65) Prior Publication Data
US 2020/0270644 A1 Aug. 27, 2020

Related U.S. Application Data

(60) Provisional application No. 62/268,932, filed on Dec. 17, 2015.

(51) Int. Cl.
*C12P 7/10* (2006.01)
*C07K 14/39* (2006.01)
*C12N 1/16* (2006.01)
*C12N 15/52* (2006.01)

(52) U.S. Cl.
CPC ............ *C12P 7/10* (2013.01); *C07K 14/39* (2013.01); *C12N 1/16* (2013.01); *C12N 15/52* (2013.01); *C12Y 302/01003* (2013.01); *C12Y 302/0101* (2013.01)

(58) Field of Classification Search
CPC ... C12P 7/10; C12P 7/06; C07K 14/39; C07K 14/37; C12N 1/16; C12N 15/52; C12Y 302/01003; C12Y 302/0101; Y02E 50/10
See application file for complete search history.

(56) References Cited

U.S. PATENT DOCUMENTS

| | | |
|---|---|---|
| 4,546,082 A | 10/1985 | Kurjan |
| 4,870,008 A | 9/1989 | Brake |
| 4,959,317 A | 9/1990 | Sauer |
| 5,024,941 A | 6/1991 | Maine |
| 5,231,017 A | 7/1993 | Lantero |
| 5,422,267 A | 6/1995 | Yocum |
| 5,521,086 A | 5/1996 | Scott |
| 5,587,290 A | 12/1996 | Klionsky |
| 5,876,988 A | 3/1999 | Selten |
| 6,214,577 B1 | 4/2001 | Yocum |
| 7,785,872 B2 | 8/2010 | Chang |
| 8,067,339 B2 | 11/2011 | Prinz |
| 8,394,622 B2 | 3/2013 | Forrester |
| 8,592,194 B2 | 11/2013 | Aehle |
| 8,664,475 B2 | 3/2014 | Puzio |
| 8,697,412 B2 | 4/2014 | Landvik |
| 8,733,149 B2 | 5/2014 | Yu |
| 8,733,321 B2 | 5/2014 | Cohn |
| 8,735,092 B2 * | 5/2014 | Hatanaka ............. C07K 14/395 435/7.1 |
| 8,735,544 B1 | 5/2014 | Prevost |
| 8,809,023 B2 | 8/2014 | Degn |
| 9,127,287 B2 * | 9/2015 | Hall ................... C12N 15/8246 |
| 10,344,288 B2 | 7/2019 | Miller |
| 10,364,421 B2 | 7/2019 | Miller |
| 10,472,656 B2 * | 11/2019 | Brady ................... C12P 7/6409 |
| 10,724,023 B2 | 7/2020 | Miller |
| 11,034,931 B2 * | 6/2021 | Solodovnikova ...... C12N 15/01 |
| 2004/0110295 A1 | 6/2004 | Punnonen |
| 2007/0015266 A1 | 1/2007 | Dunn-Coleman |
| 2007/0065905 A1 | 3/2007 | Branduardi |

(Continued)

FOREIGN PATENT DOCUMENTS

| | | |
|---|---|---|
| CN | 1069768 A | 3/1993 |
| CN | 1478097 A | 2/2004 |

(Continued)

OTHER PUBLICATIONS

Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*

(Continued)

Primary Examiner — Ganapathirama Raghu

(57) ABSTRACT

Genetically modified yeast having a heterologous sugar transporter that is capable of transporting a non-glucose sugar such as maltulose, are described. The heterologous sugar transporter can be a protein according to, or that has similarity to, SEQ ID NO: 44. Fermentation methods using enzymatically treated starch where the yeast are able to consume the non-glucose sugars, are also described. The engineered yeast can be useful for producing desired bioproducts such as high ethanol, with low amounts of residual sugars in the medium.

17 Claims, 19 Drawing Sheets

Specification includes a Sequence Listing.

(56) References Cited

U.S. PATENT DOCUMENTS

| | | | |
|---|---|---|---|
| 2007/0117186 | A1 | 5/2007 | Sahara |
| 2007/0166788 | A1 | 7/2007 | Jin |
| 2010/0317078 | A1 | 12/2010 | Mlla-Garcia |
| 2011/0033907 | A1 | 2/2011 | Forrester |
| 2011/0104331 | A1 | 5/2011 | Hatanaka |
| 2011/0209248 | A1 | 8/2011 | Frommer |
| 2011/0229968 | A1 | 9/2011 | Sohn |
| 2011/0318799 | A1 | 12/2011 | Feldman |
| 2012/0064591 | A1 | 3/2012 | Gasch |
| 2013/0137181 | A1 | 5/2013 | Choi |
| 2013/0149760 | A1 | 6/2013 | Forrester |
| 2013/0323822 | A1 | 12/2013 | Brevnova |
| 2014/0162335 | A1 | 6/2014 | Bortiri |
| 2014/0248689 | A1 | 9/2014 | Hatanaka |

FOREIGN PATENT DOCUMENTS

| | | | |
|---|---|---|---|
| CN | 101194015 | A | 6/2008 |
| CN | 101646767 | A | 2/2010 |
| CN | 101952425 | A | 1/2011 |
| CN | 102869771 | A | 1/2013 |
| CN | 103814134 | A | 5/2014 |
| CN | 104395454 | A | 3/2015 |
| CN | 104560847 | A | 4/2015 |
| EP | 0123544 | A2 | 10/1984 |
| EP | 0228254 | A2 | 7/1987 |
| EP | 2735301 | A1 | 5/2014 |
| EP | 2734490 | B1 | 9/2015 |
| JP | 62228284 | A | 10/1987 |
| WO | 9613600 | W | 5/1996 |
| WO | 9914335 | A1 | 3/1999 |
| WO | 0071738 | A1 | 11/2000 |
| WO | 0242471 | A2 | 5/2002 |
| WO | 03105889 | W | 12/2003 |
| WO | 2004042036 | A2 | 5/2004 |
| WO | 2007032792 | A2 | 3/2007 |
| WO | 2009037279 | A1 | 3/2009 |
| WO | 2011153516 | A2 | 12/2011 |
| WO | 2013011208 | A1 | 1/2013 |
| WO | 2013092840 | A1 | 6/2013 |
| WO | 2014029808 | A1 | 2/2014 |
| WO | 2014078920 | A1 | 5/2014 |
| WO | 2014081803 | A1 | 5/2014 |
| WO | 2015023989 | A1 | 2/2015 |
| WO | 2015195934 | A2 | 12/2015 |
| WO | 2016127083 | A1 | 8/2016 |
| WO | 2016160584 | A1 | 10/2016 |
| WO | 2018027131 | A1 | 2/2018 |

OTHER PUBLICATIONS

Sen et al., Developments in directed evolution for enzyme functions. Appl. Biochem. Biotechnol., 2007, vol. 143: 212-223 (Year: 2007).*
Weusthus et al., Chemostat Cultivation as a Tool for Studies on Sugar Transport in Yeasts. Microbiol. Rev., 1994, vol. 58(4): 616-630. (Year: 1994).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Accession AAP40245. Nov. 29, 1991 (Year: 1991).
Accession E9P9V2. Apr. 5, 2011 (Year: 2011).
Accession Q2VC81. Jan. 10, 2006 (Year: 2006).
Accession Q8TFE5. Jun. 1, 2002 (Year: 2002).
Accession U3N160. Dec. 11, 2013 (Year: 2013).
Alignment of SEQ ID No: 77 to SEQ ID No. 34 of U.S. Pat. No. 8,067,339. Nov. 29, 2011 (Year: 2011).
Arora et al. Renewable and Sustainable Energy Reviews. vol. 51, Nov. 2015, pp. 699-717. Available online Jul. 16, 2015. (Year: 2015).
Ballesteros, et al., Optimization of the simultaneous saccharification and fermentation process using thermotolerant yeasts, Applied Biochemistry and Biotechnology, Spring 1993, vol. 39-40, Issue 1.
Brake, et al., a-Factor-directed synthesis and secretion of mature foreign proteins in *Saccharomyces cerevisiae*, Prov. Natl. Acad. Sci., vol. 81, pp. 4642-4646, Aug. 1984 Biochemistry.
Chica, et al., Semi-rational approaches to engineering enzyme activity: combining the benefits of directed evolution and rational design, Curr. Opi. Biotechnol. 16:, 378-384.
Eva Hostinová, et al., Molecular cloning and 3D structure prediction of the first raw-starch-degrading glucoamylase without a separate starch-binding domain, XP055266201, Archives of Biochemistry and Biophysics, Mar. 1, 2003 Academic Press, US—ISSN 0003-9861, vol. 411, Issue 2.
Eva Hostinová, et al., Yeast glucoamylases: molecular-genetic and structural characterization, Biologia, SAP-Slovak Academic Press, Bratislava, SK, vol. 65 No. 4.
Favaro et al. Biotechnol Bioeng. Sep. 2015; 112(9): 1751-60. Epub Jul. 14, 2015. *Year: 2015).
Flessel, et al., The MFa1 Gene of *Saccharomyces cerevisiae*: Genetic Mapping and Mutational Analysis of Promoter Elements, Genetics 121: 223-236 (Feb. 1989).
Guomin, et al., "Integration of glucoamylase gene from Aspergillus niger into *Sacharomyces cerevisiae* genome and its stable expression", Chinese Journal of Biotechnology, Allerton Press, vol. 11 (4), 1995, 237-241.
Itoh, et al., Nucleotide sequence of the glucoamylase gene GLU1 in the yeast Saccharomycopsis fibuligera, Journal of Bacteriology, Sep. 1987 vol. 169 No. 9.
Jinxian, et al., "Expression and secretion of alpha-amylase and glucoamylase in *Saccharomyces cerevisiae*", Chinese Journal of Biotechnology, Allerton Press, vol. 10, No. 4, 1994, 241-248.
Kizer, Lance , et al., "Application of Functional Genomics to Pathway Optimization for Increased Isoprenoid Production", Appl Environ Microbiol. 74(10), May 2008, 3229-41.
Lau, et al., A Genetic Study of Signaling Processes for Repression of PH05 Transcription in *Saccharomyces cerevisiae*, Genetics Society of America 150: 1349-1359 (Dec. 1998).
Li, et al., Impediments to Secretion of Green Fluorescent Protein and Its Fusion from *Saccharomyces cerevisiae*, Biotechnol. Prog. 2002, 18, 831-838.
Nakamura, et al., Alcohol fermentation of starch by a genetic recombinant yeast having glucoamylase activity, Biotechnology and Bioengineering, Wiley etc—ISSN 0006-3592, DOI: http://dx.doi.org/10.1002/(SICI)1097-0290(19970105)53:1<21::AID-BIT4>3.0.CO;2-0, vol. 53.
P. J. Punt, et al., Intracellular and extracellular production of proteins in Aspergillus under the control of expression signals of the highly expressed Aspergillus nidulans gpdA gene, Journal of Biotechnology, Elsevier Science Publishers, Amsterdam, NL—ISSN 0168-1656, vol. 17, Nr:1.
Prather, Kristala L, et al., "De novo biosynthetic pathways: rational design of microbial chemical factories", Curr Opin Biotechnol 19(5), Oct. 19, 2008, 468-74.
R. C. Das, et al., Chapter 10: Host cell control of heterologous protein production in *Saccharomyces cerevisiae*, Marcel Dekker, Inc., New York / Basel, XP008179956.
Shi-Hwei Liu, et al., Improved secretory production of glucoamylase in Pichia pastoris by combination of genetic manipulations, Biochemical and Biophysical Research Communications, Elsevier, Available online at www.Sciencedirect.com, 817-824, 2005.
Sidhu, et al., Selection of secretory protein-enoding genes by fusion with PH05 in *Saccharomyces cerevisiae*, Gene, 107 (1991) 111-118.
Singh, Raushan Kumar., et al., Protein Engineering Approaches in the Post-Genomic Era, Curr Protein Pept Sci. 18, 1-11, 2017.
Zengran, et al., Integrative Expression of Glucoamylase Gene in a Brewer's Yeast *Saccharomyces pastorianus* Strain, Food Technol. Biotechnol. 46 (1) 32-37 (2008).
"GenBank Accession No. CAC83969.1", Apr. 15, 2005.
Ashikari T., et al. Agric. Biol. Chem. 49:2521-2523, 1985.

(56) References Cited

OTHER PUBLICATIONS

Bernhard, S. L., et al. Cysteine Analogs of Recombinant Barley Ribosome Inactivating Protein Form Antibody Conjugates with Enhanced Stability and Potency in vitro. Bioconjugate Chem., vol. 5, No. 2, pp. 126-132, 1994.
Bourbonnais et al., J. Bio. Chem. 263(30):15342, 1988.
Coutinho et al., "Structural similarities in glucoamylases by hydrophobic cluster analysis," Protein Eng., 1994 7(6):749-760.
Coutinho et al., "Structure-function relationships in the catalytic and starch binding domains of glucoamylase," Protein Eng., 1994 7(3):393-400.
Evans et al. (Gene, 91:131; 1990).
Fukuda et al., "A mutated ARO4 gene for feedback-resistant DAHP synthase which causes both o-fluoro-DL-phenylalanine resistance and beta-phenethyl-alcohol overproduction in *Saccharomyces cerevisiae*," Curr Genet. 1991, 20(6):453-6.
GenBank ABB77799.1 Rhizopus oryzae amyB, Mar. 9, 2007.
GenBank L15383, Aspergillus terreus glucoamylase, Jul. 14, 1995.
Ghose A. et al. "Characterization of glucoamylase from Aspergillus terreus 4" FEMS Microbiol Lett, 54:345-349, 1990.
Gonzalez-Siso, M.I., et al. (2015) Microb Biotechnol. 8:319-330.
Higuchi, R. In: PCR Protocols: A Guide to Methods and Applications. A. I. Michael, D. H. Gelfand, D. J. Sninsky and T. J. White (Eds.), Academic Press, pp. 177-183, 1990.
Ilmen, M., et al. (2007) Appl Environ Microbiol. 73:117-123.
Inoue, et al., Biosci Biotechnol Biochem. 2000; 64:229-236.
Ito, W., et al. A general method for introducing a series of mutations into cloned DNA using the polymerase chain reaction. GENE, vol. 102, Issue 1, pp. 67-70, Jun. 1991.
Kajiwara (Appl Microbiol Biotechnol. 2000; 53:568-74).
Kim et al., Appl Environ Microbiol. 1996; 62:1563-1569.
Li YC et al. Application of omics technology in construction of *Saccharomyces cerevisiae* strains for ethanol production [J]. China Biotechnol, 2014 34 (2): 118-128, machine translation.
Lin, S.-C., et al. (BMC Biochemistry 8:9, 2007).
Meyhack et al. (EMBO J. 6:675-680, 1982).
NCBI glucoamylase [Saccharomycopsis fibuligera]; Apr. 15, 2005.
Pascale Daran-Lapujade et al., Role of Transcriptional Regulation in Controlling Fluxes in Central Carbon Metabolism of *Saccharomyces cerevisiae*, The Journal of Biological Chemistry, vol. 279, No. 10, Issue of Mar. 15, pp. 9125-9138, 2004.
Rosario Lagunas, Sugar transport in *Saccharomyces cerevisiae*, FEMS Microbiology Reviews 104(1993) 229-242.
Sierks, M. R., and Svensson, B., 1993, Biochemistry 32:1113-1117.
Sierks, M.R., et al., 1994, Protein Eng. 7(12): 1479-1484.
Takagi et al., Appl Environ Microbiol. 2005; 71:8656-8662.
Tamakawa, H. et al. (2011) Biosci Biotechnol Biochem. 75:1994-2000.
UniProt O60087 Sachizosaccharomyces pombe meu17, Aug. 1, 1998.
UniProt O74254 Candida albicvans (strain SC5314/ATCC MYA-2876) GAMI, Mar. 15, 2017.
UniProt P04065 *Saccharomyces cerevisiae* STA1, Nov. 1, 1990.
UniProt P08017 Saccharomycopsis fibuligera GLU1, Aug. 1, 1988.
UniProt P22832 Aspergillus shirousami glaA, Aug. 1, 1991.
UniProt P22861 Ashwanniomyces occidentalis GAM1, Aug. 1, 1991.
UniProt P23176 Aspergillus kawachii gal, Nov. 1, 1991.
UniProt P26989 Saccharomycopsis fibuligera GLA1, Jul. 15, 1998.
UniProt *Saccharomyces cerevisiae* STA2, Apr. 1, 1993.
UniProt P36914 Aspergillus oryzae (strain Atcc 42149/RIB40), May 2, 2006.
UniProt P69327 Aspergillus awamori, Nov. 1, 1986.
UniProt Q03045, Amorphotheca resinae GAMP, Feb. 1, 1994.
UniProt Q0CPK9, Aspergillus terreus glucoamylase, Oct. 17, 2006.
UniProt Q8TFE5 Saccharomycopsis fibuligera Glm (CAC83969), Jun. 1, 2002.
Vallette, F., et al. Construction of mutant and chimeric genes using the polymerase chain reaction. Nucleic Acids Research, vol. 17, Issue 2, pp. 723-733, Jan. 1989.
Ventura L. et al., "Molecular cloning and transcriptional analysis of the Aspergillus terreus gla1 gene encoding a glucoamylase," Appl. Environ. Microbiol. 61:399-402, 1995.
Von Heijne, G., (1986) Nucleic Acids Res. 14, 4683-4690.
Waugh, D.S., Protein Expr Purif. 80(2): 283-293, 2011.
Xie, D., et al. (2015) Appl Microbiol Biotechnol. 99L 1599-1610.
Yamashita, I. et al., (1985) J. Bacteriol. 161, 567-573.
Zhang, J. et al. (2014) Bioresour Technol. 152:192-201.
Zhou et al., Microbial Cell Factories 13:44, 2014.
Carlson, M. et al. Mol. Cell. Biol. 3:439-447, 1983.
Ichiro Shibuya, Katsuya Gomi, Yuzuru Iimura, Kojiro Takahashi, Gakuzo Tamura & Shodo Hara (1990) Molecular Cloning of the Glucoamylase Gene of Aspergillus shirousami and Its Expression in Aspergillusoryzae, Agricultural and Biological Chemistry, 54:8, 1905-1914, DOI: 10.1080/00021369.1990.10870276.
Jigami et al. "Expression of synthetic human-lysozyme gene in *Saccharomyces cerevisiae*: use of a synthetic chicken-lysozyme signal sequence for secretion and processing," Gene, 43:273-279, 1986.
Kober et al., "Optimized signal peptides for the development of high expressing CHO cell lines," Biotechnology and Bioengineering, 110:1164-1173, 2013.
Kurjan J., et al. "Structure of a yeast pheromone gene (MFα): a putative α-factor precursor contains four tandem copies of mature α-factor," Cell 30:933-943, 1982.
Li W-C, et al., "Trichoderma reesei complete genome sequence, repeat-induced point mutations, and partitioning of CAZyme gene clusters," Biotechnology for Biofuels, 10, 170(2017).
UniProt A0A0H5C316, Cyberlindnera jadinii pep7, Oct. 14, 2015.
UniProt G8JZS4, Bacteroides thetaiotaomicron susB, Jan. 25, 2012.
UniProt I2K2N7, Brettanomyces bruxellensis AWRI1499_0572, Jul. 11, 2012.
UniProt P07683, Rhizopus oryzae glucoamylase, Nov. 1, 1995.
UniProt P29761, Clostridium sp. cga, Apr. 1, 1993.
UniProt P42042, Blastobotrys adeninivorans GAA, Nov. 1, 1995.
UniProt P69328, Aspergillus niger GLAA, Nov. 1, 1986.
UniProt Q0CK04, Aspergillus terreus ATEG_05980, Oct. 17, 2006.

* cited by examiner

SEQUENCE LISTING

<160> NUMBER OF SEQ ID NOS: 45

<210> SEQ ID NO 1
<211> LENGTH: 3182
<212> TYPE: DNA
<213> ORGANISM: Artificial Sequence
<220> FEATURE:
<223> OTHER INFORMATION: locus A-loxP-ARO4-OFP integration fragment

<400> SEQUENCE: 1
cctactgcgc caattgatga caatacagac gatgataaca aaccgaagtt atctgatgta      60
gaaaaggatt aaagatgcta agagatagtg atgatatttc ataaataatg taattctata     120
tatgttaatt acctttttg cgaggcatat ttatggtgaa ggataagttt tgaccatcaa      180
agaaggttaa tgtggctgtg gtttcagggt ccataaagct tttcaattca tctttttttt     240

```
ttttgttctt ttttttgatt ccggtttctt tgaaattttt ttgattcggt aatctccgag    300
cagaaggaag aacgaaggaa ggagcacaga cttagattgg tatatatacg catatgtggt    360
gttgaagaaa catgaaattg cccagtattc ttaacccaac tgcacagaac aaaaacctgc    420
aggaaacgaa gataaagcgg ccgcataact tcgtataatg tatgctatac gaagttatct    480
gccagtatac agctagcctt gaaagtgatg gaaacattg tcatcggcac ataaataaaa     540
aaattatgaa tcacgtgatc aacagcaaat tatgtactcg tatatatgca agcgcattcc    600
ttatattgac actctttcat tgggcatgag gctgtgtaaa cataagctgt aacggtctca    660
cggaacactg tgtagttgca ttactgtcag gcagttatgt tgcttaatat aaaggcaaag    720
gcatggcaga atcactttaa acgtggccc cacccgctgc accctgtgca ttttgtacgt     780
tactgcgaaa tgactcaacg atgaaatgaa aaaattttgc ttgaaatttt gaaaaaaga    840 tgtgcgggac gcattgttag ctcattgaat acatcgtgat cgaatccaat caatgtttaa    900
tttcatatta atacagaaac tttttctcat actttcttct tcttttcatt ggtatattat    960
ctatatatcg tgttaattcc tctttcgtca tttttagcat cgttataaga gtaattaaga   1020
ataactagaa gagtctctct ttatattcgt ttatttttata tatttaaccg ctaaatttag  1080
taaacaaaag aatctatcag aaatgagtga atctccaatg ttcgctgcca acggcatgcc   1140
aaaggtaaat caaggtgctg aagaagatgt cagaatttta ggttacgacc cattagcttc   1200
tccagctctc cttcaagtgc aaatcccagc cacaccaact tctttggaaa ctgccaagag   1260
aggtagaaga gaagctatag atattattac cggtaaagac gacagagttc ttgtcattgt   1320
cggtccttgt tccatccatg atctagaagc cgctcaagaa tacgctttga gattaaagaa   1380
attgtcagat gaattaaaag gtgatttatc catcattatg agagcatact tggagaagcc   1440
aagaacaacc gtcggctgga aaggtctaat taatgaccct gatgttaaca cactttcaa    1500 catcaacaag ggtttgcaat ccgctagaca attgtttgtc aacttgacaa atatcggttt   1560
gccaattggt tctgaaatgc ttgataccat ttctcctaaa tacttggctg atttggtctc   1620
cttcggtgcc attggtgcca gaaccaccga atctcaactg cacagagaat ggcctccgg    1680 tttgtctttc ccagttggtt tcaagaacgg taccgatggt accttaaatg ttgctgtgga   1740
tgcttgtcaa gccgctgctc attctcacca tttcatgggt gttactaagc atggtgttgc   1800
tgctatcacc actactaagg gtaacgaaca ctgcttcgtt attctaagag gtggtaaaaa   1860
gggtaccaac tacgacgcta agtccgttgc agaagctaag gctcaattgc ctgccggttc   1920
caacggtcta atgattgact actctcacgg taactccaat aaggatttca gaaaccaacc   1980
aaaggtcaat gacgttgttt gtgagcaaat cgctaacggt gaaaacgcca ttaccggtgt   2040
catgattgaa tcaaacatca acgaaggtaa ccaaggcatc ccagccgaag gtaaagccgg   2100
cttgaaatat ggtgtttcca tcactgatgc ttgtataggt tgggaaacta ctgaagacgt   2160
cttgaggaaa ttggctgctg ctgtcagaca aagaagagaa gttaacaaga atagatgtt   2220 tttttaatga tatatgtaac gtacattctt tcctctacca ctgccaattc ggtattattt   2280
aattgtgttt agcgctattt actaattaac tagaaactca attttttaaag gcaaagctcg   2340 ctgaccttc actgatttcg tggatgttat actatcagtt actcttctgc aaaaaaaaat    2400
tgagtcatat cgtagctttg ggattatttt tctctctctc cacggctaat taggtgatca   2460
tgaaaaaatg aaaaattcat gagaaaagag tcagacatcg aaacatacat aagttgatat   2520
tcctttgata tcgacgacta ctcaatcagg ttttaaaaga aaagaggcag ctattgaagt   2580
```

-continued

| | |
|---|---|
| agcagtatcc agtttaggtt ttttaattat ttacaagtaa agaaaagag aatgccggtc | 2640 |
| gttcacgata acttcgtata atgtatgcta tacgaagtta tgcggccgcg agaagatgcg | 2700 |
| gccagcaaaa ctaaaaaact gtattataag taaatgcatg tatactaaac tcacaaatta | 2760 |
| gagcttcaat ttaattatat cagttattac ccgggaatct cggtcgtaat gatttctata | 2820 |
| atgacgaaaa aaaaaaaatt ggaaagaaaa agcttcatgg cctttataaa aaggaactat | 2880 |
| ccaatacctc gccagaacca agtaacagta ttttacgggg cacaaatcaa gaacaataag | 2940 |
| acaggactgt aaagatggac gcattgaact ccaagaaca acaagagttc aaaaagtag | 3000 |
| tggaacaaaa gcaaatgaag gatttcatgc gtttgtactc taatctggta gaaagatgtt | 3060 |
| tcacagactg tgtcaatgac ttcacaacat caaagctaac caataaggaa caaacatgca | 3120 |
| tcatgaagtg ctcagaaaag ttcttgaagc atagcgaacg tgtagggcag cgtttccaag | 3180 |
| ag | 3182 |

<210> SEQ ID NO 2
<211> LENGTH: 3275
<212> TYPE: DNA
<213> ORGANISM: Artificial Sequence
<220> FEATURE:
<223> OTHER INFORMATION: locus A-loxP-TEF1-An amdS integration fragment

<400> SEQUENCE: 2

| | |
|---|---|
| cctactgcgc caattgatga caatacagac gatgataaca aaccgaagtt atctgatgta | 60 |
| gaaaaggatt aaagatgcta agagatagtg atgatatttc ataaataatg taattctata | 120 |
| tatgttaatt accttttttg cgaggcatat ttatggtgaa gaataagttt tgaccatcaa | 180 |
| agaaggttaa tgtggctgtg gtttcagggt ccataaagct tttcaattca tcattttttt | 240 |
| tttattcttt tttttgattc cggtttcctt gaaattttt tgattcggta atctccgaac | 300 |
| agaaggaaga acgaaggaag gagcacagac ttagattggt atatatacgc atatgtagtg | 360 |
| ttgaagaaac atgaaattgc ccagtattct taacccaact gcacagaaca aaaatctgca | 420 |
| ggaaacgaag ataaagcggc cgcataactt cgtatagcat acattatacg aagttatcgc | 480 |
| ctgttaagat ataactgaaa aaagagggga atttttagat actgaaatga tattttagaa | 540 |
| taaccagact atatataagg ataaattaca aaaaattaac taatagataa gatttaaata | 600 |
| taaaagatat gcaactagaa aagtcttatc aatctcctta tggagtgacg acgttaccca | 660 |
| acaatttacc gacttcttcg gcgatagcca aagttctctc ttcggacaat cttctaccaa | 720 |
| taacttgaac agcaacagga gcaccgtgat aagcctctgg gtcgtattct tcttgaacca | 780 |
| aagcatccaa ttcggaaaca gctttaaaag attcgttctt cttatcaata ttcttatcag | 840 |
| cgaaagtgac tgggacgaca acagaggtga atccaataa gttaataacg gaggcgtaac | 900 |
| cgtagtatct gaattgatcg tgtctgacag cggcggtagg agtaattgga gcgataatag | 960 |
| cgtccaattc cttaccagct ttttcttcag cttcacgcca cttttccaag tattccattt | 1020 |
| gatagttcca cttttgtaaa tgagtgtccc acaattcgtt catgttaaca gccttaatat | 1080 |
| ttgggttcaa caagtcctta atgttaggga tggctggctc accagaggca gaaatgtctc | 1140 |
| tcatgacgtc ggcagaacca tcagcagcat agatgtggga aatcaagtca tgaccgaaat | 1200 |
| catgcttgta tggagtccat ggagtaacgg tgtgaccagc cttggccaaa gcggcaacgg | 1260 |
| tagtttcgac accacgtaaa attggtgggt gtggcaagac gttaccgtcg aaattgtaat | 1320 |
| aaccaatgtt caaccacca ttcttaatct tagaggcaat gatgtcagat tcagattgtc | 1380 |
| tccatggcat tgggatgacc ttagagtcgt acttccaagg ttcttgaccc aagacagatt | 1440 |

```
tggtgaacaa tctcaagtct tcgacggagt gagtgatagg accaacgacg gagtgaacgg      1500
tttcttgacc ttccatagag ttagccattt tagcatatgg caatctaccg tgagatggtc      1560
tcaaaccgta taaaaagttg aaagcagctg ggactctaat ggaaccacca atgtcagtac      1620
cgacaccaat aacaccacct ctaataccaa caatagcacc ttcaccacca gaagaaccac      1680
cacaggacca atttttgttt cttggattga cagttctacc aatgatgttg ttgacggttt      1740
cacagaccat caaggtttgt gggacagagg tcttaacgta gaaaacagca ccagcttttc      1800
tcaacatggt ggttaagacg gaatcacctt catcgtattt gtttaaccag gaaatgtaac      1860
ccatggaggt ttcgtaaccc ttaacacgca attggtcctt taaagagatt ggtaaaccgt      1920
gtaatggacc aactggtctc ttatgcttag cgtagtattc atctaattct ctagcttgag      1980
ctaaagcagc atctgggaag aattcgtgag cacagttggt taattgttga gcaatagcag      2040
ctctcttaca aaaagccaaa gtgacttcaa cagaagtcaa ctcaccagcg gccaacttgg      2100
agaccaaatc agcagcagag gcttcggtaa tcttcaattc agcctcagac aaaataccgg      2160
acttctttgg gaaatcaata acggaatctt cggcaggcaa agtttgaacc ttccattcgt      2220
caggaatggt tttagccaaa cgggcacgtt tgtcggcggc caattcttcc caggattgtg      2280
gcattttgta attaaaactt agattagatt gctatgcttt cttctaatg agcaagaagt       2340 aaaaaaagtt gtaatagaac aagaaaaacg aaactgaaac ttgagaaatt gaagaccatt      2400
tattaactta aatatcaatg ggaggtcatc gaaagagaaa aaaatcaaaa aaaaattt        2460 tcaagaaaaa gaaacgtgat aaaaattttt attgcctttt tcgacgaaga aaaagaaacg      2520
aggcggtctc ttttttcttt tccaaacctt tagtacgggt aattaacgcc accctagagg      2580
aagaaagagg ggaaatttag tatgctgtgc ttgggtgttt tgaagtggta cggcgatgcg      2640
cggagtccga gaaaatctgg aagagtaaaa aaggagtaga acattttga agctatggtg       2700 tgtgggggat cacttgtggg ggattgggtg tgatgtaagg ataacttcgt atagcataca      2760
ttatacgaag ttatgcggcc gcgagaagat gcggccagca aaactaaaaa actgtattat      2820
aagtaaatgc atgtatacta aactcacaaa ttagagcttc aatttaatta tatcagttat      2880
tacccgggaa tctcggtcgt aatgattttt ataatgacga aaaaaaaaaa attggaaaga      2940
aaaagcttca tggcctttat aaaaaggaac catccaatac ctcgccagaa ccaagtaaca      3000
gtattttacg gggcacaaat caagaacaat aagacaggac tgtaaagatg gacgcattga      3060
actccaaaga acaacaagag ttccaaaaag tagtggaaca aaagcaaatg aaggatttca      3120
tgcgtttgta ctctaatctg gtagaaagat gttttacaga ctgtgtcaat gacttccacaa     3180 catcaaagct aaccaataag gaacaaacat gcatcatgaa gtgctcagaa aagttcttga     3240
agcatagcga acgtgtaggg cagcgtttcc aagag                                3275
```

<210> SEQ ID NO 3
<211> LENGTH: 1132
<212> TYPE: DNA
<213> ORGANISM: Artificial Sequence
<220> FEATURE:
<223> OTHER INFORMATION: cre recomb

<400> SEQUENCE: 3

```
ctctttttta cagatcatca aggaagtaat tatctacttt ttacaagaat tcatgtctaa        60
tttacttact gttcaccaaa acttgcctgc attaccagtt gacgcaacct ccgatgaagt       120
cagaaagaac cttatggata tgtttagaga tagacaagct ttctccgaac atacttggaa      180
```

| | |
|---|---|
| aatgttatta tccgtttgta gatcctgggc cgcttggtgt aaacttaaca atagaaaatg | 240 |
| gtttcctgct gaaccagaag acgtcagaga ttacttactt tacttacaag ctagaggttt | 300 |
| ggctgttaaa actatccaac aacacttagg tcaattgaat atgttacaca gaagatccgg | 360 |
| tttaccaaga ccatccgatt ccaacgcagt ttcccttgtt atgagaagaa ttagaaaaga | 420 |
| aaatgttgac gctggtgaaa gagctaaaca agcattagca tttgaaagaa ccgatttcga | 480 |
| tcaagttaga tccttaatgg aaaattccga tagatgtcaa gatattagaa acttagcttt | 540 |
| cttaggtatt gcttacaaca cattattaag aatcgctgaa attgctagaa ttagagttaa | 600 |
| agatatttca gaaccgatg gcggtagaat gttaatccac attggcagaa caaaaacctt | 660 |
| agtctccaca gcaggcgtcg aaaaagcatt atcattaggt gttactaaat tagttgaacg | 720 |
| ttggatttcc gtttccggtg ttgcagatga cccaaacaac tacttattct gtcgtgttag | 780 |
| aaaaaatggt gttgccgctc cttccgctac ctcacaatta tccacaagag cattagaagg | 840 |
| cattttgaa gctacccaca gacttattta tggtgcaaaa gacgattccg gtcaaagata | 900 |
| tttagcttgg tctggtcatt ccgctagagt tggtgccgca agagacatgg caagagctgg | 960 |
| tgtttctatt cctgaaatta tgcaagccgg tggttggact aatgttaaca ttgttatgaa | 1020 |
| ctatatcaga aacttagatt ccgaaacagg tgctatggtt agattacttg aagacggtga | 1080 |
| ttaagctagc taagatccgc tctaaccgaa aaggaaggag ttagacaacc tg | 1132 |

<210> SEQ ID NO 4
<211> LENGTH: 6376
<212> TYPE: DNA
<213> ORGANISM: Artificial Sequence
<220> FEATURE:
<223> OTHER INFORMATION: CYC1 t-pUC ori-ampR-2uori-URA3-pPGK integration fragment

<400> SEQUENCE: 4

| | |
|---|---|
| ctagctaaga tccgctctaa ccgaaaagga aggagttaga caacctgaag tctaggtccc | 60 |
| tatttatttt tttatagtta tgttagtatt aagaacgtta tttatatttc aaattttttct | 120 |
| ttttttctg tacagacgcg tgtacgcatg taacattata ctgaaaacct tgcttgagaa | 180 |
| ggttttggga cgctcgaaga tccagctgca ttaatgaatc ggccaacgcg cggggagagg | 240 |
| cggtttgcgt attgggcgct cttccgcttc ctcgctcact gactcgctgc gctcggtcgt | 300 |
| tcggctgcgg cgagcggtat cagctcactc aaaggcggta atacggttat ccacagaatc | 360 |
| aggggataac gcaggaaaga acatgtgagc aaaaggccag caaaaggcca ggaaccgtaa | 420 |
| aaaggccgcg ttgctggcgt ttttccatag gctccgcccc cctgacgagc atcacaaaaa | 480 |
| tcgacgctca agtcagaggt ggcgaaaccc gacaggacta taaagatacc aggcgtttcc | 540 |
| ccctggaagc tccctcgtgc gctctcctgt tccgacctg ccgcttaccg gatacctgtc | 600 |
| cgcctttctc ccttcgggaa gcgtggcgct ttctcatagc tcacgctgta ggtatctcag | 660 |
| ttcggtgtag tcgttcgct ccaagctggg ctgtgtgcac gaaccccccg ttcagcccga | 720 |
| ccgctgcgcc ttatccggta actatcgtct tgagtccaac ccggtaagac acgacttatc | 780 |
| gccactggca gcagccactg gtaacaggat tagcagagcg aggtatgtag gcggtgctac | 840 |
| agagttcttg aagtggtggc ctaactacgg ctacactaga aggacagtat ttggtatctg | 900 |
| cgctctgctg aagccagtta ccttcggaaa aagagttggt agctcttgat ccggcaaaca | 960 |
| aaccaccgct ggtagcggtg gtttttttgt ttgcaagcag cagattacgc gcagaaaaaa | 1020 |
| aggatctcaa gaagatcctt tgatcttttc tacggggtct gacgctcagt ggaacgaaaa | 1080 |

```
ctcacgttaa gggatttttgg tcatgagatt atcaaaaagg atcttcacct agatccttt    1140
aaattaaaaa tgaagtttta aatcaatcta aagtatatat gagtaaactt ggtctgacag    1200
ttaccaatgc ttaatcagtg aggcacctat ctcagcgatc tgtctatttc gttcatccat    1260
agttgcctga ctccccgtcg tgtagataac tacgatacgg gagggcttac catctggccc    1320
cagtgctgca atgataccgc gagacccacg ctcaccggct ccagatttat cagcaataaa    1380
ccagccagcc ggaagggccg agcgcagaag tggtcctgca actttatccg cctccatcca    1440
gtctattaat tgttgccggg aagctagagt aagtagttcg ccagttaata gtttgcgcaa    1500
cgttgttgcc attgctacag gcatcgtggt gtcacgctcg tcgtttggta tggcttcatt    1560
cagctccggt tcccaacgat caaggcgagt tacatgatcc cccatgttgt gcaaaaaagc    1620
ggttagctcc ttcggtcctc cgatcgttgt cagaagtaag ttggccgcag tgttatcact    1680
catggttatg gcagcactgc ataattctct tactgtcatg ccatccgtaa gatgcttttc    1740
tgtgactggt gagtactcaa ccaagtcatt ctgagaatag tgtatgcggc gaccgagttg    1800
ctcttgcccg gcgtcaatac gggataatac cgcgccacat agcagaactt taaaagtgct    1860
catcattgga aaacgttctt cggggcgaaa actctcaagg atcttaccgc tgttgagatc    1920
cagttcgatg taacccactc gtgcacccaa ctgatcttca gcatcttta ctttcaccag    1980
cgtttctggg tgagcaaaaa caggaaggca aaatgccgca aaaagggaa taagggcgac    2040
acggaaatgt tgaatactca tactcttcct ttttcaatat tattgaagca tttatcaggg    2100
ttattgtctc atgagcggat acatatttga atgtatttag aaaaataaac aatagggt     2160
tccgcgcaca tttccccgaa aagtgccacc tgaacgaagc atctgtgctt catttttgtag   2220
aacaaaaatg caacgcgaga gcgctaattt ttcaaacaaa gaatctgagc tgcatttttta   2280
cagaacagaa atgcaacgcg aaagcgctat tttaccaacg aagaatctgt gcttcatttt    2340
tgtaaaacaa aaatgcaacg cgagagcgct aatttttcaa acaaagaatc tgagctgcat    2400
ttttacagaa cagaaatgca acgcgagagc gctatttttac caacaaagaa tctatacttc    2460
ttttttgttc tacaaaaatg catcccgaga gcgctatttt tctaacaaag catcttagat    2520
tacttttttt ctcctttgtg cgctctataa tgcagtctct tgataacttt ttgcactgta    2580
ggtccgttaa ggttagaaga aggctacttt ggtgtctatt ttctcttcca taaaaaaagc    2640
ctgactccac ttcccgcgtt tactgattac tagcgaagct gcgggtgcat ttttcaaga    2700
taaaggcatc cccgattata ttctataccg atgtggattg cgcatacttt gtgaacagaa    2760
agtgatagcg ttgatgattc ttcattggtc agaaaattat gaacggtttc ttctattttg    2820
tctctatata ctacgtatag gaaatgttta cattttcgta ttgttttcga ttcactctat    2880
gaatagttct tactacaatt ttttgtcta aagagtaata ctagagataa acataaaaaa    2940
tgtagaggtc gagtttagat gcaagttcaa ggagcgaaag gtggatgggt aggttatata    3000
gggatatagc acagagatat atagcaaaga gatactttg agcaatgttt gtggaagcgg     3060
tattcgcaat attttagtag ctcgttacag tccggtgcgt ttttggtttt ttgaaagtgc    3120
gtcttcagag cgcttttggt tttcaaaagc gctctgaagt tcctatactt tctagagaat    3180
aggaacttcg gaataggaac ttcaaagcgt ttccgaaaac gagcgcttcc gaaaatgcaa    3240
cgcgagctgc gcacatacag ctcactgttc acgtcgcacc tatatctgcg tgttgcctgt    3300
atatatatat acatgagaag aacggcatag tgcgtgttta tgcttaaatg cgtacttata    3360
tgcgtctatt tatgtaggat gaaaggtagt ctagtacctc ctgtgatatt atcccattcc    3420
atgcggggta tcgtatgctt ccttcagcac tacccttag ctgttctata tgctgccact    3480
```

```
cctcaattgg attagtctca tccttcaatg ctatcatttc ctttgatatt ggatcatact    3540
aagaaaccat tattatcatg acattaacct ataaaaatag gcgtatcacg aggccctttc    3600
gtctcgcgcg tttcggtgat gacggtgaaa acctctgaca catgcagctc ccggagacgg    3660
tcacagcttg tctgtaagcg gatgccggga gcagacaagc ccgtcagggc gcgtcagcgg    3720
gtgttggcgg gtgtcgggc tggcttaact atgcggcatc agagcagatt gtactgagag    3780
tgcaccatac cacagctttt caattcaatt catcattttt tttttattct ttttttgat    3840 ttcggtttct ttgaaatttt tttgattcgg taatctccga acagaaggaa gaacgaagga    3900
aggagcacag acttagattg gtatatatac gcatatgtag tgttgaagaa acatgaaatt    3960
gcccagtatt cttaacccaa ctgcacagaa caaaacctg caggaaacga agataaatca    4020
tgtcgaaagc tacatataag gaacgtgctg ctactcatcc tagtcctgtt gctgccaagc    4080
tatttaatat catgcacgaa aagcaaacaa acttgtgtgc ttcattggat gttcgtacca    4140
ccaaggaatt actggagtta gttgaagcat taggtcccaa aatttgttta ctaaaaacac    4200
atgtggatat cttgactgat ttttccatgg agggcacagt taagccgcta aaggcattat    4260
ccgccaagta caatttttta ctcttcgaag acagaaaatt tgctgacatt ggtaatacag    4320
tcaaattgca gtactctgcg ggtgtataca gaatagcaga atgggcagac attacgaatg    4380
cacacggtgt ggtgggccca ggtattgtta gcggtttgaa gcaggcggca gaagaagtaa    4440
caaaggaacc tagaggcctt ttgatgttag cagaattgtc atgcaagggc tccctatcta    4500
ctggagaata tactaagggt actgttgaca ttgcgaagag cgacaaagat tttgttatcg    4560
gctttattgc tcaaagagac atgggtggaa gagatgaagg ttacgattgg ttgattatga    4620
cacccggtgt gggtttagat gacaagggag acgcattggg tcaacagtat agaaccgtgg    4680
atgatgtggt ctctacagga tctgacatta ttattgttgg aagaggacta tttgcaaagg    4740
gaagggatgc taaggtagag ggtgaacgtt acagaaaagc aggctgggaa gcatatttga    4800
gaagatgcgg ccagcaaaac taaaaaactg tattataagt aaatgcatgt atactaaact    4860
cacaaattag agcttcaatt taattatatc agttattacc ctatgcggtg tgaaataccg    4920
cacagatgcg taaggagaaa ataccgcatc aggaaattgt aaacgttaat attttgttaa    4980
aattcgcgtt aaattttgt taaatcagct catttttaa ccaataggcc gaaatcggca    5040
aaatccctta taaatcaaaa gaatagaccg agataggtt gagtgttgtt ccagtttgga    5100
acaagagtcc actattaaag aacgtggact ccaacgtcaa agggcgaaaa accgtctatc    5160
agggcgatgg cccactacgt gaaccatcac cctaatcaag ttttttgggg tcgaggtgcc    5220
gtaaagcact aaatcggaac cctaaaggga ccccgatt tagagcttga cggggaaagc    5280
cggcgaacgt ggcgagaaag gaagggaaga agcgaaagg agcgggcgct agggcgctgg    5340
caagtgtagc ggtcacgctg cgcgtaacca ccacacccgc cgcgcttaat gcgccgctac    5400
agggcgcgtc cattcgccat tcaggctgcg caactgttgg gaagggcgat cggtgcgggc    5460
ctcttcgcta ttacgccagc tgaattggag cgacctcatg ctatacctga gaaagcaacc    5520
tgacctacag gaaagagtta ctcaagaata agaattttcg ttttaaaacc taagagtcac    5580
tttaaaattt gtatacactt atttttttta aacttattt aataataaaa atcataaatc    5640
ataagaaatt cgcttattta gaagtgtcaa caacgtatct accaacgatt tgacccttt     5700 ccatcttttc gtaaatttct ggcaaggtag acaagccgac aaccttgatt ggagacttga    5760
ccaaacctct ggcgaagaat tgttaattaa gccagaaaaa ggaagtgttt ccctccttct    5820
```

| | |
|---|---:|
| tgaattgatg ttaccctcat aaagcacgtg gcctcttatc gagaaagaaa ttaccgtcgc | 5880 |
| tcgtgatttg tttgcaaaaa gaacaaaact gaaaaaaccc agacacgctc gacttcctgt | 5940 |
| cttcctattg attgcagctt ccaatttcgt cacacaacaa ggtcctagcg acggctcaca | 6000 |
| ggttttgtaa caagcaatcg aaggttctgg aatggcggga aagggtttag taccacatgc | 6060 |
| tatgatgccc actgtgatct ccagagcaaa gttcgttcga tcgtactgtt actctctctc | 6120 |
| tttcaaacag aattgtccga atcgtgtgac aacaacagcc tgttctcaca cactcttttc | 6180 |
| ttctaaccaa gggggtggtt tagtttagta gaacctcgtg aaacttacat ttacatatat | 6240 |
| ataaacttgc ataaattggt caatgcaaga aatacatatt tggtcttttc taattcgtag | 6300 |
| ttttcaagt tcttagatgc tttcttttc tcttttttac agatcatcaa ggaagtaatt | 6360 |
| atctactttt tacaag | 6376 |

<210> SEQ ID NO 5
<211> LENGTH: 3916
<212> TYPE: DNA
<213> ORGANISM: Artificial Sequence
<220> FEATURE:
<223> OTHER INFORMATION: Locus B-pPGK-ScIMA1-GAL10t-loxP-pTEF1-An amdS
      integration fragment

<400> SEQUENCE: 5

| | |
|---|---:|
| tttcgtattc ttacatccta tgtcgctaat acagttcccg catagagaag aaagcaaaca | 60 |
| aaagtagtca cagctatgac catgattacg ccaagcttgg taccgggccc cccctcgagg | 120 |
| ccagaaaaag gaagtgtttc cctccttctt gaattgatgt taccctcata aagcacgtgg | 180 |
| cctcttatcg agaaagaaat taccgtcgct cgtgatttgt ttgcaaaaag aacaaaactg | 240 |
| aaaaaaccca gacacgctcg acttcctgtc ttcctgttga ttgcagcttc caatttcgtc | 300 |
| acacaacaag gtcctagcga cggctcacag gttttgtaac aagcaatcga aggttctgga | 360 |
| atggcgggaa agggtttagt accacatgct atgatgccca ctgtgatctc cagagcaaag | 420 |
| ttcgttcgat cgtactgtta ctctctctct ttcaaacaga attgtccgaa tcgtgtgaca | 480 |
| acaacagcct gttctcacac actcttttct tctaaccaag ggggtggttt agtttagtag | 540 |
| aacctcgtga aacttacatt tacatatata taaacttgca taaattggtc aatgcaagaa | 600 |
| atacatattt ggtcttttct aattcgtagt ttttcaagtt cttagatgct ttctttttct | 660 |
| ctttttaca gatcatcaag gaagtaatta tctactttt acaagtctag aatgactatc | 720 |
| tcttctgctc acccagaaac tgaaccaaag tggtggaaag aggcaacttt ttaccaaatc | 780 |
| tacccagctt cattcaagga ctccaatgat gatggttggg gtgatatgaa aggtattgct | 840 |
| tccaaattag aatacattaa ggaattaggt gccgatgcta tttggattc tccattctat | 900 |
| gattctccac aagacgatat gggttatgac atcgctaact atgaaaaggt ttggccaacc | 960 |
| tatggcacta atgaggactg ttttgcatta attgagaaaa cccacaagtt gggcatgaag | 1020 |
| ttcattactg atcttgtcat taatcattgt catccgaac atgaatggtt caaggaatcc | 1080 |
| agatcctcca aaactaatcc aaaaagagat tggttttct ggagaccacc taagggttat | 1140 |
| gatgctgaag gtaagccaat tccaccaaac aattggaagt cttactttgg tggttccgca | 1200 |
| tggaccttcg acgaaaagac ccaagagttt tacttgagat tattctgctc cacccaacca | 1260 |
| gatttgaact gggaaaatga agattgtaga aaagcaatct acgaatctgc agttggctat | 1320 |
| tggttagatc acgtgttga tggtttcaga attgatgttg gttcacttta ctcaaaggtt | 1380 |
| gttggtttgc cagatgcacc agttgttgat aaaaactcta catggcaatc ttctgaccca | 1440 |

```
tacactctta atggtcctag aatccatgaa tttcatcaag agatgaacca gttcattaga       1500
aatagagtta aggatggtag agaaattatg accgttggtg aaatgcaaca tgcatctgat       1560
gaaactaaga gattatacac atcagcctcc cgtcacgaat tgtctgaatt attcaacttt       1620
tcacacacag acgttggcac atccccatta ttccgttata acttggttcc attcgaattg       1680
aaggactgga aaatcgcatt ggcagaattg tttagatata tcaatggtac tgattgttgg       1740
tctaccatct acttggaaaa ccacgaccaa ccaagatcca tcactagatt cggtgatgac       1800
tctcctaaaa accgtgtcat ttctggtaag ttactttctg tcttattatc cgccttaacc       1860
ggtactttgt acgtctatca aggccaggaa ttgggtcaaa ttaactttaa gaattggcca       1920
gtcgaaaagt atgaagatgt cgaaatcaga aacaactaca atgcaattaa ggaggaacat       1980
ggtgaaaatt cagaggaaat gaaaagtttt tggaagcta ttgctcttat ttccagagat        2040
cacgctagaa ccccaatgca atggtcaaga gaggaaccta acgctggttt ctctggtcct       2100
tccgccaagc cttggtttta cttaaacgac tccttcagag aaggtattaa cgttgaagat       2160
gaaattaagg acccaaattc cgtccttaac ttctggaagg aagcattgaa gtttagaaag       2220
gcccataagg atattaccgt ttatggttat gactttgagt ttatcgattt ggataacaaa       2280
aagttattct cattcactaa aaagtataac aacaagacct tattcgctgc tttaaacttc       2340
tcttctgatg ctactgattt caaaattcct aatgacgatt cctctttcaa gttggagttt       2400
ggtaactacc caagaagga gttgacgca tcttctcgta cattgaagcc ttgggaaggt         2460
agaatctaca tctccgagta acctgcaggt ttgccagctt actatccttc ttgaaaatat       2520
gcactctata tcttttagtt cttaattgca acacatagat ttgctgtata acgaatttta       2580
tgctattttt taaatttgga gttcagtgat aaaagtgtca cagcgaattt cctcacatgt       2640
agggaccgaa ttgtttacaa gttctctgta ccaccatgga gacatcaaaa attgaaaatc       2700
tatggaaaga tatggacggt agcaacaaga atatagcacg agccggcgac tagtaacggc       2760
cgccagtgtg ctggaattcg cccttatatt agcggccgca taacttcgta taatgtatgc       2820
tatacgaagt tatccttaca tcacacccaa tcccccacaa gtgatccccc acacaccata       2880
gcttcaaaat gtttctactc cttttttact cttccagatt ttctcggact ccgcgcatcg       2940
ccgtaccact tcaaaacacc caagcacagc atactaaatt tcccctcttt cttcctctag       3000
ggtggcgtta attcccgta ctaaaggttt ggaaaagaaa aaagagaccg cctcgtttct        3060
ttttcttcgt cgaaaaaggc aataaaaatt tttatcacgt ttcttttttct tgaaaaattt     3120 ttttttttgat tttttttctct ttcgatgacc tcccattgat atttaagtta ataaatggtc    3180
ttcaatttct caagtttcag tttcgttttt cttgttctat tacaacttttt tttacttctt     3240 gctcattaga aagaaagcat agcaatctaa tctaagtttt aattacaaaa tgccacaatc      3300
ctgggaagaa ttggccgccg acaaacgtgc ccgtttggct aaaaccattc ctgacgaatg      3360
gaaggttcaa actttgcctg ccgaagattc cgttattgat ttcccaaaga agtccggtat     3420
tttgtctgag gctgaattga agattaccga agcctctgct gctgatttgg tctccaagtt     3480
ggccgctggt gagttgactt ctgttgaagt cactttggct ttttgtaaga gagctgctat     3540
tgctcaacaa ttaaccaact gtgctcacga attcttccca gatgctgctt tagctcaagc    3600
tagagaatta gatgaatact acgctaagca taagagacca gttggtccat tacacggttt    3660
accaatctct ttaaaggacc aattgcgtgt taagggttac gaaacctcca tgggttacat     3720
ttcctggtta aacaaatacg atgaaggtga ttccgtctta accaccatgt tgagaaaagc    3780
tggtgctgtt ttctacgtta agacctctgt cccacaaacc ttgatggtct gtgaaaccgt    3840
```

```
                caacaacatc attggtagaa ctgtcaatcc aagaaacaaa aattggtcct gtggtggttc    3900
ttctggtggt gaaggt                                                     3916

<210> SEQ ID NO 6
<211> LENGTH: 1856
<212> TYPE: DNA
<213> ORGANISM: Artificial Sequence
<220> FEATURE:
<223> OTHER INFORMATION: An amdS-pTEF1-loxP-locus B integration fragment

<400> SEQUENCE: 6
gaagattacc gaagcctctg ctgctgattt ggtctccaag ttggccgctg gtgagttgac      60
ttctgttgaa gtcactttgg cttttttgtaa gagagctgct attgctcaac aattaaccaa     120
ctgtgctcac gaattcttcc cagatgctgc tttagctcaa gctagagaat tagatgaata     180
ctacgctaag cataagagac cagttggtcc attacacggt ttaccaatct ctttaaagga     240
ccaattgcgt gttaagggtt acgaaacctc catgggttac atttcctggt aaacaaata      300 cgatgaaggt gattccgtct taaccaccat gttgagaaaa gctggtgctg ttttctacgt     360
taagacctct gtcccacaaa ccttgatggt ctgtgaaacc gtcaacaaca tcattggtag     420
aactgtcaat ccaagaaaca aaaattggtc ctgtggtggt tcttctggtg gtgaaggtgc     480
tattgttggt attagaggtg gtgttattgg tgtcggtact gacattggtg gttccattag     540
agtcccagct gctttcaact ttttatacgg tttgagacca tctcacggta gattgccata     600
tgctaaaatg gctaactcta tggaaggtca agaaaccgtt cactccgtcg ttggtcctat     660
cactcactcc gtcgaagact tgagattgtt caccaaatct gtcttgggtc aagaaccttg     720
gaagtacgac tctaaggtca tcccaatgcc atggagacaa tctgaatctg acatcattgc     780
ctctaagatt aagaatggtg gtttgaacat tggttattac aatttcgacg gtaacgtctt     840
gccacaccca ccaatttac gtggtgtcga aactaccgtt gccgctttgg ccaaggctgg     900
tcacaccgtt actccatgga ctccatacaa gcatgatttc ggtcatgact tgatttccca     960
catctatgct gctgatggtt ctgccgacgt catgagagac atttctgcct ctggtgagcc    1020
agccatccct aacattaagg acttgttgaa cccaaatatt aaggctgtta acatgaacga    1080
attgtgggac actcatttac aaaagtggaa ctatcaaatg gaatacttgg aaaagtggcg    1140
tgaagctgaa gaaaaagctg gtaaggaatt ggacgctatt atcgctccaa ttactcctac    1200
cgccgctgtc agacacgatc aattcagata ctacggttac gcctccgtta ttaacttatt    1260
ggatttcacc tctgttgtcg tcccagtcac tttcgctgat aagaatattg ataagaagaa    1320
cgaatctttt aaagctgttt ccgaattgga tgctttggtt caagaagaat acgacccaga    1380
ggcttatcac ggtgctcctg ttgctgttca agttattggt agaagattgt ccgaagagag    1440
aactttggct atcgccgaag aagtcggtaa attgttgggt aacgtcgtca ctccataagg    1500
agattgataa gacttttcta gttgcatatc ttttatattt aaatcttatc tattagttaa    1560 tttttttgtaa tttatcctta tatatagtct ggttattcta aaatatcatt tcagtatcta    1620
aaaattcccc tcttttttca gttatatctt aacaggcgat aacttcgtat aatgtatgct    1680
atacgaagtt atgcggccgc taatataagg gcgaattctg cagatatcca tcacactggc    1740
ggccgctcga gcatgcatct agagggccca attcgcccta gtgattat agcctagctt       1800 taaggctact ttaaaaactt tttattttatt catacatata tattatcgaa cattcg        1856

<210> SEQ ID NO 7
```

<211> LENGTH: 1928
<212> TYPE: DNA
<213> ORGANISM: Artificial Sequence
<220> FEATURE:
<223> OTHER INFORMATION: ScMAL11

<400> SEQUENCE: 7

| | | | | | |
|---|---|---|---|---|---|
| caagctatac | caagcataca | atcaactatc | tcatatacaa | tgaaaaacat | catttcatta | 60 |
| gtttctaaga | agaaggctgc | atccaaaaat | gaagataaaa | acatctctga | atcttcaaga | 120 |
| gatatcgtta | atcaacaaga | ggttttcaat | accgaagatt | tcgaggaagg | caaaaaggac | 180 |
| tctgcattcg | aattagatca | cttggagttt | actaccaact | ccgcacaatt | aggcgactct | 240 |
| gatgaggaca | acgaaaacgt | cattaacgaa | atgaacgcaa | cagacgatgc | aaacgaagca | 300 |
| aactctgaag | agaaatccat | gaccttgaag | caagcattgt | tgaagtatcc | taaagccgca | 360 |
| ttatggtcta | ttttagtctc | cactactttg | gtcatggaag | gttacgacac | tgctttgtta | 420 |
| tccgcattat | acgctttacc | agtttttcaa | cgtaagtttg | gtacattgaa | tggtgaaggt | 480 |
| tcctatgaga | ttacatccca | atggcagatt | ggtcttaaca | tgtgcgtctt | gtgtggtgaa | 540 |
| atgattggtt | tacaaatcac | cacctatatg | gttgagttta | tgggtaacag | atacactatg | 600 |
| atcaccgctt | taggtctttt | gactgcttac | attttcattt | tgtactattg | taagtcctta | 660 |
| gccatgattg | ctgttggtca | aattttgtcc | gccatccctt | ggggttgttt | tcaatctttg | 720 |
| gctgttacct | atgcttctga | agtctgccca | ttagcactta | gatactatat | gacttcctat | 780 |
| tctaacattt | gctggttgtt | cggccaaatc | ttcgcatctg | gtatcatgaa | aaactcacaa | 840 |
| gagaacttag | gcaattccga | tcttggttac | aaacttccat | tgcttttaca | gtggatttgg | 900 |
| cctgccccac | ttatgattgg | tatttttcttt | gctccagaat | ctccttggtg | gcttgttaga | 960 |
| aaagatagag | ttgcagaagc | tagaaagtca | ttatccagaa | ttttgtctgg | taagggcgct | 1020 |
| gaaaaggata | ttcaagttga | tcttacctta | aagcagattg | aattaactat | tgaaaaggaa | 1080 |
| agattattag | cttctaagtc | tggttcattc | tttaactgtt | tcaagggtgt | taatggtcgt | 1140 |
| agaaccagat | tagcatgttt | aacctgggtt | gcccaaaaact | cctccggtgc | agttttgtta | 1200 |
| ggttattcta | cttacttttt | cgaaagagct | ggtatggcaa | cagacaaggc | tttcacattc | 1260 |
| tcattaatcc | agtactgttt | gggtcttgca | ggcaccttat | gttcatgggt | tatttcaggt | 1320 |
| agagtcggta | gatggactat | cttgacttat | ggtcttgctt | ttcaaatggt | ctgtttgttc | 1380 |
| attatcggtg | gtatgggttt | tggttctggt | tcctctgctt | ccaatggtgc | tggtggctta | 1440 |
| ttgttggcat | tatccttttt | ctacaatgca | ggcatcggtg | ctgttgtcta | ttgtattgtc | 1500 |
| gccgaaattc | cttcagcaga | attgagaacc | aagactattg | ttttggctag | aatctgttac | 1560 |
| aatttgatgg | ccgttatcaa | tgctattttg | accccataca | tgttgaacgt | ttctgactgg | 1620 |
| aactggggtg | ctaagacagg | cttgtattgg | ggtggtttca | ctgcagttac | tttggcttgg | 1680 |
| gttattatcg | acttaccaga | aaccactggt | agaacattct | ctgaaatcaa | tgaattattc | 1740 |
| aaccaaggtg | ttccagctcg | taagttcgca | tctactgtcg | tcgatccatt | cggtaagggt | 1800 |
| aagacccaac | atgattcctt | ggccgatgaa | tccatctctc | aatcttcatc | cattaagcaa | 1860 |
| agagaattga | atgcagcaga | taagtgttaa | ttaattaaac | aggcccctttt | tcctttgtcg | 1920 |
| atatcatg | | | | | 1928 |

<210> SEQ ID NO 8
<211> LENGTH: 1907
<212> TYPE: DNA
<213> ORGANISM: Artificial Sequence
<220> FEATURE:
<223> OTHER INFORMATION: ScMPH2

<400> SEQUENCE: 8

```
caagctatac caagcataca atcaactatc tcatatacaa tgaagaactt atctttcttg      60
atcaatagaa gaaaggagaa cacttctgat tccaacgttt acccaggtaa agctaaatct     120
cacgaacctt cttggattga atggatgac caaactaaga agatggttt ggacatcgtt       180
cacgtcgagt tctcccctga caccagagcc ccatctgact ccaacaaagt cattactgag     240
attttcgacg ctaccgaaga tgctaaagag gctgatgaat ccgaaagagg tatgccatta     300
gccactgctt tgaacactta ccaaaggct gccgcttgg ctttgttagt ctctaccact      360
ttgatcatgg aaggttacga tactgccatt ttaggtgctt tctacgcttt gcctattttc     420
caaagaaagt tcggttctca aaatgataag accggtgaat gggaaatttc tgcctcctgg     480
caaattggtt tgaccttgtg ttacatggct ggtgaaatcg ttggtttgca attgactggt     540
ccatccgttg atttagttgg taacagatat acttttgatta ttgctttgtt cttttttggct  600
gctttcactt tcatttttata cttctgtaat tccttgggta tgatcgctgt tggtcaagcc    660
ttgtgtggta tgccatgggg ttgttttccaa tgtttgactg tttcttacgc ttccgaaatt    720
tgtccattgg ccttgagata ctacttgact acttactcca acttgtgttg gttattcggt    780
caattgttcg ctgccggtat catgaaaaac tctcaaaaaa aatacgctga ttccgaattg    840
ggttacaagt taccttcgc cttacaatgg attttgcctg ttccattggc tttgggtatt      900
ttcttcgctc cagagtctcc atggtggtta gtcaagaagg gtagattcga cgaggctaga     960
agatccttgc gtcgtacttt atccggtaaa ggtccagaaa aagaaatctt ggttaccttg    1020
gaagtcgaca agattaaagt cactatcgac aaggaaaaga gattaacttc taaggaaggt    1080
tcctactccg actgtttcga agacaagatc aacagaagaa gaactagaat tacttgtttg    1140
tgttgggccg tcaagccac ctgtggttcc attttgatcg gttactctac ttacttctat    1200
gagaaagctg gtgtttccac tgaaatgtct ttcactttct ctattattca atactgtttg    1260
ggtatctgtg ctactttctt gtcttggtgg gcttccaagt acttcggtag atatgacttg    1320
tacgctttcg gtttggcctt ccaaactatt gttttttttca tcatcggtgg tttgggttgc   1380
tcctccactc acggttctaa gatggggttcc ggttcttttgt taatggccgt tgctttcttt  1440
tacaacttgg gtattgctcc agtcgtcttt tgtttggtct ctgagatgcc atcttctcgt    1500
ttaagaacta aaaccatcat tttggctaga aatacttata acgttgtctc tattatttgt    1560
tctgtttttga ttttgtacca attaaactct aagaagtgga actggggtgc taagtctggt   1620
ttcttctggg gtgtcttgtg tttctgcact ttgatctggg ctgtcgtcga tttgccagaa    1680
accgccggta gacttttcgt cgaaattaac gagttgttta gttgggtgt ctctgctaga    1740
aagttcaaat ccaccaaagt tgacccattc gttgtcaaga ctccattgaa aacttccttg    1800
attactaccc cacgtgaaat ttccaagttg ccattgcaaa gaaactccaa cgtctctcac    1860
cacttgtaat taattaaaca ggccccttttt cctttgtcga tatcatg                  1907
```

<210> SEQ ID NO 9
<211> LENGTH: 1815
<212> TYPE: DNA
<213> ORGANISM: Artificial Sequence
<220> FEATURE:
<223> OTHER INFORMATION: DhMAL11-1

<400> SEQUENCE: 9

```
caagctatac caagcataca atcaactatc tcatatacaa tgtccgccca acacgttgag      60
gacattgaca aaccaggtgt tgttatcgaa gttaacccat tgaacaagaa catgactgac    120
gactctatgg ctcacgaagc ccaagatttt atggacaaat ttttggacat gtctgaaaac    180
gctaaggaca acgatagaaa ggaaaagtac atgcctttaa aggaaggttt aaagaccttc    240
ccaaaggctg ccatgtggtc cgttattttg tctactgcct taatcatgga aggttacgac    300
accaatttgt taaattcttt gtacgccttc cctgatttcg ctaagaagtt cggtgaatac    360
tctgaatccg acggttccta ccaaattcca gctaaatggc aaacttcttt atccatgtgt    420
gttaacgtcg gtgaaatcat tggtttgttc atcgctggta tcatcgctga tagaattggt    480
tacagaaaaa ctttgatcgg tgccttgatg ttgactaccg gtttcatctt cattgttttc    540
tttgccgtta atgttgaaat gttgttggct ggtgaattat tgttgggttt accatggggt    600
gccttccaaa cttttgactgt ttcttacgct tctgaagttt gtccaaccac cttgagagtc    660
tacttgacca cttatgttaa cgtctgttgg gttttcggtc aattgatttc ctctggtatc    720
ttgagaggtt tggtttcctc cgacattgaa gacgtctacc gtattccttt tgccgtccaa    780
tgggtttggc caatcccaat tgccattggt atttacttgg ctccagaatc tccatggtgg    840
ttggctagaa aaaatagaat ccaagaagct aagcactcca ttaagagatt attgactgtc    900
aacgaacact gcctgacaa ggaaatcttg ctgaggcta tggttcaaaa gatccaaatg    960
actttgaagg aagaagcttt aactaacaac ggtgaatctt ttttggattg ttttaagggt    1020
caagacttga aagaaccag aattgctgct attgtttggg tttcccaaaa cttaactggt    1080
tcctccttga tggttactc tacctacttc tatcaacaag ctggtttggg tcaaaacatg    1140
tccttcactt tctctatcat tcaatactgt ttcggtatcg ttggtacttt gggttcctgg    1200
ttattgtctc aaaaggctgg tagattcact atctactttt acggtttgtg ttctttgttt    1260
tgtatcttat tcgtcgtcgg ttgtttgggt attaatccaa ccgaatcctc ttcttggggt    1320
gtcggttctt tgttgttagt ttataccttc gtttacgatt taactatcgg tccttttgtgc    1380 tactgtattg ttgctgaaat tccatccact aaattgagaa ctaaaaccat tattattgct    1440
agaaacgctt acaacattgc tggtattgtt gttgctatta tcactccata catgttgaat    1500
ccaaccgcct ggaactggaa ggccaagacc ggtttttttct ggtctggttt cgccttttc    1560 gctgccattt ggtgttggtt cgatttgcca gaaactaagg gtaagacctt cgccgaattg    1620
gatcaattgt tcgaaaacaa ggtcaaggcc agacaattca gaagactga agttgaagtt    1680 tttaatactg acgaattgat tgaaagatta ggtgaagacg gtattaaaga tttggtcgtt    1740
actgacgctt ctaaagatga atttttccgaa aaagtttaat taattaaaca ggcccctttt    1800
cctttgtcga tatca                                                    1815
```

<210> SEQ ID NO 10
<211> LENGTH: 1825
<212> TYPE: DNA
<213> ORGANISM: Artificial Sequence
<220> FEATURE:
<223> OTHER INFORMATION: DhMAL11-2

<400> SEQUENCE: 10

```
caagctatac caagcataca atcaactatc tcatatacaa tgtccgtttt gtccttcatc      60
gttaaaaacg aggttgaacc aaacatcgaa attgaaaaca aaactaagta tgaacaagtt    120
aacttcgagg tcgacccaac tgctgataaa gatattaacg actacattga aaagttttg    180 gatatctccg acaacgctag aaacaacgac aagcaagaaa aagaaatgtc tttgttggaa    240
```

```
ggtttgaaga cctatcctaa ggccgctgcc tggtccgtca tcttatctac tgctttagtc    300
atggaaggtt atgatacctc tttgatgggt tccttatacg gtatgcctgc tttcgctgaa    360
aaatttggta tgttcgagcc atcctcccaa tcctaccaaa ttccagctaa gtaccaaacc    420
attatgggta cttgtggtaa cgcttcttct atcattggtt tgtggttcgc tggtattttg    480
gctgatcgtt ttggttacag aaagactatc atcgctaact tgatcttagt tgctattttt    540
atctttattg ttttttttgc caaaaacatt ggtatgttga tggccggtaa tatcttattg    600
ggtttccctt ggggtgcctt ccaaactttg tccgttgctt acgcttctga agtctgccca    660
atggtcttaa gaatctactt aactacttac tctaacatct gttggatttt tggtcaattg    720
ttgtctgctg gtgttatgag agcctttgtt acttctactt ccgaacaatc ttacaaggtt    780
ccattcgcta tccaatgggt ttggccagtc caatcatta ttggtgtttt tttcgctcca    840
gaatccccat actggttggt caaaaacgac aagtataagg aagctaagag atctatcgaa    900
agattgatta ctgaaaataa aaacgtcgat aaaaacatct tatctgaagc tatgttgcaa    960
aagatgcaaa tgactgttaa gggtgaacaa caagaaaaga aattgccatc ttacttggaa   1020
tgtttcaagg gtgtcgaatt gagacgtacc cgtatcgccg ccttgacctg gttaacccaa   1080
aacttgtgtg gtgctacttt attgtcttac tcttcttact tttatattca agctggtatg   1140
gctccagaaa tgtctttcac tttcactatt attcaattcg ccttgggtat cgttggtacc   1200
atcggttcct ggttcttatc taagagattc ggtagattta ctatctactt cggtggttta   1260
tgtgccttag ccgtcatttt gatggtcatc ggtggtttgg gttgttccac tgataaaaac   1320
tctatgtggg gtgttggtac cttgttaatc atttacgtta tggtctacga cttgactgtt   1380
ggtccattgt gttactgtat cgttgctgaa atcccatctg ttagattgag agccaaatct   1440
atcatcatcg ctagaaattt gtacaacatc tccggtattg tcttgtctat tttaacccca   1500
tacatgttga acccaggtgc tttgggattgg tccgctaagg ttggtttctt ttggtctggt   1560
ttcactattg tctgtgctgt ctggtgtttt ttcgatttgc cagaaactaa gggtaaaacc   1620
ttcgctgact tggattattt gttccaacaa aatatcaagt ccagagattt taagaatact   1680
gaagcttctg tctttgacgc tgaatcttac attcacaaat taggtgatga cggtattaag   1740
caattggttg aacaaaatga atttgctaat aacaccggta aggtttaatt aattaaacag   1800
gccccttttc ctttgtcgat atcat                                          1825
```

<210> SEQ ID NO 11
<211> LENGTH: 1734
<212> TYPE: PRT
<213> ORGANISM: Artificial Sequence
<220> FEATURE:
<223> OTHER INFORMATION: SpSUT1

<400> SEQUENCE: 11

```
Gly Cys Thr Ala Thr Ala Cys Cys Ala Ala Gly Cys Ala Thr Ala Cys
1               5                   10                  15

Ala Ala Thr Cys Ala Ala Cys Thr Ala Thr Cys Thr Cys Ala Thr Ala
                20                  25                  30

Thr Ala Cys Ala Ala Thr Gly Thr Cys Cys Gly Thr Thr Gly Ala Cys
                35                  40                  45

Gly Ala Ala Ala Ala Cys Cys Ala Ala Thr Thr Gly Gly Ala Ala Ala
            50                  55                  60

Ala Thr Gly Gly Thr Cys Ala Ala Thr Thr Ala Thr Thr Ala Thr Cys
65              70                  75                  80
```

-continued

```
Thr Thr Cys Thr Gly Ala Ala Ala Ala Cys Gly Ala Ala Gly Cys Thr
                85                  90                  95

Thr Cys Thr Thr Cys Cys Cys Cys Ala Thr Thr Cys Ala Ala Gly Gly
            100                 105                 110

Ala Gly Thr Cys Thr Ala Thr Thr Cys Cys Thr Thr Cys Cys Ala Gly
        115                 120                 125

Ala Thr Cys Cys Thr Cys Thr Thr Thr Gly Thr Ala Cys Thr Thr Gly
    130                 135                 140

Ala Thr Cys Gly Cys Thr Thr Thr Gly Ala Cys Thr Gly Thr Thr Thr
145                 150                 155                 160

Cys Cys Thr Thr Ala Thr Thr Gly Gly Gly Thr Gly Thr Thr Cys Ala
                165                 170                 175

Ala Thr Thr Ala Ala Cys Cys Thr Gly Gly Thr Cys Thr Gly Thr Thr
            180                 185                 190

Gly Ala Ala Thr Thr Ala Gly Gly Thr Thr Ala Thr Gly Gly Ala Ala
        195                 200                 205

Cys Cys Cys Cys Ala Thr Ala Thr Thr Thr Ala Thr Thr Cys Thr Cys
    210                 215                 220

Thr Thr Thr Gly Gly Gly Thr Thr Thr Gly Ala Gly Ala Ala Ala Gly
225                 230                 235                 240

Gly Ala Ala Thr Gly Gly Ala Cys Cys Thr Cys Cys Ala Thr Cys Ala
                245                 250                 255

Thr Thr Thr Gly Gly Ala Thr Cys Gly Cys Thr Gly Gly Thr Cys Cys
            260                 265                 270

Ala Thr Thr Gly Ala Cys Thr Gly Gly Thr Ala Thr Thr Thr Thr Ala
        275                 280                 285

Ala Thr Cys Cys Ala Ala Cys Cys Ala Ala Thr Cys Gly Cys Cys Gly
    290                 295                 300

Gly Thr Ala Thr Cys Thr Thr Gly Thr Cys Cys Gly Ala Cys Ala Gly
305                 310                 315                 320

Ala Gly Thr Thr Ala Ala Cys Thr Cys Cys Ala Gly Ala Ala Thr Cys
                325                 330                 335

Gly Gly Thr Ala Gly Ala Ala Gly Ala Cys Gly Thr Cys Cys Ala Thr
            340                 345                 350

Thr Thr Ala Thr Gly Thr Thr Gly Thr Gly Thr Gly Cys Thr Thr Cys
        355                 360                 365

Cys Thr Thr Gly Thr Thr Gly Gly Gly Thr Ala Cys Thr Thr Thr Thr
    370                 375                 380

Thr Cys Thr Thr Thr Ala Thr Thr Cys Thr Thr Gly Ala Thr Gly Gly
385                 390                 395                 400

Gly Thr Thr Gly Gly Gly Cys Thr Cys Cys Thr Gly Ala Thr Ala Thr
                405                 410                 415

Thr Thr Gly Thr Thr Thr Gly Thr Thr Cys Ala Thr Cys Thr Thr Thr
            420                 425                 430

Thr Cys Cys Ala Ala Cys Gly Ala Ala Gly Thr Thr Thr Thr Ala Ala
        435                 440                 445

Thr Gly Ala Ala Ala Ala Gly Ala Gly Thr Thr Ala Cys Thr Ala Thr
    450                 455                 460

Cys Gly Thr Cys Thr Thr Gly Gly Cys Thr Ala Cys Cys Ala Thr Cys
465                 470                 475                 480

Thr Cys Thr Ala Thr Cys Thr Ala Cys Thr Thr Ala Thr Thr Gly Gly
                485                 490                 495
```

| | | | | | | | | | | | | |
|---|---|---|---|---|---|---|---|---|---|---|---|---|
|Ala|Cys|Gly|Thr|Thr|Gly|Cys|Cys|Gly|Thr|Cys|Ala|Ala|Cys|Gly|Thr|
| | | |500| | |505| | | |510| | | | | |

Ala Cys Gly Thr Thr Gly Cys Cys Gly Thr Cys Ala Ala Cys Gly Thr
                500             505             510

Cys Gly Thr Thr Ala Thr Gly Gly Cys Cys Thr Cys Ala Cys Thr
            515             520             525

Ala Gly Ala Thr Cys Cys Thr Ala Ala Thr Thr Gly Thr Thr Gly
530             535             540

Ala Cys Thr Cys Thr Gly Thr Ala Gly Ala Thr Cys Cys Gly Ala
545             550             555             560

Thr Cys Ala Ala Cys Ala Cys Ala Thr Gly Ala Ala Gly Cys Cys
            565             570             575

Ala Ala Cys Thr Cys Cys Thr Gly Gly Gly Cys Thr Gly Gly Thr Ala
            580             585             590

Gly Ala Ala Thr Gly Ala Thr Thr Gly Gly Thr Gly Thr Cys Gly Gly
595 600 605

Thr Ala Ala Cys Gly Thr Thr Thr Thr Gly Gly Gly Thr Thr Ala Cys
610 615 620

Thr Thr Gly Thr Thr Gly Gly Gly Thr Thr Ala Cys Thr Thr Ala Cys
625 630 635 640

Cys Ala Thr Thr Gly Thr Ala Cys Cys Gly Thr Ala Thr Thr Thr Thr
645 650 655

Cys Thr Cys Thr Thr Thr Cys Thr Thr Gly Ala Ala Cys Thr Thr Cys
660 665 670

Ala Cys Thr Cys Ala Ala Thr Thr Ala Cys Ala Ala Gly Thr Thr Thr
675 680 685

Thr Thr Thr Gly Cys Gly Thr Cys Thr Thr Gly Gly Cys Cys Thr Cys
690 695 700

Thr Ala Thr Thr Thr Cys Cys Thr Thr Ala Gly Thr Cys Thr Thr Gly
705 710 715 720

Ala Cys Thr Gly Thr Cys Ala Cys Thr Ala Thr Cys Ala Cys Cys Ala
725 730 735

Cys Thr Ala Thr Cys Thr Thr Cys Gly Thr Cys Thr Cys Cys Gly Ala
740 745 750

Ala Ala Gly Ala Ala Gly Ala Thr Thr Cys Cys Cys Ala Cys Cys Ala
755 760 765

Gly Thr Cys Gly Ala Ala Cys Ala Cys Gly Ala Ala Ala Ala Gly Thr
770 775 780

Cys Cys Gly Thr Thr Gly Cys Cys Gly Gly Thr Gly Ala Ala Ala Thr
785 790 795 800

Thr Thr Thr Cys Gly Ala Gly Thr Thr Cys Thr Thr Cys Ala Cys Thr
805 810 815

Ala Cys Cys Ala Thr Gly Ala Gly Ala Cys Ala Ala Thr Cys Thr Ala
820 825 830

Thr Thr Ala Cys Thr Gly Cys Thr Thr Thr Ala Cys Cys Ala Thr Thr
835 840 845

Cys Ala Cys Thr Thr Thr Ala Ala Ala Gly Ala Gly Ala Ala Thr Thr
850 855 860

Thr Gly Thr Thr Thr Cys Gly Thr Thr Cys Ala Ala Thr Thr Thr Thr
865 870 875 880

Thr Cys Gly Cys Thr Thr Ala Cys Thr Thr Cys Gly Gly Thr Thr Gly
885 890 895

Gly Thr Thr Cys Cys Cys Ala Thr Thr Cys Thr Thr Gly Thr Thr Thr
900 905 910

Thr Ala Cys Ala Thr Cys Ala Cys Thr Ala Cys Thr Thr Ala Cys Gly

```
                915                 920                 925
Thr Thr Gly Gly Thr Ala Thr Thr Thr Thr Gly Thr Ala Cys Thr Thr
            930                 935                 940
Gly Ala Gly Ala Cys Ala Cys Gly Cys Thr Cys Cys Thr Ala Ala Gly
945                 950                 955                 960
Gly Gly Thr Cys Ala Cys Gly Ala Ala Gly Ala Gly Ala Cys Thr
                965                 970                 975
Gly Gly Gly Ala Thr Ala Thr Gly Gly Cys Thr Ala Cys Thr Ala Gly
                980                 985                 990
Ala Cys Ala Ala Gly Gly Thr Thr Cys Cys Thr Thr Cys Gly Cys Thr
            995                 1000                1005
Thr Thr Ala Thr Thr Gly Thr Thr Gly Thr Thr Thr Gly Cys Thr
        1010                1015                1020
Ala Thr Thr Ala Thr Cys Thr Cys Cys Thr Thr Gly Gly Cys Cys
        1025                1030                1035
Gly Cys Cys Ala Ala Cys Ala Cys Cys Gly Cys Thr Thr Thr Gly
    1040                1045                1050
Cys Cys Ala Thr Thr Gly Thr Ala Thr Thr Gly Gly Ala Ala
    1055                1060                1065
Gly Ala Cys Ala Cys Cys Gly Ala Ala Gly Ala Thr Gly Ala Cys
    1070                1075                1080
Gly Ala Ala Gly Ala Gly Gly Ala Cys Gly Ala Ala Thr Cys Thr
    1085                1090                1095
Thr Cys Thr Gly Ala Cys Gly Cys Thr Thr Cys Cys Ala Ala Cys
    1100                1105                1110
Ala Ala Thr Gly Ala Gly Thr Ala Cys Ala Ala Cys Ala Thr Thr
    1115                1120                1125
Cys Ala Ala Gly Ala Ala Ala Gly Ala Ala Ala Cys Gly Ala Thr
    1130                1135                1140
Thr Thr Ala Gly Gly Thr Ala Ala Cys Ala Thr Thr Ala Gly Ala
    1145                1150                1155
Ala Cys Thr Gly Gly Thr Ala Cys Thr Ala Ala Cys Ala Cys Thr
    1160                1165                1170
Cys Cys Ala Ala Gly Ala Thr Thr Gly Gly Gly Thr Ala Ala Cys
    1175                1180                1185
Thr Thr Gly Thr Cys Thr Gly Ala Ala Ala Cys Thr Ala Cys Cys
    1190                1195                1200
Thr Cys Thr Thr Thr Cys Ala Gly Ala Thr Cys Thr Gly Ala Ala
    1205                1210                1215
Ala Ala Thr Gly Ala Ala Cys Cys Ala Thr Cys Cys Ala Gly Ala
    1220                1225                1230
Ala Gly Ala Ala Gly Ala Thr Thr Gly Thr Ala Cys Cys Ala
    1235                1240                1245
Thr Cys Thr Thr Cys Cys Ala Gly Ala Thr Cys Thr Ala Thr Cys
    1250                1255                1260
Ala Thr Gly Ala Cys Thr Ala Cys Thr Ala Thr Thr Cys Thr
    1265                1270                1275
Thr Cys Cys Ala Ala Gly Gly Thr Cys Cys Ala Ala Ala Thr Cys
    1280                1285                1290
Ala Ala Ala Gly Gly Thr Thr Gly Ala Cys Thr Thr Thr Gly
    1295                1300                1305
Cys Cys Thr Ala Thr Cys Thr Thr Ala Thr Gly Gly Thr Thr Gly
    1310                1315                1320
```

-continued

```
Thr Cys  Thr Thr Cys Thr Cys  Ala Cys Gly Thr Cys  Thr Thr Gly
    1325                 1330                 1335

Thr Thr  Cys Gly Gly Thr Gly  Thr Cys Thr Gly Thr  Ala Thr Gly
    1340                 1345                 1350

Thr Thr  Gly Thr Cys Thr Ala  Cys Thr Ala Thr Thr  Thr Thr Cys
    1355                 1360                 1365

Thr Thr  Gly Cys Ala Ala Ala  Cys Thr Thr Cys Thr  Thr Gly Gly
    1370                 1375                 1380

Cys Ala  Ala Gly Cys Cys Cys  Ala Ala Gly Cys Thr  Ala Thr Gly
    1385                 1390                 1395

Gly Thr  Thr Gly Cys Thr Ala  Thr Thr Thr Gly Thr  Gly Gly Thr
    1400                 1405                 1410

Thr Thr  Ala Thr Cys Cys Thr  Gly Gly Gly Cys Cys  Thr Gly Thr
    1415                 1420                 1425

Ala Cys  Thr Thr Thr Gly Thr  Gly Gly Ala Thr Thr  Cys Cys Ala
    1430                 1435                 1440

Thr Ala  Cys Thr Cys Thr Thr  Thr Ala Thr Thr Cys  Thr Cys Thr
    1445                 1450                 1455

Thr Cys  Thr Gly Ala Ala Ala  Thr Cys Gly Gly Thr  Ala Ala Gly
    1460                 1465                 1470

Thr Thr  Gly Gly Gly Thr Thr  Thr Gly Ala Gly Ala  Gly Ala Ala
    1475                 1480                 1485

Thr Cys  Cys Thr Cys Thr Gly  Gly Thr Ala Ala Gly  Ala Thr Gly
    1490                 1495                 1500

Ala Thr  Cys Gly Gly Thr Gly  Thr Thr Cys Ala Cys  Ala Ala Cys
    1505                 1510                 1515

Gly Thr  Thr Thr Thr Cys Ala  Thr Thr Thr Cys Thr  Gly Cys Cys
    1520                 1525                 1530

Cys Cys  Ala Cys Ala Ala Gly  Thr Thr Thr Thr Gly  Thr Cys Thr
    1535                 1540                 1545

Ala Cys  Cys Ala Thr Thr Ala  Thr Cys Gly Cys Thr  Ala Cys Cys
    1550                 1555                 1560

Ala Thr  Thr Gly Thr Thr Thr  Thr Cys Ala Thr Cys  Cys Ala Ala
    1565                 1570                 1575

Thr Cys  Cys Gly Ala Ala Gly  Gly Thr Thr Cys Thr  Cys Ala Cys
    1580                 1585                 1590

Ala Gly  Ala Gly Ala Thr Ala  Thr Cys Gly Cys Thr  Gly Ala Thr
    1595                 1600                 1605

Ala Ala  Cys Thr Cys Thr Ala  Thr Cys Gly Cys Thr  Thr Gly Gly
    1610                 1615                 1620

Gly Thr  Cys Thr Thr Gly Ala  Gly Ala Ala Thr Thr  Gly Gly Thr
    1625                 1630                 1635

Gly Gly  Thr Ala Thr Thr Thr  Cys Thr Gly Cys Cys  Thr Thr Cys
    1640                 1645                 1650

Thr Thr  Gly Gly Cys Cys Gly  Cys Thr Thr Ala Cys  Cys Ala Ala
    1655                 1660                 1665

Thr Gly  Thr Ala Gly Ala Cys  Ala Thr Thr Thr Gly  Thr Thr Gly
    1670                 1675                 1680

Cys Cys  Ala Ala Thr Thr Ala  Ala Cys Thr Thr Cys  Thr Ala Ala
    1685                 1690                 1695

Thr Thr  Ala Ala Thr Thr Ala  Ala Ala Cys Ala Gly  Gly Cys Cys
    1700                 1705                 1710
```

```
Cys Cys Thr Thr Thr Thr Cys Cys Thr Thr Thr Gly Thr Cys Gly
   1715                1720                1725

Ala Thr Ala Thr Cys Ala
   1730

<210> SEQ ID NO 12
<211> LENGTH: 1962
<212> TYPE: PRT
<213> ORGANISM: Artificial Sequence
<220> FEATURE:
<223> OTHER INFORMATION: TdMAL11

<400> SEQUENCE: 12

Ala Ala Gly Cys Thr Ala Thr Ala Cys Cys Ala Gly Cys Ala Thr
1               5                   10                  15

Ala Cys Ala Ala Thr Cys Ala Ala Cys Thr Ala Thr Cys Thr Cys Ala
           20                  25                  30

Thr Ala Thr Ala Cys Ala Ala Thr Gly Ala Ala Gly Thr Cys Cys Thr
           35                  40                  45

Thr Ala Gly Cys Cys Ala Ala Thr Gly Thr Cys Ala Ala
       50                  55                  60

Cys Ala Gly Ala Ala Ala Gly Ala Ala Thr Ala Ala Gly Ala Ala Gly
65                  70                  75                  80

Ala Ala Thr Thr Thr Gly Gly Ala Ala Gly Ala Ala Cys Cys Ala Gly
                85                  90                  95

Ala Thr Ala Thr Thr Gly Thr Thr Ala Gly Ala Gly Cys Thr Gly Gly
               100                 105                 110

Thr Gly Thr Thr Thr Cys Thr Thr Cys Thr Gly Gly Thr Thr Cys Cys
               115                 120                 125

Ala Gly Ala Thr Thr Ala Thr Cys Thr Thr Thr Gly Ala Ala Cys Ala
           130                 135                 140

Gly Ala Thr Cys Thr Ala Ala Cys Thr Thr Thr Gly Ala Ala Thr Thr
145                 150                 155                 160

Ala Gly Ala Ala Gly Ala Thr Ala Cys Cys Gly Ala Thr Ala Ala Gly
                165                 170                 175

Ala Ala Gly Ala Ala Gly Gly Cys Thr Thr Cys Cys Gly Ala Thr Gly
               180                 185                 190

Cys Thr Thr Thr Gly Gly Ala Ala Thr Thr Gly Gly Ala Cys Cys Ala
               195                 200                 205

Cys Thr Thr Gly Gly Ala Gly Thr Thr Cys Ala Cys Thr Thr Cys Thr
           210                 215                 220

Gly Ala Cys Gly Thr Cys Gly Cys Cys Cys Ala Ala Thr Cys Ala
225                 230                 235                 240

Ala Cys Gly Ala Ala Gly Ala Ala Gly Ala Gly Ala Cys Cys Ala
                245                 250                 255

Ala Ala Ala Cys Gly Ala Cys Cys Ala Cys Gly Cys Thr Thr Thr Gly
               260                 265                 270

Gly Gly Thr Gly Thr Cys Ala Thr Ala Ala Cys Gly Cys Cys Gly
           275                 280                 285

Cys Thr Gly Ala Thr Gly Ala Cys Gly Cys Thr Cys Ala Ala Gly Ala
           290                 295                 300

Ala Gly Cys Thr Ala Ala Thr Gly Ala Ala Gly Ala Gly Gly Ala Ala
305                 310                 315                 320

Ala Ala Ala Ala Ala Gly Ala Thr Gly Ala Cys Thr Thr Gly Gly
                325                 330                 335
```

-continued

```
Thr Cys Cys Ala Ala Gly Cys Thr Thr Thr Gly Ala Ala Gly Gly Cys
            340                 345                 350

Thr Thr Ala Cys Cys Cys Ala Ala Ala Ala Gly Cys Thr Gly Cys Thr
        355                 360                 365

Gly Cys Thr Thr Gly Gly Thr Cys Cys Gly Thr Cys Thr Thr Gly Gly
    370                 375                 380
Thr Cys Thr Cys Thr Ala Cys Cys Ala Cys Cys Thr Thr Gly Gly Thr
385                 390                 395                 400

Thr Ala Thr Gly Gly Ala Ala Gly Gly Thr Thr Ala Cys Gly Ala Thr
                405                 410                 415
Ala Cys Cys Thr Cys Cys Thr Thr Ala Thr Thr Gly Ala Ala Cys Gly
            420                 425                 430

Cys Thr Thr Thr Gly Thr Thr Cys Gly Cys Thr Thr Thr Gly Cys Cys
        435                 440                 445

Ala Gly Thr Cys Thr Thr Cys Cys Ala Ala Gly Ala Ala Ala Ala Ala
    450                 455                 460

Thr Thr Cys Gly Gly Thr Thr Cys Cys Ala Thr Thr Thr Cys Thr Ala
465                 470                 475                 480
Ala Gly Ala Cys Cys Gly Gly Thr Gly Ala Ala Thr Ala Cys Gly Ala
                485                 490                 495
Ala Ala Thr Cys Thr Cys Thr Thr Cys Thr Cys Ala Ala Thr Gly Gly
            500                 505                 510

Cys Ala Ala Ala Thr Cys Gly Gly Thr Thr Thr Gly Ala Ala Thr Ala
        515                 520                 525

Thr Gly Thr Gly Thr Ala Thr Thr Thr Thr Thr Gly Thr Cys Gly Gly
    530                 535                 540
Thr Gly Ala Ala Ala Thr Thr Ala Thr Cys Gly Gly Thr Thr Thr Ala
545                 550                 555                 560

Cys Ala Ala Ala Thr Gly Ala Cys Cys Gly Gly Thr Thr Thr Cys Thr
                565                 570                 575

Thr Gly Gly Thr Thr Gly Ala Ala Thr Gly Gly Thr Thr Cys Gly Gly
            580                 585                 590

Thr Ala Ala Cys Ala Gly Ala Thr Gly Gly Ala Cys Cys Ala Thr Gly
        595                 600                 605

Ala Thr Cys Gly Gly Thr Gly Cys Thr Thr Thr Ala Gly Gly Thr Thr
    610                 615                 620

Thr Gly Thr Thr Gly Ala Cys Thr Gly Cys Thr Thr Ala Cys Ala Thr
625                 630                 635                 640

Cys Thr Thr Cys Thr Thr Gly Thr Thr Gly Thr Ala Cys Thr Thr Cys
                645                 650                 655

Thr Gly Thr Ala Ala Ala Thr Cys Thr Thr Thr Gly Gly Cys Thr Ala
            660                 665                 670

Thr Gly Ala Thr Cys Gly Cys Thr Gly Thr Thr Gly Cys Thr Cys Ala
        675                 680                 685

Ala Ala Thr Cys Thr Thr Gly Thr Cys Cys Gly Cys Thr Ala Thr Gly
    690                 695                 700

Cys Cys Ala Thr Gly Gly Gly Gly Thr Thr Gly Thr Thr Thr Cys Cys
705                 710                 715                 720

Ala Ala Thr Cys Thr Thr Thr Gly Gly Cys Thr Gly Thr Cys Ala Cys
                725                 730                 735

Cys Thr Ala Cys Gly Cys Thr Thr Cys Thr Gly Ala Ala Gly Thr Cys
            740                 745                 750

Thr Gly Thr Cys Cys Ala Thr Thr Ala Ala Cys Cys Thr Thr Gly Ala
```

-continued

```
            755                 760                 765
Gly Ala Thr Ala Cys Thr Ala Thr Thr Ala Ala Cys Cys Ala Cys
            770                 775                 780
Thr Thr Ala Thr Thr Cys Thr Ala Ala Cys Ala Thr Gly Thr Gly Thr
785                 790                 795                 800
Thr Gly Gly Thr Thr Gly Thr Thr Cys Gly Gly Thr Cys Ala Ala Ala
                805                 810                 815
Thr Thr Thr Thr Cys Thr Cys Cys Gly Cys Thr Gly Gly Thr Ala Thr
            820                 825                 830
Thr Ala Thr Gly Ala Ala Gly Ala Ala Cys Thr Cys Thr Cys Ala Ala
            835                 840                 845
Thr Cys Thr Ala Ala Cys Thr Thr Gly Gly Gly Thr Ala Ala Cys Thr
            850                 855                 860
Cys Thr Gly Ala Thr Thr Thr Gly Gly Gly Thr Thr Ala Cys Ala Ala
865                 870                 875                 880
Gly Ala Thr Gly Cys Cys Ala Thr Thr Cys Gly Cys Thr Thr Thr Gly
                885                 890                 895
Cys Ala Ala Thr Gly Gly Ala Thr Cys Thr Gly Gly Cys Cys Ala Gly
                900                 905                 910
Cys Thr Cys Cys Ala Thr Thr Gly Gly Cys Thr Thr Thr Gly Gly Gly
            915                 920                 925
Thr Ala Thr Thr Thr Ala Cys Thr Thr Gly Gly Cys Thr Cys Cys Ala
            930                 935                 940
Gly Ala Ala Thr Cys Cys Cys Ala Thr Gly Gly Thr Ala Cys Thr
945                 950                 955                 960
Thr Gly Gly Thr Thr Ala Gly Ala Ala Ala Gly Thr Cys Cys Ala Ala
                965                 970                 975
Gly Thr Thr Cys Gly Cys Thr Gly Ala Ala Gly Cys Thr Ala Ala Gly
                980                 985                 990
Ala Ala Gly Thr Cys Thr Thr Thr Gly Ala Ala Cys Ala Gly Ala Ala
                995                1000                1005
Thr Cys Thr Thr Gly Thr Cys Thr Gly Gly Thr Thr Cys Cys Gly
     1010                1015                1020
Gly Thr Cys Cys Ala Cys Ala Ala Ala Gly Gly Ala Ala Ala
     1025                1030                1035
Thr Thr Cys Ala Ala Gly Thr Gly Ala Thr Thr Gly Ala
     1040                1045                1050
Ala Thr Thr Thr Gly Ala Ala Gly Cys Ala Ala Ala Thr Thr Gly
     1055                1060                1065
Ala Ala Thr Thr Ala Ala Cys Cys Ala Thr Cys Gly Ala Ala Ala
     1070                1075                1080
Ala Gly Gly Ala Ala Cys Gly Thr Ala Ala Gly Thr Thr Gly Ala
     1085                1090                1095
Ala Ala Cys Ala Ala Ala Gly Ala Ala Gly Gly Gly Thr Thr
     1100                1105                1110
Cys Cys Thr Thr Cys Thr Gly Gly Gly Ala Cys Thr Gly Cys Thr
     1115                1120                1125
Thr Cys Ala Ala Gly Gly Thr Gly Thr Gly Ala Thr Gly
     1130                1135                1140
Gly Thr Cys Gly Thr Ala Gly Ala Ala Cys Cys Ala Gly Ala Ala
     1145                1150                1155
Thr Cys Ala Cys Cys Thr Gly Thr Thr Thr Gly Ala Cys Cys Thr
     1160                1165                1170
```

```
Gly Gly Gly Thr Cys Thr Cys Cys Ala Ala Ala Cys Ala
        1175            1180            1185

Cys Thr Thr Cys Cys Gly Gly Thr Thr Cys Thr Gly Cys Thr Thr
        1190            1195            1200

Thr Gly Thr Thr Gly Gly Gly Thr Thr Ala Cys Thr Cys Cys Ala
        1205            1210            1215

Cys Cys Thr Ala Cys Thr Thr Cys Thr Cys Gly Ala Ala Ala
        1220            1225            1230

Gly Ala Gly Cys Cys Gly Gly Thr Ala Thr Gly Ala Cys Ala
        1235            1240            1245

Cys Cys Thr Cys Thr Ala Ala Cys Gly Cys Thr Thr Cys Ala
        1250            1255            1260

Cys Thr Thr Thr Cys Thr Cys Cys Ala Thr Thr Ala Thr Thr Thr
        1265            1270            1275

Cys Thr Thr Ala Cys Thr Thr Gly Thr Gly Gly Gly Thr Thr
        1280            1285            1290

Thr Gly Gly Thr Thr Gly Gly Thr Ala Cys Thr Ala Thr Gly Ala
        1295            1300            1305

Cys Cys Thr Cys Cys Thr Gly Gly Ala Thr Cys Ala Thr Thr Thr
        1310            1315            1320

Cys Thr Gly Gly Thr Ala Gly Ala Thr Thr Ala Gly Gly Thr Ala
        1325            1330            1335

Gly Ala Thr Gly Gly Cys Ala Ala Thr Cys Thr Thr Gly Gly
        1340            1345            1350

Cys Thr Gly Gly Thr Gly Gly Thr Thr Thr Gly Thr Gly Thr Thr
        1355            1360            1365

Thr Cys Cys Ala Ala Ala Thr Gly Thr Thr Gly Gly Thr Cys Thr
        1370            1375            1380

Thr Gly Thr Thr Thr Gly Thr Cys Ala Thr Cys Gly Gly Thr Gly
        1385            1390            1395

Gly Thr Thr Thr Ala Gly Gly Thr Thr Thr Cys Thr Cys Cys Gly
        1400            1405            1410

Ala Cys Thr Cys Cys Cys Ala Gly Gly Thr Gly Cys Thr Thr
        1415            1420            1425

Cys Thr Ala Ala Cys Gly Gly Thr Gly Cys Thr Gly Gly Thr Gly
        1430            1435            1440

Gly Thr Thr Thr Gly Thr Thr Gly Thr Thr Ala Gly Cys Cys Thr
        1445            1450            1455

Thr Gly Thr Cys Thr Thr Thr Thr Thr Thr Cys Thr Cys Cys Ala
        1460            1465            1470

Ala Cys Gly Thr Cys Gly Gly Thr Ala Thr Thr Gly Gly Thr Thr
        1475            1480            1485

Cys Thr Gly Thr Cys Thr Gly Thr Thr Ala Cys Thr Gly Thr Ala
        1490            1495            1500

Thr Thr Gly Thr Cys Gly Cys Cys Gly Ala Ala Ala Thr Gly Cys
        1505            1510            1515

Cys Ala Thr Cys Thr Gly Cys Thr Gly Ala Ala Thr Thr Gly Ala
        1520            1525            1530

Gly Ala Ala Cys Thr Cys Ala Ala Ala Cys Thr Ala Thr Thr Gly
        1535            1540            1545

Thr Thr Thr Thr Gly Gly Cys Thr Ala Gly Ala Ala Ala Cys Thr
        1550            1555            1560
```

-continued

```
Gly Thr  Thr Ala Cys Ala Ala  Cys Thr Thr Gly Ala  Thr Gly Gly
    1565                 1570                 1575

Cys Thr  Ala Thr Thr Gly Thr  Cys Ala Ala Cys Gly  Cys Cys Ala
    1580                 1585                 1590

Thr Cys  Thr Thr Gly Ala Cys  Thr Cys Cys Ala Thr  Ala Thr Ala
    1595                 1600                 1605

Thr Gly  Thr Thr Gly Ala Ala  Cys Ala Cys Cys Gly  Gly Thr Gly
    1610                 1615                 1620

Ala Thr  Thr Gly Gly Ala Ala  Thr Thr Gly Gly Gly  Gly Thr Gly
    1625                 1630                 1635

Cys Cys  Ala Ala Ala Ala Cys  Thr Gly Gly Thr Thr  Thr Gly Thr
    1640                 1645                 1650

Ala Thr  Thr Gly Gly Gly Gly  Thr Gly Gly Thr Ala  Thr Gly Ala
    1655                 1660                 1665

Cys Thr  Gly Cys Cys Thr Thr  Gly Ala Cys Cys Thr  Thr Gly Gly
    1670                 1675                 1680

Cys Cys  Thr Gly Gly Gly Thr  Cys Ala Thr Cys Ala  Thr Cys Gly
    1685                 1690                 1695

Ala Cys  Thr Thr Gly Cys Cys  Ala Gly Ala Ala Ala  Cys Cys Gly
    1700                 1705                 1710

Cys Thr  Gly Gly Thr Ala Gly  Ala Ala Cys Cys Thr  Thr Cys Thr
    1715                 1720                 1725

Cys Thr  Gly Ala Gly Ala Thr  Thr Ala Ala Cys Gly  Ala Ala Thr
    1730                 1735                 1740

Thr Ala  Thr Thr Cys Gly Cys  Cys Cys Gly Thr Gly  Gly Thr Gly
    1745                 1750                 1755

Thr Cys  Cys Cys Ala Gly Cys  Thr Ala Gly Ala Ala  Ala Gly Thr
    1760                 1765                 1770

Thr Cys  Ala Ala Gly Thr Cys  Cys Ala Cys Thr Gly  Thr Thr Gly
    1775                 1780                 1785

Thr Thr  Gly Ala Cys Cys Cys  Ala Thr Thr Cys Gly  Cys Thr Ala
    1790                 1795                 1800

Ala Ala  Gly Gly Thr Ala Gly  Ala Ala Thr Cys Gly  Cys Cys Gly
    1805                 1810                 1815

Ala Cys  Gly Ala Cys Ala Thr  Thr Gly Cys Thr Gly  Ala Ala Gly
    1820                 1825                 1830

Ala Thr  Gly Ala Cys Thr Thr  Gly Gly Ala Cys Gly  Cys Cys Gly
    1835                 1840                 1845

Ala Ala  Gly Thr Thr Ala Cys  Thr Thr Cys Thr Gly  Thr Thr Thr
    1850                 1855                 1860

Thr Cys  Ala Gly Ala Gly Ala  Ala Gly Ala Cys Gly  Ala Cys Gly
    1865                 1870                 1875

Thr Thr  Gly Ala Ala Thr Thr  Gly Gly Gly Thr Thr  Cys Thr Gly
    1880                 1885                 1890

Cys Cys  Thr Gly Thr Gly Ala  Thr Cys Cys Ala Gly  Gly Thr Ala
    1895                 1900                 1905

Ala Gly  Ala Cys Thr Thr Cys  Thr Thr Thr Gly Thr  Ala Ala Thr
    1910                 1915                 1920

Thr Ala  Ala Thr Thr Ala Ala  Ala Cys Ala Gly Gly  Cys Cys Cys
    1925                 1930                 1935

Cys Thr  Thr Thr Thr Cys Cys  Thr Thr Thr Gly Thr  Cys Gly Ala
    1940                 1945                 1950

Thr Ala  Thr Cys Ala Thr Gly  Thr Ala
```

-continued

```
        1955            1960

<210> SEQ ID NO 13
<211> LENGTH: 5836
<212> TYPE: PRT
<213> ORGANISM: Artificial Sequence
<220> FEATURE:
<223> OTHER INFORMATION: CYC1-AmpR-ScCEN-URA3-pADH integration fragment

<400> SEQUENCE: 13

Thr Ala Ala Ala Cys Ala Gly Gly Cys Cys Cys Thr Thr Thr Thr
1               5                   10                  15

Cys Cys Thr Thr Thr Gly Thr Cys Gly Ala Thr Ala Thr Cys Ala Thr
            20                  25                  30

Gly Thr Ala Ala Thr Thr Ala Gly Thr Thr Ala Thr Gly Thr Cys Ala
        35                  40                  45

Cys Gly Cys Thr Thr Ala Cys Ala Thr Thr Cys Ala Cys Gly Cys Cys
    50                  55                  60

Cys Thr Cys Cys Thr Cys Cys Ala Cys Ala Thr Cys Cys Gly Cys
65              70                  75                  80

Thr Cys Thr Ala Ala Cys Cys Gly Ala Ala Ala Gly Gly Ala Ala
                85                  90                  95

Gly Gly Ala Gly Thr Ala Gly Ala Cys Ala Cys Cys Thr Gly
            100                 105                 110

Ala Ala Gly Thr Cys Thr Ala Gly Gly Thr Cys Cys Cys Thr Ala Thr
        115                 120                 125

Thr Thr Ala Thr Thr Thr Thr Thr Thr Ala Thr Ala Gly Thr Thr
    130                 135                 140

Ala Thr Gly Thr Thr Ala Gly Thr Ala Thr Ala Ala Gly Ala Ala
145                 150                 155                 160

Cys Gly Thr Thr Ala Thr Thr Ala Thr Ala Thr Thr Cys Ala
        165                 170                 175

Ala Ala Thr Thr Thr Thr Cys Thr Thr Thr Thr Thr Thr Thr Thr
    180                 185                 190

Cys Thr Gly Thr Ala Cys Ala Ala Ala Cys Gly Cys Gly Thr Gly Thr
        195                 200                 205

Ala Cys Gly Cys Ala Thr Gly Thr Ala Ala Cys Ala Thr Thr Ala Thr
    210                 215                 220

Ala Cys Thr Gly Ala Ala Ala Ala Cys Cys Thr Thr Gly Cys Thr
225                 230                 235                 240

Thr Gly Cys Thr Thr Ala Thr Cys Gly Ala Thr Ala Cys Cys Gly Thr
            245                 250                 255

Cys Gly Ala Cys Cys Thr Cys Gly Ala Gly Gly Gly Gly Gly Gly
        260                 265                 270

Cys Cys Cys Gly Gly Thr Ala Cys Cys Ala Gly Cys Thr Thr Thr Thr
    275                 280                 285

Gly Thr Thr Cys Cys Cys Thr Thr Thr Ala Gly Thr Gly Ala Gly Gly
        290                 295                 300

Gly Thr Thr Ala Ala Thr Thr Cys Cys Gly Ala Gly Cys Thr Thr Gly
305                 310                 315                 320

Gly Cys Gly Thr Ala Ala Thr Cys Ala Thr Gly Gly Thr Cys Ala Thr
            325                 330                 335

Ala Gly Cys Thr Gly Thr Thr Thr Cys Cys Thr Gly Thr Gly Thr Gly
        340                 345                 350

Ala Ala Ala Thr Thr Gly Thr Thr Ala Thr Cys Cys Gly Cys Thr Cys
```

```
                355                 360                 365
Ala Cys Ala Ala Thr Thr Cys Cys Ala Cys Ala Ala Cys Ala
370                 375                 380
Thr Ala Gly Gly Ala Gly Cys Cys Gly Gly Ala Ala Gly Cys Ala Thr
385                 390                 395                 400
Ala Ala Ala Gly Thr Gly Thr Ala Ala Gly Cys Cys Thr Gly Gly
            405                 410                 415
Gly Gly Thr Gly Cys Cys Thr Ala Ala Thr Gly Ala Gly Thr Gly Ala
            420                 425                 430
Gly Gly Thr Ala Ala Cys Thr Cys Ala Cys Thr Thr Ala Ala Thr
            435                 440                 445
Thr Gly Cys Gly Thr Thr Gly Cys Gly Cys Thr Cys Ala Cys Thr Gly
        450                 455                 460
Cys Cys Cys Gly Cys Thr Thr Thr Cys Cys Ala Gly Thr Cys Gly Gly
465                 470                 475                 480
Gly Ala Ala Ala Cys Cys Thr Gly Thr Cys Gly Thr Gly Cys Cys Ala
            485                 490                 495
Gly Cys Thr Gly Cys Ala Thr Thr Ala Ala Thr Gly Ala Ala Thr Cys
        500                 505                 510
Gly Gly Cys Cys Ala Ala Cys Gly Cys Gly Cys Gly Gly Gly Gly Ala
        515                 520                 525
Gly Ala Gly Gly Cys Gly Gly Thr Thr Thr Gly Cys Gly Thr Ala Thr
530                 535                 540
Thr Gly Gly Gly Cys Gly Cys Thr Cys Thr Thr Cys Cys Gly Cys Thr
545                 550                 555                 560
Thr Cys Cys Thr Cys Gly Cys Thr Cys Ala Cys Thr Gly Ala Cys Thr
            565                 570                 575
Cys Gly Cys Thr Gly Cys Gly Cys Thr Cys Gly Gly Thr Cys Gly Thr
            580                 585                 590
Thr Cys Gly Gly Cys Thr Gly Cys Gly Gly Cys Gly Ala Gly Cys Gly
            595                 600                 605
Gly Thr Ala Thr Cys Ala Gly Cys Thr Cys Ala Cys Thr Cys Ala Ala
        610                 615                 620
Ala Gly Gly Cys Gly Gly Thr Ala Ala Thr Ala Cys Gly Gly Thr Thr
625                 630                 635                 640
Ala Thr Cys Cys Ala Cys Ala Gly Ala Ala Thr Cys Ala Gly Gly Gly
            645                 650                 655
Gly Ala Thr Ala Ala Cys Gly Cys Ala Gly Gly Ala Ala Ala Gly Ala
            660                 665                 670
Ala Cys Ala Thr Gly Thr Gly Ala Gly Cys Ala Ala Ala Ala Gly Gly
        675                 680                 685
Cys Cys Ala Gly Cys Ala Ala Ala Ala Gly Gly Cys Cys Ala Gly Gly
        690                 695                 700
Ala Ala Cys Cys Gly Thr Ala Ala Ala Ala Ala Gly Gly Cys Cys Gly
705                 710                 715                 720
Cys Gly Thr Thr Gly Cys Thr Gly Gly Cys Gly Thr Thr Thr Thr Thr
            725                 730                 735
Cys Cys Ala Thr Ala Gly Gly Cys Thr Cys Cys Gly Cys Cys Cys Cys
            740                 745                 750
Cys Cys Thr Gly Ala Cys Gly Ala Gly Cys Ala Thr Cys Ala Cys Ala
            755                 760                 765
Ala Ala Ala Ala Thr Cys Gly Ala Cys Gly Cys Thr Cys Ala Ala Gly
            770                 775                 780
```

-continued

```
Thr Cys Ala Gly Ala Gly Gly Thr Gly Gly Cys Gly Ala Ala Ala Cys
785                 790                 795                 800

Cys Cys Gly Ala Cys Ala Gly Gly Ala Cys Thr Ala Thr Ala Ala Ala
                805                 810                 815

Gly Ala Thr Ala Cys Cys Ala Gly Gly Cys Gly Thr Thr Cys Cys Cys
            820                 825                 830

Cys Cys Cys Thr Gly Gly Ala Ala Gly Cys Thr Cys Cys Cys Thr Cys
        835                 840                 845

Gly Thr Gly Cys Gly Cys Thr Cys Thr Cys Cys Thr Gly Thr Thr Cys
    850                 855                 860

Cys Gly Ala Cys Cys Cys Thr Gly Cys Cys Gly Cys Thr Thr Ala Cys
865                 870                 875                 880

Cys Gly Gly Ala Thr Ala Cys Cys Thr Gly Thr Cys Cys Gly Cys Cys
                885                 890                 895

Thr Thr Thr Cys Thr Cys Cys Cys Thr Thr Cys Gly Gly Gly Ala Ala
            900                 905                 910

Gly Cys Gly Thr Gly Gly Cys Gly Cys Thr Thr Thr Cys Thr Cys Ala
        915                 920                 925

Ala Thr Gly Cys Thr Cys Ala Cys Gly Cys Thr Gly Thr Ala Gly Gly
    930                 935                 940

Thr Ala Thr Cys Thr Cys Ala Gly Thr Thr Cys Gly Gly Thr Gly Thr
945                 950                 955                 960

Ala Gly Gly Thr Cys Gly Thr Thr Cys Gly Cys Thr Cys Cys Ala Ala
                965                 970                 975

Gly Cys Thr Gly Gly Gly Cys Thr Gly Thr Gly Thr Gly Cys Ala Cys
            980                 985                 990

Gly Ala Ala Cys Cys Cys Cys Cys  Cys Gly Thr Thr Cys  Ala Gly Cys
        995                 1000                1005

Cys Cys  Gly Ala Cys Cys Gly  Cys Thr Gly Cys Gly  Cys Cys Thr
    1010                1015                1020

Thr Ala  Thr Cys Cys Gly Gly  Thr Ala Ala Cys Thr  Ala Thr Cys
    1025                1030                1035

Gly Thr  Cys Thr Thr Gly Ala  Gly Thr Cys Cys Ala  Ala Cys Cys
    1040                1045                1050

Cys Gly  Gly Thr Ala Ala Gly  Ala Cys Ala Cys Gly  Ala Cys Thr
    1055                1060                1065

Thr Ala  Thr Cys Gly Cys Cys  Ala Cys Thr Gly Gly  Cys Ala Gly
    1070                1075                1080

Cys Ala  Gly Cys Cys Ala Cys  Thr Gly Gly Thr Ala  Ala Cys Ala
    1085                1090                1095

Gly Gly  Ala Thr Thr Ala Gly  Cys Ala Gly Ala Gly  Cys Gly Ala
    1100                1105                1110

Gly Gly  Thr Ala Thr Gly Thr  Ala Gly Gly Cys Gly  Gly Thr Gly
    1115                1120                1125

Cys Thr  Ala Cys Ala Gly Ala  Gly Thr Thr Cys Thr  Thr Gly Ala
    1130                1135                1140

Ala Gly  Thr Gly Gly Thr Gly  Gly Cys Cys Thr Ala  Ala Cys Thr
    1145                1150                1155

Ala Cys  Gly Gly Cys Thr Ala  Cys Ala Cys Thr Ala  Gly Ala Ala
    1160                1165                1170

Gly Gly  Ala Cys Ala Gly Thr  Ala Thr Thr Thr Gly  Gly Thr Ala
    1175                1180                1185
```

```
Thr Cys Thr Gly Cys Gly Cys Thr Cys Thr Gly Cys Thr Gly Ala
    1190            1195                1200
Ala Gly Cys Cys Ala Gly Thr Thr Ala Cys Cys Thr Thr Cys Gly
    1205            1210                1215
Gly Ala Ala Ala Ala Ala Gly Ala Gly Thr Thr Gly Gly Thr Ala
    1220            1225                1230
Gly Cys Thr Cys Thr Thr Gly Ala Thr Cys Cys Gly Gly Cys Ala
    1235            1240                1245
Ala Ala Cys Ala Ala Ala Cys Cys Ala Cys Cys Gly Cys Thr Gly
    1250            1255                1260
Gly Thr Ala Gly Cys Gly Gly Thr Gly Gly Thr Thr Thr Thr Thr
    1265            1270                1275
Thr Thr Gly Thr Thr Thr Gly Cys Ala Ala Gly Cys Ala Gly Cys
    1280            1285                1290
Ala Gly Ala Thr Thr Ala Cys Gly Cys Gly Cys Ala Gly Ala Ala
    1295            1300                1305
Ala Ala Ala Ala Ala Gly Gly Ala Thr Cys Thr Cys Ala Ala Gly
    1310            1315                1320
Ala Ala Gly Ala Thr Cys Cys Thr Thr Thr Gly Ala Thr Cys Thr
    1325            1330                1335
Thr Thr Thr Cys Thr Ala Cys Gly Gly Gly Gly Thr Cys Thr Gly
    1340            1345                1350
Ala Cys Gly Cys Thr Cys Ala Gly Thr Gly Gly Ala Ala Cys Gly
    1355            1360                1365
Ala Ala Ala Ala Cys Thr Cys Ala Cys Gly Thr Thr Ala Ala Gly
    1370            1375                1380
Gly Gly Ala Thr Thr Thr Thr Gly Gly Thr Cys Ala Thr Gly Ala
    1385            1390                1395
Gly Ala Thr Thr Ala Thr Cys Ala Ala Ala Ala Ala Gly Gly Ala
    1400            1405                1410
Thr Cys Thr Thr Cys Ala Cys Cys Thr Ala Gly Ala Thr Cys Cys
    1415            1420                1425
Thr Thr Thr Ala Ala Ala Thr Thr Ala Ala Ala Ala Ala Ala Thr
    1430            1435                1440
Gly Ala Ala Gly Thr Thr Thr Thr Ala Ala Ala Thr Cys Ala Ala
    1445            1450                1455
Thr Cys Thr Ala Ala Ala Gly Thr Ala Thr Ala Thr Ala Thr Gly
    1460            1465                1470
Ala Gly Thr Ala Ala Ala Cys Thr Thr Gly Gly Thr Cys Thr Gly
    1475            1480                1485
Ala Cys Ala Gly Thr Thr Ala Cys Cys Ala Ala Thr Gly Cys Thr
    1490            1495                1500
Thr Ala Ala Thr Cys Ala Gly Thr Gly Ala Gly Gly Cys Ala Cys
    1505            1510                1515
Cys Thr Ala Thr Cys Thr Cys Ala Gly Cys Gly Ala Thr Cys Thr
    1520            1525                1530
Gly Thr Cys Thr Ala Thr Thr Thr Cys Gly Thr Thr Cys Ala Thr
    1535            1540                1545
Cys Cys Ala Thr Ala Gly Thr Thr Gly Cys Cys Thr Gly Ala Cys
    1550            1555                1560
Thr Gly Cys Cys Cys Gly Thr Cys Gly Thr Gly Thr Ala Gly Ala
    1565            1570                1575
Thr Ala Ala Cys Thr Ala Cys Gly Ala Thr Ala Cys Gly Gly Gly
```

-continued

```
    1580                1585                1590

Ala Gly  Gly Gly Cys Thr Thr  Ala Cys Cys Ala Thr  Cys Thr Gly
    1595                1600                1605

Gly Cys  Cys Cys Cys Ala Gly  Thr Gly Cys Thr Gly  Cys Ala Ala
    1610                1615                1620

Thr Gly  Ala Thr Ala Cys Cys  Gly Cys Gly Ala Gly  Ala Cys Cys
    1625                1630                1635

Cys Ala  Cys Gly Cys Thr Cys  Ala Cys Cys Gly Gly  Cys Thr Cys
    1640                1645                1650

Cys Ala  Gly Ala Thr Thr Thr  Ala Thr Cys Ala Gly  Cys Ala Ala
    1655                1660                1665

Thr Ala  Ala Ala Cys Cys Ala  Gly Cys Cys Ala Gly  Cys Cys Gly
    1670                1675                1680

Gly Ala  Ala Gly Gly Gly Cys  Cys Gly Ala Gly Cys  Gly Cys Ala
    1685                1690                1695

Gly Ala  Ala Gly Thr Gly Gly  Thr Cys Cys Thr Gly  Cys Ala Ala
    1700                1705                1710

Cys Thr  Thr Thr Ala Thr Cys  Cys Gly Cys Cys Thr  Cys Cys Ala
    1715                1720                1725

Thr Cys  Cys Ala Gly Thr Cys  Thr Ala Thr Thr Ala  Ala Thr Thr
    1730                1735                1740

Gly Thr  Thr Gly Cys Cys Gly  Gly Gly Ala Ala Gly  Cys Thr Ala
    1745                1750                1755

Gly Ala  Gly Thr Ala Ala Gly  Thr Ala Gly Thr Thr  Cys Gly Cys
    1760                1765                1770

Cys Ala  Gly Thr Thr Ala Ala  Thr Ala Gly Thr Thr  Thr Gly Cys
    1775                1780                1785

Gly Cys  Ala Ala Cys Gly Thr  Thr Gly Thr Thr Gly  Cys Cys Ala
    1790                1795                1800

Thr Thr  Gly Cys Thr Ala Cys  Ala Gly Gly Cys Ala  Thr Cys Gly
    1805                1810                1815

Thr Gly  Gly Thr Gly Thr Cys  Ala Cys Gly Cys Thr  Cys Gly Thr
    1820                1825                1830

Cys Gly  Thr Thr Thr Gly Gly  Thr Ala Thr Gly Gly  Cys Thr Thr
    1835                1840                1845

Cys Ala  Thr Thr Cys Ala Gly  Cys Thr Cys Cys Gly  Gly Thr Thr
    1850                1855                1860

Cys Cys  Cys Ala Ala Cys Gly  Ala Thr Cys Ala Ala  Gly Gly Cys
    1865                1870                1875

Gly Ala  Gly Thr Thr Ala Cys  Ala Thr Gly Ala Thr  Cys Cys Cys
    1880                1885                1890

Cys Cys  Ala Thr Gly Thr Thr  Gly Thr Gly Ala Ala  Ala Ala Ala
    1895                1900                1905

Ala Ala  Gly Cys Gly Gly Thr  Thr Ala Gly Cys Thr  Cys Cys Thr
    1910                1915                1920

Thr Cys  Gly Gly Thr Cys Cys  Thr Cys Cys Gly Ala  Thr Cys Gly
    1925                1930                1935

Thr Thr  Gly Thr Cys Ala Gly  Ala Ala Gly Thr Ala  Ala Gly Thr
    1940                1945                1950

Thr Gly  Gly Cys Cys Gly Cys  Ala Gly Thr Gly Thr  Thr Ala Thr
    1955                1960                1965

Cys Ala  Cys Thr Cys Ala Thr  Gly Gly Thr Thr Ala  Thr Gly Gly
    1970                1975                1980
```

Cys Ala Gly Cys Ala Cys Thr Gly Cys Ala Thr Ala Ala Thr Thr
1985 1990 1995

Cys Thr Cys Thr Thr Ala Cys Thr Gly Thr Cys Ala Thr Gly Cys
2000 2005 2010

Cys Ala Thr Cys Cys Gly Thr Ala Ala Gly Ala Thr Gly Cys Thr
2015 2020 2025

Thr Thr Thr Cys Thr Gly Thr Gly Ala Cys Thr Gly Gly Thr Gly
2030 2035 2040

Ala Gly Thr Ala Cys Thr Cys Ala Ala Cys Cys Ala Ala Gly Thr
2045 2050 2055

Cys Ala Thr Thr Cys Thr Gly Ala Gly Ala Ala Thr Ala Gly Thr
2060 2065 2070

Gly Thr Ala Thr Gly Cys Gly Gly Cys Gly Ala Cys Cys Gly Ala
2075 2080 2085

Gly Thr Thr Gly Cys Thr Cys Thr Thr Gly Cys Cys Cys Gly Gly
2090 2095 2100

Cys Gly Thr Cys Ala Ala Thr Ala Cys Gly Gly Gly Ala Thr Ala
2105 2110 2115

Ala Thr Ala Cys Cys Gly Cys Gly Cys Cys Ala Cys Ala Thr Ala
2120 2125 2130

Gly Cys Ala Gly Ala Ala Cys Thr Thr Thr Ala Ala Ala Ala Gly
2135 2140 2145

Thr Gly Cys Thr Cys Ala Thr Cys Ala Thr Thr Gly Gly Ala Ala
2150 2155 2160

Ala Ala Cys Gly Thr Thr Cys Thr Thr Cys Gly Gly Gly Gly Cys
2165 2170 2175

Gly Ala Ala Ala Ala Cys Thr Cys Thr Cys Ala Ala Gly Gly Ala
2180 2185 2190

Thr Cys Thr Thr Ala Cys Cys Gly Cys Thr Gly Thr Thr Gly Ala
2195 2200 2205

Gly Ala Thr Cys Cys Ala Gly Thr Thr Cys Gly Ala Thr Gly Thr
2210 2215 2220

Ala Ala Cys Cys Cys Ala Cys Thr Cys Gly Thr Gly Cys Ala Cys
2225 2230 2235

Cys Cys Ala Ala Cys Thr Gly Ala Thr Cys Thr Thr Cys Ala Gly
2240 2245 2250

Cys Ala Thr Cys Thr Thr Thr Thr Ala Cys Thr Thr Thr Cys Ala
2255 2260 2265

Cys Cys Ala Gly Cys Gly Thr Thr Thr Cys Thr Gly Gly Gly Thr
2270 2275 2280

Gly Ala Gly Cys Ala Ala Ala Ala Ala Cys Ala Gly Gly Ala Ala
2285 2290 2295

Gly Gly Cys Ala Ala Ala Ala Thr Gly Cys Cys Gly Cys Ala Ala
2300 2305 2310

Ala Ala Ala Ala Gly Gly Gly Ala Ala Thr Ala Ala Gly Gly Gly
2315 2320 2325

Cys Gly Ala Cys Ala Cys Gly Gly Ala Ala Ala Thr Gly Thr Thr
2330 2335 2340

Gly Ala Ala Thr Ala Cys Thr Cys Ala Thr Ala Cys Thr Cys Thr
2345 2350 2355

Thr Cys Cys Thr Thr Thr Thr Thr Cys Ala Ala Thr Ala Thr Thr
2360 2365 2370

| | | | | | | | | | | |
|---|---|---|---|---|---|---|---|---|---|---|
|Ala|Thr|Thr|Gly|Ala|Ala|Gly|Cys|Ala|Thr|Thr|Ala|Thr|Cys|
| |2375| | | | |2380| | | |2385| | | |

Ala Thr Thr Gly Ala Ala Gly Cys Ala Thr Thr Ala Thr Cys
    2375                2380              2385

Ala Gly Gly Gly Thr Thr Ala Thr Thr Gly Thr Cys Thr Cys Ala
    2390                2395              2400

Thr Gly Ala Gly Cys Gly Gly Ala Thr Ala Cys Ala Thr Ala Thr
    2405                2410              2415

Thr Thr Gly Ala Ala Thr Gly Thr Ala Thr Thr Ala Gly Ala
    2420                2425              2430

Ala Ala Ala Ala Thr Ala Ala Ala Cys Ala Ala Ala Thr Ala Gly
    2435                2440              2445

Gly Gly Gly Thr Thr Cys Cys Gly Cys Gly Cys Ala Cys Ala Thr
    2450                2455              2460

Thr Thr Cys Cys Cys Cys Gly Ala Ala Ala Gly Thr Gly Cys
    2465                2470              2475

Cys Ala Cys Cys Thr Gly Gly Gly Thr Cys Cys Thr Thr Thr
    2480                2485              2490

Cys Ala Thr Cys Ala Cys Gly Thr Gly Cys Thr Ala Thr Ala Ala
    2495                2500              2505

Ala Ala Ala Thr Ala Ala Thr Thr Ala Thr Ala Ala Thr Thr Thr
    2510                2515              2520

Ala Ala Ala Thr Thr Thr Thr Thr Thr Ala Ala Thr Ala Thr Ala
    2525                2530              2535

Ala Ala Thr Ala Thr Ala Thr Ala Ala Ala Thr Thr Ala Ala Ala
    2540                2545              2550

Ala Ala Thr Ala Gly Ala Ala Ala Gly Thr Ala Ala Ala Ala Ala
    2555                2560              2565

Ala Ala Gly Ala Ala Ala Thr Thr Ala Ala Ala Gly Ala Ala Ala
    2570                2575              2580

Ala Ala Ala Thr Ala Gly Thr Thr Thr Thr Thr Gly Thr Thr Thr
    2585                2590              2595

Thr Cys Cys Gly Ala Ala Gly Ala Thr Gly Thr Ala Ala Ala Ala
    2600                2605              2610

Gly Ala Cys Thr Cys Thr Ala Gly Gly Gly Gly Ala Thr Cys
    2615                2620              2625

Gly Cys Cys Ala Ala Cys Ala Ala Ala Thr Ala Cys Thr Ala Cys
    2630                2635              2640

Cys Thr Thr Thr Thr Ala Thr Cys Thr Thr Gly Cys Thr Cys Thr
    2645                2650              2655

Thr Cys Cys Thr Gly Cys Thr Cys Thr Cys Ala Gly Gly Thr Ala
    2660                2665              2670

Thr Thr Ala Ala Thr Gly Cys Cys Gly Ala Ala Thr Thr Gly Thr
    2675                2680              2685

Thr Thr Cys Ala Thr Cys Thr Thr Gly Thr Cys Thr Gly Thr Gly
    2690                2695              2700

Thr Ala Gly Ala Ala Gly Ala Cys Cys Ala Cys Ala Cys Ala Cys
    2705                2710              2715

Gly Ala Ala Ala Ala Thr Cys Cys Thr Gly Thr Gly Ala Thr Thr
    2720                2725              2730

Thr Thr Thr Ala Cys Ala Thr Thr Thr Thr Ala Cys Thr Thr Ala Thr
    2735                2740              2745

Cys Gly Thr Thr Ala Ala Thr Cys Gly Ala Ala Thr Gly Thr Ala
    2750                2755              2760

Thr Ala Thr Cys Thr Ala Thr Thr Thr Ala Ala Thr Cys Thr Gly 2765                2770                2775
Cys Thr Thr Thr Thr Cys Thr Thr Gly Thr Cys Thr Ala Ala Thr
    2780                2785                2790
Ala Ala Ala Thr Ala Thr Ala Thr Ala Thr Gly Thr Ala Ala Ala
    2795                2800                2805
Gly Thr Ala Cys Gly Cys Thr Thr Thr Thr Gly Thr Thr Gly
    2810                2815                2820
Ala Ala Ala Thr Thr Thr Thr Thr Thr Ala Ala Ala Cys Cys Thr
    2825                2830                2835
Thr Thr Gly Thr Thr Thr Ala Thr Thr Thr Thr Thr Thr Thr
    2840                2845                2850
Thr Cys Thr Thr Cys Ala Thr Thr Cys Cys Gly Thr Ala Ala Cys
    2855                2860                2865
Thr Cys Thr Thr Cys Thr Ala Cys Cys Thr Thr Cys Thr Thr Thr
    2870                2875                2880
Ala Thr Thr Thr Ala Cys Thr Thr Cys Thr Ala Ala Ala Ala
    2885                2890                2895
Thr Cys Cys Ala Ala Ala Thr Ala Cys Ala Ala Ala Cys Ala
    2900                2905                2910
Thr Ala Ala Ala Ala Ala Thr Ala Ala Ala Thr Ala Ala Ala Cys
    2915                2920                2925
Ala Cys Ala Gly Ala Gly Thr Ala Ala Ala Thr Cys Cys Cys
    2930                2935                2940
Ala Ala Ala Thr Thr Ala Thr Thr Cys Cys Ala Thr Cys Ala Thr
    2945                2950                2955
Thr Ala Ala Ala Ala Gly Ala Thr Ala Cys Gly Ala Gly Gly Cys
    2960                2965                2970
Gly Cys Gly Thr Gly Thr Ala Ala Gly Thr Thr Ala Cys Ala Gly
    2975                2980                2985
Gly Cys Ala Ala Gly Cys Gly Ala Thr Cys Cys Gly Thr Cys Cys
    2990                2995                3000
Thr Ala Ala Gly Ala Ala Ala Cys Cys Ala Thr Thr Ala Thr Thr
    3005                3010                3015
Ala Thr Cys Ala Thr Gly Ala Cys Ala Thr Thr Ala Ala Cys Cys
    3020                3025                3030
Thr Ala Thr Ala Ala Ala Ala Ala Thr Ala Gly Gly Cys Gly Thr
    3035                3040                3045
Ala Thr Cys Ala Cys Gly Ala Gly Gly Cys Cys Cys Thr Thr Thr
    3050                3055                3060
Cys Gly Thr Cys Thr Cys Gly Cys Gly Cys Gly Thr Thr Thr Cys
    3065                3070                3075
Gly Gly Thr Gly Ala Thr Gly Ala Cys Gly Gly Thr Gly Ala Ala
    3080                3085                3090
Ala Ala Cys Cys Thr Cys Thr Gly Ala Cys Ala Cys Ala Thr Gly
    3095                3100                3105
Cys Ala Gly Cys Thr Cys Cys Cys Gly Gly Ala Gly Ala Cys Gly
    3110                3115                3120
Gly Thr Cys Ala Cys Ala Gly Cys Thr Thr Gly Thr Cys Thr Gly
    3125                3130                3135
Thr Ala Ala Gly Cys Gly Gly Ala Thr Gly Cys Cys Gly Gly Gly
    3140                3145                3150
Ala Gly Cys Ala Gly Ala Cys Ala Ala Gly Cys Cys Cys Gly Thr
    3155                3160                3165

-continued

Cys Ala Gly Gly Gly Cys Gly Cys Gly Thr Cys Ala Gly Cys Gly
3170                3175                3180

Gly Gly Thr Gly Thr Thr Gly Gly Cys Gly Gly Thr Gly Thr
    3185                3190                3195

Cys Gly Gly Gly Cys Thr Gly Gly Cys Thr Thr Ala Ala Cys
3200                3205                3210

Thr Ala Thr Gly Cys Gly Gly Cys Ala Thr Cys Ala Gly Ala Gly
    3215                3220                3225

Cys Ala Gly Ala Thr Thr Gly Thr Ala Cys Thr Gly Ala Gly Ala
3230                3235                3240

Gly Thr Gly Cys Ala Cys Cys Ala Cys Gly Cys Thr Thr Thr
    3245                3250                3255

Cys Ala Ala Thr Thr Cys Ala Ala Thr Thr Cys Ala Thr Cys Ala
3260                3265                3270

Thr Thr Thr Thr Thr Thr Thr Thr Thr Ala Thr Thr Cys Thr
    3275                3280                3285

Thr Thr Thr Thr Thr Thr Thr Gly Ala Thr Thr Cys Gly Gly
    3290                3295                3300

Thr Thr Thr Cys Thr Thr Thr Gly Ala Ala Ala Thr Thr Thr Thr
3305                3310                3315

Thr Thr Thr Gly Ala Thr Thr Cys Gly Gly Thr Ala Ala Thr Cys
3320                3325                3330

Thr Cys Cys Gly Ala Ala Cys Ala Gly Ala Ala Gly Gly Ala Ala
3335                3340                3345

Gly Ala Ala Cys Gly Ala Ala Gly Gly Ala Ala Gly Gly Ala Gly
    3350                3355                3360

Cys Ala Cys Ala Gly Ala Cys Thr Thr Ala Gly Ala Thr Thr Gly
3365                3370                3375

Gly Thr Ala Thr Ala Thr Ala Thr Ala Cys Gly Cys Ala Thr Ala
    3380                3385                3390

Thr Gly Thr Ala Gly Thr Gly Thr Thr Gly Ala Ala Gly Ala Ala
    3395                3400                3405

Ala Cys Ala Thr Gly Ala Ala Ala Thr Thr Gly Cys Cys Cys Ala
    3410                3415                3420

Gly Thr Ala Thr Thr Cys Thr Thr Ala Ala Cys Cys Cys Ala Ala
    3425                3430                3435

Cys Thr Gly Cys Ala Cys Ala Gly Ala Ala Cys Ala Ala Ala Ala
3440                3445                3450

Ala Cys Cys Thr Gly Cys Ala Gly Gly Ala Ala Ala Cys Gly Ala
3455                3460                3465

Ala Gly Ala Thr Ala Ala Ala Thr Cys Ala Thr Gly Thr Cys Gly
    3470                3475                3480

Ala Ala Ala Gly Cys Thr Ala Cys Ala Thr Ala Thr Ala Ala Gly
    3485                3490                3495

Gly Ala Ala Cys Gly Thr Gly Cys Thr Gly Cys Thr Ala Cys Thr
    3500                3505                3510

Cys Ala Thr Cys Cys Thr Ala Gly Thr Cys Cys Thr Gly Thr Thr
3515                3520                3525

Gly Cys Thr Gly Cys Cys Ala Ala Gly Cys Thr Ala Thr Thr Thr
    3530                3535                3540

Ala Ala Thr Ala Thr Cys Ala Thr Gly Cys Ala Cys Gly Ala Ala
    3545                3550                3555

-continued

```
Ala Ala  Gly Cys Ala Ala Ala  Cys Ala Ala Ala Cys  Thr Thr Gly
    3560                 3565                 3570

Thr Gly  Thr Gly Cys Thr Thr  Cys Ala Thr Thr Gly  Gly Ala Thr
    3575                 3580                 3585

Gly Thr  Thr Cys Gly Thr Ala  Cys Cys Ala Cys Cys  Ala Ala Gly
    3590                 3595                 3600

Gly Ala  Ala Thr Thr Ala Cys  Thr Gly Gly Ala Gly  Thr Thr Ala
    3605                 3610                 3615

Gly Thr  Thr Gly Ala Ala Gly  Cys Ala Thr Thr Ala  Gly Gly Thr
    3620                 3625                 3630

Cys Cys  Cys Ala Ala Ala Ala  Thr Thr Thr Gly Thr  Thr Thr Ala
    3635                 3640                 3645

Cys Thr  Ala Ala Ala Ala Ala  Cys Ala Cys Ala Thr  Gly Thr Gly
    3650                 3655                 3660

Gly Ala  Thr Ala Thr Cys Thr  Thr Gly Ala Cys Thr  Gly Ala Thr
    3665                 3670                 3675

Thr Thr  Thr Thr Cys Cys Ala  Thr Gly Gly Ala Gly  Gly Gly Cys
    3680                 3685                 3690

Ala Cys  Ala Gly Thr Thr Ala  Ala Gly Cys Cys Gly  Cys Thr Ala
    3695                 3700                 3705

Ala Ala  Gly Gly Cys Ala Thr  Thr Ala Thr Cys Cys  Gly Cys Cys
    3710                 3715                 3720

Ala Ala  Gly Thr Ala Cys Ala  Ala Thr Thr Thr Thr  Thr Thr Ala
    3725                 3730                 3735

Cys Thr  Cys Thr Thr Cys Gly  Ala Ala Gly Ala Cys  Ala Gly Ala
    3740                 3745                 3750

Ala Ala  Ala Thr Thr Thr Gly  Cys Thr Gly Ala Cys  Ala Thr Thr
    3755                 3760                 3765

Gly Gly  Thr Ala Ala Thr Ala  Cys Ala Gly Thr Cys  Ala Ala Ala
    3770                 3775                 3780

Thr Thr  Gly Cys Ala Gly Thr  Ala Cys Thr Cys Thr  Gly Cys Gly
    3785                 3790                 3795

Gly Gly  Thr Gly Thr Ala Thr  Ala Cys Ala Gly Ala  Ala Thr Ala
    3800                 3805                 3810

Gly Cys  Ala Gly Ala Ala Thr  Gly Gly Gly Cys Ala  Gly Ala Cys
    3815                 3820                 3825

Ala Thr  Thr Ala Cys Gly Ala  Ala Thr Gly Cys Ala  Cys Ala Cys
    3830                 3835                 3840

Gly Gly  Thr Gly Thr Gly Gly  Thr Gly Gly Gly Cys  Cys Cys Ala
    3845                 3850                 3855

Gly Gly  Thr Ala Thr Thr Gly  Thr Thr Ala Gly Cys  Gly Gly Thr
    3860                 3865                 3870

Thr Thr  Gly Ala Ala Gly Cys  Ala Gly Gly Cys Gly  Gly Cys Ala
    3875                 3880                 3885

Gly Ala  Ala Gly Ala Ala Gly  Thr Ala Ala Cys Ala  Ala Ala Gly
    3890                 3895                 3900

Gly Ala  Ala Cys Cys Thr Ala  Gly Ala Gly Gly Cys  Cys Thr Thr
    3905                 3910                 3915

Thr Thr  Gly Ala Thr Gly Thr  Thr Ala Gly Cys Ala  Gly Ala Ala
    3920                 3925                 3930

Thr Thr  Gly Thr Cys Ala Thr  Gly Cys Ala Ala Gly  Gly Gly Cys
    3935                 3940                 3945

Thr Cys  Cys Cys Thr Ala Thr  Cys Thr Ala Cys Thr  Gly Gly Ala
```

|   |   |   |   |   |   |   |   |   |   |
|---|---|---|---|---|---|---|---|---|---|
|   | 3950 |   |   | 3955 |   |   | 3960 |   |   |
| Gly | Ala | Ala | Thr | Ala | Thr | Ala | Cys | Thr | Ala |
| Ala | Gly | Gly | Thr |   |   |   |   |   |   |
|   | 3965 |   |   | 3970 |   |   | 3975 |   |   |
| Ala | Cys | Thr | Gly | Thr | Thr | Gly | Ala | Cys | Ala |
| Thr | Thr | Gly | Cys | Gly |   |   |   |   |   |
|   | 3980 |   |   | 3985 |   |   | 3990 |   |   |
| Ala | Ala | Gly | Ala | Gly | Cys | Gly | Ala | Cys | Ala |
| Ala | Ala | Gly | Ala | Thr |   |   |   |   |   |
|   | 3995 |   |   | 4000 |   |   | 4005 |   |   |
| Thr | Thr | Thr | Gly | Thr | Thr | Ala | Thr | Cys | Gly |
| Gly | Cys | Thr | Thr | Thr |   |   |   |   |   |
|   | 4010 |   |   | 4015 |   |   | 4020 |   |   |
| Ala | Thr | Thr | Gly | Cys | Thr | Cys | Ala | Ala | Gly |
| Ala | Gly | Ala | Cys |   |   |   |   |   |   |
|   | 4025 |   |   | 4030 |   |   | 4035 |   |   |
| Ala | Thr | Gly | Gly | Gly | Thr | Gly | Gly | Ala | Ala |
| Gly | Ala | Gly | Ala | Thr |   |   |   |   |   |
|   | 4040 |   |   | 4045 |   |   | 4050 |   |   |
| Gly | Ala | Ala | Gly | Gly | Thr | Thr | Ala | Cys | Gly |
| Ala | Thr | Thr | Gly | Gly |   |   |   |   |   |
|   | 4055 |   |   | 4060 |   |   | 4065 |   |   |
| Thr | Thr | Gly | Ala | Thr | Ala | Thr | Gly | Ala | Cys |
| Ala | Cys | Cys | Cys |   |   |   |   |   |   |
|   | 4070 |   |   | 4075 |   |   | 4080 |   |   |
| Gly | Gly | Thr | Gly | Thr | Gly | Gly | Thr | Thr | Ala |
| Gly | Ala | Thr |   |   |   |   |   |   |   |
|   | 4085 |   |   | 4090 |   |   | 4095 |   |   |
| Gly | Ala | Cys | Ala | Ala | Gly | Gly | Gly | Ala | Gly |
| Ala | Cys | Gly | Cys | Ala |   |   |   |   |   |
|   | 4100 |   |   | 4105 |   |   | 4110 |   |   |
| Thr | Thr | Gly | Gly | Gly | Thr | Cys | Ala | Ala | Cys |
| Ala | Gly | Thr | Ala | Thr |   |   |   |   |   |
|   | 4115 |   |   | 4120 |   |   | 4125 |   |   |
| Ala | Gly | Ala | Ala | Cys | Cys | Gly | Thr | Gly | Gly |
| Ala | Thr | Gly | Ala | Thr |   |   |   |   |   |
|   | 4130 |   |   | 4135 |   |   | 4140 |   |   |
| Gly | Thr | Gly | Gly | Thr | Cys | Thr | Cys | Thr | Ala |
| Cys | Ala | Gly | Gly | Ala |   |   |   |   |   |
|   | 4145 |   |   | 4150 |   |   | 4155 |   |   |
| Thr | Cys | Thr | Gly | Ala | Cys | Ala | Thr | Thr | Ala |
| Thr | Thr | Ala | Thr | Thr |   |   |   |   |   |
|   | 4160 |   |   | 4165 |   |   | 4170 |   |   |
| Gly | Thr | Thr | Gly | Gly | Ala | Ala | Gly | Ala | Gly |
| Gly | Ala | Cys | Thr | Ala |   |   |   |   |   |
|   | 4175 |   |   | 4180 |   |   | 4185 |   |   |
| Thr | Thr | Thr | Gly | Cys | Ala | Ala | Ala | Gly | Gly |
| Gly | Ala | Ala | Gly | Gly |   |   |   |   |   |
|   | 4190 |   |   | 4195 |   |   | 4200 |   |   |
| Gly | Ala | Thr | Gly | Cys | Thr | Ala | Ala | Gly | Gly |
| Thr | Ala | Gly | Ala | Gly |   |   |   |   |   |
|   | 4205 |   |   | 4210 |   |   | 4215 |   |   |
| Gly | Gly | Thr | Gly | Ala | Ala | Cys | Gly | Thr | Thr |
| Ala | Cys | Ala | Gly | Ala |   |   |   |   |   |
|   | 4220 |   |   | 4225 |   |   | 4230 |   |   |
| Ala | Ala | Ala | Gly | Cys | Ala | Gly | Gly | Cys | Thr |
| Gly | Gly | Gly | Ala | Ala |   |   |   |   |   |
|   | 4235 |   |   | 4240 |   |   | 4245 |   |   |
| Gly | Cys | Ala | Thr | Ala | Thr | Thr | Thr | Gly | Ala |
| Gly | Ala | Ala | Gly | Ala |   |   |   |   |   |
|   | 4250 |   |   | 4255 |   |   | 4260 |   |   |
| Thr | Gly | Cys | Gly | Gly | Cys | Cys | Ala | Gly | Cys |
| Ala | Ala | Ala | Ala | Cys |   |   |   |   |   |
|   | 4265 |   |   | 4270 |   |   | 4275 |   |   |
| Thr | Ala | Ala | Ala | Ala | Ala | Ala | Cys | Thr | Gly |
| Thr | Ala | Thr | Thr | Ala |   |   |   |   |   |
|   | 4280 |   |   | 4285 |   |   | 4290 |   |   |
| Thr | Ala | Ala | Gly | Thr | Ala | Ala | Ala | Thr | Gly |
| Cys | Ala | Thr | Gly | Thr |   |   |   |   |   |
|   | 4295 |   |   | 4300 |   |   | 4305 |   |   |
| Ala | Thr | Ala | Cys | Thr | Ala | Ala | Ala | Cys | Thr |
| Cys | Ala | Cys | Ala | Ala |   |   |   |   |   |
|   | 4310 |   |   | 4315 |   |   | 4320 |   |   |
| Ala | Thr | Thr | Ala | Gly | Ala | Gly | Cys | Thr | Thr |
| Cys | Ala | Ala | Thr | Thr |   |   |   |   |   |
|   | 4325 |   |   | 4330 |   |   | 4335 |   |   |
| Thr | Ala | Ala | Thr | Thr | Ala | Thr | Ala | Thr | Cys |
| Ala | Gly | Thr | Thr | Ala |   |   |   |   |   |
|   | 4340 |   |   | 4345 |   |   | 4350 |   |   |

-continued

```
Thr Thr Ala Cys Cys Cys Thr Gly Cys Gly Gly Thr Gly Thr Gly
4355                4360                4365
Ala Ala Ala Thr Ala Cys Cys Gly Cys Ala Cys Ala Gly Ala Thr
4370                4375                4380
Gly Cys Gly Thr Ala Ala Gly Gly Ala Gly Ala Ala Ala Ala Thr
4385                4390                4395
Ala Cys Cys Gly Cys Ala Thr Cys Ala Gly Gly Ala Ala Ala Thr
4400                4405                4410
Thr Gly Thr Ala Ala Ala Cys Gly Thr Ala Ala Thr Ala Thr
4415                4420                4425
Thr Thr Thr Gly Thr Thr Ala Ala Ala Ala Thr Thr Cys Gly Cys
4430                4435                4440
Gly Thr Thr Ala Ala Ala Thr Thr Thr Thr Thr Gly Thr Thr Ala
4445                4450                4455
Ala Ala Thr Cys Ala Gly Cys Thr Cys Ala Thr Thr Thr Thr Thr
4460                4465                4470
Thr Ala Ala Cys Cys Ala Ala Thr Ala Gly Gly Cys Cys Gly Ala
4475                4480                4485
Ala Ala Thr Cys Gly Gly Cys Ala Ala Ala Ala Thr Cys Cys Cys
4490                4495                4500
Thr Thr Ala Thr Ala Ala Ala Thr Cys Ala Ala Ala Ala Gly Ala
4505                4510                4515
Ala Thr Ala Gly Ala Cys Cys Gly Ala Gly Ala Thr Ala Gly Gly
4520                4525                4530
Gly Thr Thr Gly Ala Gly Thr Gly Thr Thr Gly Thr Thr Cys Cys
4535                4540                4545
Ala Gly Thr Thr Thr Gly Gly Ala Ala Cys Ala Ala Gly Ala Gly
4550                4555                4560
Thr Cys Cys Ala Cys Thr Ala Thr Thr Ala Ala Ala Gly Ala Ala
4565                4570                4575
Cys Gly Thr Gly Gly Ala Cys Thr Cys Cys Ala Ala Cys Gly Thr
4580                4585                4590
Cys Ala Ala Ala Gly Gly Gly Cys Gly Ala Ala Ala Ala Ala Cys
4595                4600                4605
Cys Gly Thr Cys Thr Ala Thr Cys Ala Gly Gly Gly Cys Gly Ala
4610                4615                4620
Thr Gly Gly Cys Cys Cys Ala Cys Thr Ala Cys Gly Thr Gly Ala
4625                4630                4635
Ala Cys Cys Ala Thr Cys Ala Cys Cys Cys Thr Ala Ala Thr Cys
4640                4645                4650
Ala Ala Gly Thr Thr Thr Thr Thr Thr Gly Gly Gly Gly Thr Cys
4655                4660                4665
Gly Ala Gly Gly Thr Gly Cys Cys Gly Thr Ala Ala Ala Gly Cys
4670                4675                4680
Ala Cys Thr Ala Ala Ala Thr Cys Gly Gly Ala Ala Cys Cys Cys
4685                4690                4695
Thr Ala Ala Ala Gly Gly Gly Ala Gly Cys Cys Cys Cys Cys Gly
4700                4705                4710
Ala Thr Thr Thr Ala Gly Ala Gly Cys Thr Thr Gly Ala Cys Gly
4715                4720                4725
Gly Gly Gly Ala Ala Ala Gly Cys Cys Gly Gly Cys Gly Ala Ala
4730                4735                4740
```

```
Cys Gly Thr Gly Gly Cys Gly Ala Ala Ala Gly Gly Ala
    4745            4750            4755

Ala Gly Gly Gly Ala Ala Gly Ala Ala Gly Cys Gly Ala Ala
    4760            4765            4770

Ala Gly Gly Ala Gly Cys Gly Gly Gly Cys Gly Cys Thr Ala Gly
    4775            4780            4785

Gly Gly Cys Gly Cys Thr Gly Gly Cys Ala Ala Gly Thr Gly Thr
    4790            4795            4800

Ala Gly Cys Gly Gly Thr Cys Ala Cys Gly Cys Thr Gly Cys Gly
    4805            4810            4815

Cys Gly Thr Ala Ala Cys Cys Ala Cys Cys Ala Cys Ala Cys Cys
    4820            4825            4830

Cys Gly Cys Cys Gly Cys Gly Cys Thr Thr Ala Ala Thr Gly Cys
    4835            4840            4845

Gly Cys Cys Gly Cys Thr Ala Cys Ala Gly Gly Gly Cys Gly Cys
    4850            4855            4860

Gly Thr Cys Gly Cys Gly Cys Cys Ala Thr Thr Cys Gly Cys Cys
    4865            4870            4875

Ala Thr Thr Cys Ala Gly Gly Cys Thr Gly Cys Gly Cys Ala Ala
    4880            4885            4890

Cys Thr Gly Thr Thr Gly Gly Gly Ala Ala Gly Gly Gly Cys Gly
    4895            4900            4905

Ala Thr Cys Gly Gly Thr Gly Cys Gly Gly Gly Cys Cys Thr Cys
    4910            4915            4920

Thr Thr Cys Gly Cys Thr Ala Thr Thr Ala Cys Gly Cys Cys Ala
    4925            4930            4935

Gly Cys Thr Gly Gly Cys Gly Ala Ala Gly Gly Gly Gly Gly Gly
    4940            4945            4950

Ala Thr Gly Thr Gly Cys Thr Gly Cys Ala Ala Gly Gly Cys Gly
    4955            4960            4965

Ala Thr Thr Ala Ala Gly Thr Thr Gly Gly Gly Thr Ala Ala Cys
    4970            4975            4980

Gly Cys Cys Ala Gly Gly Gly Thr Thr Thr Thr Cys Cys Cys Ala
    4985            4990            4995

Gly Thr Cys Ala Cys Gly Ala Cys Gly Thr Thr Gly Thr Ala Ala
    5000            5005            5010

Ala Ala Cys Gly Ala Cys Gly Gly Cys Cys Ala Gly Thr Gly Ala
    5015            5020            5025

Ala Thr Thr Gly Thr Ala Ala Thr Ala Cys Gly Ala Cys Thr Cys
    5030            5035            5040

Ala Cys Thr Ala Thr Ala Gly Gly Gly Cys Gly Ala Ala Thr Thr
    5045            5050            5055

Gly Gly Ala Gly Cys Thr Cys Cys Ala Cys Cys Gly Cys Gly Gly
    5060            5065            5070

Thr Gly Gly Cys Gly Gly Cys Cys Gly Cys Thr Cys Thr Ala Gly
    5075            5080            5085

Ala Ala Cys Thr Ala Gly Thr Gly Gly Ala Thr Cys Cys Cys Cys
    5090            5095            5100

Gly Gly Gly Cys Thr Gly Cys Ala Gly Gly Ala Ala Thr Thr Cys
    5105            5110            5115

Gly Ala Thr Ala Thr Cys Ala Ala Gly Cys Thr Thr Ala Thr Cys
    5120            5125            5130

Ala Thr Cys Gly Ala Thr Ala Cys Cys Gly Thr Cys Gly Ala Cys
```

-continued

```
    5135                5140                5145

Thr Gly  Gly Ala Cys Thr Thr  Cys Cys Thr Cys Thr  Thr Thr Thr
    5150                5155                5160

Cys Thr  Gly Gly Cys Ala Ala  Cys Cys Ala Ala Ala  Cys Cys Cys
    5165                5170                5175

Ala Thr  Ala Cys Ala Thr Cys  Gly Gly Gly Ala Thr  Thr Cys Cys
    5180                5185                5190

Thr Ala  Thr Ala Ala Thr Ala  Cys Cys Thr Thr Cys  Gly Thr Thr
    5195                5200                5205

Gly Gly  Thr Cys Thr Cys Cys  Cys Thr Ala Ala Cys  Ala Thr Gly
    5210                5215                5220

Thr Ala  Gly Gly Thr Gly Gly  Cys Gly Gly Ala Gly  Gly Gly Gly
    5225                5230                5235

Ala Gly  Ala Thr Ala Thr Ala  Cys Ala Ala Thr Ala  Gly Ala Ala
    5240                5245                5250

Cys Ala  Gly Ala Thr Ala Cys  Cys Ala Gly Ala Cys  Ala Ala Gly
    5255                5260                5265

Ala Cys  Ala Thr Ala Ala Thr  Gly Gly Gly Cys Thr  Ala Ala Ala
    5270                5275                5280

Cys Ala  Ala Gly Ala Cys Thr  Ala Cys Ala Cys Cys  Ala Ala Thr
    5285                5290                5295

Thr Ala  Cys Ala Cys Thr Gly  Cys Cys Thr Cys Ala  Thr Thr Gly
    5300                5305                5310

Ala Thr  Gly Gly Thr Gly Gly  Thr Ala Cys Ala Thr  Ala Ala Cys
    5315                5320                5325

Gly Ala  Ala Cys Thr Ala Ala  Thr Ala Cys Thr Gly  Thr Ala Gly
    5330                5335                5340

Cys Cys  Cys Thr Ala Gly Ala  Cys Thr Thr Gly Ala  Thr Ala Gly
    5345                5350                5355

Cys Cys  Ala Thr Cys Ala Thr  Cys Ala Thr Ala Thr  Cys Gly Ala
    5360                5365                5370

Ala Gly  Thr Thr Thr Cys Ala  Cys Thr Ala Cys Cys  Cys Thr Thr
    5375                5380                5385

Thr Thr  Thr Cys Cys Ala Thr  Thr Thr Gly Cys Cys  Ala Thr Cys
    5390                5395                5400

Thr Ala  Thr Thr Gly Ala Ala  Gly Thr Ala Ala Thr  Ala Ala Thr
    5405                5410                5415

Ala Gly  Gly Cys Gly Cys Ala  Thr Gly Cys Ala Ala  Cys Thr Thr
    5420                5425                5430

Cys Thr  Thr Thr Thr Cys Thr  Thr Thr Thr Thr Thr  Thr Thr Thr
    5435                5440                5445

Cys Thr  Thr Thr Thr Cys Thr  Cys Thr Cys Thr Cys  Cys Cys Cys
    5450                5455                5460

Cys Gly  Thr Thr Gly Thr Thr  Gly Thr Cys Thr Cys  Ala Cys Cys
    5465                5470                5475

Ala Thr  Ala Thr Cys Cys Gly  Cys Ala Ala Thr Gly  Ala Cys Ala
    5480                5485                5490

Ala Ala  Ala Ala Ala Ala Thr  Gly Ala Thr Gly Gly  Ala Ala Gly
    5495                5500                5505

Ala Cys  Ala Cys Thr Ala Ala  Ala Gly Gly Ala Ala  Ala Ala Ala
    5510                5515                5520

Ala Thr  Thr Ala Ala Cys Gly  Ala Cys Ala Ala Ala  Gly Ala Cys
    5525                5530                5535
```

| Ala | Gly | Cys | Ala | Cys | Cys | Ala | Ala | Cys | Ala | Gly | Ala | Thr | Gly | Thr |
|---|---|---|---|---|---|---|---|---|---|---|---|---|---|---|
| | 5540 | | | | 5545 | | | | 5550 | | | | | |

| Cys | Gly | Thr | Thr | Gly | Thr | Thr | Cys | Cys | Ala | Gly | Ala | Gly | Cys | Thr |
|---|---|---|---|---|---|---|---|---|---|---|---|---|---|---|
| | 5555 | | | | 5560 | | | | 5565 | | | | | |

| Gly | Ala | Thr | Gly | Gly | Gly | Gly | Gly | Thr | Ala | Thr | Cys | Thr | Cys |
|---|---|---|---|---|---|---|---|---|---|---|---|---|---|
| | 5570 | | | | 5575 | | | | 5580 | | | | |

| Gly | Ala | Ala | Gly | Cys | Ala | Cys | Ala | Cys | Gly | Ala | Ala | Ala | Cys | Thr |
|---|---|---|---|---|---|---|---|---|---|---|---|---|---|---|
| | 5585 | | | | 5590 | | | | 5595 | | | | | |

| Thr | Thr | Thr | Thr | Cys | Thr | Thr | Cys | Cys | Thr | Thr | Cys | Ala | Thr |
|---|---|---|---|---|---|---|---|---|---|---|---|---|---|
| | 5600 | | | | 5605 | | | | 5610 | | | | |

| Thr | Cys | Ala | Cys | Gly | Cys | Ala | Cys | Ala | Cys | Thr | Ala | Cys | Thr | Cys |
|---|---|---|---|---|---|---|---|---|---|---|---|---|---|---|
| | 5615 | | | | 5620 | | | | 5625 | | | | | |

| Thr | Cys | Thr | Ala | Ala | Thr | Gly | Ala | Gly | Cys | Ala | Ala | Cys | Gly | Gly |
|---|---|---|---|---|---|---|---|---|---|---|---|---|---|---|
| | 5630 | | | | 5635 | | | | 5640 | | | | | |

| Thr | Ala | Thr | Ala | Cys | Gly | Gly | Cys | Cys | Thr | Thr | Cys | Thr | Thr |
|---|---|---|---|---|---|---|---|---|---|---|---|---|---|
| | 5645 | | | | 5650 | | | | 5655 | | | | |

| Cys | Cys | Ala | Gly | Thr | Thr | Ala | Cys | Thr | Thr | Gly | Ala | Ala | Thr | Thr |
|---|---|---|---|---|---|---|---|---|---|---|---|---|---|---|
| | 5660 | | | | 5665 | | | | 5670 | | | | | |

| Thr | Gly | Ala | Ala | Ala | Thr | Ala | Ala | Ala | Ala | Ala | Ala | Gly | Thr |
|---|---|---|---|---|---|---|---|---|---|---|---|---|---|
| | 5675 | | | | 5680 | | | | 5685 | | | | |

| Thr | Thr | Gly | Cys | Thr | Gly | Thr | Cys | Thr | Thr | Gly | Cys | Thr | Ala | Thr |
|---|---|---|---|---|---|---|---|---|---|---|---|---|---|---|
| | 5690 | | | | 5695 | | | | 5700 | | | | | |

| Cys | Ala | Ala | Gly | Thr | Ala | Thr | Ala | Ala | Thr | Ala | Gly | Ala | Cys |
|---|---|---|---|---|---|---|---|---|---|---|---|---|---|
| | 5705 | | | | 5710 | | | | 5715 | | | | |

| Cys | Thr | Gly | Cys | Ala | Ala | Thr | Thr | Ala | Thr | Thr | Ala | Ala | Thr | Cys |
|---|---|---|---|---|---|---|---|---|---|---|---|---|---|---|
| | 5720 | | | | 5725 | | | | 5730 | | | | | |

| Thr | Thr | Thr | Thr | Gly | Thr | Thr | Thr | Cys | Cys | Thr | Cys | Gly | Thr | Cys |
|---|---|---|---|---|---|---|---|---|---|---|---|---|---|---|
| | 5735 | | | | 5740 | | | | 5745 | | | | | |

| Ala | Thr | Thr | Gly | Thr | Thr | Cys | Thr | Cys | Gly | Thr | Thr | Cys | Cys | Cys |
|---|---|---|---|---|---|---|---|---|---|---|---|---|---|---|
| | 5750 | | | | 5755 | | | | 5760 | | | | | |

| Thr | Thr | Thr | Cys | Thr | Thr | Cys | Cys | Thr | Thr | Gly | Thr | Thr | Thr | Cys |
|---|---|---|---|---|---|---|---|---|---|---|---|---|---|---|
| | 5765 | | | | 5770 | | | | 5775 | | | | | |

| Thr | Thr | Thr | Thr | Thr | Cys | Thr | Gly | Cys | Ala | Cys | Ala | Ala | Thr | Ala |
|---|---|---|---|---|---|---|---|---|---|---|---|---|---|---|
| | 5780 | | | | 5785 | | | | 5790 | | | | | |

| Thr | Thr | Thr | Cys | Ala | Ala | Gly | Cys | Thr | Ala | Thr | Ala | Cys | Cys | Ala |
|---|---|---|---|---|---|---|---|---|---|---|---|---|---|---|
| | 5795 | | | | 5800 | | | | 5805 | | | | | |

| Ala | Gly | Cys | Ala | Thr | Ala | Cys | Ala | Ala | Thr | Cys | Ala | Ala | Cys | Thr |
|---|---|---|---|---|---|---|---|---|---|---|---|---|---|---|
| | 5810 | | | | 5815 | | | | 5820 | | | | | |

| Ala | Thr | Cys | Thr | Cys | Ala | Thr | Ala | Thr | Ala | Cys | Ala | Thr |
|---|---|---|---|---|---|---|---|---|---|---|---|---|
| | 5825 | | | | 5830 | | | | 5835 | | | |

<210> SEQ ID NO 14
<211> LENGTH: 1961
<212> TYPE: DNA
<213> ORGANISM: Artificial Sequence
<220> FEATURE:
<223> OTHER INFORMATION: SmMAL11-1

<400> SEQUENCE: 14

```
caagctatac caagcataca atcaactatc tcatatacaa tgaagaactt catatcactg      60
gtgaacaaga aaagggtac cctggatgat aggaatagta gcgttccgga atcttccagt     120
ggtataatac accaacgtgg agctttaaac actgaggatt ttgaagaagg aaagaaagat     180
ggtgcattcg aattgggtca cctcgaattc accaccaatt cagcccaatt gggtgattca     240
```

```
gacgatgata atgataatgc aattaagata gcgaatgctg ccactgatga agccaatgag    300
gctaatagtg aagaaaaaag catgaccttA aggcaagctt tgagaaaata tccaaaggca    360
gccctatggt ccatcttggt gtctactacc ttagtcatgg aaggttatga tactgcgctt    420
ttgagtgcac tttatgcatt accggttttc cagaggaaat tcggtactat gaatgcggaa    480
ggctcctacg aaattacctc gcagtggcaa attggtttga acatgtgtgt cctttgtggt    540
gaaatgattg gtttacagat gaccacttac atggtcgagt tcatgggtaa tcgttacaca    600
atgattacgg cgctcggctt gttgactgct tatatttta tcctttacta ctgcaaaagt    660
ttggccatga tcgctgtagg gcaaattctg tctgctatgc catggggttg cttccagagt    720
ctggctgtta cctatgcttc ggaggtttgc ccctagcgc tgagatatta catgaccagt    780
tactccaata tttgttggtt gtttggtcaa attttcgctt ctggtatcat gaaaaactcc    840
caggagaatt tgggagactc cgatttaggc tacaagttgc catttgcctt acaatggatc    900
tggcctgcac ctttgattat tggtatcttc tttgctcctg agtcgccttg gtggctggtg    960
agaaagaata agattgcgga ggccaaaaag tccttgaata gaatcctgag cggcactgct    1020
gccgagaggg agattcaagt ggatatcact ttaaagcaaa ttgagatgac cattgagaag    1080
gagagacttc tggcatctaa atcagggtcg ttcttcaact gtttcaaagg cgttgatgga    1140
agaagaacaa ggcttgcgtg tttgacttgg gttgctcaaa acagtagtgg tgccgtttta    1200
ctaggttact cgacgtattt ctttgaaagg cagggatgg ccactgacaa ggcgtttact    1260
ttctcgctta tccagtactg tctaggttta gcaggcactc tttgttcctg ggtgatatct    1320
ggccgtgttg gtagatggag tatcctggct tatggtcttg catttcaaat ggtgtgtcta    1380
ttcatcattg gtggaatggg gtttgcatcc ggaagcaatg ccagtaatgg tgctggtggt    1440
ctactgctgg ctttatcgtt cttttacaac gctggtatcg gagctgtcgt ttactgtatt    1500
gtggctgaaa ttccgtctgc agaattaagg accaaaacta ttgtaatggc tcgtatttgc    1560
tataatttga tggccgtcat caatgccatt ttaacgccat atatgctgaa cgtgagtgac    1620
tggaactggg gtgctaaaac cggcctatac tggggtggtt tcactgcagt cactttggct    1680
tgggttatca ttgatttgcc tgagacaact ggtagaacat ttagcgaaat taatgagctt    1740
ttcaatcaag gtgtccctgc tagaaaattt gcatctactg tagttgatcc tttcgggaag    1800
ggacagcgtc aaaatgattc gcaagtggat aacgtcattg accagtcctc aagcgcaatg    1860
cagcaagagc taaatgaagc taacgaattc taattaatta aacaggcccc ttttcctttg    1920
tcgatatcat gtaattagtt atgtcacgct tacattcacg c                       1961
```

<210> SEQ ID NO 15
<211> LENGTH: 1955
<212> TYPE: PRT
<213> ORGANISM: Artificial Sequence
<220> FEATURE:
<223> OTHER INFORMATION: Sm MAL11-2

<400> SEQUENCE: 15

Cys Ala Ala Gly Cys Thr Ala Thr Ala Cys Cys Ala Ala Gly Cys Ala
1               5                   10                  15

Thr Ala Cys Ala Ala Thr Cys Ala Ala Cys Thr Ala Thr Cys Thr Cys
                20                  25                  30

Ala Thr Ala Thr Ala Cys Ala Ala Thr Gly Ala Ala Gly Ala Ala Thr
            35                  40                  45

Ala Thr Cys Ala Thr Cys Thr Cys Gly Cys Thr Gly Gly Thr Ala Gly
        50                  55                  60

Gly Cys Ala Gly Gly Ala Ala Ala Gly Ala Ala Thr Gly Cys
65                  70                  75                  80

Cys Cys Cys Ala Gly Ala Gly Ala Ala Thr Gly Ala Gly Ala Thr Cys
                85                  90                  95

Ala Cys Ala Ala Ala Cys Cys Thr Cys Cys Gly Gly Ala Cys Thr
            100                 105                 110

Cys Thr Thr Cys Ala Ala Gly Cys Gly Cys Thr Ala Cys Ala Gly Thr
        115                 120                 125

Cys Ala Thr Gly Cys Ala Ala Gly Cys Ala Ala Gly Ala Gly Thr
        130                 135                 140

Thr Thr Ala Gly Ala Cys Ala Cys Cys Gly Ala Cys Gly Ala Thr Thr
145                 150                 155                 160

Thr Thr Gly Ala Ala Gly Ala Ala Gly Gly Ala Ala Gly Ala Ala
                165                 170                 175

Ala Gly Ala Cys Gly Gly Cys Gly Cys Ala Thr Thr Gly Ala Gly
                180                 185                 190

Thr Thr Gly Gly Gly Thr Cys Ala Cys Thr Thr Gly Gly Ala Gly Thr
        195                 200                 205

Thr Cys Ala Cys Cys Ala Cys Cys Ala Ala Thr Gly Cys Ala Gly Cys
        210                 215                 220

Ala Cys Ala Gly Cys Thr Ala Gly Gly Cys Gly Ala Thr Thr Cys Thr
225                 230                 235                 240

Gly Ala Cys Gly Ala Gly Gly Ala Cys Ala Gly Cys Gly Thr Ala Ala
            245                 250                 255

Ala Cys Gly Cys Ala Ala Thr Cys Ala Gly Ala Gly Thr Gly Gly Cys
            260                 265                 270

Ala Gly Ala Cys Gly Cys Thr Ala Cys Gly Gly Ala Thr Gly Ala Thr
            275                 280                 285

Gly Cys Gly Ala Ala Cys Gly Ala Ala Gly Cys Thr Ala Ala Cys Ala
            290                 295                 300

Ala Thr Gly Ala Gly Gly Ala Gly Ala Ala Ala Ala Gly Cys Ala Thr
305                 310                 315                 320

Gly Ala Cys Thr Thr Thr Gly Ala Gly Gly Cys Ala Ala Gly Cys Thr
            325                 330                 335

Thr Thr Gly Cys Gly Ala Ala Ala Ala Thr Ala Thr Cys Cys Ala Ala
            340                 345                 350

Ala Gly Gly Cys Ala Gly Cys Cys Cys Thr Gly Thr Gly Gly Thr Cys
            355                 360                 365

Thr Ala Thr Thr Thr Thr Gly Gly Thr Gly Thr Cys Cys Ala Cys Gly
        370                 375                 380

Ala Cys Gly Cys Thr Gly Gly Thr Thr Ala Thr Gly Gly Ala Gly Gly
385                 390                 395                 400

Gly Thr Thr Ala Thr Gly Ala Thr Ala Cys Thr Gly Cys Gly Cys Thr
            405                 410                 415

Thr Thr Thr Gly Ala Gly Thr Gly Cys Ala Cys Thr Thr Ala Thr
                420                 425                 430

Gly Cys Ala Thr Thr Gly Cys Cys Gly Gly Thr Thr Thr Cys Cys
            435                 440                 445

Ala Gly Ala Gly Gly Ala Ala Gly Thr Thr Cys Gly Gly Thr Ala Cys
            450                 455                 460

Thr Ala Thr Gly Ala Ala Thr Gly Cys Gly Gly Ala Ala Gly Gly Cys
465                 470                 475                 480

-continued

```
Thr Cys Cys Thr Ala Cys Gly Ala Gly Ala Thr Ala Cys Cys Thr
                485                 490                 495
Cys Gly Cys Ala Gly Thr Gly Gly Cys Ala Ala Thr Thr Gly Gly
                500                 505                 510
Thr Thr Thr Gly Ala Ala Cys Ala Thr Gly Gly Thr Gly Thr Cys
                515                 520                 525
Cys Thr Thr Thr Gly Thr Gly Gly Thr Gly Ala Ala Ala Thr Gly Ala
530                 535                 540
Thr Thr Gly Gly Thr Thr Thr Ala Cys Ala Ala Thr Gly Ala Cys
545                 550                 555                 560
Cys Ala Cys Thr Thr Ala Cys Ala Thr Gly Gly Thr Cys Gly Ala Gly
                565                 570                 575
Thr Thr Cys Ala Thr Gly Gly Thr Ala Ala Thr Cys Gly Thr Thr
                580                 585                 590
Ala Cys Ala Cys Ala Ala Thr Gly Ala Thr Thr Ala Cys Gly Gly Cys
                595                 600                 605
Gly Cys Thr Cys Gly Gly Cys Thr Thr Gly Thr Thr Gly Ala Cys Thr
                610                 615                 620
Gly Cys Thr Thr Ala Thr Ala Thr Thr Thr Thr Ala Thr Cys Cys
625                 630                 635                 640
Thr Thr Thr Ala Cys Thr Ala Cys Thr Gly Cys Ala Ala Ala Gly
                645                 650                 655
Thr Thr Thr Gly Gly Cys Cys Ala Thr Gly Ala Thr Cys Gly Cys Thr
                660                 665                 670
Gly Thr Ala Gly Gly Cys Ala Ala Ala Thr Thr Cys Thr Gly Thr
                675                 680                 685
Cys Thr Gly Cys Thr Ala Thr Gly Cys Ala Thr Gly Gly Gly Gly
                690                 695                 700
Thr Thr Gly Cys Thr Thr Cys Cys Ala Gly Ala Gly Thr Cys Thr Gly
705                 710                 715                 720
Gly Cys Thr Gly Thr Thr Ala Cys Cys Thr Ala Cys Gly Thr Thr
                725                 730                 735
Cys Gly Gly Ala Gly Gly Thr Thr Thr Gly Cys Cys Cys Cys Thr
                740                 745                 750
Ala Gly Cys Gly Thr Thr Gly Ala Gly Ala Thr Ala Cys Thr Ala Cys
                755                 760                 765
Ala Thr Gly Ala Cys Cys Ala Gly Thr Thr Ala Cys Thr Cys Cys Ala
770                 775                 780
Ala Cys Ala Thr Cys Thr Gly Thr Thr Gly Gly Thr Gly Thr Thr
785                 790                 795                 800
Thr Gly Gly Thr Cys Ala Ala Thr Thr Thr Cys Gly Cys Thr
                805                 810                 815
Thr Cys Thr Gly Gly Thr Ala Thr Cys Ala Thr Gly Ala Ala Ala Ala
                820                 825                 830
Ala Cys Thr Cys Cys Cys Ala Gly Gly Ala Gly Ala Ala Thr Thr Thr
                835                 840                 845
Gly Gly Gly Ala Gly Ala Cys Thr Cys Cys Gly Ala Gly Thr Thr Gly
                850                 855                 860
Gly Gly Cys Thr Ala Cys Ala Ala Gly Thr Thr Gly Cys Cys Ala Thr
865                 870                 875                 880
Thr Thr Gly Cys Cys Thr Thr Ala Cys Ala Ala Thr Gly Gly Ala Thr
                885                 890                 895
Cys Thr Gly Gly Cys Cys Thr Gly Cys Ala Cys Cys Thr Thr Thr Gly
```

```
                    900             905             910
Ala Thr Thr Ala Thr Gly Gly Thr Ala Thr Cys Thr Thr Cys Thr
            915             920             925
Thr Cys Gly Cys Thr Cys Cys Thr Gly Ala Gly Thr Cys Gly Cys
            930             935             940
Thr Thr Gly Gly Thr Gly Gly Cys Thr Gly Gly Thr Gly Ala Gly Ala
945             950             955             960
Ala Ala Gly Ala Ala Thr Ala Ala Gly Ala Thr Cys Gly Cys Gly Gly
                965             970             975
Ala Gly Gly Cys Cys Ala Ala Ala Ala Gly Thr Cys Cys Thr Thr
            980             985             990
Gly Ala Ala Thr Ala Gly Gly Ala  Thr Thr Cys Thr Gly  Ala Gly Cys
            995             1000            1005
Gly Gly  Cys Ala Cys Thr Gly  Cys Thr Gly Cys Thr  Gly Ala Gly
            1010            1015            1020
Ala Gly  Gly Gly Ala Gly Ala  Thr Thr Cys Ala Ala  Gly Thr Gly
            1025            1030            1035
Gly Ala  Thr Ala Thr Thr Ala  Cys Thr Thr Gly  Ala Ala Gly
            1040            1045            1050
Cys Ala  Ala Ala Thr Thr Gly  Ala Gly Ala Thr Gly  Ala Cys Cys
            1055            1060            1065
Ala Thr  Thr Gly Ala Gly Ala  Ala Gly Gly Ala Ala  Ala Gly Ala
            1070            1075            1080
Cys Thr  Thr Cys Thr Gly Gly  Cys Ala Thr Cys Thr  Ala Ala Ala
            1085            1090            1095
Thr Cys  Ala Gly Gly Gly Thr  Cys Thr Thr Thr Cys  Thr Thr Thr
            1100            1105            1110
Cys Ala  Cys Thr Gly Thr Thr  Thr Cys Ala Ala Gly  Gly Gly Cys
            1115            1120            1125
Gly Thr  Thr Gly Ala Thr Gly  Ala Ala Gly Ala  Ala Gly Ala
            1130            1135            1140
Ala Cys  Ala Ala Gly Ala Cys  Thr Thr Gly Cys Ala  Thr Gly Thr
            1145            1150            1155
Thr Thr  Gly Ala Cys Thr Thr  Gly Gly Gly Thr Thr  Gly Cys Thr
            1160            1165            1170
Cys Ala  Ala Ala Ala Cys Ala  Gly Thr Ala Gly Thr  Gly Gly Thr
            1175            1180            1185
Gly Cys  Thr Gly Thr Thr Thr  Thr Gly Cys Thr Thr  Gly Gly Cys
            1190            1195            1200
Thr Ala  Cys Thr Cys Gly Ala  Cys Ala Thr Ala Thr  Thr Thr Cys
            1205            1210            1215
Thr Thr  Thr Gly Ala Ala Ala  Gly Gly Gly Cys Ala  Gly Gly Cys
            1220            1225            1230
Ala Thr  Gly Gly Cys Cys Ala  Cys Thr Gly Ala Cys  Cys Ala Gly
            1235            1240            1245
Gly Cys  Gly Thr Thr Thr Ala  Cys Thr Thr Cys  Thr Cys Gly
            1250            1255            1260
Cys Thr  Thr Ala Thr Cys Cys  Ala Gly Thr Ala Cys  Thr Gly Thr
            1265            1270            1275
Cys Thr  Thr Gly Gly Thr Thr  Thr Gly Gly Cys Ala  Gly Gly Thr
            1280            1285            1290
Ala Cys  Thr Cys Thr Thr Thr  Gly Thr Thr Cys Cys  Thr Gly Gly
            1295            1300            1305
```

```
Gly Thr Gly Ala Thr Ala Thr Cys Thr Gly Gly Thr Cys Gly Thr
    1310                1315                1320

Gly Thr Thr Gly Gly Thr Ala Gly Ala Thr Gly Gly Ala Cys Thr
    1325                1330                1335
Ala Thr Cys Cys Thr Gly Ala Cys Gly Thr Ala Thr Gly Gly Thr
    1340                1345                1350

Cys Thr Thr Gly Cys Ala Thr Thr Cys Cys Ala Ala Ala Thr Gly
    1355                1360                1365

Gly Thr Thr Thr Gly Thr Cys Thr Ala Thr Thr Thr Ala Thr Cys
    1370                1375                1380

Ala Thr Thr Gly Gly Thr Gly Gly Ala Ala Thr Gly Gly Gly Gly
    1385                1390                1395
Thr Thr Thr Gly Cys Ala Thr Cys Cys Gly Gly Ala Ala Gly Cys
    1400                1405                1410
Ala Ala Thr Gly Cys Cys Ala Gly Thr Ala Ala Thr Gly Gly Thr
    1415                1420                1425
Gly Cys Cys Gly Gly Thr Gly Gly Thr Cys Thr Ala Cys Thr Gly
    1430                1435                1440
Cys Thr Gly Gly Cys Thr Thr Thr Ala Thr Cys Gly Thr Thr Cys
    1445                1450                1455
Thr Thr Cys Thr Ala Cys Ala Ala Cys Gly Cys Thr Gly Gly Thr
    1460                1465                1470
Ala Thr Cys Gly Gly Ala Gly Cys Thr Gly Thr Cys Gly Thr Thr
    1475                1480                1485
Thr Ala Thr Thr Gly Thr Ala Thr Cys Gly Thr Thr Gly Cys Ala
    1490                1495                1500
Gly Ala Gly Ala Thr Cys Cys Cys Ala Thr Cys Cys Gly Cys Ala
    1505                1510                1515
Gly Ala Gly Thr Thr Ala Ala Gly Gly Ala Cys Cys Ala Ala Gly
    1520                1525                1530
Ala Cys Thr Ala Thr Thr Gly Thr Gly Cys Thr Gly Gly Cys Gly
    1535                1540                1545
Cys Gly Thr Ala Thr Thr Thr Gly Thr Thr Ala Cys Ala Ala Thr
    1550                1555                1560

Cys Thr Ala Ala Thr Gly Gly Cys Cys Gly Thr Cys Thr Thr Cys
    1565                1570                1575

Ala Ala Cys Gly Cys Thr Ala Thr Thr Cys Thr Ala Ala Cys Thr
    1580                1585                1590

Cys Cys Ala Thr Ala Thr Ala Thr Gly Cys Thr Gly Ala Ala Cys
    1595                1600                1605

Gly Thr Gly Ala Gly Cys Gly Ala Cys Thr Gly Gly Ala Ala Cys
    1610                1615                1620

Thr Gly Gly Gly Gly Thr Gly Cys Cys Ala Ala Ala Ala Cys Thr
    1625                1630                1635

Gly Gly Thr Cys Thr Ala Thr Ala Cys Thr Gly Gly Gly Gly Thr
    1640                1645                1650

Gly Gly Thr Thr Thr Cys Ala Cys Cys Gly Cys Ala Cys Thr Cys
    1655                1660                1665

Ala Cys Thr Cys Thr Gly Gly Cys Thr Thr Gly Gly Gly Thr Cys
    1670                1675                1680

Ala Thr Cys Ala Thr Thr Gly Ala Thr Thr Thr Gly Cys Cys Cys
    1685                1690                1695
```

```
Gly Ala  Gly Ala Cys Ala Ala  Cys Thr Gly Gly Cys  Ala Gly Ala
    1700             1705                 1710

Ala Cys  Cys Thr Thr Thr Ala  Gly Thr Gly Ala Ala  Ala Thr Thr
    1715             1720                 1725

Ala Ala  Thr Gly Ala Ala Cys  Thr Thr Thr Thr Cys  Ala Ala Thr
    1730             1735                 1740

Cys Ala  Ala Gly Gly Thr Gly  Thr Thr Cys Cys Thr  Gly Cys Cys
    1745             1750                 1755

Ala Gly  Ala Ala Ala Ala Thr  Thr Cys Gly Cys Ala  Thr Cys Thr
    1760             1765                 1770

Ala Cys  Thr Gly Thr Ala Gly  Thr Thr Gly Ala Thr  Cys Cys Thr
    1775             1780                 1785

Thr Thr  Cys Cys Gly Thr Ala  Ala Gly Gly Gly Thr  Gly Ala Gly
    1790             1795                 1800

Cys Thr  Thr Cys Ala Ala Ala  Ala Thr Gly Ala Thr  Cys Thr Gly
    1805             1810                 1815

Cys Ala  Ala Gly Thr Cys Gly  Ala Cys Gly Thr Thr  Ala Thr Thr
    1820             1825                 1830

Gly Ala  Thr Cys Ala Ala Thr  Cys Cys Thr Cys Ala  Ala Gly Cys
    1835             1840                 1845

Gly Thr  Ala Ala Ala Gly Cys  Ala Gly Cys Gly Gly  Gly Ala Gly
    1850             1855                 1860

Thr Cys  Ala Gly Cys Thr Gly  Ala Ala Gly Cys Thr  Ala Ala Cys
    1865             1870                 1875

Ala Cys  Gly Thr Thr Cys Thr  Ala Ala Thr Thr Ala  Ala Thr Thr
    1880             1885                 1890

Ala Ala  Ala Cys Ala Gly Gly  Cys Cys Cys Cys Thr  Thr Thr Thr
    1895             1900                 1905

Cys Cys  Thr Thr Thr Gly Thr  Cys Gly Ala Thr Ala  Thr Cys Ala
    1910             1915                 1920

Thr Gly  Thr Ala Ala Thr Thr  Ala Gly Thr Thr Ala  Thr Gly Thr
    1925             1930                 1935

Cys Ala  Cys Gly Cys Thr Thr  Ala Cys Ala Thr Thr  Cys Ala Cys
    1940             1945                 1950

Gly Cys
    1955

<210> SEQ ID NO 16
<211> LENGTH: 1952
<212> TYPE: DNA
<213> ORGANISM: Artificial Sequence
<220> FEATURE:
<223> OTHER INFORMATION: Sc RM11-1a MAL11

<400> SEQUENCE: 16
caagctatac caagcataca atcaactatc tcatatacaa tgaagggatt atcctcatta      60
ataaacagaa aaaagacag gaacgactca cacttagatg agatcgagaa tggcgtgaac      120
gctaccgaat tcaactcgat agagatggag gagcaaggta agaaaagtga ttttgatctt     180
tcccatcttg agtacggtcc aggttcacta ataccaaacg ataataatga agaagtcccc     240
gaccttctcg atgaagctat gcaggacgcc aaagaggcag atgaaagtga gaggggaatg     300
ccactcatga cagctttgaa gacatatcca aaagctgctg cttggtcact attagttttcc    360 acaacattga ttcaagaggg ttatgacaca gccattctag gagctttcta tgccctgcct     420 gttttttcaaa aaaatatgg ttctttgaat agcaatacag gagattatga aatttcagtt     480
```

```
tcctggcaaa tcggtctatg tctatgctac atggcaggtg agattgtcgg tttgcaaatg        540
actgggcctt ctgtagatta catgggcaac cgttacactc tgatcatggc gttgttcttt        600
ttagcggctt tcattttcat tctgtatttt tgcaagagtt tgggtatgat tgccgtggga        660
caggcattgt gtggtatgcc atggggttgt ttccaatgtt tgaccgtttc ttatgcttct        720
gaaatttgtc ctttggccct aagatactat ttgacgactt attctaattt atgttgggcg        780
ttcggtcaac ttttcgctgc tggtattatg aaaaattccc agaacaaata tgccaactca        840
gaactaggat ataagctacc ttttgctttg cagtggatct ggccccttcc tttggcggta        900 ggtattttt ttgcaccaga gtctccatgg tggctggtta aaaaggaag gattgatcaa         960 gcgaggagat cacttgaaag aacattaagt ggtaaaggac ccgagaaaga attactagtg       1020
actatggaac tcgataaaat caaaactact atagaaaagg agcagaaaat gtctgatgaa       1080
ggaacttact gggattgtgt gaaagatggt attaacagga gaagaacgag aatagcttgt       1140
ttatgttgga tcggtcaatg ctcctgtggt gcatcattaa ttggttattc aacttacttt       1200
tatgaaaaag ctggtgttag cactgatacg gcttttactt tcagtattat ccaatattgt       1260
cttggtattg ctgcaacgtt tatatcctgg tgggcttcaa aatattgtgg cagatttgac       1320
ctttatgctt ttgggctggc ttttcaggct attatgttct tcattatcgg tggtttagga       1380
tgttcagaca ctcatggcgc taaaatggg agtggtgctc ttctaatggt tgtcgcgttc        1440
ttttacaacc tcggtattgc acctgttgtt ttttgcttag tgtctgaaat accgtcttca       1500
aggctaagaa ccaaaacaat tattttggct cgtaatgctt acaatgtgat ccaagttgta       1560
gttacagttt tgatcatgta ccaattgaac tcagagaaat ggaattgggg tgctaaatca       1620
ggctttttct ggggaggatt ttgtctggcc acttttagctt gggctgttgt cgatttacca       1680
gaaaccgctg gcaggacttt tattgagata aatgaattgt ttagacttgg tgttccagca       1740
agaaagttca gtcgactaa agtcgaccct tttgcagctg ccaaagcagc agctgcagaa        1800
attaatgtta aagatccgaa ggaagatttg gaaacttctg tggtagatga agggcgaaac       1860
acctcatctg ttgtgaacaa ataattaatt aaacaggccc cttttccttt gtcgatatca       1920
tgtaattagt tatgtcacgc ttacattcac gc                                     1952
```

<210> SEQ ID NO 17
<211> LENGTH: 1955
<212> TYPE: DNA
<213> ORGANISM: Artificial Sequence
<220> FEATURE:
<223> OTHER INFORMATION: Sp MAL11

<400> SEQUENCE: 17

```
caagctatac caagcataca atcaactatc tcatatacaa tgaaaaatat catctcgctg         60
gtaagcagga aagaaatgt gccagaggat gagatcgcaa atattccgga ctcttcaagc        120
ggtacagtca tgcgagcaaa gattttagac gcggaggatt tagaagaaga gaagaaagac       180
ggcgcatttg aattggacca cttggagttc accactaatg gtggacagct aggcgattct       240
gaaggggaca gcgaaagtga atcagagtt gcagacgctg ctgatgatgc gaacgaagct        300
aacaatgagg agaaaagcat gacttgagg caagctttgc gaaatatcc aaaggctgcc        360 ttatggtcta ttttagtgtc cactacgctg gttatggagg ttatgatac tgcgcttttg       420 agtgcacttt atgcattgcc agtttttcca ggaagttcg gtactatgaa tgcggaaggc        480
tcctacgaaa ttacctcgca gtggcaaatt ggtttgaaca tgtgtgttct ttgtggtgaa       540
```

| | |
|---|---|
| atgattggtt tacagattac cacttacatg gtcgaattca tgggcaaccg ttatacaatg | 600 |
| attacggcgc ttggtttgtt gactgcttat agtttcatcc tttactactg taaaagtttg | 660 |
| gccatgatcg ctgtagggca aattctgtcg gctatgccat ggggctgctt ccagagtctg | 720 |
| gctgttactt acgcttcgga agtttgtccc ctagcgttga gatattacat gaccagttac | 780 |
| tccaatatct gttggttgtt tggccaaatt ttcgcctctg gtattatgaa aaactctcag | 840 |
| gagaacttgg gagattctga cctaggttac aaattgccat cgccttaca atggatttgg | 900 |
| cctgcacctt tgattgttgg tattttcttt gctcctgagt cgccttggtg gctggtgaga | 960 |
| aagaataaga ttgcggaggc caaaaagtcc ttgaatagga ttctgagtgg cactgctgct | 1020 |
| gagaaggaga ttcaagtgga tattacttta aagcaaattg atgacgat tgagaaggaa | 1080 |
| agacttctgg catcgaaatc agggtcgttc ttcaattgtt tcaagggcgt tgatggaaga | 1140 |
| agaacaagac ttgcgtgttt gacttgggtt gctcagaata gcagcggtgc cgttttactt | 1200 |
| ggttactcga catatttctt tgaaaggggca ggcatggcca ctgacaaggc gttcactttt | 1260 |
| tcgcttattc agtactgtct aggtttagca ggcacccttt gttcctgggt aatatctggc | 1320 |
| cgtgttggga gatggactat actgacttat ggtcttgcat ttcaaatggt ttgtctattt | 1380 |
| atcattggtg gaatggggtt tgcttctgga agcaatgcta gtaacggtgc cggtggttta | 1440 |
| ctgttggctt tatcgttctt ctacaacgcc ggtatcgggg ctgtagttta ctgtatcgtt | 1500 |
| gcagagatcc catccgcaga attaaggacc aagactattg tgctggcccg tatttgctac | 1560 |
| aatttgatgg ccgtcatcaa tgccattcta acgccatata tgcttaatgt gagcgactgg | 1620 |
| aactggggcg ccaaaaccgg tctatattgg ggcggtttca ccgcagtcac tttggcttgg | 1680 |
| gtcatcattg atttgcctga acaactggt agaacctta gtgaaattaa tgaactttc | 1740 |
| aatcaaggtg tccctgctag aaaatttgcg tctactgtag ttgatccttt ccggaaggga | 1800 |
| gagtctcaaa atgatccgca agttgacgtt gttgatcagt cctcaagcgc aaagcagcag | 1860 |
| gagctagatg aagctaacac attctaatta attaaacagg ccccttttcc tttgtcgata | 1920 |
| tcatgtaatt agttatgtca cgcttacatt cacgc | 1955 |

<210> SEQ ID NO 18
<211> LENGTH: 1838
<212> TYPE: DNA
<213> ORGANISM: Artificial Sequence
<220> FEATURE:
<223> OTHER INFORMATION: Kl MAL11

<400> SEQUENCE: 18

| | |
|---|---|
| caagctatac caagcataca atcaactatc tcatatacaa tggattcttc atcgtccgtg | 60 |
| cttcagaaag acacaaaaca ggtcgatatt gaacataggg aagaagcaag ctccaacgat | 120 |
| cagttagtag atcaaaatgc cttattagat agcttccttg gtgacgtcga tggtgctgcg | 180 |
| agcgctgatg cgactgaaaa aagtatgtct ctcttagaag ggttgcgcaa gtacccgaaa | 240 |
| gctgtaggtt ggtccttagt ggtttcaacc ggcttaatca tggaagggta cgacactgct | 300 |
| ttcattaaca atctgtttgc tcttccaatt tttcgaacca ctttcggtga atacaatcaa | 360 |
| gcgaatgaca tttgggagat tccttccaaa tggcaaattg gtttggggat gtgtgttgcc | 420 |
| tgtggtgaga ttattggttt gcagataact ggtatattcg cagatcgtta cggttacagg | 480 |
| cttgtgttga ttgctggctt ggttcttttg attgctttca atttttattct ctactttgca | 540 |
| aacagtttga ctatgattgc tataggccaa atttaagtg gtatcccatg gggctcattc | 600 |
| caaacactct gcgtttcata tgctagtgag gtctgtccat tggttttgag atactatttg | 660 |

```
acaacataca tcaatttatg ttggcttatc gggcaagtga ttgccgctgg agttttgaag      720
gcatgtcagg aacatcttgc caatgatgag ctaggttgga gacttccatt tgcgttacag      780
tggatatggc cggttccttt gattgtaggt atttaccttg ctccagaatc tccttggtgg      840
ttggttagaa agggcaggat cgatcaagcc aaacgatccg tcacaagaat tctaaccctg      900
cccacttctg aaaaggacaa gctaactgac ataatgatca caaaaatgag aatgactgtc      960
gagaaagaaa accgtcttgc ttccgaatca agttcttata tggactgttt caagggcatt     1020
gatgcgagaa gaaccaggat aacgtgtctc acatgggtca tgcaaaattt aacgggatcc     1080
gctttgatgg gatactccac ctatttctat gaaaaagccg ggttggacac ttctgcagcc     1140 ttcactttt ccatcattca atacgtgatt ggtattgttg gtaccttaac atcatggttc      1200
ctatcttcca gagctggtcg cttcacgatt ctcttttggg gtgtcttttt ccagacgata     1260
gttatgttca ttactggtgg cctcggattc agcagctctg aaggtgccag ttggggtgct     1320
ggttccatgt tgctgatcta caacttcttt tacaactcca ccttaggtcc tgttgtttac     1380
tgtgtggtgt cagaaattcc tagtgacaga ttgagaacta aaactgtagt tctagcacgt     1440
aactcctaca acttgatagc tattgtaaat tctattttga caccgtatat gttaaactcc     1500
gaccaatgga actggggtgc aaagacaggt ttgttctggg gtggattagc tgccatctca     1560
ttagtttggg cttacttcga tctcccagaa actaagggca aacatttgc agagcttgat      1620 gagttattcc atcaaagagt tccagcaagg aagtttaaca gtacacatgt ggagcctttc     1680
tctcgtgaga caataatgaa agacctggat gtgaaccctg aggtttggtt ggaaacaatc     1740
gaagaagggg acaccgacat caaaaagtaa ttaattaaac aggcccctttt tcctttgtcg     1800 atatcatgta attagttatg tcacgcttac attcacgc                              1838

<210> SEQ ID NO 19
<211> LENGTH: 1853
<212> TYPE: DNA
<213> ORGANISM: Artificial Sequence
<220> FEATURE:
<223> OTHER INFORMATION: Ps MAL11

<400> SEQUENCE: 19
caagctatac caagcataca atcaactatc tcatatacaa tggttactga atacgttgaa       60
gacgtcaaga acccagaaaa gactattgct gttgactcta tcaccaaaaa gaccactgac      120
gactcttctt tgaattctgt cgatgactat gtcgccagat tcttggatat gtctaacgaa      180
gctagagaca acgaccataa ggaaaaagtt atgccattac gtgaaggttt gaagactttt      240
ccaaaggccg tcatgtggtc catcattttg tctaccgctt tggttatgga aggttatgat      300
accaacttat tgaactcttt gttcggtttc caagctttca caaaaaagtt cggtcatttt      360
gatgaaagat tgaacgtcta cattattgag gccagatggc aaaccggttt aaacatgggt      420
tataactgtg gttgtgtcat tggtttggct attgctggtt ttatcgctga tctctacggt      480
tacagaagaa ctttgatgac tgctttagct acttccgtcg gtttgatctt tttgcaattt      540
tttgctccaa acaaggaagt tttgttattg gcttacgttt tattgggtat taactggggt      600
tcttaccaaa ccttgaccgt cacctacgct tctgaagtcg ctccaaccac cttgagagtt      660
tatttaacca cttacgttaa cgtctgttgg gtcttcggtc aattgatttc ctccggtgtt      720
ttgaaaggtg tcacttctat ggctgaaact ccaaattcct acagaattcc tttcgctgtt      780
caatgggttt ggccaattcc tttgttcatt ggtgttact tggctccaga atccccatgg      840
```

```
ttcttggtta agagaggtag agacgaagaa gctaagagat ctttgaagag attgttgtcc    900
gaaaactctc acatgccaga caaggacgtt ttggctcaag ccatgttggc taagattcaa    960
atgactgtcc aagaagaaga caccgctgac gccggtacct tccgtgattg tttccgtggt   1020
actaatttca gacgtaccag aatcgctgcc ttcacttggt tatttcaatc tatcactggt   1080
tcctccttga tgggttattc cactatcttc taccaacaag ctggtttggc tgtttccatg   1140
tcctttactt tctccattat ccaatactgt ttgggtatta ttggtaccgt cggttcttgg   1200
tttgtctccc aaaaggtcgg tcgtagacca atttacttct tcggtttgtg tactatgttc   1260
gtcttgttga ttttggttgg tggtttgggt gtcgccaata ctactggtgc taaatggggt   1320
atcggtactt tgttgttaat tttcactttc gtctatgact tgaccgttgg tccaatgtgc   1380
tattgtattg ttgctgaaat cccatcttct aagttgagaa ccaagaccgt catgttgtct   1440
cgtaatatgt acaacgttgc caatattatt gtcggtgttg ttaccccata tatgttgtcc   1500
ccaaccgctt gggactggaa agctaagacc ggtttctttt gggccggttt ttccttattg   1560
ggttctattt gggtttactt cgaattgcca gaaactagaa ccgtactta tgccgaattg    1620
gatattttat ccaagacaa ggttccagcc agaaaattca agaccaccga agttgaagtt    1680
ttcgatgctg gtaagttaat ggaaagatac ggtgaaagag gtattaagca atttgttgaa   1740
cacgttgata aggctgaaga agaagaaatt tttgaaaagg cctaattaat taaacaggcc   1800
ccttttcctt tgtcgatatc atgtaattag ttatgtcacg cttacattca cgc           1853

<210> SEQ ID NO 20
<211> LENGTH: 1859
<212> TYPE: DNA
<213> ORGANISM: Artificial Sequence
<220> FEATURE:
<223> OTHER INFORMATION: PsMAL11

<400> SEQUENCE: 20
caagctatac caagcataca atcaactatc tcatatacaa tgtcgactga gtacgttgaa     60
gacaacaaga acccagataa gtcaaccaca gttggctcta tcaccaaaaa aattctttca    120
gatgactctt ccaccaactc ggtagacgac tatgtcgcca gtttttgga catgtcaaat     180
gaagccagag aaaatgataa taaagaaaag aacatgcccc tcaaggaatg tttgaggact    240
ttccctaagg ctgttatgtg gtctatcatc ctttccactg ctattgttat ggaaggttat    300
gataccaatc ttttgaactc tttgtttggt ttcccagctt caacaaaaa gtttggtcac    360
tttgacgaaa gacttgacag atacattatt gaagcaagat ggcaaactgg tttgaacatg    420
gcttataact gtggatgtgt tgttggtctt acaattgctg gttttttgc tgatatcttt     480
ggttacagga aaactttgat gacagctttg gctacttccg tcggtttgat ctttcttcaa    540
ttcttttctc caaataagga ggtcttattg cttgcttacg ttcttttggg tattaactgg    600
ggatcttatc agactttaac tgtcacatac gcttctgaag ttgcaccaac aactttacgt    660
gtgtatctta ctacttatgt taatgtgtgt tgggtgtttg gtcagttaat ctcttctggt    720
gtcatcaagg gagttagtag tataaatgac aaccctaact cttacagaat tccgtttgcg    780
gttcaatggg tgtggcccat cccattattt attggtgtct acttagctcc tgaatccccc    840
tggttttgg tcaagagagg tagaaaccag gacgccaaga actctttgaa gcgtctctta    900
tctgaaaatc ctaatttacc tgacaaggac gcattggctc aagctatgtt gaccaagatt    960
caaatgactg tacaagagga ggactcagac gaccaaggtt cattcagaga atgtttcagg   1020
ggtaccaatt tcagaagaac cagagtcgct gctatggctt ggatgttgca aagtattacc   1080
```

```
ggttcatgtt tgattggtta ctctactatt ttctatcagc aagctggttt agctgttagt    1140
atgtctttca acttctcgat catccaatac tgtttaggta ttattggtac agtcggatcc    1200
tggtttcttg ctcagagagt aggtagattc aaaatctact tctatggtct ttgtgcaatg    1260
tttgttatct taattattgt tggtggttta ggtgtttcca attccaacgg tgctaagtgg    1320
ggtattggta cgctcttgtt gattttcaac tttgtatacg atttgacaat tggtccaatg    1380
gcttactgta tcgttgccga aattccttct tccaagttac gtacaaagac agtcatgctt    1440
tccagaaatt tgtacaacgt tgccaacatt atcgttggta ttgtcactcc atacatgtta    1500
agtcctactg cttggaactg gagagcaaag actggtttct tctgggctgg tttcgcactt    1560
cttggttgtg tctgggtttg gtttgaattg cctgaaacca aggacagaac atatgctgaa    1620
ttggatgtct tgttccagga cggtgttaag gctagagatt caagcacac cgaagttgaa    1680 gttttcgatg ccggtaagtt gatggaaaag ttcggtgaaa atggaatcaa acattttgta    1740
gaacatgttg acaacaagga tgacaacaac gaaatctttg aaaaagctta attaattaaa    1800 caggccccttt tcctttgtc gatatcatgt aattagttat gtcacgctta cattcacgc    1859
```

<210> SEQ ID NO 21
<211> LENGTH: 1853
<212> TYPE: DNA
<213> ORGANISM: Artificial Sequence
<220> FEATURE:
<223> OTHER INFORMATION: Ps MAL11

<400> SEQUENCE: 21

```
caagctatac caagcataca atcaactatc tcatatacaa tgagctcggt gtttgttgaa      60
gatataaaaa atccagaaaa ggtcgtcata gtgaactcag ttgctaaaaa ggcctctgat     120
gactcgtcct tgaattcagt agacgactat gtgtctaggt tcttagatat gtccaatgag     180
gctagagata cgatcacaa tgaaaaaaga atgccactta gagaaggttt aaaaacattt     240
ccaaaggcag taatgtggtc catcattctc tctactgctt tggtaatgga gggatatgat     300
acttaccttt tgaattcttt gtttggtttt caggcgttca acaaaaagtt tggtcacttc     360
gataaaagac tcaacaaata tattatcgaa gctaaatggc aaactggttt gaatatgggc     420
tataatagtg gttgtgttat tggacttgca atttctggtt ttgtagctga tatttatggt     480
tacagaaaaa ctttaatgac agctttggct tcttccatag ctttgatttt tcttcagttt     540
ttctctccta caaggaagt tttgttgctt gcatacgttc ttttggggat caactggggc     600
tcttatcaaa cattaactgt tacatacgcc agtgaagttc tccaacaac tttgcgtgta     660 tatctcacta cgtatgtcaa tatgtgttgg gtatttggcc agttgcttgg ttctggtgtg     720
cttaaggctg tttctagtat gtcagaaacg ccgaattcat acagaattcc ttttgctgtt     780
caatgggtat ggccaattcc gttaatcatc ggtgtatacc ttgctcctga gtcaccatgg     840
ttcttagtca aaagaggaag agatcaggat gctaagaatt ccttgaagcg tcttttgtct     900
gagaatccac tcatgccaga caaagatgta ttatcccaag caatgttgac aaaaatccag     960
atgactgtca gagaagaaga tgcaaaagat gttggaaatt ttagcgattg tttcaaggga    1020
acaaactgga gacgaactag aattgctggt ttgacttggt ttttcaatg tttctgtgga    1080 tcttctttga tgggctattc aactgtattt taccaacaag cgggattacc tgttagtatg    1140
tcatttactt tttctatcat acaatactgt ttaggtattg ttggtactgt tagttcttgg    1200
tttctttccc aaaaggtagg aagaagaaaa atttatttaa ccgggttaag tacaatgagc    1260
```

-continued

| | |
|---|---|
| cttttgatgt tgctagtagg aggattggga acctccagct ctaaaagtgc aaagtggggt | 1320 |
| gtcggtactc tcctattact ttttacattt gtttatgatt tatcagtggg tccaatgtgc | 1380 |
| tactgtattg ttgctgaaat gccatcttcc aagttgcgta ccaagactgt tatgcttgcc | 1440 |
| agaaatactt acaacgttgc tcacattgtt gctggtgtgg tcactcctta catgttgagc | 1500 |
| ccaactgctt ggaattggaa agccaaaact gggttttttct gggctggaac tgctttcgtt | 1560 |
| ggttctgttt gggtcttttt tgaattgcct gaaactaaaa acaggactta tgctgaattg | 1620 |
| gatattttat tccaagatgg agtttcttct cgcaaattta atagcaccga cgttgaggta | 1680 |
| tttgatgctg gaaagttgat ggaaaaatat ggtgcaactg gtattaaaca gattattgag | 1740 |
| catgtcgaca aaaccaatta tgatattctt gaacaaaacc gttaattaat taaacaggcc | 1800 |
| ccttttcctt tgtcgatatc atgtaattag ttatgtcacg cttacattca cgc | 1853 |

```
<210> SEQ ID NO 22
<211> LENGTH: 1676
<212> TYPE: DNA
<213> ORGANISM: Artificial Sequence
<220> FEATURE:
<223> OTHER INFORMATION: Hp MAL11

<400> SEQUENCE: 22
```

| | |
|---|---|
| caagctatac caagcataca atcaactatc tcatatacaa tgtcgctgaa ggaaggtctg | 60 |
| aaaactttcc caaaagctgc ctgctggtcg attgtgcttt ccacagccat catcatggaa | 120 |
| ggatacgata ccacgctcct gaacagtctg tactcaatgc aatctttcgc caaaaagtac | 180 |
| ggcaagtact acccagaaat tgaccagtac caggtccctg ccaagtggca gacatcgctt | 240 |
| tcgatgtcga cttatgtcgg tgaaattgtc ggactgtaca ttgcaggtct tgttgccgag | 300 |
| aaatggggat acaggcgtac gttaatatcg ttcatggcag ccgttgtggg tttaatcttc | 360 |
| attctttttct ttgcggtcga cgtgcagatg ctgcttgccg gcgagctgct ctgtggtatt | 420 |
| gtctggggtg cattccagac cctcacagtg tcatacgcct cggaagtgtg tccagtagtt | 480 |
| ctgagaatct accttaccac ttatgtcaat gcttgctggg ttatcggaca gttgattgct | 540 |
| gcttgtttgc tgagaggcac tatgaccctg accagcgagt ggtcatacaa gattcctttc | 600 |
| gctgtccagt ggatctggcc tgtgccaatc atgattggaa tctacctggc cccggagtcg | 660 |
| ccctggtggc tggttaaaaa gaaccgagac gcagaagcta agaaaagtat cacaaggctt | 720 |
| ttgagtccaa acaccgaggt gccagatgtt gctccgctag ccgaggcaat gctgaataaa | 780 |
| atgcaactaa ccatcaagga agagtctgcg cgcacgtcca atgtctcgta ctttgactgc | 840 |
| ttcaaacacg ggaacttcag aagaacaagg attgccgcca tgatctggct catccagaat | 900 |
| atcactggat ctgtcttgat gggctattcg acctactttt acatccaggc aggacttgac | 960 |
| agcagtatgt ctttcactttt ctctatcatc caatatgcac tcggtcttct tggaacactt | 1020 |
| gcctcgtggc tcctctcgca aaaattgggc cgttttgaca tctacttctt gggtctgagc | 1080 |
| ataaacacgt gcattctgat aattgtcgga ggtttgggct tttcttcgtc gacgagtgcg | 1140 |
| tcttgggcaa ttggctcgct gctccttgtc ttcacttttg tctacgactc gtccatcggt | 1200 |
| cccatcacct actgcacggt tgcagaaatc ccttcgtcga cggtgcgtgc caagaccgtt | 1260 |
| gcccttgcaa gaaactggta caatctgtct caaattccgc tctccattgt cactccgtac | 1320 |
| atgctgaacc cgactgcttg gaactggaaa gcaaaagcgg ccctttttatg gcaggcttg | 1380 |
| tctatttgct cactgatcta catctggttt gaattcccag aaacaaaagg aagaactttat | 1440 |
| gctgaactgg acatcctctt caaaaacggt accagtgccc gtaaatttag gtccactcag | 1500 |

```
gtggaaacat tcaatcctca ggaaatgtta aaaaaaatga ataatgagga tattatacag   1560
gttgttgatg gcgacctgga cgccggtgcg gccactgcta aagtttaatt aattaaacag   1620
gccccttttc ctttgtcgat atcatgtaat tagttatgtc acgcttacat tcacgc       1676
```

<210> SEQ ID NO 23
<211> LENGTH: 1874
<212> TYPE: DNA
<213> ORGANISM: Artificial Sequence
<220> FEATURE:
<223> OTHER INFORMATION: Ca MAL11

<400> SEQUENCE: 23

```
caagctatac caagcataca atcaactatc tcatatacaa tgactattga agagtacaga     60
ccagaatctg atgagaagaa cgtctctacc ccatctattg tttccttaga cgacaagacc    120
actaacgcct cccatatctc caacgctgcc aagaaaatg tcgatgatta cattgctaag    180
ttcttagata tgtctaacac cgctaaggct gaggacgaaa gagacaaaac catgccattg    240
aaggaatgta ttaagacctt ccaaaggct tgtttctggt ccgtcgtttt gtcttccgct    300
ttgatcatgg aaggttacga tactaatttg ttagcttctt tttacgctta tcaaggtttt    360
gctaaaaaat tcggtagata ctacgaaaac ttgggtgaat accaagtccc agccaaggat    420
caattgggtt tgtctatgtg ttaccaaact ggtcaattgg tcggtgtcta cattggtgct    480
catttggtcg atattatcgg ttaccgttac actttaattc cagctttggc ttcttctatt    540
ggtttgatct tcattcaatt ttttgctcca aacgtccacg tcttgatggt ttcttacgtt    600 tgttgggta ttaactgggg ttcttaccaa actgtttgtg tttcttacgc tatggacatt    660
gccccaacca ccttaagatt gtacttgacc acttatatta attgttgttg gttttttggt    720
caattgattt cctctggtgt cgtcaaggct atttcccaat cctctgatcc acacgcctac    780
agaatcgctt ttgccatcca atggatctgg ccaattccaa ttatgactgg tattttcttt    840
gctccagaat ctccatggtt tttagttaga aagggtagat tggaacaagc taaacacgcc    900
ttggaaagat tattgtccca atccgaacat atcccagata agtccattat ctctcaatct    960
atgttgacca aaattcaaat gaccattaag gaagaagatg ccgtctctgc tggttcttct   1020
attattgaat gttttaaggg taccaacttc agaagaacca gaattgctgc tttcacttgg   1080
ttgattcaaa acatcactgg ttcttctttg atgggttatt ccacttactt ttaccaaaac   1140
gctggtgtcc cagtttctat gtcctttact ttctctatca ttcaatactg tttaggtatt   1200
gttggtacta tcggttcttg gttcttgtct caaaagtgtg gtagatttac catttacttc   1260
tatggtttat gtgccatgac tgtcttgtta ttattgaccg gtggtatggg tacctctgac   1320
aagaaatctt tgtctatggc tgtcggttct atgttgttgg tttacacttt cgtttacgat   1380
ttgactattg gtccaatgtg ctactgtatt gtcggtgaaa tgccatcttc taagttaaga   1440
gctaaaactg tcatgttggc tagaaacttg tacaacatcg ctggtattat cgttgctatt   1500
gttactccat acatgttgaa tccaactcaa tggaattgga aggccaagtc cgccttttg    1560 tgggctggtt tcgctatttt atccgctatc tgggtttact tgagttgcc agagactaaa    1620 ggtcgtacct tcgccgaatt ggataagatg tttgaagata agttccagc tagaaagttc    1680 aagtatacca cccctactac tttcgatgct ggtgaaatga tggaaaagat gggtaactct   1740
ggtttgaagt ctattgttca tgacactgaa cacgtcgaat cttctcatat tgaaactaag   1800
gcctaattaa ttaaacaggc cccttttcct ttgtcgatat catgtaatta gttatgtcac   1860
```

```
gcttacattc acgc                                                        1874
```

<210> SEQ ID NO 24
<211> LENGTH: 1871
<212> TYPE: DNA
<213> ORGANISM: Artificial Sequence
<220> FEATURE:
<223> OTHER INFORMATION: Cd MAL11

<400> SEQUENCE: 24

```
caagctatac caagcataca atcaactatc tcatatacaa tgaccattga agaataccgt      60
ccagaccaaa agaatgtctc cacccatct attgtttctg ttgatgataa aactaccaac     120
gcttctcaca tttctaacgc tggtcaagat aacgttgacg actacatctc caagttcttg     180
gatatgtcta acaccgctaa ggctgaagat gaaagagaca agactatgcc attgaaagaa     240
tgtatcagaa cttcccctaa agcttgtttc tggtccgttg tcttgtctac cgctttgatt     300
atggaaggtt acgacactaa cttattggcc tccttctacg cctaccaagg tttcgccaag     360
aaattcggta gatactacga agatttaggt gaataccaag ttcctgctaa ggatcaattg     420
ggtttgtcta tgtgttatca aaccggtcaa ttggttggtg tttatatcgg tgctcatttg     480
gttgacatta ttggttacag atacactttg attccagcct ggcttcctc cattggtttg     540
attttttattc aattcttcgc tccaaacgtt tctgtcttaa tggtctctta cgttttgttg     600
ggtatcaact ggggttctta ccaaactgtc tgtgtttctt atgccatgga tatcgctcct     660
accactttga gattgtactt aactacctac attaactgtt gttgggtctt cggtcaatta     720
atctcctccg tgttgtcaa ggccgtcttg gaaatgactg acccacatgc ttaccgtatc     780
gcttttgcta ttcaatggat ctggccaatc ccaattatga ctggtatttt tttcgctcca     840
gaatctccat ggttcttagc cagaaaaggt agattggaag aagctaagca ttccttggaa     900
agattgttgt ctcaaaacaa acatattcca gataagtcta ttgtttctca atctatgttg     960
actaagatcc aaatgactat caaggaggaa gacgctgtct ctgccggttc ctccatcatt    1020
gaatgtttca agggtaccaa cttcagaaga accagaatcg ccgctttcac ttggttaatt    1080
caaaacatca ccggttcttc tttgatgggt tactccacct acttctacca aaacgctggt    1140
gttcctgttt ccatgtcttt caacttttct atcatccaat attgcttggg tattttgggt    1200
accattggtt cttggttctt gtctcaaaag tgtggtcgtt ttactatcta cttctatggt    1260
ttatgcacca tgactttgtt gttattgttg accggtggta tgggtacctc cgacaagaaa    1320
tccttgtcca tggccgttgg ttccatgttg ttggtctaca ccttcgtcta cgatttgact    1380
attggtccaa tgtgttactg tattgttggt gaaatgccat cctctaagtt gagagctaag    1440
actgttatgt tagccagaaa cttgttcaac attgctggta ttattatcgc tatcgttact    1500
ccatacatgt tgaacccaac ccaatggaat tggaaggcca agtctgcctt cttgtgggct    1560
ggtttcgcta ttttatctgc tatttggggtt tacttcgaat tgccagaaac taagggtaga    1620
accttagctg aattggacaa gatgttcgaa gacaaggtcc cagcccgtaa gttcaagtat    1680
actaccccaa acaccttcga cgccggtgag atgatggaaa agatgggtaa tactggtttg    1740
aagtctattg ttttagacac cgaacacgtt gaagaagctt cccacattga atctaaggtc    1800
taattaatta aacaggcccc ttttcctttg tcgatatcat gtaattagtt atgtcacgct    1860
tacattcacg c                                                          1871
```

<210> SEQ ID NO 25
<211> LENGTH: 1727

<212> TYPE: DNA
<213> ORGANISM: Artificial Sequence
<220> FEATURE:
<223> OTHER INFORMATION: Ao MAL11

<400> SEQUENCE: 25

```
caagctatac caagcataca atcaactatc tcatatacaa tgactccaga gaaggccgct      60
atgtctgaac atattgaaaa cgataaccca gcgaggcatg atgatatcga cctccccaac     120
agtagcgagg cacataccgc cattgcgaaa gaacgtgaga tgactctatg gcaagcgcta     180
agactttatc cgaaggcggt ggcgtggtct cttctgttct cctgtgccat tatcatggaa     240
ggctacgatg ttgttcttat cggttccttc ctcgcatttc ctgccttcaa cgaaaaatac     300
ggaggtctca tgtccgacgg gacatatggg ctcgaagcta ggtggcaagc aggtgttaac     360
aacgcgatgg cctgcggcca gattatcgga cttttctca atggactggt ctcagagcgc     420
ttgggatacc gaaagaccct gatggcatgc cttgccgcga ccgttggttt cgttttcatt     480
ctgttctttg cgcccaatat tcaaactctc gttgtcggcg agctctttat gggcatccct     540
cttggtgtat accaaacccct cgttgtgaca tacgcatccg aagtgtgccc tgtcgcattg     600
cgcgcatatc tcaccaccta tgttaaccttt gctgggtgc taggtcaatt gctcgcctct     660
ggcgtgctga agggtctggc cgagcgcacc gatcaatggg cataccgtat ccccttttgct    720
ctgcagtgga tctggccaat tcccattttc atcggggtgt ttctggcccc cgagagcccc    780
tggtggctcg ttcgacaaga ccgccgcgaa gatgccgtca aggcattgaa acgactgacc    840
agcgctaacg cagacttcaa cgccgaagaa accgtcgcaa tgatcgtata caccgacgca    900
ctcgagcgac gtgctgaaac cggtacctcc taccttgact gcttcaagaa aagcgactta    960
cgccgaaccg aaatctcctg ctgcgcatgg cggcgcagag tctatgtgg cgcaggcctc   1020
atgggctatt cgactgtctt ttaccagcgc gcaggtctcg ccgtgtcgca gtccttcacc    1080
atgtcgctcg tgcaatatgc cctaggcgtg gtggggacat tcgtctcctg gacactaatg    1140
tcgtacttcg gccgtcgcac cctctacgtc ggcggtctat ttatcctagc catcgtatta    1200
ttcgtcatcg ggttcgtctc catcgctcca tccacacccg ccatctcctg gccaccggc     1260
tccatgcttc tcgtctatac cttatctac gactcctcca tcggccccgt ctgcttcgcc    1320
ctcgtctccg aaatcccatc ctccagactc cgtaccaaga ccgtcgtgct ggcccgaaac    1380
gtctacaata tcctcaacct cgtcaccgga atcattatcc cgtatatgct gaacgtcgac    1440
gcatggaact ggcgcggtaa atcaggtttc ttctggggtg cactctgcgt ttgctgcttg    1500
acgtggtcgt tcttccggct gccagaacct aagggacggt cgtatgctga gttggatctg    1560
ttgtttgaga gagggtgaa gacgagggag tttgcgactg ctaagactgg gttggaggat    1620
ttgcagggcg aggggaagga tgatatggtg aaggtttaat taattaaaca ggccccttt    1680
cctttgtcga tatcatgtaa ttagttatgt cacgcttaca ttcacgc                   1727
```

<210> SEQ ID NO 26
<211> LENGTH: 1754
<212> TYPE: DNA
<213> ORGANISM: Artificial Sequence
<220> FEATURE:
<223> OTHER INFORMATION: Af MAL11

<400> SEQUENCE: 26

```
caagctatac caagcataca atcaactatc tcatatacaa tggagattga gaagtcgacc      60
ggaatcgaac atgtggagga ggaagctgcc tcacgcaggc cccatcccca gcctgcgagc    120
```

| | |
|---|---|
| caccaggacc tcattgccag cagtgaggcc caggcggcgc tcgagaagga gcacagcatg | 180 |
| acactgtggc aggcactgaa gatctacccc aaggccgtgg ggtggtcaat tctcctgtcg | 240 |
| tgtgccatca tcatggaggg ctatgatgtc gtcctgatcg gctctttctt cgcttacccc | 300 |
| caattcaacc agaagtacgg ccatatcatg tcggacggaa actacggtct cgctgccaag | 360 |
| tggcaagcgg ccttgaccaa ctcgatgagc tgcggccaga ttatcggcct gttcatcaac | 420 |
| ggcgtcgtct cggaacgttt cgggtaccgg cggacccctca tggcttgcct agccgcgaca | 480 |
| gtggggtttg tgttcatttt gttctttgcg cccaacatcg agaccctcgt ggccggcgag | 540 |
| ctgctcatgg ggatccccct cggcgtgtac cagaccctca ccgtcaccta tgcatcggaa | 600 |
| gtatgtcccg tcgctattcg gggctatctc actacctatg tgaacctgtg ctgggtccta | 660 |
| ggtcaactga ttgcctccgg tgtcctaaag ggcttacagg ggcgcacgga tgagtggggc | 720 |
| taccgcatcc ccttcgccat ccagtgggtg tggcccgtcc ccatcttcat cggcgtcttc | 780 |
| ttcgcccccg agagccctg gtggctcatc cgccgagacc gccggacga cgccgtcaaa | 840 |
| gcgctcaacc ggctggccag aaccggacat ccggacttca cgccgagga ccgcgtcg | 900 |
| atgatcgtct acaccaacac gctggaaaaa caggtcgaga caggcacatc ctacgtggac | 960 |
| tgcttccgcg gatgcgacct cgccgcacc gagatctcct gtctcgtctg ggccgcccag | 1020 |
| agtctctgcg gcgcgggct catgggctac tcgaccttct tctatcggcg tgctggcctc | 1080 |
| gccgtctccc agtccttcac catgtcgctc gtccagtacg ccatcggcgt cgtgggaacc | 1140 |
| tttctctcct gggttatgat gacctacttc ggtcgtcgca cgctatatgt cggtggactg | 1200 |
| gcactgctgg ccatcgttct cttcgtcatc ggctttatct ccatccctca ctccaccccg | 1260 |
| gccctctcct gggccaccgg gtccatgctc ctcgtctaca ccttcatcta cgattcaacc | 1320 |
| atcggcccgc tctgcttctc tctcgtctcc gaaatcccct catcccgact ccgcaccaag | 1380 |
| actgtggtgc tagcccgtaa cctgtacaac gtgatcaatc tggtttcggg aatcatcatc | 1440 |
| ccgtacatgc tcaacgtgga cgcatggaac tggagaggca gtcggggtt cttctggggc | 1500 |
| tcgttctgca cctgctgttt gatctgggcg ttcttccgca tcccggagcc caagggtcgg | 1560 |
| tcctatgccg agctggatat tctgtttgag cgtagagtcc gcacgcggga gtttgcaact | 1620 |
| gccgagacgg gcttggtgga ggggagaagc gattacaagg ttgatccact tgctgttagg | 1680 |
| gtttaattaa ttaaacaggc cccttttcct ttgtcgatat catgtaatta gttatgtcac | 1740 |
| gcttacattc acgc | 1754 |

<210> SEQ ID NO 27
<211> LENGTH: 1958
<212> TYPE: DNA
<213> ORGANISM: Artificial Sequence
<220> FEATURE:
<223> OTHER INFORMATION: Sc ZTW MAL11

<400> SEQUENCE: 27

| | |
|---|---|
| caagctatac caagcataca atcaactatc tcatatacaa tgaaaaatat catttcattg | 60 |
| gtaagcaaga agaaggctgc ctcaaaaaat gaggataaaa acatttctga gtcttcaaga | 120 |
| gatattgtaa accaacagga ggttttcaat actgaagatt ttgaagaagg gaaaaaggat | 180 |
| agtgcctttg agctagacca cttagagttc accaccaatt cagcccagtt aggagattct | 240 |
| gacgaagata cgagaatgt gattaatgag atgaacgcta ctgatgatgc aaatgaagct | 300 |
| aacagcgagg aaaaaagcat gactttgaag caggcgttgc taaatatcc aaaagcagcc | 360 |
| ctgtggtcca tattagtgtc tactaccctg gttatggaag gttatgatac cgcactactg | 420 |

```
agcgcactgt atgccctgcc agttttttcag agaaaattcg gtactttgaa cggggagggt    480
tcttacgaaa ttacttccca atggcagatt ggtttaaaca tgtgtgtcct ttgtggtgag    540
atgattggtt tgcaaatcac gacttatatg gttgaattta tggggaatcg ttatacgatg    600
attacagcac ttggtttgtt aactgctat atctttatcc tctactactg taaaagttta    660
gctatgattg ctgtgggaca agttctctca gctatgccat ggggttgttt ccaaagtttg    720
gctgttactt atgcttcgga agtttgcccct ttagcattaa gatattacat gaccagttac    780
tccaacattt gttggttatt tggtcaaatc ttcgcctctg gtattatgaa aaactcacaa    840
gagaatttag ggaactccga cttgggctat aaattgccat tgctttaca atggatttgg    900 cctgctcctt taatgatcgg tatcttttttc gctcctgagt cgccctggtg gttggtgaga    960
aaggataggg tcgctgaggc aagaaaatct ttaagcagaa ttttgagtgg taaaggcgcc    1020
gagaaggaca ttcaagttga tcttacttta aagcagattg aattgactat tgaaaaagaa    1080
agacttttag catctaaatc aggatcattc tttaattgtt tcaagggagt taatggaaga    1140
agaacgagac ttgcatgttt aacttgggta gctcaaaata gtagcggtgc cgttttactt    1200
ggttactcga catattttttt tgaaagagca ggtatggcca ccgacaaggc gtttactttt    1260
tctctaattc agtactgtct tgggttagcg ggtacacttt gctcctgggt aatatctggc    1320
cgtgttggta gatggacaat actgacctat ggtcttgcat ttcaaatggt ctgcttattt    1380
attattggtg gaatgggttt tggttctgga agcagcgcta gtaatggtgc cggtggttta    1440
ttgctggctt tatcattctt ttacaatgct ggtatcggtg cagttgttta ctgtatcgtt    1500
gctgaaattc catcagcgga gttgagaact aagactatag tgctggcccg tatttgctac    1560
aatctcatgg ccgttattaa cgctatatta acgccctata tgctaaacgt gagcgattgg    1620
aactggggtg ccaaaactgg tctatactgg ggtggtttca cagcagtcac tttagcttgg    1680
gtcatcatcg atctgcctga gacaactggt agaaccttca gtgaaattaa tgaacttttc    1740
aaccaagggg ttcctgccag aaaatttgca tctactgtgg ttgatccatt cggaaaggga    1800
aaaactcaac atgattcgct agctgatgag agtatcagtc agtcctcaag cataaaacag    1860
cgagaattaa atgcagctga taaatgctaa ttaattaaac aggccccttt tcctttgtcg    1920
atatcatgta attagttatg tcacgcttac attcacgc                             1958
```

<210> SEQ ID NO 28
<211> LENGTH: 1853
<212> TYPE: DNA
<213> ORGANISM: Artificial Sequence
<220> FEATURE:
<223> OTHER INFORMATION: Sc CBS7690 MAL11

<400> SEQUENCE: 28

```
caagctatac caagcataca atcaactatc tcatatacaa tgaaaaatat catttcattg     60
gtaagcaaga agaaggctgc ctcaaaaaat gaggataaaa acatttctga gtcttcaaga   120
gatattgtaa accaacagga ggttttcaat actgaaaatt ttgaagaagg gaaaaaggat   180 agtgccttttg agctagacca cttagagttc accaccaatt cagcccagtt aggagattct   240
gacgaagata acgagaatgt gattaatgag acgaacgcta ctgatgatgc aaatgaagct   300
aacagcgagg aaaaaagcat gactttaaag caggcgttgc taatatatcc aaaagcagcc   360
ctgtggtcca tattagtgtc tactaccctg gttatggaag gttatgatac cgcactactg   420
aacgcactgt atgccctgcc agttttttcag agaaaattcg gtactttgaa cggggagggt   480
```

```
tcttacgaaa ttacttccca atggcagatt ggtttaaaca tgtgtgtcca atgtggtgag    540
atgattggtt tgcaaatcac gccttatatg gttgaattta tggggaatcg ttatacgatg    600
attacagcac ttggtttgtt aactgcttat atctttatcc tctactactg taaaagttta    660
gctatgattg ctgtgggaca agttctctca gctatgccat ggggttgttt ccagggtttg    720
actgttactt atgcttcgga agtttgccct ttagcattaa gatattacat gaccagttac    780
tccaacattt gttggttatt tggtcaaatc ttcgcctctg gtattatgaa aaactcacaa    840
gagaatttag ggaactctga cttgggctat aaattgccat ttgctttaca atggatttgg    900
cctgctcctt taatgatcgg tatcttttc gctcctgagt cgccctggtg gttggtgaga    960
aaggataggg tcgctgaggc aagaaaatct ttaagcagaa ttttgagtgg taaaggcgcc   1020
gagaaggaca ttcaaattga tcttacttta aagcagattg aattgactat tgaaaaagaa   1080
agacttttag catctaaatc aggatcattc tttgattgtt tcaagggagt taatggaaga   1140
agaacgagac ttgcatgttt agcttgggta gctcaaaata ctagcggtgc ctgtttactt   1200
ggttactcga catatttttt tgaaagagca ggtatggcca ccgacaaggc gtttactttt   1260
tctgtaattc agtactgtct tgggttagcg ggtacacttt gctcctgggt aatatctggc   1320
cgtgttggta gatggacaat actgacctat ggtcttgcat ttcaaatggt ctgcttattt   1380
gttattggtg gaatgggttt tggttctgga agcggcgcta gtaatggtgc cggtggttta   1440
ttgctggctt tatcattctt ttacaatgct ggtatcggtg cagttgttta ctgtatcgta   1500
actgaaattc catcagcgga gttgagaact aagactatag tgctggcccg tatttgctac   1560
aatatcatgg ccgttatcaa cgctatatta acgccctata tgctaaacgt gagcgattgg   1620
aactggggtg ccaaaactgg tctatactgg ggtggtttca cagcagtcac tttagcttgg   1680
gtcatcatcg atctgcctga gacaagtggt agaaccttca gtgaaattaa tgaacttttc   1740
aacccagggg gttcctgcca gaaaatttgc atctactgtg gataattaat taaacaggcc   1800
ccttttcctt tgtcgatatc atgtaattag ttatgtcacg cttacattca cgc           1853
```

<210> SEQ ID NO 29
<211> LENGTH: 1679
<212> TYPE: DNA
<213> ORGANISM: Artificial Sequence
<220> FEATURE:
<223> OTHER INFORMATION: Sc FO MAL11

<400> SEQUENCE: 29

```
caagctatac caagcataca atcaactatc tcatatacaa tgactttaaa gcaggcgttg     60
ctaatatatc caaaagcagc cctgtggtcc atattagtgt ctactaccct ggttatggaa    120
ggttatgata ccgcactact gaacgcactg tatgccctgc agttttttca gagaaaattc    180
ggtactttga acggggaggg ttcttacgaa attacttccc aatggcagat tggtttaaac    240
atgtgtgtcc aatgtggtga gataattggt ttgcaaatca cgcctttatat ggttgaattt    300 atggggaatc gttatacgat gattacagca cttggtttgt taactgctta tgtctttatc    360
ctctactact gtaaaagttt agctatgatt gctgtgggac aagttctctc agctatgcca    420
tggggttgtt tccagggttt gactgttact tatgcttcgg aagtttgccc tttagcatta    480
agatattata tgaccagtta ctccaacatt tgttggttat ttggtcaaat cttcgcctct    540
ggtattatga aaaactcaca agagaattta gggaactctg acttgggcta taaattgcca    600
tttgctttac aatggatttg gcctgctcct ttaatgatcg gtatcttttt cgctcctgag    660
tcgccctggt ggttggtgag aaaggatagg gtcgctgagg caagaaaatc tttaagcaga    720
```

```
attttgagtg gtaaaggcgc cgagaaggac attcaaattg atcttacttt aaagcagatt      780
gaattgacta ttgaaaaaga aagacttta gcatctaaat caggatcatt ctttgattgt      840
ttcaagggag ttaatggaag aagaacgaga cttgcatgtt taacttgggt agctcaaaat      900
actagcggtg cctgtttact tggttactcg acatattttt ttgaaagagc aggtatggcc      960
accgacaagg cgtttacttt ttctgtaatt cagtactgtc ttgggttagc gggtacactt     1020
tgctcctggg taatatctgg ccgtgttggt agatggacaa tactgaccta tggtcttgca     1080
tttcaaatgg tctgcttatt tattattggt ggaatgggtt ttggttctgg aagcggcgct     1140
agtaatggtg ccggtggttt attgctggct ttatcattct tttacaatgc tggtatcggt     1200
gcagttgttt actgtatcgt aactgaaatt ccatcagcgg agttgagaac taagactata     1260
gtgctggccc gtatttgcta caatatcatg gccgttatca acgctatatt aacgccctat     1320
atgctaaacg tgagcgattg aactggggt gccaaaactg gtctatactg gggtggtttc     1380
acagcagtca ctttagcttg ggtcatcatc gatctgcctg agacaagtgg tagaaccttc     1440
agtgaaatta atgaactttt caaccaaggg gttcctgcca gaaaatttgc atctactgtg     1500
gttgatccat tcggaaaggg aaaaactcaa catgattcgc tagatgatga gagtatcagt     1560
cagtcctcaa gcataaaaca gcgagaatta aatgcagctg ataaatgcta attaattaaa     1620
caggcccctt ttcctttgtc gatatcatgt aattagttat gtcacgctta cattcacgc     1679
```

<210> SEQ ID NO 30
<211> LENGTH: 4887
<212> TYPE: DNA
<213> ORGANISM: Artificial Sequence
<220> FEATURE:
<223> OTHER INFORMATION: URA3-lacZ-AmpR-CEN6 integration fragment

<400> SEQUENCE: 30

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accacgcttt tcaattcaat tcatcatttt ttttttattc ttttttttga tttcggtttc      240
tttgaaattt ttttgattcg gtaatctccg aacagaagga agaacgaagg aaggagcaca      300
gacttagatt ggtatatata cgcatatgta gtgttgaaga acatgaaat tgcccagtat      360 tcttaaccca actgcacaga acaaaaacct gcaggaaacg aagataaatc atgtcgaaag      420
ctacatataa ggaacgtgct gctactcatc ctagtcctgt tgctgccaag ctatttaata      480
tcatgcacga aaagcaaaca aacttgtgtg cttcattgga tgttcgtacc accaaggaat      540
tactggagtt agttgaagca ttaggtccca aaatttgttt actaaaaaca catgtggata      600
tcttgactga ttttttccatg gagggcacag ttaagccgct aaaggcatta tccgccaagt      660 acaattttt actcttcgaa gacagaaaat ttgctgacat tggtaataca gtcaaattgc      720
agtactctgc gggtgtatac agaatagcag aatgggcaga cattacgaat gcacacggtg      780
tggtgggccc aggtattgtt agcggtttga agcaggcggc agaagaagta acaaaggaac      840
ctagaggcct tttgatgtta gcagaattgt catgcaaggg ctccctatct actggagaat      900
atactaaggg tactgttgac attgcgaaga gcgacaaaga ttttgttatc ggctttattg      960
ctcaaagaga catgggtgga agagatgaag gttacgattg gttgattatg acacccggtg     1020
tgggtttaga tgacaaggga gacgcattgg gtcaacagta tagaaccgtg gatgatgtgg     1080
```

-continued

```
tctctacagg atctgacatt attattgttg aagaggact atttgcaaag ggaagggatg    1140
ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta acgttaata ttttgttaaa attcgcgtta    1380 aattttgtt aaatcagctc atttttaac caataggccg aaatcggcaa atcccttat    1440 aaatcaaaag aatagaccga datagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttgggt cgaggtgccg taaagcacta    1620
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa gggggatgt gctgcaaggc gattaagttg ggtaacgcca    1920 gggtttccc agtcacgacg ttgtaaaacg acggccagtg aattgtaata cgactcacta    1980
tagggcgaat tggagctcca ccgcggtggc ggccgctcta gaactagtgg atccccggg    2040 ctgcaggaat tcgatatcaa gcttatcgat accgtcgacc tcgagggggg gcccggtacc    2100
cagcttttgt tccctttagt gagggttaat tccgagcttg gcgtaatcat ggtcatagct    2160
gtttcctgtg tgaaattgtt atccgctcac aattccacac aacataggag ccggaagcat    2220
aaagtgtaaa gcctggggtg cctaatgagt gaggtaactc acattaattg cgttgcgctc    2280
actgcccgct ttccagtcgg gaaacctgtc gtgccagctg cattaatgaa tcggccaacg    2340
cgcggggaga ggcggtttgc gtattgggcg ctcttccgct tcctcgctca ctgactcgct    2400
gcgctcggtc gttcggctgc ggcgagcggt atcagctcac tcaaaggcgg taatacggtt    2460
atccacagaa tcaggggata acgcaggaaa gaacatgtga gcaaaaggcc agcaaaaggc    2520
caggaaccgt aaaaaggccg cgttgctggc gtttttccat aggctcggcc cccctgacga    2580
gcatcacaaa aatcgacgct caagtcagag gtggcgaaac ccgacaggac tataaagata    2640
ccaggcgttc cccctggaa gctccctcgt gcgctctcct gttccgaccc tgccgcttac    2700
cggatacctg tccgcctttc tcccttcggg aagcgtggcg ctttctcaat gctcacgctg    2760
taggtatctc agttcggtgt aggtcgttcg ctccaagctg ggctgtgtgc acgaaccccc    2820
cgttcagccc gaccgctgcg ccttatccgg taactatcgt cttgagtcca acccggtaag    2880
acacgactta tcgccactgg cagcagccac tggtaacagg attagcagag cgaggtatgt    2940
aggcggtgct acagagttct tgaagtggtg gcctaactac ggctacacta aggacagt    3000 atttggtatc tgcgctctgc tgaagccagt taccttcgga aaagagttg gtagctcttg    3060 atccggcaaa caaccaccg ctggtagcgg tggtttttt gtttgcaagc agcagattac    3120
gcgcagaaaa aaggatctc aagaagatcc tttgatcttt tctacggggt ctgacgctca    3180
gtggaacgaa aactcacgtt aagggatttt ggtcatgaga ttatcaaaaa ggatcttcac    3240
ctagatcctt ttaaattaaa aatgaagttt taaatcaatc taaagtatat atgagtaaac    3300
ttggtctgac agttaccaat gcttaatcag tgaggcacct atctcagcga tctgtctatt    3360
tcgttcatcc atagttgcct gactgcccgt cgtgtagata actacgatac gggagggctt    3420
accatctggc cccagtgctg caatgatacc gcgagaccca cgctcaccgg ctccagattt    3480
```

```
atcagcaata aaccagccag ccggaagggc cgagcgcaga agtggtcctg caactttatc    3540
cgcctccatc cagtctatta attgttgccg ggaagctaga gtaagtagtt cgccagttaa    3600
tagtttgcgc aacgttgttg ccattgctac aggcatcgtg gtgtcacgct cgtcgtttgg    3660
tatggcttca ttcagctccg gttcccaacg atcaaggcga gttacatgat cccccatgtt    3720
gtgaaaaaaa gcggttagct ccttcggtcc tccgatcgtt gtcagaagta agttggccgc    3780
agtgttatca ctcatggtta tggcagcact gcataattct cttactgtca tgccatccgt    3840
aagatgcttt tctgtgactg gtgagtactc aaccaagtca ttctgagaat agtgtatgcg    3900
gcgaccgagt tgctcttgcc cggcgtcaat acgggataat accgcgccac atagcagaac    3960
tttaaaagtg ctcatcattg gaaaacgttc ttcgggcga aaactctcaa ggatcttacc    4020
gctgttgaga tccagttcga tgtaacccac tcgtgcaccc aactgatctt cagcatcttt    4080
tactttcacc agcgtttctg ggtgagcaaa acaggaagg caaaatgccg caaaaaggg    4140 aataagggcg acacggaaat gttgaatact catactcttc cttttcaat attattgaag    4200 catttatcag ggttattgtc tcatgagcgg atacatattt gaatgtattt agaaaaataa    4260
acaaataggg gttccgcgca catttccccg aaaagtgcca cctgggtcct ttcatcacg    4320 tgctataaaa ataattataa tttaaatttt ttaatataaa tatataaatt aaaaatagaa    4380
agtaaaaaaa gaaattaaag aaaaaatagt ttttgttttc cgaagatgta aaagactcta    4440
gggggatcgc caacaaatac tacctttat cttgctcttc ctgctctcag gtattaatgc    4500
cgaattgttt catcttgtct gtgtagaaga ccacacacga aaatcctgtg atttttacatt    4560 ttacttatcg ttaatcgaat gtatatctat ttaatctgct tttcttgtct aataaatata    4620
tatgtaaagt acgcttttg ttgaaatttt ttaaacctttt gtttattttt tttctttcat    4680
tccgtaactc ttctaccttc ttttatttact ttctaaaatc caaatacaaa acataaaaat    4740
aaataaacac agagtaaatt cccaaattat tccatcatta aaagatacga ggcgcgtgta    4800
agttacaggc aagcgatccg tcctaagaaa ccattattat catgacatta acctataaaa    4860
ataggcgtat cacgaggccc tttcgtc                                        4887
```

<210> SEQ ID NO 31
<211> LENGTH: 8086
<212> TYPE: DNA
<213> ORGANISM: Artificial Sequence
<220> FEATURE:
<223> OTHER INFORMATION: Locus C-Sc pPGK-IMA1-GAL10t-loxP-Sc URA3-Sc
    pADH1--SmMAL11-1-CYC1t integration fragment

<400> SEQUENCE: 31

```
ccgggaaacc atccacttca cgagactgat ctcctctgcc ggaacaccgg gcatctccaa      60
cttataagtt ggagaaataa gagaatttca gattgagaga atgaaaaaaa aaaaaaaga     120 cagaggagag cataaaaatg gggttcactt tttggtaaag ctatagcatg cctatcacat    180
ataaatagag tgccagtagc gacttttttc acactcgaaa tactcttact actgctctct    240
tgttgttttt atcacttctt gtttcttctt ggtaaataga atatcaagct acaaaaagca    300
tacctcgagg ccagaaaaag gaagtgtttc cctccttctt gaattgatgt taccctcata    360
aagcacgtgg cctcttatcg agaaagaaat taccgtcgct cgtgatttgt ttgcaaaaag    420
aacaaaactg aaaaaaccca gacacgctcg acttcctgtc ttcctgttga ttgcagcttc    480
caatttcgtc acacaacaag gtcctagcga cggctcacag gttttgtaac aagcaatcga    540
aggttctgga atggcgggaa agggtttagt accacatgct atgatgccca ctgtgatctc    600
```

-continued

```
cagagcaaag ttcgttcgat cgtactgtta ctctctctct ttcaaacaga attgtccgaa    660
tcgtgtgaca caacagcct gttctcacac actcttttct tctaaccaag ggggtggttt    720
agtttagtag aacctcgtga aacttacatt tacatatata taaacttgca taaattggtc    780
aatgcaagaa atacatattt ggtcttttct aattcgtagt ttttcaagtt cttagatgct    840
ttctttttct cttttttaca gatcatcaag gaagtaatta tctacttttt acaagtctag    900
aatgactatc tcttctgctc acccagaaac tgaaccaaag tggtggaaag aggcaacttt    960
ttaccaaatc tacccagctt cattcaagga ctccaatgat gatggttggg gtgatatgaa   1020
aggtattgct tccaaattag aatacattaa ggaattaggt gccgatgcta tttggatttc   1080
tccattctat gattctccac aagacgatat gggttatgac atcgctaact atgaaaaggt   1140
ttggccaacc tatggcacta atgaggactg ttttgcatta attgagaaaa cccacaagtt   1200
gggcatgaag ttcattactg atcttgtcat taatcattgt tcatccgaac atgaatggtt   1260
caaggaatcc agatcctcca aaactaatcc aaaaagagat tggttttttct ggagaccacc   1320 taagggttat gatgctgaag gtaagccaat tccaccaaac aattggaagt cttactttgg   1380
tggttccgca tggaccttcg acgaaaagac ccaagagttt tacttgagat tattctgctc   1440
cacccaacca gatttgaact gggaaaatga agattgtaga aaagcaatct acgaatctgc   1500
agttggctat tggttagatc acggtgttga tggtttcaga attgatgttg gttcactta   1560 ctcaaaggtt gttggttttgc cagatgcacc agttgttgat aaaaactcta catggcaatc   1620
ttctgaccca tacactctta atggtcctag aatccatgaa tttcatcaag agatgaacca   1680
gttcattaga aatagagtta aggatggtag agaaattatg accgttggtg aaatgcaaca   1740
tgcatctgat gaaactaaga gattatacac atcagcctcc cgtcacgaat tgtctgaatt   1800
attcaacttt tcacacacag acgttggcac atccccatta ttccgttata acttggttcc   1860
attcgaattg aaggactgga aaatcgcatt ggcagaattg tttagatata tcaatggtac   1920
tgattgttgg tctaccatct acttggaaaa ccacgaccaa ccaagatcca tcactagatt   1980
cggtgatgac tctcctaaaa accgtgtcat ttctggtaag ttactttctg tcttattatc   2040
cgccttaacc ggtactttgt acgtctatca aggccaggaa ttgggtcaaa ttaactttaa   2100
gaattggcca gtcgaaaagt atgaagatgt cgaaatcaga aacaactaca atgcaattaa   2160
ggaggaacat ggtgaaaatt cagaggaaat gaaaagttt ttggaagcta ttgctcttat   2220
ttccagagat cacgctagaa ccccaatgca atggtcaaga gaggaaccta acgctggttt   2280
ctctggtcct tccgccaagc cttggtttta cttaaacgac tccttcagag aaggtattaa   2340
cgttgaagat gaaattaagg acccaaattc cgtccttaac ttctggaagg aagcattgaa   2400
gtttagaaag gcccataagg atattaccgt ttatggttat gactttgagt ttatcgattt   2460
ggataacaaa aagttattct cattcactaa aaagtataac aacaagacct tattcgctgc   2520
tttaaacttc tcttctgatg ctactgattt caaaattcct aatgacgatt cctcttttcaa   2580 gttggagttt ggtaactacc caagaaggga agttgacgca tcttctcgta cattgaagcc   2640
ttgggaaggt agaatctaca ctctccgagta acctgcaggt tgccagctt actatccttc   2700 ttgaaaatat gcactctata tcttttagtt cttaattgca acacatagat ttgctgtata   2760
acgaatttta tgctattttt taaatttgga gttcagtgat aaaagtgtca cagcgaattt   2820
cctcacatgt agggaccgaa ttgtttacaa gttctctgta ccaccatgga gacatcaaaa   2880
attgaaaatc tatggaaaga tatggacggt agcaacaaga atatagcacg agccggcgac   2940
```

```
tagtaacggc cgccagtgtg ctggaattcg gccggccata acttcgtata atgtatgcta    3000
tacgaagtta tggcaacggt tcatcatctc atggatctgc acatgaacaa acaccagagt    3060
caaacgacgt tgaaattgag gctactgcgc caattgatga caatacagac gatgataaca    3120
aaccgaagtt atctgatgta gaaaggatt agagatgcta agagatagtg atgatatttc    3180
ataaataatg taattctata tatgttaatt acctttttg cgaggcatat ttatggtgaa    3240
ggataagttt tgaccatcaa agaaggttaa tgtggctgtg gtttcagggt ccataaagct    3300
tttcaattca tcttttttt tttgttcttt ttttgattc cggtttcttt gaaattttt    3360 tgattcggta atctccgagc agaaggaaga acgaaggaag gagcacagac ttagattggt    3420
atatatacgc atatgtggtg ttgaagaaac atgaaattgc ccagtattct aacccaact    3480 gcacagaaca aaaacctgca ggaaacgaag ataaatcatg tcgaaagcta catataagga    3540
acgtgctgct actcatccta gtcctgttgc tgccaagcta tttaatatca tgcacgaaaa    3600
gcaaacaaac ttgtgtgctt cattggatgt tcgtaccacc aaggaattac tggagttagt    3660
tgaagcatta ggtcccaaaa tttgtttact aaaaacacat gtggatatct tgactgattt    3720
ttccatggag ggcacagtta agccgctaaa ggcattatcc gccaagtaca attttttact    3780
cttcgaagac agaaaatttg ctgacattgg taatacagtc aaattgcagt actctgcggg    3840
tgtatacaga atagcagaat gggcagacat tacgaatgcg cacggtgtgg tgggcccagg    3900
tattgttagc ggtttgaagc aggcggcgga agaagtaaca aaggaaccta gaggcctttt    3960
gatgttagca gaattgtcat gcaagggctc cctagctact ggagaatata ctaagggtac    4020
tgttgacatt gcgaagagcg acaaagattt tgttatcggc tttattgctc aaagagacat    4080
gggtggaaga gatgaaggtt acgattggtt gattatgaca cccggtgtgg gtttagatga    4140
caagggagac gcattgggtc aacagtatag agccgtggat gatgtggtct ctacaggatc    4200
tgacattatt attgttggaa gaggactatt tgcaaaggga agggatgcta aggtagaggg    4260
tgaacgttac agaaaagcag gctgggaagc atatttgaga agatgcggcc agcaaaacta    4320
aaaaactgta ttataagtaa atgcatgtat actaaactca caaattagag cttcaattta    4380
attatatcag ttattacccg ggaatctcgg tcgtaatgat tttttataatg acgaaaaaaa    4440 aaaattggaa agaaaaagct tcatggcctt tataaaaagg aaccatccaa tacctcgcca    4500
gaaccaagta acagtatttt acggggcaca aatcaagaac aataagacag gactgtaaag    4560
atggacgcat tgaactccaa agaacaacaa gagttccaaa aagtagtgga acaaaagcaa    4620
atgaaggatt tcatgcgttt gataacttcg tataatgtat gctatacgaa gttatgcggc    4680
cgcctcgaga tctcccctaa accgtggaat atttcggata tccttttgtt gtttccgggt    4740
gtacaatatg gacttcctct tttctggcaa ccaaacccat acatcgggat tcctataata    4800
ccttcgttgg tctccctaac atgtaggtgg cggaggggag atatacaata gaacagatac    4860
cagacaagac ataatgggct aaacaagact acaccaatta cactgcctca ttgatggtgg    4920
tacataacga actaatactg tagccctaga cttgatagcc atcatcatat cgaagtttca    4980
ctaccctttt tccatttgcc atctattgaa gtaataatag gcgcatgcaa cttctttct    5040 tttttttct tttctctctc cccgttgtt gtctcaccat atccgcaatg acaaaaaaat    5100
gatggaagac actaaaggaa aaaattaacg acaaagacag caccaacaga tgtcgttgtt    5160
ccagagctga tggggggtat ctcgaagcac acgaaacttt ttccttcctt cattcacgca    5220
cactactctc taatgagcaa cggtatacgg ccttccttcc agttacttga atttgaaata    5280
aaaaaagttt gctgtcttgc tatcaagtat aaatagacct gcaattatta atcttttgtt    5340
```

| | |
|---|---|
| tcctcgtcat tgttctcgtt cccttcttc cttgtttctt tttctgcaca atatttcaag | 5400 |
| ctataccaag catacaatca actatctcat atacaatgaa gaacttcata tcactggtga | 5460 |
| acaagaaaaa gggtaccctg gatgatagga atagtagcgt tccggaatct tccagtggta | 5520 |
| taatacacca acgtggagct ttaaacactg aggattttga agaaggaaag aaagatggtg | 5580 |
| cattcgaatt gggtcacctc gaattcacca ccaattcagc ccaattgggt gattcagacg | 5640 |
| atgataatga taatgcaatt aagatagcga atgctgccac tgatgaagcc aatgaggcta | 5700 |
| atagtgaaga aaaaagcatg accttaaggc aagctttgag aaaatatcca aaggcagccc | 5760 |
| tatggtccat cttggtgtct actaccttag tcatggaagg ttatgatact gcgcttttga | 5820 |
| gtgcacttta tgcattaccg gttttccaga ggaaattcgg tactatgaat gcggaaggct | 5880 |
| cctacgaaat tacctcgcag tggcaaattg gtttgaacat gtgtgtcctt tgtggtgaaa | 5940 |
| tgattggttt acagatgacc acttacatgg tcgagttcat gggtaatcgt tacacaatga | 6000 |
| ttacggcgct cggcttgttg actgcttata ttttatcct ttactactgc aaaagtttgg | 6060 |
| ccatgatcgc tgtagggcaa attctgtctg ctatgccatg gggttgcttc cagagtctgg | 6120 |
| ctgttaccta tgcttcggag gtttgccccc tagcgctgag atattacatg accagttact | 6180 |
| ccaatatttg ttggttgttt ggtcaaattt tcgcttctgg tatcatgaaa aactcccagg | 6240 |
| agaatttggg agactccgat ttaggctaca agttgccatt tgccttacaa tggatctggc | 6300 |
| ctgcaccttt gattattggt atcttctttg ctcctgagtc gccttggtgg ctggtgagaa | 6360 |
| agaataagat tgcggaggcc aaaaagtcct tgaatagaat cctgagcggc actgctgccg | 6420 |
| agagggagat tcaagtggat atcactttaa agcaaattga tgaccatt gagaaggaga | 6480 |
| gacttctggc atctaaatca gggtcgttct tcaactgttt caaggcgtt gatggaagaa | 6540 |
| gaacaaggct tgcgtgtttg acttgggttg ctcaaaacag tagtggtgcc gttttactag | 6600 |
| gttactcgac gtatttcttt gaagggcag ggatggccac tgacaaggcg tttacttct | 6660 |
| cgcttatcca gtactgtcta ggtttagcag gcactctttg ttcctgggtg atatctggcc | 6720 |
| gtgttggtag atggagtatc ctggcttatg gtcttgcatt tcaaatggtg tgtctattca | 6780 |
| tcattggtgg aatgggtttt gcatccggaa gcaatgccag taatggtgct ggtggtctac | 6840 |
| tgctggcttt atcgttcttt tacaacgctg gtatcggagc tgtcgtttac tgtattgtgg | 6900 |
| ctgaaattcc gtctgcagaa ttaaggacca aaactattgt aatggctcgt atttgctata | 6960 |
| atttgatggc cgtcatcaat gccatttaa cgccatatat gctgaacgtg agtgactgga | 7020 |
| actggggtgc taaaaccggc ctatactggg gtggtttcac tgcagtcact ttggcttggg | 7080 |
| ttatcattga tttgcctgag acaactggta gaacatttag cgaaattaat gagcttttca | 7140 |
| atcaaggtgt ccctgctaga aaatttgcat ctactgtagt tgatccttc gggaagggac | 7200 |
| agcgtcaaaa tgattcgcaa gtggataacg tcattgacca gtcctcaagc gcaatgcagc | 7260 |
| aagagctaaa tgaagctaac gaattctaat taattaaaca ggccccttt cctttgtcga | 7320 |
| tatcatgtaa ttagttatgt cacgcttaca ttcacgccct cctcccacat ccgctctaac | 7380 |
| cgaaaaggaa ggagttagac aacctgaagt ctaggtccct atttatttt ttatagttat | 7440 |
| gttagtatta agaacgttat ttatatttca aattttctt ttttttctgt acaaacgcgt | 7500 |
| gtacgcatgt aacgggcaga cgaattcgat atcaagctta tcgataccgt cgacgcggat | 7560 |
| ctcttatgtc tttacgattt atagttttca ttatcaagta tgcctatatt agtatatagc | 7620 |
| atctttagat gacagtgttc gaagtttcac gaataaaaga taatattcta ctttttgctc | 7680 |

```
ccaccgcgtt tgctagcacg agtgaacacc atccctcgcc tgtgagttgt acccattcct    7740
ctaaactgta gacatggtag cttcagcagt gttcgttatg tacggcatcc tccaacaaac    7800
agtcggttat agtttgtcct gctcctctga atcgtctccc tcgatatttc tcattttcct    7860
tcgcatgcca gcattgaaat gatcgaagtt caatgatgaa acggtaattc ttctgtcatt    7920
tactcatctc atctcatcaa gttatataat tctatacgga tgtaattttt cacttttcgt    7980
cttgacgtcc accctataat ttcaattatt gaaccctcac aaatgatgca ctgcaatgta    8040
cacaccctca tatagtttct cagggcttga tcagggttcc gtagag                  8086
```

<210> SEQ ID NO 32
<211> LENGTH: 8685
<212> TYPE: DNA
<213> ORGANISM: Artificial Sequence
<220> FEATURE:
<223> OTHER INFORMATION: Locus C-Sc pPGK-IMA1-GAL10t-loxP-Sc TEFt--An amdS-Sc TEF1t-loxP-Sc CYC1t-Sm MAL11 integration fragment

<400> SEQUENCE: 32

```
ccgggaaacc atccacttca cgagactgat ctcctctgcc ggaacaccgg gcatctccaa      60
cttataagtt ggagaaataa gagaatttca gattgagaga atgaaaaaaa aaaaaaaaga     120
cagaggagag cataaaaatg gggttcactt tttggtaaag ctatagcatg cctatcacat     180
ataaatagag tgccagtagc gacttttttc acactcgaaa tactcttact actgctctct     240
tgttgttttt atcacttctt gtttcttctt ggtaaataga atatcaagct acaaaaagca     300
tacctcgagg ccagaaaaag gaagtgtttc cctccttctt gaattgatgt taccctcata     360
aagcacgtgg cctcttatcg agaaagaaat taccgtcgct cgtgatttgt ttgcaaaaag     420
aacaaaactg aaaaaaccca gacacgctcg acttcctgtc ttcctgttga ttgcagcttc     480
caatttcgtc acacaacaag gtcctagcga cggctcacag gttttgtaac aagcaatcga     540
aggttctgga atggcgggaa agggtttagt accacatgct atgatgccca ctgtgatctc     600
cagagcaaag ttcgttcgat cgtactgtta ctctctctct ttcaaacaga attgtccgaa     660
tcgtgtgaca acaacagcct gttctcacac actctttttct tctaaccaag ggggtggttt     720
agtttagtag aacctcgtga aacttacatt tacatatata taaacttgca taaattggtc     780
aatgcaagaa atacatattt ggtcttttct aattcgtagt ttttcaagtt cttagatgct     840 ttcttttttct ctttttttaca gatcatcaag gaagtaatta tctacttttt acaagtctag     900
aatgactatc tcttctgctc acccagaaac tgaaccaaag tggtggaaag aggcaacttt     960
ttaccaaatc tacccagctt cattcaagga ctccaatgat gatggttggg gtgatatgaa    1020
aggtattgct tccaaattag aatacattaa ggaattaggt gccgatgcta tttggatttc    1080
tccattctat gattctccac aagacgtatt gggttatgac atcgctaact atgaaaaggt    1140
ttggccaacc tatggcacta atgaggactg ttttgcatta attgagaaaa cccacaagtt    1200
gggcatgaag ttcattactg atcttgtcat taatcattgt tcatccgaac atgaatggtt    1260
caaggaatcc agatcctcca aaactaatcc aaaaagagat tggtttttct ggagaccacc    1320
taagggttat gatgctgaag gtaagccaat tccaccaaac aattggaagt cttactttgg    1380
tggttccgca tggaccttcg acgaaaagac ccaagagttt tacttgagat tattctgctc    1440
cacccaacca gatttgaact gggaaaatga agattgtaga aaagcaatct acgaatctgc    1500
agttggctat tggttagatc acggtgttga tggtttcaga attgatgttg gttcactttta    1560 ctcaaaggtt gttggtttgc cagatgcacc agttgttgat aaaaactcta catggcaatc    1620
```

```
ttctgaccca tacactctta atggtcctag aatccatgaa tttcatcaag agatgaacca   1680
gttcattaga aatagagtta aggatggtag agaaattatg accgttggtg aaatgcaaca   1740
tgcatctgat gaaactaaga gattatacac atcagcctcc cgtcacgaat tgtctgaatt   1800
attcaacttt tcacacacag acgttggcac atccccatta ttccgttata acttggttcc   1860
attcgaattg aaggactgga aaatcgcatt ggcagaattg tttagatata tcaatggtac   1920
tgattgttgg tctaccatct acttggaaaa ccacgaccaa ccaagatcca tcactagatt   1980
cggtgatgac tctcctaaaa accgtgtcat ttctggtaag ttactttctg tcttattatc   2040
cgccttaacc ggtactttgt acgtctatca aggccaggaa ttgggtcaaa ttaactttaa   2100
gaattggcca gtcgaaaagt atgaagatgt cgaaatcaga aacaactaca atgcaattaa   2160
ggaggaacat ggtgaaaatt cagaggaaat gaaaaagttt ttggaagcta ttgctcttat   2220
ttccagagat cacgctagaa ccccaatgca atggtcaaga gaggaaccta acgctggttt   2280
ctctggtcct tccgccaagc cttggtttta cttaaacgac tccttcagag aaggtattaa   2340
cgttgaagat gaaattaagg acccaaattc cgtccttaac ttctggaagg aagcattgaa   2400
gtttagaaag gcccataagg atattaccgt ttatggttat gactttgagt ttatcgattt   2460
ggataacaaa aagttattct cattcactaa aaagtataac aacaagacct tattcgctgc   2520
tttaaacttc tcttctgatg ctactgattt caaaattcct aatgacgatt cctctttcaa   2580
gttggagttt ggtaactacc caagaaagga agttgacgca tcttctcgta cattgaagcc   2640
ttgggaaggt agaatctaca tctccgagta acctgcaggt ttgccagctt actatccttc   2700
ttgaaaatat gcactctata tcttttagtt cttaattgca acacatagat ttgctgtata   2760
acgaatttta tgctattttt taaatttgga gttcagtgat aaaagtgtca cagcgaattt   2820
cctcacatgt agggaccgaa ttgtttacaa gttctctgta ccaccatgga gacatcaaaa   2880
attgaaaatc tatggaaaga tatggacggt agcaacaaga atatagcacg agccggcgac   2940
tagtaacggc cgccagtgtg ctggaattcg gccggccagg ccgcataact tcgtatagca   3000
tacattatac gaagttatcg cctgttaaga tataactgaa aaagaggggg aattttttaga   3060 tactgaaatg atattttaga ataaccagac tatatataag gataaattac aaaaaattaa   3120
ctaatagata agatttaaat ataaaagata tgcaactaga aaagtcttat caatctcctt   3180
atggagtgac gacgttaccc aacaatttac cgacttcttc ggcgatagcc aaagttctct   3240
cttcggacaa tcttctacca ataacttgaa cagcaacagg agcaccgtga taagcctctg   3300
ggtcgtattc ttcttgaacc aaagcatcca attcggaaac agctttaaaa gattcgttct   3360
tcttatcaat attcttatca gcgaaagtga ctgggacgac aacagaggtg aaatccaata   3420
agttaataac ggaggcgtaa ccgtagtatc tgaattgatc gtgtctgaca gcggcggtag   3480
gagtaattgg agcgataata gcgtccaatt ccttaccagc ttttcttca gcttcacgcc   3540 acttttccaa gtattccatt tgatagtcc acttttgtaa atgagtgtcc cacaattcgt   3600
tcatgttaac agccttaata tttgggttca acaagtcctt aatgttaggg atggctggct   3660
caccagaggc agaaatgtct ctcatgacgt cggcagaacc atcagcagca tagatgtggg   3720
aaatcaagtc atgaccgaaa tcatgcttgt atggagtcca tggagtaacg gtgtgaccag   3780
ccttggccaa agcggcaacg gtagtttcga caccacgtaa aattggtggg tgtggcaaga   3840
cgttaccgtc gaaattgtaa taaccaatgt tcaaaccacc attcttaatc ttagaggcaa   3900
tgatgtcaga ttcagattgt ctccatggca ttgggatgac cttagagtcg tacttccaag   3960
gttcttgacc caagacagat ttggtgaaca atctcaagtc ttcgacggag tgagtgatag   4020
```

```
gaccaacgac ggagtgaacg gtttcttgac cttccataga gttagccatt ttagcatatg   4080
gcaatctacc gtgagatggt ctcaaaccgt ataaaaagtt gaaagcagct gggactctaa   4140
tggaaccacc aatgtcagta ccgacaccaa taacaccacc tctaatacca acaatagcac   4200
cttcaccacc agaagaacca ccacaggacc aattttttgtt tcttggattg acagttctac   4260
caatgatgtt gttgacggtt tcacagacca tcaaggtttg tgggacagag gtcttaacgt   4320
agaaaacagc accagctttt ctcaacatgg tggttaagac ggaatcacct tcatcgtatt   4380
tgtttaacca ggaaatgtaa cccatggagg tttcgtaacc cttaacacgc aattggtcct   4440
ttaaagagat tggtaaaccg tgtaatggac caactggtct cttatgctta gcgtagtatt   4500
catctaattc tctagcttga gctaaagcag catctgggaa gaattcgtga gcacagttgg   4560
ttaattgttg agcaatagca gctctcttac aaaaagccaa agtgacttca acagaagtca   4620
actcaccagc ggccaacttg gagaccaaat cagcagcaga ggcttcggta atcttcaatt   4680
cagcctcaga caaaataccg gacttctttg ggaaatcaat aacggaatct tcggcaggca   4740
aagtttgaac cttccattcg tcaggaatgg ttttagccaa acgggcacgt tgtcggcgg   4800 ccaattcttc ccaggattgt ggcattttgt aattaaaact tagattagat tgctatgctt   4860
tctttctaat gagcaagaag taaaaaaagt tgtaatagaa caagaaaaac gaaactgaaa   4920
cttgagaaat tgaagaccat ttattaactt aaatatcaat gggaggtcat cgaaagagaa   4980
aaaaatcaaa aaaaaatttt tcaagaaaa agaaacgtga taaaaatttt tattgccttt   5040
ttcgacgaag aaaagaaac gaggcggtct ctttttcttt ttccaaacct ttagtacggg   5100
taattaacgc caccctagag gaagaaagag gggaaattta gtatgctgtg cttgggtgtt   5160
ttgaagtggt acggcgatgc gcggagtccg agaaaatctg gaagagtaaa aaggagtag    5220 aaacattttg aagctatggt gtgtggggga tcacttgtgg gggattgggt gtgatgtaag   5280
gataacttcg tatagcatac attatacgaa gttatgcggc cgcgtctgcc cgttacatgc   5340
gtacacgcgt ttgtacagaa aaaaagaaa aatttgaaat ataaataacg ttcttaatac   5400
taacataact ataaaaaaat aaatagggac ctagacttca ggttgtctaa ctccttcctt   5460
ttcggttaga gcggatgtgg gaggagggcg tgaatgtaag cgtgacataa ctaattacat   5520
gatatcgaca aaggaaaagg ggcctgttta attaattaga attcgttagc ttcatttagc   5580
tcttgctgca ttgcgcttga ggactggtca atgacgttat ccacttgcga atcattttga   5640
cgctgtccct tcccgaaagg atcaactaca gtagatgcaa attttctagc agggacacct   5700
tgattgaaaa gctcattaat ttcgctaaat gttctaccag ttgtctcagg caaatcaatg   5760
ataacccaag ccaaagtgac tgcagtgaaa ccaccccagt ataggccggt tttagcaccc   5820
cagttccagt cactcacgtt cagcatatat ggcgttaaaa tggcattgat gacggccatc   5880
aaattatagc aaatacgagc cattacaata gttttggtcc ttaattctgc agacggaatt   5940
tcagccacaa tacagtaaac gacagctccg ataccagcgt tgtaaaagaa cgataaagcc   6000
agcagtagac caccagcacc attactggca ttgcttccgg atgcaaaccc cattccacca   6060
atgatgaata gacacaccat ttgaaatgca agaccataag ccaggatact ccatctacca   6120
acacggccag atatcaccca ggaacaaaga gtgcctgcta aacctagaca gtactggata   6180
agcgagaaag taaacgcctt gtcagtggcc atccctgccc tttcaaagaa atacgtcgag   6240
taacctagta aaacggcacc actactgttt tgagcaaccc aagtcaaaca cgcaagcctt   6300
gttcttcttc catcaacgcc tttgaaacag ttgaagaacg accctgattt agatgccaga   6360
```

-continued

```
agtctctcct tctcaatggt catctcaatt tgctttaaag tgatatccac ttgaatctcc    6420
ctctcggcag cagtgccgct caggattcta ttcaaggact ttttggcctc cgcaatctta    6480
ttctttctca ccagccacca aggcgactca ggagcaaaga agataccaat aatcaaaggt    6540
gcaggccaga tccattgtaa ggcaaatggc aacttgtagc ctaaatcgga gtctcccaaa    6600
ttctcctggg agttttctcat gataccagaa gcgaaaattt gaccaaacaa ccaacaaata    6660
ttggagtaac tggtcatgta atatctcagc gctaggggc aaacctccga agcataggta     6720
acagccagac tctggaagca accccatggc atagcagaca gaatttgccc tacagcgatc    6780
atggccaaac ttttgcagta gtaaaggata aaaatataag cagtcaacaa gccgagcgcc    6840
gtaatcattg tgtaacgatt acccatgaac tcgaccatgt aagtggtcat ctgtaaacca    6900
atcatttcac cacaaaggac acacatgttc aaaccaattt gccactgcga ggtaatttcg    6960
taggagcctt ccgcattcat agtaccgaat ttcctctgga aaaccggtaa tgcataaagt    7020
gcactcaaaa gcgcagtatc ataaccttcc atgactaagg tagtagacac caagatggac    7080
catagggctg cctttggata ttttctcaaa gcttgcctta aggtcatgct ttttttcttca   7140 ctattagcct cattggcttc atcagtggca gcattcgcta tcttaattgc attatcatta   7200
tcatcgtctg aatcacccaa ttgggctgaa ttggtggtga attcgaggtg acccaattcg   7260
aatgcaccat ctttctttcc ttcttcaaaa tcctcagtgt ttaaagctcc acgttggtgt   7320
attataccac tggaagattc cggaacgcta ctattcctat catccagggt accctttttc   7380
ttgttcacca gtgatatgaa gttcttcatt gtatatgaga tagttgattg tatgcttggt   7440
atagcttgaa atattgtgca gaaaagaaa caaggaagaa agggaacgag aacaatgacg    7500
aggaaacaaa agattaataa ttgcaggtct atttatactt gatagcaaga cagcaaactt    7560
tttttatttc aaattcaagt aactggaagg aaggccgtat accgttgctc attagagagt    7620
agtgtgcgtg aatgaaggaa ggaaaaagtt tcgtgtgctt cgagataccc cccatcagct    7680
ctggaacaac gacatctgtt ggtgctgtct ttgtcgttaa tttttcctt tagtgtcttc     7740 catcattttt ttgtcattgc ggatatggtg agacaacaac gggggagaga gaaaagaaaa   7800
aaaaagaaaa gaagttgcat gcgcctatta ttacttcaat agatggcaaa tggaaaaagg   7860
gtagtgaaac ttcgatatga tgatggctat caagtctagg gctacagtat tagttcgtta   7920
tgtaccacca tcaatgaggc agtgtaattg gtgtagtctt gtttagccca ttatgtcttg   7980
tctggtatct gttctattgt atatctcccc tccgccacct acatgttagg gagaccaacg    8040
aaggtattat aggaatcccg atgtatgggt ttggttgcca gaaaagagga agtccatatt    8100
gtacacccgg aaacaacaaa aggatatccg aaatattcca cggtttaggt cgacgcggat    8160
ctcttatgtc tttacgattt atagttttca ttatcaagta tgcctatatt agtgtatagc    8220
atctttagat gacagtgttc gaagtttcac gaataaaaga taatattcta cttttgctc    8280 ccaccgcgtt tgctagcacg agtgaacacc atccctcgcc tgtgagttgt acccattcct   8340
ctaaactgta gacatggtag cttcagcagt gttcgttatg tacggcatcc tccaacaaac    8400
agtcggttat agtttgtcct gctcctctga atcgtctccc tcgatatttc tcattttcct   8460
tcgcatgcca gcattgaaat gatcgaagtt caatgatgaa acggtaattc ttctgtcatt    8520
tactcatctc atctcatcaa gttatataat tctatacgga tgtaattttt cacttttcgt    8580
cttgacgtca ccctataatt tcaattgttg aaccctcaca aatgatgcac tgcaatgtac    8640
acaccctcat atagtttctc agggcttgat cagggttccg tagag                    8685
```

<210> SEQ ID NO 33
<211> LENGTH: 3426
<212> TYPE: DNA
<213> ORGANISM: Artificial Sequence
<220> FEATURE:
<223> OTHER INFORMATION: locus C-Sc pPGK-Dasher GFP-Sc CYC1t-loxP-Io
    URA3-loxP integration fragment

<400> SEQUENCE: 33

| | | | | | |
|---|---|---|---|---|---|
| ggtaaataga | atatcaagct | acaaaaagca | tacaatcaac | tatcaactat | taactatatc | 60 |
| gtaatacaca | cagctatgac | catgattacg | ccaagctatt | taggtgacac | tatagaatac | 120 |
| tcaagctatg | catcaagctt | ggtaccgggc | cccccctcga | ggccagaaaa | aggaagtgtt | 180 |
| tccctccttc | ttgaattgat | gttaccctca | taaagcacgt | ggcctcttat | cgagaaagaa | 240 |
| attaccgtcg | ctcgtgattt | gtttgcaaaa | agaacaaaac | tgaaaaaacc | cagacacgct | 300 |
| cgacttcctg | tcttcctatt | gattgcagct | tccaatttcg | tcacacaaca | aggtcctagc | 360 |
| gacggctcac | aggttttgta | acaagcaatc | gaaggttctg | gaatggcggg | aaagggttta | 420 |
| gtaccacatg | ctatgatgcc | cactgtgatc | tccagagcaa | agttcgttcg | atcgtactgt | 480 |
| tactctctct | ctttcaaaca | gaattgtccg | aatcgtgtga | caacaacagc | ctgttctcac | 540 |
| acactctttt | cttctaacca | aggggtggt | ttagtttagt | agaacctcgt | gaaacttaca | 600 |
| tttacatata | tataaacttg | cataaattgg | tcaatgcaag | aaatacatat | ttggtctttt | 660 |
| ctaattcgta | gtttttcaag | ttcttagatg | ctttcttttt | tcttttttta | cagatcatca | 720 |
| aggaagtaat | tatctacttt | ttacaagtct | agaatgaccg | cactaacaga | aggagctaaa | 780 |
| ctattcgaaa | aggagattcc | ttacattaca | gaattgaggg | tgatgtcga | aggaatgaaa | 840 |
| ttcattatca | agggcgaggg | tactggtgac | gctactaccg | gtacgattaa | agcaaagtac | 900 |
| atctgtacaa | caggtgaccct | tcctgttccg | tgggctactc | tggtgagcac | tttgtcttat | 960 |
| ggagttcaat | gttttgctaa | ataccccttcg | cacattaaag | acttttttcaa | aagtgcaatg | 1020 |
| cctgagggct | atactcagga | gagaacaata | tctttcgaag | gagatggtgt | gtataagact | 1080 |
| agggctatgg | tcacgtatga | agaggatcc | atctacaata | gagtaacttt | aactggtgaa | 1140 |
| aacttcaaaa | aggacggtca | catccttaga | aagaatgttg | cctttcaatg | cccaccatcc | 1200 |
| atcttgtaca | ttttgccaga | cacagttaac | aatggtatca | gagttgagtt | taaccaagct | 1260 |
| tatgacatag | agggtgtcac | cgaaaagttg | gttacaaaat | gttcacagat | gaatcgtccc | 1320 |
| ctggcaggat | cagctgccgt | ccatatccca | cgttaccatc | atatcactta | tcataccaag | 1380 |
| ctgtccaaag | atcgtgatga | gagaagggat | cacatgtgtt | tggttgaagt | ggtaaaggcc | 1440 |
| gtggatttgg | atacttacca | aggttgatta | attaagctag | ctaagatccg | ctctaaccga | 1500 |
| aaaggaagga | gttagacaac | ctgaagtcta | ggtccctatt | tatttttttt | aatagttatg | 1560 |
| ttagtattaa | gaacgttatt | tatatttcaa | atttttcttt | ttttctgta | caaacgcgtg | 1620 |
| tacgcatgta | acattatact | gaaaaccttg | cttgagaagg | ttttgggacg | ctcgaaggaa | 1680 |
| ttcctgcagc | ccgggggatc | cactagttct | agagcggccg | ccaccgcggt | ggagctcgga | 1740 |
| tccactagta | acggccgcca | gtgtgctgga | attcgccctt | agaattcgcc | cttacatatg | 1800 |
| ataacttcgt | ataatgtatg | ctatacgaag | ttatcatagc | ctcatgaaat | cagccatttg | 1860 |
| cttttgttca | acgatctttt | gaaattgttg | ttgttcttgg | tagttaagtt | gatccatctt | 1920 |
| ggcttatgtt | gtgtgtatgt | tgtagttatt | cttagtatat | tcctgtcctg | agtttagtga | 1980 |
| aacataatat | cgccttgaaa | tgaaaatgct | gaaattcgtc | gacatacaat | ttttcaaact | 2040 |
| tttttttttt | cttggtgcac | ggacatgttt | ttaaaggaag | tactctatac | cagttattct | 2100 |

```
tcacaaattt aattgctgga gaatagatct tcaacgcttt aataaagtag tttgtttgtc    2160
aaggatggcg tcatacaaag aaagatcaga atcacacact tccctgttg ctaggagact    2220 tttctccatc atggaggaaa agaagtctaa cctttgtgca tcattggata ttactgaaac    2280
tgaaaagctt ctctctattt tggacactat tggtccttac atctgtctag ttaaaacaca    2340
catcgatatt gtttctgatt ttacgtatga aggaactgtg ttgcctttga aggagcttgc    2400
caagaaacat aattttatga tttttgaaga tagaaaattt gctgatattg gtaacactgt    2460
taaaaatcaa tataaatctg gtgtcttccg tattgccgaa tgggctgaca tcactaatgc    2520
acatggtgta acgggtgcag gtattgtttc tggcttgaag gaggcagccc aagaaacaac    2580
cagtgaacct agaggtttgc taatgcttgc tgagttatca tcaaagggtt ctttagcata    2640
tggtgaatat acagaaaaaa cagtagaaat tgctaaatct gataaagagt ttgtcattgg    2700
ttttattgcg caacacgata tgggcggtag agaagaaggt tttgactgga tcattatgac    2760 tccagggggtt ggtttagatg acaaaggtga tgcacttggt caacaatata gaactgttga    2820
tgaagttgta aagactggaa cggatatcat aattgttggt agaggtttgt acggtcaagg    2880
aagagatcct atagagcaag ctaaaagata ccaacaagct ggttggaatg cttatttaaa    2940
cagatttaaa tgattcttac acaaagattt gatacatgta cactagttta aataagcatg    3000 aaagaatta cacaagcaaa aaaaaaaaaa taaatgaggt actttacgtt cacctacaac    3060
caaaaaaact agatagagta aaatcttaag atttagaaaa agttgtttaa caaaggcttt    3120
agtatgtgaa tttttaatgt agcaaagcga taactaataa acataaacaa aagtatggtt    3180
ttctttatca gtcaaatcat tatcgattga ttgttccgcg tatctgcaga taacttcgta    3240
taatgtatgc tatacgaagt tatagatccg cggccgcagg gcgaattctg cagatatcca    3300
tcacactggc ggccgctcga gcatgcatct agagggccca attcgcccta gtgtgagcgg    3360
atctcttatg tctttacgat ttatagtttt cattatcaag tatgcctata ttagtatata    3420
gcatct                                                             3426
```

<210> SEQ ID NO 34
<211> LENGTH: 4205
<212> TYPE: DNA
<213> ORGANISM: Artificial Sequence
<220> FEATURE:
<223> OTHER INFORMATION: Locus C-Sc pPGK-Dasher GFP-Sc CYC1-loxP-Sc
      TEF1-An amdS-Sc TEF1t-loxP integration fragment

<400> SEQUENCE: 34

```
ggtaaataga atatcaagct acaaaaagca tacaatcaac tatcaactat taactatatc     60
gtaatacaca cagctatgac catgattacg ccaagcttgg taccgggccc ccctcgagg    120 ccagaaaaag gaagtgtttc cctccttctt gaattgatgt taccctcata aagcacgtgg    180
cctcttatcg agaaagaaat taccgtcgct cgtgatttgt ttgcaaaaag aacaaaactg    240
aaaaaaccca gacacgctcg acttcctgtc ttcctattga ttgcagcttc caatttcgtc    300
acacaacaag gtcctagcga cggctcacag gttttgtaac aagcaatcga aggttctgga    360
atggcgggaa agggtttagt accacatgct atgatgccca ctgtgatctc cagagcaaag    420
ttcgttcgat cgtactgtta ctctctctct ttcaaacaga attgtccgaa tcgtgtgaca    480
acaacagcct gttctcacac actctttttct tctaaccaag ggggtggttt agtttagtag    540
aacctcgtga aacttacatt tacatatata taaacttgca taaattggtc aatgcaagaa    600
atacatattt ggtcttttct aattcgtagt ttttcaagtt cttagatgct ttctttttct    660
```

```
cttttttaca gatcatcaag gaagtaatta tctactttt acaagtctag aatgaccgca    720
ctaacagaag gagctaaact attcgaaaag gagattcctt acattacaga attagagggt    780
gatgtcgaag gaatgaaatt cattatcaag ggcgagggta ctggtgacgc tactaccggt    840
acgattaaag caaagtacat ctgtacaaca ggtgaccttc ctgttccgtg gctactctg    900 gtgagcactt tgtcttatgg agttcaatgt tttgctaaat acccttcgca cattaaagac    960
tttttcaaaa gtgcaatgcc tgagggctat actcaggaga gaacaatatc tttcgaagga   1020
gatggtgtgt ataagactag gctatggtc acgtatgaaa aggatccat ctacaataga    1080 gtaactttaa ctggtgaaaa cttcaaaaag gacggtcaca tccttagaaa gaatgttgcc   1140
tttcaatgcc caccatccat cttgtacatt tgccagaca cagttaacaa tggtatcaga    1200
gttgagttta accaagctta tgacatagag ggtgtcaccg aaaagttggt tacaaaatgt   1260
tcacagatga atcgtcccct ggcaggatca gctgccgtcc atatcccacg ttaccatcat   1320
atcacttatc ataccaagct gtccaaagat cgtgatgaga aagggatca catgtgtttg    1380 gttgaagtgg taaaggccgt ggatttggat acttaccaag gttgattaat taagctagct   1440
aagatccgct ctaaccgaaa aggaaggagt tagacaacct gaagtctagg tccctattta   1500 tttttttaa tagttatgtt agtattaaga acgttattta tatttcaaat ttttctttt    1560 tttctgtaca aacgcgtgta cgcatgtaac attatactga aaaccttgct tgagaaggtt   1620
ttgggacgct cgaaggaatt cctgcagccc ggggatcca ctagtaacgg ccgccagtgt    1680
gctggaattc gcccttatat tagcggccgc ataacttcgt ataatgtatg ctatacgaag   1740
ttatccttac atcacaccca atcccccaca agtgatcccc cacacaccat agcttcaaaa   1800
tgtttctact cctttttac tcttccagat tttctcggac tccgcgcatc gccgtaccac    1860
ttcaaaacac ccaagcacag catactaaat ttcccctctt tcttcctcta gggtggcgtt   1920
aattacccgt actaaaggtt tggaaaagaa aaagagacc gcctcgtttc tttttcttcg    1980
tcgaaaaagg caataaaaat ttttatcacg tttcttttc ttgaaaaatt ttttttga    2040 ttttttctc tttcgatgac ctcccattga tatttaagtt aataaatggt cttcaatttc    2100
tcaagtttca gtttcgtttt tcttgttcta ttacaacttt ttttacttct tgctcattag   2160
aaagaaagca tagcaatcta atctaagttt taattacaaa atgccacaat cctgggaaga   2220
attggccgcc gacaaacgtg cccgtttggc taaaaccatt cctgacgaat ggaaggttca   2280
aactttgcct gccgaagatt ccgttattga tttcccaaag aagtccggta ttttgtctga   2340
ggctgaattg aagattaccg aagcctctgc tgctgatttg gtctccaagt tggccgctgg   2400
tgagttgact tctgttgaag tcactttggc ttttttgtaag agagctgcta ttgctcaaca   2460
attaaccaac tgtgctcacg aattcttccc agatgctgct ttagctcaag ctagagaatt   2520
agatgaatac tacgctaagc ataagagacc agttggtcca ttacacggtt taccaatctc   2580
tttaaaggac caattgcgtg ttaagggtta cgaaacctcc atgggttaca tttcctggtt   2640
aaacaaatac gatgaaggtg attccgtctt aaccaccatg ttgagaaaag ctggtgctgt   2700
tttctacgtt aagacctctg tcccacaaac cttgatggtc tgtgaaaccg tcaacaacat   2760
cattggtaga actgtcaatc caagaaacaa aaattggtcc tgtggtggtt cttctggtgg   2820
tgaaggtgct attgttggta ttagaggtgg tgttattggt gtcggtactg acattggtgg   2880
ttccattaga gtcccagctg cttcaactt ttatacggt ttgagaccat ctcacggtag    2940
attgccatat gctaaaatgg ctaactctat ggaaggtcaa gaaaccgttc actccgtcgt   3000
```

```
tggtcctatc actcactccg tcgaagactt gagattgttc accaaatctg tcttgggtca    3060
agaaccttgg aagtacgact ctaaggtcat cccaatgcca tggagacaat ctgaatctga    3120
catcattgcc tctaagatta agaatggtgg tttgaacatt ggttattaca atttcgacgg    3180
taacgtcttg ccacacccac caattttacg tggtgtcgaa actaccgttg ccgctttggc    3240
caaggctggt cacaccgtta ctccatggac tccatacaag catgatttcg gtcatgactt    3300
gatttcccac atctatgctg ctgatggttc tgccgacgtc atgagagaca tttctgcctc    3360
tggtgagcca gccatcccta acattaagga cttgttgaac ccaaatatta aggctgttaa    3420
catgaacgaa ttgtgggaca ctcatttaca aaagtggaac tatcaaatgg aatacttgga    3480
aaagtggcgt gaagctgaag aaaaagctgg taaggaattg gacgctatta tcgctccaat    3540
tactcctacc gccgctgtca gacacgatca attcagatac tacggttacg cctccgttat    3600
taacttattg gatttcacct ctgttgtcgt cccagtcact ttcgctgata agaatattga    3660
taagaagaac gaatctttta aagctgtttc cgaattggat gctttggttc aagaagaata    3720
cgacccagag gcttatcacg gtgctcctgt tgctgttcaa gttattggta agagattgtc    3780
cgaagagaga actttggcta tcgccgaaga agtcggtaaa ttgttgggta acgtcgtcac    3840
tccataagga gattgataag acttttctag ttgcatatct tttatattta aatcttatct    3900
attagttaat tttttgtaat ttatccttat atatagtctg gttattctaa aatatcattt    3960
cagtatctaa aaattcccct ctttttttcag ttatatctta acaggcgata acttcgtata    4020
atgtatgcta tacgaagtta tgcggccgct aatataaggg cgaattctgc agatatccat    4080
cacactggcg gccgctcgag catgcatcta gagggcccaa ttcgccctat agtgagcgga    4140
tctcttatgt ctttacgatt tatagttttc attatcaagt atgcctatat tagtatatag    4200
catct                                                                 4205

<210> SEQ ID NO 35
<211> LENGTH: 4632
<212> TYPE: DNA
<213> ORGANISM: Artificial Sequence
<220> FEATURE:
<223> OTHER INFORMATION: Locus B-Sc pTDH3-Sf GA-Sc CYCt-loxP-Sc URA3
      integration fragment

<400> SEQUENCE: 35
cagagcctct tatattcact ctgttcctcc atcgcctatt gagaaacgtt ggaataaaac      60
tctaaaaata tcatctagtt ggttagtttt tattttacca gtacattgtc acttgcggag     120
ggaggatgac ataagattg agacgcagtc atttaatgaa gtttaaacgc aggtatttga     180
taaagtaata cgatattgaa tcatgacgta taaagtgaaa tgaacaaatg attacgtaaa     240
aaatgtcgat tttctcttga gagactccca tagcctctaa gaggccttct actacgttcc     300
atatatctaa gaatggggcc atatccagtg gaatcccagc aattatttaa ggatcaccta     360
tttctcagcc gatattttag caaaatcact accaatatca gggggcaata gttgatcgcc     420
tactttaaca aaaaatgttg ctcacgtatt aacacaggca acaaaaagga tattacgcaa     480
gaacgtagta tccacatgcc atcctccttg ttgcatcttt ttttttccga aatgattccc     540
tttcctgcac aacacgagat ctttcacgca tacatcggga ggatcacccc ccactcaagt     600
cgttgcattg ctaacatgtg gcattctgcc cattttttttc acgaaaattc tctctctata     660
atgaagaccc ttgtgccctg gactctgtaa tacttgaaac tacttcctca ataatcgctt     720
ggagacctac ccccacgctt ttcaaacaag gcgctagcaa aaagcctgcc gatatctcct     780
```

```
tgccccctcc ttctgttcga gagaactacg acccgaccaa taataatgtc atacaagaac    840
cgccaagaac caactgctga accttagatc tccaatactt cagttggagt atgtgaatat    900
ataagtacct ggtcgactaa tcttcttgca tcttttcgta ttcttacatc ctatgtcgct    960
aatacagttc ccgcatagag aagaaagcaa acaaaagtag tcactcgaga tctcccgagt   1020
ttatcattat caatactgcc atttcaaaga atacgtaaat aattaatagt agtgattttc   1080
ctaactttat ttagtcaaaa aattggcctt ttaattctgc tgtaacccgt acatgcccaa   1140
aataggggc gggttacaca gaatatataa catcataggt gtctgggtga acagtttatt   1200
cctggcatcc actaaatata atggagcccg cttttttta gctggcatcc agaaaaaaaa   1260
agaatcccag caccaaaata ttgttttctt caccaaccat cagttcatag gtccattctc   1320
ttagcgcaac tacacagaac aggggcacaa acaggcaaaa aacgggcaca acctcaatgg   1380
agtgatgcaa cctgcttgga gtaaatgatg acacaaggca attgacctac gcatgtatct   1440
atctcatttt cttacacctt ctattacctt ctgctctctc tgatttggaa aaagctgaaa   1500
aaaaaggttg aaaccagttc cctgaaatta ttccccctatt tgactaataa gtatataaag   1560
acggtaggta ttgattgtaa ttctgtaaat ctatttctta aacttcttaa attctacttt   1620
tatagttagt cttttttta gtttaaaaca ccaagaactt agtttcgaat aaacacacat   1680
aaacaaacaa atctagaatg attagattaa ccgtattcct cactgcagtt tttgcagcag   1740
tcgcttcctg tgttccagtt gaattggata agagaaatac aggccatttc caagcatatt   1800
ctggttacac cgtagctaga tcaaacttta ctcaatggat tcacgagcaa ccagccgtat   1860
catggtacta tttgcttcag aatatagact atccagaagg acaattcaag tctgccaagc   1920
cagggtcgt tgtggcttcc ccttctacat ccgaacctga ttacttctac caatggacta   1980
gagatactgc tatcaccttc ttgtcactta tcgcggaagt tgaggatcat tcttttcaa   2040
atactacact agccaaggtg gttgaatact acatctctaa tacttacaca ttacaaagag   2100
tttccaaccc atctggtaac ttcgacagtc caaatcacga cggtttggga gaaccaaagt   2160
ttaatgttga tgatacagct tatactgcat cttggggtag accacaaaat gatggcccag   2220
cgttgagagc atacgcaatt tcaagatacc ttaacgcagt agcaaaacac aacaacggta   2280
agttactgct cgctggacaa aacggtattc cttactcttc agcttctgat atctactgga   2340
agattatcaa gccagatctt caacatgtgt caacccattg gtctacatct ggttttgatt   2400
tgtgggaaga gaatcaggga acacatttct ttactgcgtt ggtccagcta aaagcactta   2460
gttacggcat tcctttaagt aagacctaca acgatcctgg tttcactagt tggctagaaa   2520
agcaaaagga tgctttaaac tcttatatca acagctctgg tttcgtaaac tctggcaaaa   2580
agcatatagt gggagagccct caactatctt caagaggagg gttggatagc gccacataca   2640
ttgcagcctt aatcacacat gatattggcg acgacgacac ttacacacct ttcaacgttg   2700
acaactccta tgtcttgaac tcactgtatt accttctagt cgataacaaa aaccgttaca   2760
aaatcaatgg taactacaag gccggtgctg ctgttggtag atacccagag gatgtttaca   2820
acggtgttgg gacatcagaa ggcaatccat ggcaattagc tacagcctac gccggccaaa   2880
cattttacac actggcttac aactcattga aaaacaaaaa aaacttagtg attgaaaagt   2940
tgaactacga cctctacaat tctttcatag cagatttatc caagatcgat agttcttacg   3000
catcaaaaga ctccttgact ttgacctacg gttctgacaa ctacaaaaac gtcataaagt   3060
cactattaca gtttgagat tcattcctga aggtcttgct cgatcacatt gatgataatg   3120
gacaattaac agaagagatc aatagataca cagggttcca ggctggtgct gttagtttga   3180
```

```
catggtcctc tggttcatta cttcagcaa accgtgcgag aaataagttg attgaactat    3240
tgtagttaat taaacaggcc ccttttcctt tgtcgatatc atgtaattag ttatgtcacg    3300
cttacattca cgccctcctc ccacatccgc tctaaccgaa aaggaaggag ttagacaacc    3360
tgaagtctag gtcccatatt attttttat agttatgtta gtattaagaa cgttatttat    3420
atttcaaatt tttctttttt ttctgtacaa acgcgtgtac gcatgtaacg ggcagacggc    3480
cggccataac ttcgtataat gtatgctata cgaagttatg gcaacggttc atcatctcat    3540
ggatctgcac atgaacaaac accagagtca aacgacgttg aaattgaggc tactgcgcca    3600
attgatgaca atacagacga tgataacaaa ccgaagttat ctgatgtaga aaaggattag    3660
agatgctaag agatagtgat gatatttcat aaataatgta attctatata tgttaattac    3720
cttttttgcg aggcatattt atggtgaagg ataagttttg accatcaaag aaggttaatg    3780
tggctgtggt ttcagggtcc ataaagcttt tcaattcatc ttttttttt ttgttctttt    3840 ttttgattcc ggtttctttg aaattttttt gattcggtaa tctccgagca gaaggaagaa    3900
cgaaggaagg agcacagact tagattggta tatatacgca tatgtggtgt tgaagaaaca    3960
tgaaattgcc cagtattctt aacccaactg cacagaacaa aaacctgcag gaaacgaaga    4020
taaatcatgt cgaaagctac atataaggaa cgtgctgcta ctcatcctag tcctgttgct    4080
gccaagctat ttaatatcat gcacgaaaag caaacaaact tgtgtgcttc attggatgtt    4140
cgtaccacca aggaattact ggagttagtt gaagcattag gtcccaaaat ttgtttacta    4200
aaaacacatg tggatatctt gactgatttt tccatggagg gcacagttaa gccgctaaag    4260
gcattatccg ccaagtacaa tttttactc ttcgaagaca gaaaatttgc tgacattggt    4320
aatacagtca aattgcagta ctctgcgggt gtatacagaa tagcagaatg ggcagacatt    4380
acgaatgcac acggtgtggt gggcccaggt attgttagcg gtttgaagca ggcggcggaa    4440
gaagtaacaa aggaacctag aggccttttg atgttagcag aattgtcatg caagggctcc    4500
ctagctactg gagaatatac taagggtact gttgacattg cgaagagcga caaagatttt    4560
gttatcggct ttattgctca aagagacatg ggtggaagag atgaaggtta cgattggttg    4620
attatgacac gc                                                         4632

<210> SEQ ID NO 36
<211> LENGTH: 4363
<212> TYPE: DNA
<213> ORGANISM: Artificial Sequence
<220> FEATURE:
<223> OTHER INFORMATION: Sc URA3-loxP-Sc pPGK-Sf GA-Sc RPL3-locus B
      integration fragment

<400> SEQUENCE: 36
ggccgctcca tggagggcac agttaagccg ctaaaggcat tatccgccaa gtacaatttt     60
ttactcttcg aagacagaaa atttgctgac attggtaata cagtcaaatt gcagtactct    120
gcgggtgtat acagaatagc agaatgggca gacattacga atgcacacgg tgtggtgggc    180
ccaggtattg ttagcggttt gaagcaggcg gcggaagaag taacaaagga acctagaggc    240
cttttgatgt tagcagaatt gtcatgcaag ggctccctag ctactggaga atatactaag    300
ggtactgttg acattgcgaa gagcgacaaa gattttgtta tcggctttat tgctcaaaga    360
gacatgggtg gaagagatga aggttacgat tggttgatta tgacacccgg tgtgggttta    420
gatgacaagg gagacgcatt gggtcaacag tatagaaccg tggatgatgt ggtctctaca    480
ggatctgaca ttattattgt tggaagagga ctatttgcaa agggaaggga tgctaaggta    540
```

```
gagggtgaac gttacagaaa agcaggctgg gaagcatatt tgagaagatg cggccagcaa    600
aactaaaaaa ctgtattata agtaaatgca tgtatactaa actcacaaat tagagcttca    660
atttaattat atcagttatt acccgggaat ctcggtcgta atgattttta taatgacgaa    720
aaaaaaaaaa ttggaaagaa aaagcttcat ggcctttata aaaaggaacc atccaatacc    780
tcgccagaac caagtaacag tattttacgg ggcacaaatc aagaacaata agacaggact    840
gtaaagatgg acgcattgaa ctccaaagaa caacaagagt tccaaaaagt agtgaacaa     900 aagcaaatga aggatttcat gcgtttgata acttcgtata atgtatgcta tacgaagtta    960
tctcgagggc cagaaaaagg aagtgttttcc ctccttcttg aattgatgtt accctcataa   1020
agcacgtggc ctcttatcga gaaagaaatt accgtcgctc gtgatttgtt tgcaaaaaga   1080
acaaaactga aaaacccag acacgctcga cttcctgtct tcctgttgat gcagcttcc     1140 aatttcgtca cacaacaagg tcctagcgac ggctcacagg ttttgtaaca agcaatcgaa   1200
ggttctggaa tggcgggaaa gggtttagta ccacatgcta tgatgcccac tgtgatctcc   1260
agagcaaagt tcgttcgatc gtactgttac tctctctctt tcaaacagaa ttgtccgaat   1320
cgtgtgacaa caacagcctg ttctcacaca ctcttttctt ctaaccaagg gggtggttta   1380
gtttagtaga acctcgtgaa acttacattt acatatatat aaacttgcat aaattggtca   1440
atgcaagaaa tacatatttg gtcttttcta attcgtagtt tttcaagttc ttagatgctt   1500
tctttttctc ttttttacag atcatcaagg aagtaattat ctacttttta caagtctaga   1560
atgatcagac ttcagttttt cctaacagcc gttttcgccg ccgttgcatc atgtgtccca   1620
gtagaattgg ataagagaaa caccggccat ttccaagcat attcaggata caccgttgca   1680
cgttctaatt tcacacaatg gattcatgag cagcctgctg tgtcctggta ctacttatta   1740 caaacattg attatcctga gggacaattc aagtcagcga accaggcgt tgtggttgct     1800 tctccatcca cttcagaacc agactacttc taccagtgga cccgtgacac agcaataact   1860
ttcttatctt tgatagcaga agtagaagat cactcatttt caaatacaac tctagctaag   1920
gttgtcgaat actacatctc taacacatac accctacaaa gagtttctaa cccatctggt   1980
aatttcgata gcccaaatca cgatggtctg ggtgaaccaa agttcaacgt tgacgacact   2040
gcttacactg catcatgggg cagacctcaa aacgacggtc cagccttaag agcttacgcg   2100
atctcaagat atttgaacgc agttgccaag cataacaacg gtaagctatt gctcgcgggt   2160
caaaatggta ttccttactc atctgcatca gatatctact ggaagattat caagccagat   2220
ttacaacatg taagtactca ctggagtaca tctggttttg acttatggga agagaatcaa   2280
ggtacacatt tctttactgc acttgtccag ttaaaagctc tttcatacgg tatacctttg   2340
tctaagacat ataacgatcc aggatttact tcttggttgg aaaagcagaa ggatgccttg   2400
aactcttaca tcaattccag cggcttcgtc aactccggga aaaagcacat tgtcgaatct   2460
cctcaattat ctagtagagg gggtcttgat agcgctactt acatcgctgc tctaattaca   2520
catgatattg gtgatgatga tacatacact ccttttaacg tagataattc ttatgtgctg   2580
aactctttat actatctgct tgtagacaac aaaaacagat acaagatcaa cgggaactac   2640
aaagcaggag ctgcagttgg tagatacca gaagatgtgt acaatggagt gggaacctca    2700
gagggaaacc catggcaatt ggcgacagca tacgccggcc aaacctttta cacactggct   2760
tacaattctc tcaaaaacaa aaaaaatttg gttattgaga agttgaatta cgatctatac   2820 aactcccttta tagctgactt aagtaagatt gactcctctt acgcttctaa ggattcattg   2880
```

| | |
|---|---|
| acattgacct acggctcaga taactacaaa aatgtcatta agtcacttt acaattcggg | 2940 |
| gattctttct tgaaagtctt gttggaccat attgatgata atggtcagct aacagaggaa | 3000 |
| atcaacagat atacaggttt tcaagctggc gcagtttccc tcacttggag tagtggttca | 3060 |
| ctcttatctg caaacagagc cagaaacaag ttgatcgaat tgctttagtt aattaagaag | 3120 |
| ttttgttaga aaataaatca tttttaatt gagcattctt attcctattt tatttaaata | 3180 |
| gttttatgta ttgttagcta catacaacag tttaaatcaa attttctttt tcccaagtcc | 3240 |
| aaaatggagg tttattttga tgacccgcat gcgattatgt tttgaaagta taagactaca | 3300 |
| tacatgtaca tatatttaaa catgtaaacc cgtccattat attgccgggc agacggccgg | 3360 |
| ccttatagcc tagctttaag gctactttaa aaactttta tttattcata cacatatatt | 3420 |
| atcgaacatt cgtataactt aatatcattc aaaaaaaaa aaaaaaaaa aagaaaacat | 3480 |
| atacacatat atatttatgt ttatagagag agagagagaa aatttgaatt tttgaatcat | 3540 |
| ttgcaaagtt atatgtttta tacattattt attcatttt tttggtgtcg aggacattgt | 3600 |
| gctgttcaga gaaccactta aaatacgcat cgttctgtaa atatccactt tcattaaaaa | 3660 |
| ccttattcac ttctaacttt gccttcaact ccttcttgga gttttctccc tttttttct | 3720 |
| gaacaagctc aaccagatat aatggttcgt tcttttcgaa ctttgtcttt acatatattt | 3780 |
| cctcctttgt acctcttctc tttcccacat aaacagtccc cttttcaata aaacgagaga | 3840 |
| aataccagaa aagtagcgag agaacaaaat atgcgcctac caaaagcttt tgatacgtaa | 3900 |
| caatctgatc tctctcaaat tttttatcca agaagaaact caaaccagct acaacagcta | 3960 |
| tggaataacc tatgtacaat ttagcatcga gtaaagcgta tgatctctcg taatttaatc | 4020 |
| tcgcgaaaac agaaggtagg gcttcatcta aagcttggtt caactccggg attgaatata | 4080 |
| cattaatagg tttagcagaa ctcatcttga acaggcgtct cttttccta caataacttg | 4140 |
| tgcttttcct tctataattc cgtttcaacg tgtacaattg tcattttg tctggtatga | 4200 |
| ttttgcagaa ctgaaaaaat ctcttaaatg ttccgcctca tcaagaaggc atattccttt | 4260 |
| acaaaagtac attgatctta caagaagcta gctaatggta ctatttaaaa aacaactaca | 4320 |
| ctccatcaat acataaaatt gttatgatag acttgaggga cgg | 4363 |

<210> SEQ ID NO 37
<211> LENGTH: 5015
<212> TYPE: DNA
<213> ORGANISM: Artificial Sequence
<220> FEATURE:
<223> OTHER INFORMATION: Locus B-Sc pTDH3-Sf GA-Sc CYCt-loxP-Sc pTEF1-An amdS integration fragment

<400> SEQUENCE: 37

| | |
|---|---|
| cagagcctct tatattcact ctgttcctcc atcgcctatt gagaaacgtt ggaataaaac | 60 |
| tctaaaaata tcatctagtt ggttagtttt tattttacca gtacattgtc acttgcggag | 120 |
| ggaggatgac ataagattg agacgcagtc atttaatgaa gttaaacgc aggtatttga | 180 |
| taaagtaata cgatattgaa tcatgacgta taaagtgaaa tgaacaaatg attacgtaaa | 240 |
| aaatgtcgat tttctcttga gagactccca tagcctctaa gaggccttct actacgttcc | 300 |
| atatatctaa gaatggggcc atatccagtg gaatcccagc aattatttaa ggatcaccta | 360 |
| tttctcagcc gatattttag caaaatcact accaatatca gggggcaata gttgatcgcc | 420 |
| tactttaaca aaaaatgttg ctcacgtatt aacacaggca acaaaaagga tattacgcaa | 480 |
| gaacgtagta tccacatgcc atcctccttg ttgcatcttt ttttttccga atgattccc | 540 |

```
tttcctgcac aacacgagat ctttcacgca tacatcggaa ggatcacccc ccactcaagt    600
cgttgcattg ctaacatgtg gcattctgcc cattttttc acgaaaattc tctctctata    660
atgaagaccc ttgtgccctg gactctgtaa tacttgaaac tacttcctca ataatcgctt    720
ggagacctac ccccacgctt ttcaaacaag gcgctagcaa aaagcctgcc gatatctcct    780 tgcccctcc ttctgttcga gagaactacg acccgaccaa taataatgtc atacaagaac    840
cgccaagaac caactgctga accttagatc tccaatactt cagttggagt atgtgaatat    900
ataagtacct ggtcgactaa tcttcttgca tcttttcgta ttcttacatc ctatgtcgct    960
aatacagttc ccgcatagag aagaaagcaa acaaaagtag tcactcgaga tctcccgagt   1020
ttatcattat caatactgcc atttcaaaga atacgtaaat aattaatagt agtgattttc   1080
ctaactttat ttagtcaaaa aattggcctt ttaattctgc tgtaacccgt acatgcccaa   1140 aataggggc gggttacaca gaatatataa catcataggt gtctgggtga acagtttatt   1200
cctggcatcc actaaatata atggagcccg ctttttttaa gctggcatcc agaaaaaaaa   1260
agaatcccag caccaaaata ttgttttctt caccaaccat cagttcatag gtccattctc   1320
ttagcgcaac tacacagaac aggggcacaa acaggcaaaa aacgggcaca acctcaatgg   1380
agtgatgcaa cctgcttgga gtaaatgatg acacaaggca attgacctac gcatgtatct   1440
atctcatttt cttacacctt ctattacctt ctgctctctc tgatttggaa aaagctgaaa   1500
aaaaaggttg aaaccagttc cctgaaatta ttcccctatt tgactaataa gtatataaag   1560
acggtaggta ttgattgtaa ttctgtaaat ctatttctta aacttcttaa attctacttt   1620
tatagttagt cttttttta gtttaaaaca ccaagaactt agtttcgaat aaacacacat   1680
aaacaaacaa atctagaatg atcagactta ctgttttcct cacagccgtt tttgcagcag   1740
tagcttcttg tgttccagtt gaattggata agagaaatac aggtcatttc caagcttact   1800
ctggttacac tgtggctaga tctaacttca cacaatggat tcatgaacag cctgccgtga   1860
gttggtacta tttgctacaa acattgatt accctgaggg tcaattcaaa tcagctaagc   1920
caggtgttgt tgtcgcgagc ccatcaactt ctgaaccaga ttacttctac caatggacta   1980
gagataccgc aataaccttc ttatctctaa tcgcagaggt agaagatcac tctttttcaa   2040
atactaccct ggcaaaagtg gtcgagtact acatctcaaa cacatacacc ttgcagagag   2100
tctcaaaccc atcaggaaac ttcgattctc ctaatcatga cggcttagga gaaccaaagt   2160
ttaatgttga cgataccgct tatactgcat cttggggtag accacagaat gatggccctg   2220
ccttacgtgc atacgccatt tccagatatc tcaacgctgt agcgaagcac aacaacggta   2280
agctgctttt agctggtcaa aatgggatac catactcttc cgcttcagac atttactgga   2340
agattatcaa accagacttg cagcatgtca gtacacattg gtcaacttct ggttttgatt   2400
tgtgggaaga gaaccaaggc actcacttct ttacagcctt ggttcaacta aaggcattgt   2460
cttacggaat ccctttgtcc aagacataca atgatcctgg attcactagt tggctagaaa   2520
agcaaaagga tgcactgaac tcatacatta acagttcagg ctttgtgaac tccgtaaaa   2580 agcatattgt tgaaagccca caactatcta gcagaggtgg tttagattct gcaacctaca   2640
tagcagcctt gatcacacac gacattgggg atgacgatac atacacacca ttcaacgtcg   2700
acaattcata cgttttgaat agcttatact acctactggt agataacaaa aacagatata   2760
agatcaatgg caactacaag gccggtgctg ccgtaggaag ataccctgaa gatgtctaca   2820
acggagttgg tacatcagaa ggtaacccat ggcaattagc aacagcatat gcgggccaga   2880
cattttacac tttggcttac aattcattga aaaacaaaaa aaatttagtg atagaaaagc   2940
```

```
ttaactatga cctttacaac tctttcattg ccgatttatc caagattgat tcctcctacg   3000
catcaaagga ctccttgaca cttacatacg gttctgacaa ctacaaaaat gttatcaagt   3060
ctctcttgca atttggtgat tctttcttga aggttttact cgatcatatc gatgataatg   3120
gtcaactaac tgaggaaatc aacagataca ctgggttcca agctggagct gtctctttaa   3180
catggagttc agggagtttg ttatctgcta acagagcgcg taacaaactt attgagcttc   3240
tgtagttaat taaacaggcc ccttttcctt tgtcgatatc atgtaattag ttatgtcacg   3300
cttacattca cgccctcctc ccacatccgc tctaaccgaa aaggaaggag ttagacaacc   3360
tgaagtctag gtccctattt attttttttat agttatgtta gtattaagaa cgttatttat   3420
atttcaaatt tttcttttt ttctgtacaa acgcgtgtac gcatgtaacg ggcagacggc   3480
cggccataac ttcgtataat gtatgctata cgaagttatc cttacatcac acccaatccc   3540
ccacaagtga tcccccacac accatagctt caaaatgttt ctactccttt tttactcttc   3600
cagattttct cggactccgc gcatcgccgt accacttcaa acacccaag cacagcatac   3660 taaatttccc ctctttcttc ctctagggtg gcgttaatta cccgtactaa aggtttggaa   3720
aagaaaaaag agaccgcctc gtttcttttt cttcgtcgaa aaaggcaata aaaatttta    3780 tcacgtttct ttttcttgaa aaattttttt tttgattttt ttctctttcg atgacctccc   3840
attgatattt aagttaataa atggtcttca atttctcaag tttcagtttc gttttcttg    3900 ttctattaca acttttttta cttcttgctc attagaaaga aagcatagca atctaatcta   3960
agttttaatt acaaaatgcc acaatcctgg gaagaattgg ccgccgacaa acgtgcccgt   4020
ttggctaaaa ccattcctga cgaatggaag gttcaaactt gcctgccga agattccgtt    4080 attgatttcc caaagaagtc cggtattttg tctgaggctg aattgaagat taccgaagcc   4140
tctgctgctg atttggtctc caagttggcc gctggtgagt tgacttctgt tgaagtcact   4200
ttggcttttt gtaagagagc tgctattgct caacaattaa ccaactgtgc tcacgaattc   4260
ttcccagatg ctgctttagc tcaagctaga gaattagatg aatactacgc taagcataag   4320
agaccagttg gtccattaca cggttttacca atctctttaa aggaccaatt gcgtgttaag   4380
ggttacgaaa cctccatggg ttacatttcc tggttaaaca aatacgatga aggtgattcc   4440
gtcttaacca ccatgttgag aaaagctggt gctgttttct acgttaagac ctctgtccca   4500
caaaccttga tggtctgtga aaccgtcaac aacatcattg gtagaactgt caatccaaga   4560
aacaaaaatt ggtcctgtgg tggttcttct ggtggtgaag gtgctattgt tggtattaga   4620
ggtggtgtta ttggtgtcgg tactgacatt ggtggttcca ttagagtccc agctgctttc   4680
aactttttat acggtttgag accatctcac ggtagattgc catatgctaa aatggctaac   4740
tctatggaag gtcaagaaac cgttcactcc gtcgttggtc ctatcactca ctccgtcgaa   4800
gacttgagat tgttcaccaa atctgtcttg ggtcaagaac cttggaagta cgactctaag   4860
gtcatcccca tgccatggag acaatctgaa tctgacatca ttgcctctaa gattaagaat   4920 ggtggttga acattggtta ttacaatttc gacggtaacg tcttgccaca cccaccaatt   4980
ttacgtggtg tcgaaactac cgttgccgct ttggc                             5015
```

<210> SEQ ID NO 38
<211> LENGTH: 4771
<212> TYPE: DNA
<213> ORGANISM: Artificial Sequence
<220> FEATURE:
<223> OTHER INFORMATION: An amdS-Sc ADH1t-loxP-Sc pPGK-Sf GA-Sc RPL3t-locus B integration fragment

<400> SEQUENCE: 38

```
ggccgcgaag gtgctattgt tggtattaga ggtggtgtta ttggtgtcgg tactgacatt      60
ggtggttcca ttagagtccc agctgctttc aacttttat acggtttgag accatctcac     120
ggtagattgc catatgctaa aatggctaac tctatggaag gtcaagaaac cgttcactcc     180
gtcgttggtc ctatcactca ctccgtcgaa gacttgagat tgttcaccaa atctgtcttg     240
ggtcaagaac cttggaagta cgactctaag gtcatcccaa tgccatggag acaatctgaa     300
tctgacatca ttgcctctaa gattaagaat ggtggtttga acattggtta ttacaatttc     360
gacggtaacg tcttgccaca cccaccaatt ttacgtggtg tcgaaactac cgttgccgct     420
ttggccaagg ctggtcacac cgttactcca tggactccat acaagcatga tttcggtcat     480
gacttgattt cccacatcta tgctgctgat ggttctgccg acgtcatgag agacatttct     540
gcctctggtg agccagccat ccctaacatt aaggacttgt tgaacccaaa tattaaggct     600
gttaacatga acgaattgtg ggacactcat ttacaaaagt ggaactatca aatggaatac     660
ttggaaaagt ggcgtgaagc tgaagaaaaa gctggtaagg aattggacgc tattatcgct     720
ccaattactc ctaccgccgc tgtcagacac gatcaattca gatactacgg ttacgcctcc     780
gttattaact tattggattt cacctctgtt gtcgtcccag tcactttcgc tgataagaat     840
attgataaga agaacgaatc ttttaaagct gttttccgaat tggatgcttt ggttcaagaa     900
gaatacgacc cagaggctta tcacggtgct cctgttgctg ttcaagttat tggtagaaga     960
ttgtccgaag agaaactttt ggctatcgcc gaagaagtcg gtaaattgtt gggtaacgtc    1020
gtcactccat aagcgaattt cttatgattt atgatttta ttattaaata agttataaaa    1080
aaaataagtg tatacaaatt ttaaagtgac tcttaggttt taaaacgaaa attcttattc    1140
ttgagtaact cttttcctgta ggtcaggttg ctttctcagg tatagcatga ggtcgctctt    1200
attgaccaca cctctaccgg catgccgagc aaatgcctgc aaatcgctcc ccatttcacc    1260
caattgtaga tatgctaact ccagcaatga gttgatgaat ctcggtgtgt atttttatgtc    1320
ctcagaggac aacacataac ttcgtataat gtatgctata cgaagttatc tcgagggcca    1380
gaaaaaggaa gtgtttccct ccttcttgaa ttgatgttac cctcataaag cacgtggcct    1440
cttatcgaga aagaaattac cgtcgctcgt gatttgtttg caaaaagaac aaaactgaaa    1500
aaacccagac acgctcgact tcctgtcttc ctgttgattg cagcttccaa tttcgtcaca    1560
caacaaggtc ctagcgacgg ctcacaggtt ttgtaacaag caatcgaagg ttctggaatg    1620
gcgggaaagg gtttagtacc acatgctatg atgcccactg tgatctccag agcaaagttc    1680
gttcgatcgt actgttactc tctctctttc aaacagaatt gtccgaatcg tgtgacaaca    1740
acagcctgtt ctcacacact ctttttcttct aaccaagggg gtggtttagt ttagtagaac    1800
ctcgtgaaac ttacatttac atatatataa acttgcataa attggtcaat gcaagaaata    1860
catatttggt cttttctaat tcgtagtttt tcaagttctt agatgctttc ttttctctt     1920
ttttacagat catcaaggaa gtaattatct actttttaca agtctagaat gattagatta    1980
acagtatttc ttacagccgt tttcgcagcc gtcgcatcct gtgttccagt agaattagat    2040
aagcgtaata caggacattt tcaagcttac tctggctata cagttgcgag atctaacttt    2100
acacaatgga ttcacgaaca gccagcagtt tcttggtact atttgctcca aacatcgac    2160
taccctgaag gccaattcaa gtctgcaaag ccaggagtgg tcgtcgcttc tcctagtact    2220
tcagaaccag attacttcta ccagtggaca agagacactg ctattacctt cctgagctta    2280
```

```
atcgctgaag ttgaagatca ctcttttcct aatacaacac tggccaaagt agttgagtac   2340
tacatctcta acacttacac tctacaaaga gtgtcaaacc cttctgggaa cttcgacagc   2400
ccaaaccatg atggtttggg ggagccaaaa ttcaacgttg atgatacagc ctacaccgca   2460
tcttggggta gaccacaaaa cgacggacca gctttaagag catacgcaat atctcgttac   2520
cttaatgctg ttgcaaagca caataatgga aagttgttgt tggctggtca aaacggtatt   2580
ccttactctt cagcatctga tatctactgg aagattatca agccagatct tcaacacgta   2640
tccacacatt ggtcaacctc cggcttcgat ttatgggagg aaaatcaggg tacacatttc   2700
ttcaccgctc tagtgcaatt gaaggctttg agttacggca ttccattgtc taagacttac   2760
aacgatcctg gtttcacctc atggcttgaa aagcagaagg atgccctgaa tagctacatc   2820
aactcatctg gttttgttaa ctcagggaaa aagcatatag ttgaatcccc acaactatca   2880
tcaagaggag gtttagactc cgccacatac attgctgcct tgattacaca tgatattggg   2940
gatgatgaca catatactcc atttaacgtc gataacagtt atgtccttaa ttccttatac   3000
tatttgttgg tcgataacaa aaatagatac aaaatcaacg gcaactacaa ggctggcgca   3060
gcggtgggta gatacctga ggatgtttac aatggtgtag gtacatctga aggcaatcca   3120
tggcaattag cgactgctta cgctggacaa actttctaca cacttgcgta caactcattg   3180
aaaaacaaaa aaaacctagt cattgaaaag ttgaattacg atctgtacaa ctctttcatc   3240
gcagacctat caaagattga ctcatcttat gcaagtaaag attcactaac tttaacctac   3300
ggtagtgata actacaaaaa cgttatcaag tctttactcc agtttggtga ttcattcttg   3360
aaggtgttgt tagatcatat agacgacaat ggtcaactca cagaggagat aaacagatac   3420
actggttttc aagcaggagc tgtttcactt acttggtcaa gtggttcttt gctttccgcc   3480
aacagagcca gaaacaagct catcgaatta ctatagttaa ttaagaagtt tgttagaaa   3540 ataaatcatt ttttaattga gcattcttat cctattttta tttaaatagt tttatgtatt   3600
gttagctaca tacaacagtt taaatcaaat tttcttttc ccaagtccaa aatggaggtt   3660
tattttgatg acccgcatgc gattatgttt tgaaagtata agactacata catgtacata   3720
tatttaaaca tgtaaacccg tccattatat tgccgggcag acggccggcc ttatagccta   3780
gctttaaggc tactttaaaa acttttttatt tattcataca catatattat cgaacattcg   3840
tataacttaa tatcattcaa aaaaaaaaa aaaaaaaaa gaaaacatat acacatatat   3900
atttatgttt atagagagag agagagaaaa tttgaatttt tgaatcattt gcaaagttat   3960
atgttttata cattatttat tcatttttt tggtgtcgag acattgtgc tgttcagaga   4020 accacttaaa atacgcatcg ttctgtaaat atccactttc attaaaaacc ttattcactt   4080
ctaactttgc cttcaactcc ttcttggagt tttctccctt ttttttctga acaagctcaa   4140
ccagatataa tggttcgttc ttttcgaact ttgtctttac atatatttcc tcctttgtac   4200
ctcttctctt tcccacataa acagtcccct tttcaataaa acgagagaaa taccagaaaa   4260
gtagcgagag aacaaaatat gcgcctacca aaagcttttg atacgtaaca atctgatctc   4320
tctcaaattt tttatccaag aagaaactca aaccagctac aacagctatg aataaccta   4380 tgtacaattt agcatcgagt aaagcgtatg atctctcgta atttaatctc gcgaaaacag   4440
aaggtagggc ttcatctaaa gcttggttca actccgggat tgaatataca ttaataggtt   4500
tagcagaact catcttgaac aggcgtctct tttccttaca ataacttgtg cttttccttc   4560
tataattccg tttcaacgtg tacaattgtc atttttgtc tggtatgatt ttgcagaact   4620
gaaaaaatct cttaaatgtt ccgcctcatc aagaaggcat attcctttac aaaagtacat   4680
```

```
tgatcttaca agaagctagc taatggtact atttaaaaaa caactacact ccatcaatac    4740
ataaaattgt tatgatagac ttgagggacg g                                  4771

<210> SEQ ID NO 39
<211> LENGTH: 8719
<212> TYPE: DNA
<213> ORGANISM: Artificial Sequence
<220> FEATURE:
<223> OTHER INFORMATION: Sc pTEF1-Sc ARO4-OFP-Sc pPGK-cre recomb-Sc
      CYC1t-Sc URA3-Amp R integration fragment

<400> SEQUENCE: 39
atcacatagg aagcaacagg cgcgttggac ttttaatttt cgaggaccgc gaatccttac      60
atcacaccca atcccccaca agtgatcccc cacacaccat agcttcaaaa tgtttctact     120 cctttttac  tcttccagat tttctcggac tccgcgcatc gccgtaccac ttcaaaacac     180
ccaagcacag catactaaat ttcccctctt tcttcctcta gggtgtcgtt aattacccgt     240
actaaaggtt tggaaaagaa aaaagagacc gcctcgtttc tttttcttcg tcgaaaaagg     300
caataaaaat tttatcacg  tttcttttc  ttgaaaattt tttttttga  ttttttctc     360 tttcgatgac ctcccattga tatttaagtt aataaacggt cttcaatttc tcaagtttca     420
gtttcatttt tcttgttcta ttacaacttt tttacttct  tgctcattag aaagaaagca     480
tagcaatcta atctaagttt taattacaaa tctagaatga gtgaatctcc aatgttcgct     540
gccaacggca tgccaaaggt aaatcaaggt gctgaagaag atgtcagaat tttaggttac     600
gacccattag cttctccagc tctccttcaa gtgcaaatcc cagccacacc aacttctttg     660
gaaactgcca agagaggtag aagagaagct atagatatta ttaccggtaa agacgacaga     720
gttcttgtca ttgtcggtcc ttgttccatc catgatcttg aagccgctca agaatacgct     780
ttgagattaa agaaattgtc agatgaatta aaaggtgatt tatccatcat tatgagagca     840
tacttggaga agccaagaac aaccgtcggc tggaaaggtc taattaatga ccctgatgtt     900
aacaacactt tcaacatcaa caagggtttg caatccgcta gacaattgtt tgtcaacttg     960
acaaatatcg gtttgccaat tggttctgaa atgcttgata ccatttctcc taaatacttg    1020
gctgatttgg tctccttcgg tgccattggt gccagaacca ccgaatctca actgcacaga    1080
gaattggcct ccggtttgtc tttcccagtt ggtttcaaga acggtaccga tggtaccta     1140 aatgttgctg tggatgcttg tcaagccgct gctcattctc accatttcat gggtgttact     1200
aagcatggtg ttgctgctat caccactact aagggtaacg aacactgctt cgttattcta    1260
agaggtggta aaagggtac  caactacgac gctaagtccg ttgcagaagc taaggctcaa    1320
ttgcctgccg gttccaacgg tctaatgatt gactactctc acggtaactc caataaggat    1380
ttcagaaacc aaccaaaggt caatgacgtt gtttgtgagc aaatcgctaa cggtgaaaac    1440
gccattaccg gtgtcatgat tgaatcaaac atcaacgaag gtaaccaagg catcccagcc    1500
gaaggtaaag ccggcttgaa atatggtgtt tccatcactg atgcttgtat aggttgggaa    1560
actactgaag acgtcttgag gaaattggct gctgctgtca gacaaagaag agaagttaac    1620
aagaaataga tgttttttta atgatatatg taacgtacat tctttcctct accactgcca    1680
attcggtatt atttaattgt gtttagcgct atttactaat taactagaaa ctcaattttt    1740
aaaggcaaag ctcgctgacc tttcactgat ttcgtggatg ttatactatc agttactctt    1800
ctgcaaaaaa aaattgagtc atatcgtagc tttgggatta ttttttctctc tctccacggc    1860 taattaggtg atcatgaaaa aatgaaaaat tcatgagaaa agagtcagac atcgaaacat    1920
```

```
acataagttg atattccttt gatatcgacg actactcaat caggttttaa aagaaaagag   1980
gcagctattg aagtagcagt atccagttta ggttttttaa ttatttacaa gtaaagaaaa   2040
agagaatgcc ggtcgttcac ggcggccgcg ccagaaaaag gaagtgtttc cctccttctt   2100
gaattgatgt taccctcata aagcacgtgg cctcttatcg agaaagaaat taccgtcgct   2160
cgtgatttgt ttgcaaaaag aacaaaactg aaaaaaccca gacacgctcg acttcctgtc   2220
ttcctattga ttgcagcttc caatttcgtc acacaacaag gtcctagcga cggctcacag   2280
gttttgtaac aagcaatcga aggttctgga atggcgggaa agggtttagt accacatgct   2340
atgatgccca ctgtgatctc cagagcaaag ttcgttcgat cgtactgtta ctctctctct   2400
ttcaaacaga attgtccgaa tcgtgtgaca acaacagcct gttctcacac actctttttct  2460 tctaaccaag ggggtggttt agtttagtag aacctcgtga aacttacatt tacatatata   2520
taaacttgca taaattggtc aatgcaagaa atacatattt ggtcttttct aattcgtagt   2580
ttttcaagtt cttagatgct ttcttttttct cttttttaca gatcatcaac tctttttttac  2640 agatcatcaa ggaagtaatt atctactttt tacaagaatt catgtctaat ttacttactg   2700
ttcaccaaaa cttgcctgca ttaccagttg acgcaacctc cgatgaagtc agaaagaacc   2760
ttatggatat gtttagagat agacaagctt tctccgaaca tacttggaaa atgttattat   2820
ccgtttgtag atcctgggcc gcttggtgta aacttaacaa tagaaaatgg tttcctgctg   2880
aaccagaaga cgtcagagat tacttacttt acttacaagc tagaggtttg gctgttaaaa   2940
ctatccaaca acacttaggt caattgaata tgttacacag aagatccggt ttaccaagac   3000
catccgattc caacgcagtt tcccttgtta tgagaagaat tagaaaagaa aatgttgacg   3060
ctggtgaaag agctaaacaa gcattagcat ttgaaagaac cgatttcgat caagttagat   3120
ccttaatgga aaattccgat agatgtcaag atattagaaa cttagctttc ttaggtattg   3180
cttacaacac attattaaga atcgctgaaa ttgctagaat tagagttaaa gatatttcaa   3240
gaaccgatgg cggtagaatg ttaatccaca ttggcagaac aaaaaccttta gtctccacag   3300 caggcgtcga aaaagcatta tcattaggtg ttactaaatt agttgaacgt tggatttccg   3360
tttccggtgt tgcagatgac ccaaacaact acttattctg tcgtgttaga aaaaatggtg   3420
ttgccgctcc ttccgctacc tcacaattat ccacaagagc attagaaggc attttttgaag  3480 ctacccacag acttatttat ggtgcaaaag acgattccgg tcaaagatat ttagcttggt   3540
ctggtcattc cgctagagtt ggtgccgcaa gagacatggc aagagctggt gtttctattc   3600
ctgaaattat gcaagccggt ggttggacta atgttaacat tgttatgaac tatatcagaa   3660
acttagattc cgaaacaggt gctatggtta gattacttga agacggtgat taagctagct   3720
aagatccgct ctaaccgaaa aggaaggagt tagacaacct gaagtctagg tcccctatta   3780
tttttttata gttatgttag tattaagaac gttatttata tttcaaattt ttctttttt     3840 tctgtacaga cgcgtgtacg catgtaacat tatactgaaa accttgcttg agaaggtttt   3900
gggacgctcg aaggagctcc aattcgccct atagtgagtc gtattacaat tcactggccg   3960
tcgttttaca acgtcgtgac tgggaaaacc ctggcgttac ccaacttaat cgccttgcag   4020
cacatccccc cttcgccagc tggcgtaata gcgaagaggc ccgcaccgat cgcccttccc   4080
aacagttgcg cagcctgaat ggcgaatggc gcgacgcgcc ctgtagcggc gcattaagcg   4140
cggcgggtgt ggtggttacg cgcagcgtga ccgctacact tgccagcgcc ctagcgcccg   4200
ctcctttcgc tttcttccct tcctttctcg ccacgttcgc cggctttccc cgtcaagctc   4260
```

```
taaatcgggg gctcccttta gggttccgat ttagtgcttt acggcacctc gaccccaaaa   4320
aacttgatta gggtgatggt tcacgtagtg ggccatcgcc ctgatagacg gttttttcgcc  4380 ctttgacgtt ggagtccacg ttctttaata gtggactctt gttccaaact ggaacaacac   4440
tcaaccctat ctcggtctat tcttttgatt tataagggat tttgccgatt tcggcctatt   4500
ggttaaaaaa tgagctgatt taacaaaaat ttaacgcgaa ttttaacaaa atattaacgt   4560
ttacaatttc ctgatgcggt attttctcct tacgcatctg tgcggtattt cacaccgcag   4620
ggtaataact gatataatta aattgaagct ctaatttgtg agtttagtat acatgcattt   4680
acttataata cagttttta gttttgctgg ccgcatcttc tcaaatatgc ttcccagcct    4740
gcttttctgt aacgttcacc ctctacctta gcatcccttc cctttgcaaa tagtcctctt   4800
ccaacaataa taatgtcaga tcctgtagag accacatcat ccacggttct atactgttga   4860
cccaatgcgt ctcccttgtc atctaaaccc acaccgggtg tcataatcaa ccaatcgtaa   4920
ccttcatctc ttccacccat gtctctttga gcaataaagc cgataacaaa atctttgtcg   4980
ctcttcgcaa tgtcaacagt acccttagta tattctccag tagatagga gcccttgcat   5040 gacaattctg ctaacatcaa aaggcctcta ggttcctttg ttacttcttc tgccgcctgc   5100
ttcaaaccgc taacaatacc tgggcccacc acaccgtgtg cattcgtaat gtctgcccat   5160
tctgctattc tgtatacacc cgcagagtac tgcaatttga ctgtattacc aatgtcagca   5220
aattttctgt cttcgaagag taaaaaattg tacttggcgg ataatgcctt tagcggctta   5280
actgtgccct ccatggaaaa atcagtcaag atatccacat gtgtttttag taaacaaatt   5340
ttgggaccta atgcttcaac taactccagt aattccttgg tggtacgaac atccaatgaa   5400
gcacacaagt ttgtttgctt ttcgtgcatg atattaaata gcttggcagc aacaggacta   5460
ggatgagtag cagcacgttc cttatatgta gctttcgaca tgatttatct tcgtttcctg   5520 caggttttg ttctgtgcag ttgggttaag aatactgggc aatttcatgt ttcttcaaca    5580
ctacatatgc gtatatatac caatctaagt ctgtgctcct tccttcgttc ttccttctgt   5640
tcggagatta ccgaatcaaa aaatttcaa agaaaccgaa atcaaaaaaa agaataaaaa    5700
aaaaatgatg aattgaattg aaaagcgtgg tgcactctca gtacaatctg ctctgatgcc   5760
gcatagttaa gccagccccg acacccgcca acacccgctg acgcgccctg acgggcttgt   5820
ctgctcccgg catccgctta cagacaagct gtgaccgtct ccgggagctg catgtgtcag   5880
aggttttcac cgtcatcacc gaaacgcgcg agacgaaagg gcctcgtgat acgcctattt   5940
ttataggtta atgtcatgat aataatggtt tcttaggacg gatcgcttgc ctgtaactta   6000
cacgcgcctc gtatctttta atgatggaat aatttgggaa tttactctgt gtttatttat   6060
ttttatgttt tgtatttgga ttttagaaag taaataaaga aggtagaaga gttacggaat   6120
gaagaaaaaa aaataaacaa aggtttaaaa aatttcaaca aaaagcgtac tttacatata   6180
tatttattag acaagaaaag cagattaaat agatatacat tcgattaacg ataagtaaaa   6240
tgtaaaatca caggattttc gtgtgtggtc ttctacacag acaagatgaa acaattcggc   6300
attaatacct gagagcagga agagcaagat aaaaggtagt atttgttggc gatcccccta   6360
gagtctttta catcttcgga aaacaaaaac tattttttct ttaatttctt ttttacttt    6420 ctatttttaa tttatatatt tatattaaaa aatttaaatt ataattattt ttatagcacg   6480
tgatgaaaag gacccaggtg gcactttcg gggaaatgtg cgcggaaccc ctatttgttt    6540 attttctaa atacattcaa atatgtatcc gctcatgaga caataaccct gataaatgct   6600
tcaataatat tgaaaaagga agagtatgag tattcaacat ttccgtgtcg cccttattcc  6660
```

-continued

```
cttttttgcg gcattttgcc ttcctgtttt tgctcaccca gaaacgctgg tgaaagtaaa    6720
agatgctgaa gatcagttgg gtgcacgagt gggttacatc gaactggatc tcaacagcgg    6780
taagatcctt gagagttttc gccccgaaga acgttttcca atgatgagca cttttaaagt    6840
tctgctatgt ggcgcggtat tatcccgtat tgacgccggg caagagcaac tcggtcgccg    6900
catacactat tctcagaatg acttggttga gtactcacca gtcacagaaa agcatcttac    6960
ggatggcatg acagtaagag aattatgcag tgctgccata accatgagtg ataacactgc    7020
ggccaactta cttctgacaa cgatcggagg accgaaggag ctaaccgctt ttttcacaa    7080 catgggggat catgtaactc gccttgatcg ttgggaaccg gagctgaatg aagccatacc    7140
aaacgacgag cgtgacacca cgatgcctgt agcaatggca acaacgttgc gcaaactatt    7200
aactggcgaa ctacttactc tagcttcccg gcaacaatta atagactgga tggaggcgga    7260
taaagttgca ggaccacttc tgcgctcggc ccttccggct ggctggttta ttgctgataa    7320
atctggagcc ggtgagcgtg ggtctcgcgg tatcattgca gcactgggc cagatggtaa    7380 gccctcccgt atcgtagtta tctacacgac gggcagtcag gcaactatgg atgaacgaaa    7440
tagacagatc gctgagatag gtgcctcact gattaagcat tggtaactgt cagaccaagt    7500
ttactcatat atactttaga ttgatttaaa acttcatttt taatttaaaa ggatctaggt    7560
gaagatcctt tttgataatc tcatgaccaa aatcccttaa cgtgagtttt cgttccactg    7620
agcgtcagac cccgtagaaa agatcaaagg atcttcttga gatcctttt ttctgcgcgt    7680 aatctgctgc ttgcaaacaa aaaaaccacc gctaccagcg gtggtttgtt tgccggatca    7740
agagctacca actctttttc cgaaggtaac tggcttcagc agagcgcaga taccaaatac    7800
tgtccttcta gtgtagccgt agttaggcca ccacttcaag aactctgtag caccgcctac    7860
atacctcgct ctgctaatcc tgttaccagt ggctgctgcc agtggcgata agtcgtgtct    7920
taccgggttg gactcaagac gatagttacc ggataaggcg cagcggtcgg gctgaacggg    7980
gggttcgtgc acacagccca gcttggagcg aacgacctac accgaactga gatacctaca    8040
gcgtgagcat tgagaaagcg ccacgcttcc cgaaggga gaaggcggaca ggtatccggt    8100 aagcggcagg gtcggaacag gagagcgcac gagggagctt ccaggggga acgcctggta    8160 tctttatagt cctgtcgggt ttcgccacct ctgacttgag cgtcgatttt tgtgatgctc    8220
gtcagggggg ccgagcctat ggaaaaacgc cagcaacgcg gcctttttac ggttcctggc    8280
cttttgctgg ccttttgctc acatgttctt tcctgcgtta tcccctgatt ctgtggataa    8340
ccgtattacc gcctttgagt gagctgatac cgctcgccgc agccgaacga ccgagcgcag    8400
cgagtcagtg agcgaggaag cggaagagcg cccaatacgc aaaccgcctc tccccgcgcg    8460
ttggccgatt cattaatgca gctggcacga caggtttccc gactggaaag cgggcagtga    8520
gcgcaacgca attaatgtga gttacctcac tcattaggca ccccaggctt tacactttat    8580
gcttccggct cctatgttgt gtggaattgt gagcggataa caatttcaca caggaaacag    8640
ctatgaccat gattacgcca agctcggaat taaccctcac taaagggaac aaaagctggg    8700
taccgggccc cccctcgag                                                 8719
```

<210> SEQ ID NO 40
<211> LENGTH: 1980
<212> TYPE: DNA
<213> ORGANISM: Artificial Sequence
<220> FEATURE:
<223> OTHER INFORMATION: Locus C-Sc URA3 integration fragment

<400> SEQUENCE: 40

```
agatgctata tactaatata ggcatacttg ataatgaaaa ctataaatcg taaagacata      60
agagatccgc tcactatagg gcgaattggg ccctctagat gcatgctcga gcggccgcca     120
gtgtgatgga tatctgcaga attcgcccct gctagcggca acggttcatc atctcatgga     180
tctgcacatg aacaaacacc agagtcaaac gacgttgaaa ttgaggctac tgcgccaatt    240
gatgacaata cagacgatga taacaaaccg aagttatctg atgtagaaaa ggattagaga     300
tgctaagaga tagtgatgat atttcataaa taatgtaatt ctatatatgt taattacctt     360
ttttgcgagg catatttatg gtgaaggata agttttgacc atcaaagaag gttaatgtgg     420
ctgtggtttc agggtccata aagcttttca attcatcttt ttttttttg ttcttttttt      480
tgattccggt ttctttgaaa tttttttgat tcggtaatct ccgagcagaa ggaagaacga     540
aggaaggagc acagacttag attggtatat atacgcatat gtggtgttga agaaacatga    600
aattgcccag tattcttaac ccaactgcac agaacaaaaa cctgcaggaa acgaagataa    660
atcatgtcga aagctacata taaggaacgt gctgctactc atcctagtcc tgttgctgcc     720
aagctattta atatcatgca cgaaaagcaa acaaacttgt gtgcttcatt ggatgttcgt     780
accaccaagg aattactgga gttagttgaa gcattaggtc ccaaaatttg tttactaaaa     840
acacatgtgg atatcttgac tgattttttcc atggagggca cagttaagcc gctaaaggca    900
ttatccgcca agtacaattt tttactcttc gaagacagaa aatttgctga cattggtaat    960
acagtcaaat tgcagtactc tgcgggtgta tacagaatag cagaatgggc agacattacg   1020
aatgcacacg gtgtggtggg cccaggtatt gttagcggtt tgaagcaggc ggcggaagaa   1080
gtaacaaagg aacctagagg cccttttgatg ttagcagaat tgtcatgcaa gggctcccta    1140
gctactggag aatatactaa gggtactgtt gacattgcga agagcgacaa agattttgtt    1200
atcggctttta ttgctcaaag agacatgggt ggaagagatg aaggttacga ttggttgatt    1260
atgacacccg gtgtgggttt agatgacaag ggagacgcat gggtcaaca gtatagaacc    1320
gtggatgatg tggtctctac aggatctgac attattattg ttggaagagg actatttgca   1380
aagggaaggt atgctaaggt agagggtgaa cgttacagaa aagcaggctg ggaagcatat   1440
ttgagaagat gcggccagca aaactaaaaa actgtattat aagtaaatgc atgtatacta   1500
aactcacaaa ttagagcttc aatttaatta tatcagttat tacccgggaa tctcggtcgt   1560
aatgattttt ataatgacga aaaaaaaaaa attggaaaga aaaagcttca tggcctttat   1620
aaaaaggaac catccaatac ctcgccagaa ccaagtaaca gtattttacg gggcacaaat   1680
caagaacaat aagacaggac tgtaaagatg gacgcattga actccaaaga acaacaagag   1740
ttccaaaaag tagtggaaca aaagcaaatg aaggatttca tgcgtttgcc gcgggcggcc   1800
gcaagggcga attccagcac actggcggcc gttactagtg gatccgagct cggtaccaag   1860
cttgatgcat agcttgagta ttctatagtg tcacctaaat agcttggcgt aatcatggtc   1920
atagctgtgt gtattacgat atagttaata gttgatagtt gattgtatgc ttttttgtagc   1980
```

<210> SEQ ID NO 41
<211> LENGTH: 3476
<212> TYPE: DNA
<213> ORGANISM: Artificial Sequence
<220> FEATURE:
<223> OTHER INFORMATION: Locus C-Sc URA3-loxP-Sc TEF1t-An amdS-Sc pTEF1-loxP -Sc URA3 integration fragment

<400> SEQUENCE: 41

-continued

| | | | | | |
|---|---|---|---|---|---|
| ggtaaataga | atatcaagct | acaaaaagca | tacaatcaac | tatcaactat | taactatatc | 60 |
| gtaatacaca | cagctatgac | catgattacg | ccaagcttgg | taccgagctc | ctactgcgcc | 120 |
| aattgatgac | aatacagacg | atgataacaa | accgaagtta | tctgatgtag | aaaaggatta | 180 |
| aagatgctaa | gagatagtga | tgatatttca | taaataatgt | aattctatat | atgttaatta | 240 |
| cctttttgc | gaggcatatt | tatggtgaag | aataagtttt | gaccatcaaa | gaaggttaat | 300 |
| gtggctgtgg | tttcagggtc | cataaagctt | ttcaattcat | catttttttt | ttattctttt | 360 |
| ttttgattcc | ggtttccttg | aaattttttt | gattcggtaa | tctccgaaca | gaaggaagaa | 420 |
| cgaaggaagg | agcacagact | tagattggta | tatatacgca | tatgtagtgt | tgaagaaaca | 480 |
| tgaaattgcc | cagtattctt | aacccaactg | cacagaacaa | aaatctgcag | gaaacgaaga | 540 |
| taaagcggcc | gcataacttc | gtatagcata | cattatacga | agttatcgcc | tgttaagata | 600 |
| taactgaaaa | aagaggggaa | ttttagata | ctgaaatgat | attttagaat | aaccagacta | 660 |
| tatataagga | taaattacaa | aaaattaact | aatagataag | atttaaatat | aaaagatatg | 720 |
| caactagaaa | agtcttatca | atctccttat | ggagtgacga | cgttacccaa | caatttaccg | 780 |
| acttcttcgg | cgatagccaa | agttctctct | tcggacaatc | ttctaccaat | aacttgaaca | 840 |
| gcaacaggag | caccgtgata | agcctctggg | tcgtattctt | cttgaaccaa | agcatccaat | 900 |
| tcggaaacag | cttaaaaga | ttcgttcttc | ttatcaatat | tcttatcagc | gaaagtgact | 960 |
| gggacgacaa | cagaggtgaa | atccaataag | ttaataacgg | aggcgtaacc | gtagtatctg | 1020 |
| aattgatcgt | gtctgacagc | ggcggtagga | gtaattggag | cgataatagc | gtccaattcc | 1080 |
| ttaccagctt | tttcttcagc | ttcacgccac | ttttccaagt | attccatttg | atagttccac | 1140 |
| ttttgtaaat | gagtgtccca | caattcgttc | atgttaacag | ccttaatatt | tgggttcaac | 1200 |
| aagtccttaa | tgttagggat | ggctggctca | ccagaggcag | aaatgtctct | catgacgtcg | 1260 |
| gcagaaccat | cagcagcata | gatgtgggaa | atcaagtcat | gaccgaaatc | atgcttgtat | 1320 |
| ggagtccatg | gagtaacggt | gtgaccagcc | ttggccaaag | cggcaacggt | agtttcgaca | 1380 |
| ccacgtaaaa | ttggtgggtg | tggcaagacg | ttaccgtcga | aattgtaata | accaatgttc | 1440 |
| aaaccaccat | tcttaatctt | agaggcaatg | atgtcagatt | cagattgtct | ccatggcatt | 1500 |
| gggatgacct | tagagtcgta | cttccaaggt | tcttgaccca | agacagattt | ggtgaacaat | 1560 |
| ctcaagtctt | cgacggagtg | agtgatagga | ccaacgacgg | agtgaacggt | ttcttgacct | 1620 |
| tccatagagt | tagccatttt | agcatatggc | aatctaccgt | gagatggtct | caaaccgtat | 1680 |
| aaaaagttga | aagcagctgg | gactctaatg | gaaccaccaa | tgtcagtacc | gacaccaata | 1740 |
| acaccacctc | taataccaac | aatagcacct | tcaccaccag | aagaaccacc | acaggaccaa | 1800 |
| tttttgtttc | ttggattgac | agttctacca | atgatgttgt | tgacggtttc | acagaccatc | 1860 |
| aaggtttgtg | ggacagaggt | cttaacgtag | aaaacagcac | cagcttttct | caacatggtg | 1920 |
| gttaagacgg | aatcaccttc | atcgtatttg | tttaaccagg | aaatgtaacc | catggaggtt | 1980 |
| tcgtaaccct | taacacgcaa | ttggtccttt | aaagagattg | gtaaaccgtg | taatggacca | 2040 |
| actggtctct | tatgcttagc | gtagtattca | tctaattctc | tagcttgagc | taaagcagca | 2100 |
| tctgggaaga | attcgtgagc | acagttggtt | aattgttgag | caatagcagc | tctcttacaa | 2160 |
| aaagccaaag | tgacttcaac | agaagtcaac | tcaccagcgg | ccaacttgga | gaccaaatca | 2220 |
| gcagcagagg | cttcggtaat | cttcaattca | gcctcagaca | aaataccgga | cttctttggg | 2280 |
| aaatcaataa | cggaatcttc | ggcaggcaaa | gtttgaacct | tccattcgtc | aggaatggtt | 2340 |
| ttagccaaac | gggcacgttt | gtcggcggcc | aattcttccc | aggattgtgg | cattttgtaa | 2400 |

```
ttaaaactta gattagattg ctatgctttc tttctaatga gcaagaagta aaaaaagttg    2460
taatagaaca agaaaaacga aactgaaact tgagaaattg aagaccattt attaacttaa    2520
atatcaatgg gaggtcatcg aaagagaaaa aaatcaaaaa aaaattttt caagaaaaag     2580 aaacgtgata aaaatttta ttgccttttt cgacgaagaa aaagaaacga ggcggtctct    2640 ttttctttt ccaaacettt agtacgggta attaacgcca ccctagagga agaaagaggg     2700
gaaatttagt atgctgtgct tgggtgtttt gaagtggtac ggcgatgcgc ggagtccgag    2760
aaaatctgga agagtaaaaa aggagtagaa acattttgaa gctatggtgt gtggggatc    2820 acttgtgggg gattgggtgt gatgtaagga taacttcgta tagcatacat tatacgaagt    2880
tatgcggccg cgagaagatg cggccagcaa aactaaaaaa ctgtattata agtaaatgca    2940
tgtatactaa actcacaaat tagagcttca atttaattat atcagttatt acccgggaat    3000
ctcggtcgta atgattttta taatgacgaa aaaaaaaaa ttggaaagaa aaagcttcat     3060
ggcctttata aaaaggaacc atccaatacc tcgccagaac caagtaacag tattttacgg    3120
ggcacaaatc aagaacaata agacaggact gtaaagatgg acgcattgaa ctccaaagaa    3180
caacaagagt tccaaaaagt agtggaacaa agcaaatgaa aggatttcat gcgtttgtac    3240
tctaatctgg tagaaagatg ttttacagac tgtgtcaatg acttcacaac atcaaagcta    3300
accaataagg aacaaacatg catcatgaag tgctcagaaa agttcttgaa gcatagcgaa    3360
cgtgtagggc agcgtttcca agagggccca attcgcccta tagtgagcgg atctcttatg    3420
tctttacgat ttatagtttt cattatcaag tatgcctata ttagtatata gcatct        3476
```

<210> SEQ ID NO 42
<211> LENGTH: 2662
<212> TYPE: DNA
<213> ORGANISM: Artificial Sequence
<220> FEATURE:
<223> OTHER INFORMATION: Locus C-loxP-Sc TEF1t-An amdS-Sc pTEF1-loxP
      integration fragment

<400> SEQUENCE: 42

```
ggtaaataga atatcaagct acaaaaagca tacaatcaac tatcaactat taactatatc     60
gtaatacaca cagctatgac catgattacg ccaagcttgg taccgagctc ggatccacta    120
gtaacggccg ccagtgtgct ggaattcgcc cttatattag cggccgcata acttcgtata    180
gcatacatta tacgaagtta tcgcctgtta agatataact gaaaaaagag gggaattttt    240
agatactgaa atgatatttt agaataacca gactatatat aaggataaat tacaaaaaat    300
taactaatag ataagattta aatataaaag atatgcaact agaaaagtct tatcaatctc    360
cttatggagt gacgacgtta cccaacaatt taccgacttc ttcggcgata gccaaagttc    420
tctcttcgga caatcttcta ccaataactt gaacagcaac aggagcaccg tgataagcct    480
ctgggtcgta ttcttcttga accaaagcat ccaattcgga aacagcttta aaagattcgt    540
tcttcttatc aatattctta tcagcgaaag tgactgggac gacaacagag gtgaaatcca    600
ataagttaat aacggaggcg taaccgtagt atctgaattg atcgtgtctg acagcggcgg    660
taggagtaat tggagcgata atagcgtcca attccttacc agcttttttct tcagcttcac    720 gccactttc caagtattcc atttgatagt tccacttttg taaatgagtg tcccacaatt     780
cgttcatgtt aacagccta atatttgggt tcaacaagtc cttaatgtta gggatggctg    840
gctcaccaga ggcagaaatg tctctcatga cgtcggcaga accatcagca gcatagatgt    900
gggaaatcaa gtcatgacag aaatcatgct tgtatggagt ccatggagta acggtgtgac    960
```

-continued

| | |
|---|---|
| cagccttggc caaagcggca acggtagttt cgacaccacg taaaattggt gggtgtggca | 1020 |
| agacgttacc gtcgaaattg taataaccaa tgttcaaacc accattctta atcttagagg | 1080 |
| caatgatgtc agattcagat tgtctccatg gcattgggat gaccttagag tcgtacttcc | 1140 |
| aaggttcttg acccaagaca gatttggtga acaatctcaa gtcttcgacg gagtgagtga | 1200 |
| taggaccaac gacggagtga acggtttctt gaccttccat agagttagcc attttagcat | 1260 |
| atggcaatct accgtgagat ggtctcaaac cgtataaaaa gttgaaagca gctgggactc | 1320 |
| taatggaacc accaatgtca gtaccgacac caataacacc acctctaata ccaacaatag | 1380 |
| caccttcacc accagaagaa ccaccacagg accaattttt gtttcttgga ttgacagttc | 1440 |
| taccaatgat gttgttgacg gtttcacaga ccatcaaggt ttgtgggaca gaggtcttaa | 1500 |
| cgtagaaaac agcaccagct tttctcaaca tggtggttaa gacggaatca ccttcatcgt | 1560 |
| atttgtttaa ccaggaaatg taacccatgg aggtttcgta acccttaaca cgcaattggt | 1620 |
| cctttaaaga gattggtaaa ccgtgtaatg gaccaactgg tctcttatgc ttagcgtagt | 1680 |
| attcatctaa ttctctagct tgagctaaag cagcatctgg gaagaattcg tgagcacagt | 1740 |
| tggttaattg ttgagcaata gcagctctct tacaaaaagc caaagtgact tcaacagaag | 1800 |
| tcaactcacc agcggccaac ttggagacca aatcagcagc agaggcttcg gtaatcttca | 1860 |
| attcagcctc agacaaaata ccggacttct ttgggaaatc aataacgaaa tcttcggcag | 1920 |
| gcaaagtttg aaccttccat tcgtcaggaa tggttttagc caaacgggca cgtttgtcgg | 1980 |
| cggccaattc ttcccaggat tgtggcattt tgtaattaaa acttagatta gattgctatg | 2040 |
| ctttctttct aatgagcaag aagtaaaaaa agttgtaata gaacaagaaa aacgaaactg | 2100 |
| aaacttgaga aattgaagac catttattaa cttaaatatc aatgggaggt catcgaaaga | 2160 |
| gaaaaaaatc aaaaaaaaaa ttttttcaaga aaaagaaacg tgataaaaat ttttattgcc | 2220 |
| tttttcgacg aagaaaaaga aacgaggcgg tctctttttt cttttccaaa cctttagtac | 2280 |
| gggtaattaa cgccacccta gaggaagaaa gaggggaaat ttagtatgct gtgcttgggt | 2340 |
| gttttgaagt ggtacggcga tgcgcggagt ccgagaaaat ctggaagagt aaaaaaggag | 2400 |
| tagaaacatt ttgaagctat ggtgtgtggg ggatcacttg tgggggattg ggtgtgatgt | 2460 |
| aaggataact tcgtatagca tacattatac gaagttatgc ggccgctaat ataagggcga | 2520 |
| attctgcaga tatccatcac actggcggcc gctcgagcat gcatctagag ggcccaattc | 2580 |
| gccctatagt gagcggatct cttatgtctt tacgatttat agttttcatt atcaagtatg | 2640 |
| cctatattag tatatagcat ct | 2662 |

<210> SEQ ID NO 43
<211> LENGTH: 1684
<212> TYPE: DNA
<213> ORGANISM: Artificial Sequence
<220> FEATURE:
<223> OTHER INFORMATION: Sc URA3

<400> SEQUENCE: 43

| | |
|---|---|
| ggccgccagt gtgatggata tctgcagaat tcgcccttgc tagcggcaac ggttcatcat | 60 |
| ctcatggatc tgcacatgaa caaacaccag agtcaaacga cgttgaaatt gaggctactg | 120 |
| cgccaattga tgacaataca gacgatgata caaaccgaa gttatctgat gtagaaaagg | 180 |
| attagagatg ctaagagata gtgatgatat tcataaaata atgtaattct atatatgtta | 240 |
| attaccttttt ttgcgaggca tatttatggt gaaggataag ttttgaccat caagaaggt | 300 |

```
taatgtggct gtggtttcag ggtccataaa gcttttcaat tcatctttt ttttttttgtt    360
cttttttttg attccggttt ctttgaaatt tttttgattc ggtaatctcc gagcagaagg    420
aagaacgaag gaaggagcac agacttagat tggtatatat acgcatatgt ggtgttgaag    480
aaacatgaaa ttgcccagta ttcttaaccc aactgcacag aacaaaaacc tgcaggaaac    540
gaagataaat catgtcgaaa gctacatata aggaacgtgc tgctactcat cctagtcctg    600
ttgctgccaa gctatttaat atcatgcacg aaaagcaaac aaacttgtgt gcttcattgg    660
atgttcgtac caccaaggaa ttactggagt tagttgaagc attaggtccc aaaatttgtt    720
tactaaaaac acatgtggat atcttgactg attttccat ggagggcaca gttaagccgc    780
taaaggcatt atccgccaag tacaattttt tactcttcga agacagaaaa tttgctgaca    840
ttggtaatac agtcaaattg cagtactctg cgggtgtata cagaatagca gaatgggcag    900
acattacgaa tgcacacggt gtggtgggcc caggtattgt tagcggtttg aagcaggcgg    960
cggaagaagt aacaaaggaa cctagaggcc ttttgatgtt agcagaattg tcatgcaagg   1020
gctccctagc tactggagaa tatactaagg gtactgttga cattgcgaag agcgacaaag   1080
attttgttat cggctttatt gctcaaagag acatgggtgg aagagatgaa ggttacgatt   1140
ggttgattat gacaccggt gtgggtttag atgacaaggg agacgcattg ggtcaacagt   1200
atagaaccgt ggatgatgtg gtctctacag gatctgacat tattattgtt ggaagaggac   1260
tatttgcaaa gggaagggat gctaaggtag agggtgaacg ttacagaaaa gcaggctggg   1320
aagcatattt gagaagatgc ggccagcaaa actaaaaaac tgtattataa gtaaatgcat   1380
gtatactaaa ctcacaaatt agagcttcaa tttaattata tcagttatta cccgggaatc   1440
tcggtcgtaa tgatttttat aatgacgaaa aaaaaaaaat tggaaagaaa aagcttcatg   1500
gcctttataa aaaggaacca tccaatacct cgccagaacc aagtaacagt attttacggg   1560
gcacaaatca agaacaataa gacaggactg taaagatgga cgcattgaac tccaaagaac   1620
aacaagagtt ccaaaaagta gtggaacaaa agcaaatgaa ggatttcatg cgtttgccgc   1680
gggc                                                                 1684
```

<210> SEQ ID NO 44
<211> LENGTH: 617
<212> TYPE: PRT
<213> ORGANISM: Saccharomyces mikatae

<400> SEQUENCE: 44

```
Met Lys Asn Phe Ile Ser Leu Val Asn Lys Lys Gly Thr Leu Asp
1               5                   10                  15

Asp Arg Asn Ser Ser Val Pro Glu Ser Ser Ser Gly Ile Ile His Gln
            20                  25                  30

Arg Gly Ala Leu Asn Thr Glu Asp Phe Glu Gly Lys Lys Asp Gly
        35                  40                  45

Ala Phe Glu Leu Gly His Leu Glu Phe Thr Thr Asn Ser Ala Gln Leu
    50                  55                  60

Gly Asp Ser Asp Asp Asp Asn Asp Asn Ala Ile Lys Ile Ala Asn Ala
65                  70                  75                  80

Ala Thr Asp Glu Ala Asn Glu Ala Asn Ser Glu Glu Lys Ser Met Thr
                85                  90                  95

Leu Arg Gln Ala Leu Arg Lys Tyr Pro Lys Ala Ala Leu Trp Ser Ile
            100                 105                 110

Leu Val Ser Thr Thr Leu Val Met Glu Gly Tyr Asp Thr Ala Leu Leu
        115                 120                 125
```

Ser Ala Leu Tyr Ala Leu Pro Val Phe Gln Arg Lys Phe Gly Thr Met
130                 135                 140

Asn Ala Glu Gly Ser Tyr Glu Ile Thr Ser Gln Trp Gln Ile Gly Leu
145                 150                 155                 160

Asn Met Cys Val Leu Cys Gly Glu Met Ile Gly Leu Gln Met Thr Thr
                165                 170                 175

Tyr Met Val Glu Phe Met Gly Asn Arg Tyr Thr Met Ile Thr Ala Leu
                180                 185                 190

Gly Leu Leu Thr Ala Tyr Ile Phe Ile Leu Tyr Tyr Cys Lys Ser Leu
                195                 200                 205

Ala Met Ile Ala Val Gly Gln Ile Leu Ser Ala Met Pro Trp Gly Cys
210                 215                 220

Phe Gln Ser Leu Ala Val Thr Tyr Ala Ser Glu Val Cys Pro Leu Ala
225                 230                 235                 240

Leu Arg Tyr Tyr Met Thr Ser Tyr Ser Asn Ile Cys Trp Leu Phe Gly
                245                 250                 255

Gln Ile Phe Ala Ser Gly Ile Met Lys Asn Ser Gln Glu Asn Leu Gly
                260                 265                 270

Asp Ser Asp Leu Gly Tyr Lys Leu Pro Phe Ala Leu Gln Trp Ile Trp
                275                 280                 285

Pro Ala Pro Leu Ile Ile Gly Ile Phe Phe Ala Pro Glu Ser Pro Trp
                290                 295                 300

Trp Leu Val Arg Lys Asn Lys Ile Ala Glu Ala Lys Lys Ser Leu Asn
305                 310                 315                 320

Arg Ile Leu Ser Gly Thr Ala Ala Glu Arg Glu Ile Gln Val Asp Ile
                325                 330                 335

Thr Leu Lys Gln Ile Glu Met Thr Ile Glu Lys Glu Arg Leu Leu Ala
                340                 345                 350

Ser Lys Ser Gly Ser Phe Phe Asn Cys Phe Lys Gly Val Asp Gly Arg
                355                 360                 365

Arg Thr Arg Leu Ala Cys Leu Thr Trp Val Ala Gln Asn Ser Ser Gly
                370                 375                 380

Ala Val Leu Leu Gly Tyr Ser Thr Tyr Phe Phe Glu Arg Ala Gly Met
385                 390                 395                 400

Ala Thr Asp Lys Ala Phe Thr Phe Ser Leu Ile Gln Tyr Cys Leu Gly
                405                 410                 415

Leu Ala Gly Thr Leu Cys Ser Trp Val Ile Ser Gly Arg Val Gly Arg
                420                 425                 430

Trp Ser Ile Leu Ala Tyr Gly Leu Ala Phe Gln Met Val Cys Leu Phe
                435                 440                 445

Ile Ile Gly Gly Met Gly Phe Ala Ser Gly Ser Asn Ala Ser Asn Gly
                450                 455                 460

Ala Gly Gly Leu Leu Leu Ala Leu Ser Phe Phe Tyr Asn Ala Gly Ile
465                 470                 475                 480

Gly Ala Val Val Tyr Cys Ile Val Ala Glu Ile Pro Ser Ala Glu Leu
                485                 490                 495

Arg Thr Lys Thr Ile Val Met Ala Arg Ile Cys Tyr Asn Leu Met Ala
                500                 505                 510

Val Ile Asn Ala Ile Leu Thr Pro Tyr Met Leu Asn Val Ser Asp Trp
                515                 520                 525

Asn Trp Gly Ala Lys Thr Gly Leu Tyr Trp Gly Gly Phe Thr Ala Val
530                 535                 540

-continued

Thr Leu Ala Trp Val Ile Ile Asp Leu Pro Glu Thr Thr Gly Arg Thr
545                 550                 555                 560

Phe Ser Glu Ile Asn Glu Leu Phe Asn Gln Gly Val Pro Ala Arg Lys
            565                 570                 575

Phe Ala Ser Thr Val Val Asp Pro Phe Gly Lys Gly Gln Arg Gln Asn
            580                 585                 590

Asp Ser Gln Val Asp Asn Val Ile Asp Gln Ser Ser Ser Ala Met Gln
            595                 600                 605

Gln Glu Leu Asn Glu Ala Asn Glu Phe
            610                 615

<210> SEQ ID NO 45
<211> LENGTH: 515
<212> TYPE: PRT
<213> ORGANISM: Saccharomycopsis fibuligera

<400> SEQUENCE: 45

Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
            20                  25                  30

Ala Tyr Ser Gly Tyr Thr Val Ala Arg Ser Asn Phe Thr Gln Trp Ile
            35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
            115                 120                 125

Thr Tyr Thr Leu Gln Arg Val Ser Asn Pro Ser Gly Asn Phe Asp Ser
130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
            165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
            195                 200                 205

Ala Ser Asp Ile Tyr Trp Lys Ile Ile Lys Pro Asp Leu Gln His Val
            210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
            245                 250                 255

Gly Ile Pro Leu Ser Lys Thr Tyr Asn Asp Pro Gly Phe Thr Ser Trp
            260                 265                 270

Leu Glu Lys Gln Lys Asp Ala Leu Asn Ser Tyr Ile Asn Ser Ser Gly
            275                 280                 285

Phe Val Asn Ser Gly Lys Lys His Ile Val Glu Ser Pro Gln Leu Ser
            290                 295                 300

-continued

```
Ser Arg Gly Gly Leu Asp Ser Ala Thr Tyr Ile Ala Ala Leu Ile Thr
305                 310                 315                 320

His Asp Ile Gly Asp Asp Thr Tyr Thr Pro Phe Asn Val Asp Asn
                325                 330                 335

Ser Tyr Val Leu Asn Ser Leu Tyr Tyr Leu Leu Val Asp Asn Lys Asn
                340                 345                 350

Arg Tyr Lys Ile Asn Gly Asn Tyr Lys Ala Gly Ala Ala Val Gly Arg
            355                 360                 365

Tyr Pro Glu Asp Val Tyr Asn Gly Val Gly Thr Ser Glu Gly Asn Pro
        370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Lys Asn Leu Val Ile Glu Lys Leu Asn
                405                 410                 415

Tyr Asp Leu Tyr Asn Ser Phe Ile Ala Asp Leu Ser Lys Ile Asp Ser
                420                 425                 430

Ser Tyr Ala Ser Lys Asp Ser Leu Thr Leu Thr Tyr Gly Ser Asp Asn
            435                 440                 445

Tyr Lys Asn Val Ile Lys Ser Leu Leu Gln Phe Gly Asp Ser Phe Leu
    450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515
```

SUGAR TRANSPORTER-MODIFIED YEAST STRAINS AND METHODS FOR BIOPRODUCT PRODUCTION

CROSS-REFERENCE TO RELATED APPLICATIONS

This application is a national phase application of international application PCT/US2016/067314, filed Dec. 16, 2016, which claims the benefit of U.S. Provisional Patent Application No. 62/268,932, filed Dec. 17, 2015, each of which is hereby incorporated by reference in its entirety.

SEQUENCE LISTING

The entire contents of the ASCII text file entitled "N00309 ST25.txt" created on Jun. 15, 2018, and having a size of 270 kilobytes, is incorporated herein by reference in its entirety.

FIELD OF THE INVENTION

The current invention relates to genetically modified yeast capable of consuming maltulose, genetically modified yeast having a heterologous sugar transporter, and methods for producing ethanol using genetically modified yeast.

BACKGROUND

Ethanol production by fermentation is a well know industrial process. However increasing ethanol yields can be technically difficult. There are various factors that make it challenging for microorganisms to grow in fermentation conditions designed for increased ethanol production. For example, the fermentation media may have increased substrate concentrations to promote ethanol production, but these conditions can have a negative impact on cell growth. Also, increased ethanol concentration and accumulation of undesirable byproducts can be detrimental to cell health. Yeast strains have been selected for tolerance to these conditions, which can result in improved ethanol yields. In particular, the ethanol tolerant strains of the yeast *Saccharomyces cerevisiae* have been used in industrial settings as a workhorse microorganism for producing ethanol.

The components of the fermentation media can have a significant impact on ethanol production. In fermentation processes, a carbohydrate or carbohydrate mixture is present in the media. Starch is a widely available and inexpensive carbohydrate source and can be obtained from a variety of plant sources such as corn, wheat, rice, barley, and the like. Many organisms used for fermentation are not capable of metabolizing starch directly, or else metabolize it slowly and inefficiently. Therefore, it is common to treat starch before feeding it into the fermentation process, in order to break it down into monosaccharides that the organism can ferment easily.

Usually, starch is hydrolyzed to form a mixture of starch hydrolysis products containing glucose (dextrose) which is the predominant monomeric sugar and preferred by fermenting organisms. Starch hydrolysis is typically performed using a strong acid, and will result in a composition that includes starch degradation products. The composition can then be neutralized with a base to increase the pH. Since complete hydrolysis of starch to glucose using acid can be difficult and expensive, it is often not run to completion thereby resulting in a partially hydrolyzed starch composition. The partially-hydrolyzed starch composition is then often treated by adding α-amylase, which can cleave 1,4-bonds in internal regions of the starch molecule resulting in a loss of viscosity of the composition. However, even after treatment with α-amylase some sugar oligomers remain. As such, the acid and α-amylase treated starch composition can further be treated with glucoamylase to promote degradation of these sugar oligomers.

The steps of chemically and enzymatically treating the starch compositions for preparing a fermentation feedstock can result in the formation of low molecular weight sugars that are poorly fermented. For example, in conditions following acid treatment and then neutralization of the composition, isomerization of low molecular weight sugar products may occur. These isomerizations can result in the formation of products such as certain disaccharides that cannot be utilized well by yeast, or that are refractory to the conversion to useful products. Also, the presence of a glucoamylase can contribute to the production of oligosaccharides generated from the reverse conversion of glucose to glucose oligomers by glucoamylases. During fermentation such products can accumulate in the fermentation media and can compromise the fermentation process.

SUMMARY OF THE INVENTION

The current invention is directed to fermentation methods, engineered yeast, and production of bioproducts, such as ethanol. Methods of the invention use a fermentation media comprising starch product, such as partially hydrolyzed starch, comprising one or more oligo sugar(s) such as maltulose, isomaltose, and/or panose. The oligo sugars may be formed in a partially hydrolyzed starch composition at a neutral pH, or which includes a glucoamylase enzyme to form a fermentable carbohydrate composition. Engineered yeast of the invention comprise a heterologous sugar transporter, and are capable of fermentation of the carbohydrate composition while minimizing accumulation of oligo sugars during the fermentation process.

In one embodiment, the invention provides a fermentation method that includes steps of (a) providing a fermentation medium comprising a hydrolyzed starch composition comprising maltulose and an engineered yeast comprising a heterologous di- or tri-glucopyranosyl sugar transporter, wherein maltulose is present at a first concentration of 0.5 g/L or greater at a first time point; and (b) fermenting the carbohydrate composition over a period of time to a second time point, with the maltulose being at a second concentration at this second time point. The second concentration of maltulose is less than a concentration of maltose obtained using a yeast that does have the heterologous sugar transporter, but otherwise identical to the engineered yeast, and under the same fermentation conditions.

The benefits of the engineered yeast of the invention can be understood in its ability to grow in a medium with maltulose as the primary carbon source. Therefore, in another aspect the invention provides a genetically modified yeast comprising a heterologous sugar transporter, wherein the yeast is capable of growing at a rate of 0.02 or greater on modified standard yeast media comprising a carbohydrate composition comprising maltulose is at a concentration of at least 97% (wt), and grown under standard conditions.

In another embodiment, the invention provides a genetically modified Crabtree-positive yeast comprising a heterologous polypeptide (which is a di- or tri-glucopyranosyl sugar transporter) having 90% or greater identity to SEQ ID NO:44. The engineered yeast may further include other genetic modifications in addition to the heterologous sugar transporter, such as a genetic modification that increases alphaglucose cytases, e.g., intracellular isomaltase activity, and/or a heterologous starch-degrading polypeptide, such as a glucoamylase.

In embodiments, the engineered yeast is used in a fermentation method for producing ethanol, such as where the ethanol is produced at a concentration in the range of 80 g/L to 140 g/L in the fermentation medium.

Methods and engineered cells of the invention can provide particular benefit when used to ferment partially hydrolyzed starch compositions that have been treated with an amylolytic enzyme, such as a glucoamylase. Low molecular weight non-glucose sugars, such as maltulose, isomaltose, and panose have been found to form in significant quantities in enzyme-treated starch product compositions. Low molecular weight sugars (e.g., maltulose, etc.) increase as the DE increases. These sugars may also be formed in a hydrolyzed starch composition having a neutral pH. It has been found that these types of sugars are not desirable components in the fermentation media particularly at the later stages of fermentation. These low molecular weight sugars may interfere with product yield not only by hindering fermentation, but also by reacting with fermentation products. While one could add an enzyme to the starch hydrolysate to convert the non-glucose sugars into glucose, it has been found that addition of such an enzyme to a starch hydrolysate material having high glucose concentration tends to render the enzyme less effective.

The present invention provides a robust way to effectively utilize these low molecular weight non-glucose sugars, such as maltulose, during fermentation. The engineered organism of the invention can consume these non-glucose sugars present in the fermentation broth and prevent their accumulation which would otherwise compromise various aspects of the fermentation process. Further, the engineered cell can also include one or more genetic modification(s) that provide enzyme(s) that facilitate conversion of non-glucose sugars into glucose once they are transported into the cell.

In one aspect, the disclosure provides a fermentation method comprising: fermenting a liquid medium comprising glucose oligomers with a genetically engineered yeast comprising a glucoamylase (GA) expressing gene, wherein the amount of ethanol produced in the fermentation is at least 80 g/L at 36 hours or longer after inoculation, the glucose concentration of the medium does not exceed 70 g/L during fermentation, and the total amount of acetaldehyde produced during the fermentation is reduced compared to a fermentation process using a yeast and with a glucose concentration exceeding 80 g/L within 10 hours or less of inoculation. In some embodiments, the genetically engineered yeast is any of the yeasts described herein. In some embodiments, the glucose concentration of the medium does not exceed 80, 75, 70, 65, 60, 55, 50, 45, or 40 g/L during fermentation and the total amount of acetaldehyde produced during the fermentation is reduced compared to a fermentation process using a yeast and with a glucose concentration exceeding 80, 95, 90, 95, 100, or 105 g/L. In some embodiments, the dextrose equivalent (DE) of the medium is less than 20, 25, 30, 35, 40, 45, or 50 within 5 hours or less of inoculation. In some embodiments, the amount of ethanol produced in the fermentation is at least 85, 90, 95, 100, or 105 g/L at 36 hours or longer after inoculation. In some embodiments, the glucose concentration of the medium does not exceed 75, 70, 65, 60, 55, 50, 45, 40, 35, 30, 25, or 20 g/L during fermentation.

In some embodiments, the total amount of acetaldehyde produced during the fermentation is reduced compared to a process where the GA activity is at least 0.8 times the 1×GA activity. In some embodiments, the total amount of acetaldehyde emitted in the fermentation effluent gas is less than 250, 225, 200, 175, 150, 125, 100, or 75 ppm when the carbon dioxide evolution rate (CER) is 100 mmol $CO_2$/(L-h) or greater. In some embodiments, the total amount of acetaldehyde emitted in the fermentation effluent gas is less than 250, 225, 200, 175, 150, or 125 ppm when the carbon dioxide evolution rate (CER) is 50 or greater. In some embodiments, the total amount of acetaldehyde produced in the fermentation is reduced by 30, 40, 50, 60, 70, 80, or 90% compared to a fermentation process using a yeast with a glucose concentration exceeding 90 g/L within 10 hours or less of inoculation.

In some embodiments, the total GA activity of the process is less than 0.8 times the 1×GA activity. In some embodiments, the total GA activity of the process is in the range of 0.675 to 0.8 times the 1×GA activity. In some embodiments, the total GA activity of the process is at least 0.5, 0.55, 0.6, 0.65, or 0.7 times the 1×GA activity and less than 0.8 times the 1×GA activity.

It is also to be understood that the elements or aspects of any embodiment of the processes, methods, or compositions described above can be applied to any other embodiment, as would be understood by a person skilled in the art.

DETAILED DESCRIPTION

Figure 1:
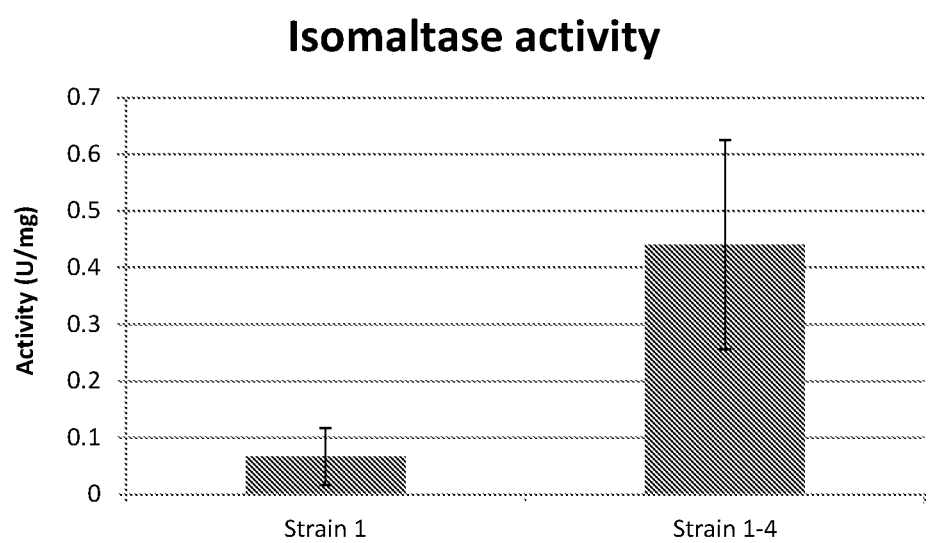
FIG. 1 is a graph showing isomaltase activity in Strain 1 and Strain 1-4.

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

Embodiments of the invention are related to fermentation methods and engineered yeast strains expressing a di- or tri-glucopyranosyl sugar transporter which are able ferment a carbohydrate composition in a fermentation medium which is formed from hydrolyzed (e.g., glucoamylase-treated) starch, wherein the carbohydrate composition comprises one or more oligo sugar(s) such as maltulose, isomaltose, and/or panose.

In preferred embodiments, the genetically modified yeast can be one that expresses a heterologous polypeptide that is a di- or tri-glucopyranosyl sugar transporter and that has 90% or greater identity to SEQ ID NO:44, which is a previously uncharacterized protein. The engineered yeast may further include other genetic modifications in addition to the heterologous sugar transporter, such as a genetic modification that increases intracellular isomaltase activity, and/or a heterologous starch-degrading polypeptide, such as a glucoamylase.

The term "exogenous" as used herein, means that a molecule, such as a nucleic acid, or an activity, such as an enzyme activity, is introduced into the host organism. An exogenous nucleic acid can be introduced in to the host organism by well-known techniques and can be maintained external to the hosts chromosomal material (e.g., maintained on a non-integrating vector), or can be integrated into the host's chromosome, such as by a recombination event. An exogenous nucleic acid can encode an enzyme, or portion thereof, that is either homologous or heterologous to the host organism.

The term "heterologous" refers to a molecule, activity, or genetic arrangement that is different than the molecule, activity, or genetic arrangement naturally found in a referenced organism. Accordingly, a gene or protein that is heterologous to a referenced organism can be a gene or protein not found in that organism, such as a gene or protein that is from a different organism or a gene or protein that is a modified version of a native gene or protein that is introduced into the organism. In the context of the disclosure, a "heterologous di- or tri-glucopyranosyl sugar transporter" refers to a di- or tri-glucopyranosyl sugar transporter polypeptide that is different from a di- or tri-glucopyranosyl sugar transporter polypeptide native to the host organism, if present in the host organism. For example, a specific di- or tri-glucopyranosyl sugar transporter gene found in a first fungal species and exogenously introduced into a second fungal species that is the host organism is "heterologous" to the second fungal organism.

Fermentation using a host cell expressing the heterologous di- or tri-glucopyranosyl sugar transporter gene can be performed in the presence of an enzymatically-treated starch-containing plant material. Starch-containing plant materials can be obtained from any plant and plant part, such as tubers, roots, stems, leaves and seeds. Starch-containing plant materials can be obtained from cereal, such as barley, wheat, maize, rye, sorghum, millet, barley, potatoes, cassava, or rice, and any combination thereof. The plant materials can be processed, such as by methods such as milling, malting, or partially malting. In some embodiments, the starch material is from corn flour, milled corn endosperm, sorghum flour, soybean flour, wheat flour, biomass derived starch, barley flour, or combinations thereof.

A variety of techniques can be used to obtain starch from a plant material. In one technique, a corn wet milling process can be used to provide steep-water, which can provide a starch composition for fermentation. Corn kernels can be steeped and then milled, and separated into their major constituent fractions. Light steep water is a byproduct of the steeping process, and contains a mixture of soluble proteins, amino acids, organic acids, carbohydrates, vitamins, and minerals.

Fermentation methods of the disclosure typically use a treated starch. A starch-containing composition can be treated prior to its introduction into the fermentation medium, while it is in the fermentation medium, or both prior to and while it is in the fermentation medium.

Fermentation methods of the disclosure can also utilize a partially hydrolyzed starch. Partially hydrolyzed starches and preparation thereof are well known in the art. A partially hydrolyzed starch refers to one that has a dextrose equivalent ("DE") of less than 100. If a partially hydrolyzed starch is used, it preferably has a DE of less than about 75, or less than about 70, and preferably greater than about 15, greater than about 25, greater than about 35, or greater than about 45, or within any range between the upper and lower of these number sets. For example, a partially hydrolyzed starch composition can have a DE in the range of about 45 to about 75, or about 50 to about 70. The partially hydrolyzed starch can include high molecular weight dextrins and high molecular weight maltodextrins. Partially hydrolyzed starches can be prepared by heating the starch with an acid such as hydrochloric or sulfuric acid at a high temperature and then neutralizing the hydrolysis mixture with a suitable base such as sodium carbonate. A partially hydrolyzed starch is one type of "starch product."

After acid hydrolysis the pH of the hydrolyzed starch composition can be neutralized with a base. In neutral pH conditions, isomerization of low molecular weight sugar products may occur. These isomerizations can result in the formation of products such as certain disaccharides that cannot be utilized well by yeast, or that are refractory to the conversion to useful products, but that can be advantageously utilized with the engineered yeast of the current disclosure.

In some modes of practice the starch-containing composition can be treated with a starch-degrading enzyme. The starch-degrading enzyme can be added to the fermentation medium at one or more points during the fermentation process, such as in the presence of the engineered cells. For example, the starch-degrading enzyme in a purified or partially purified form can be added to the fermentation medium to promote degradation of the starch or starch product and formation of low molecular weight sugars for consumption by the engineered yeast during fermentation. Starch-degrading enzymes, such as amylases, are commercially available or can be prepared by art known techniques. The process of adding a starch-degrading enzyme to the fermentation medium may be referred to as an "external" addition of the starch-degrading enzyme. In some modes of practice a starch-degrading enzyme is added to a partially hydrolyzed starch composition, such as one having a DE in the range of about 50 to about 70.

In other modes of practice, the starch-degrading enzyme can be produced by a microorganism in the fermentation medium. For example, the starch-degrading enzyme can be produced by an microorganism, which can be the engineered yeast having the heterologous sugar transporter, or another microorganism that is different, such as a second yeast strain that can secrete an amylolytic enzyme. Therefore, in some embodiments, engineered yeast includes genetic modifications including a heterologous sugar transporter as well as a genetic modification that results in increased starch degradation in the fermentation medium by secretion of an amylolytic enzyme from the engineered yeast into the medium. The amylolytic enzyme that is secreted from the engineered yeast may be one that is endogenous or exogenous to the yeast cell. Fermentation methods of the invention can also include those where external purified starch-degrading enzyme is added in addition to starch-degrading enzyme that is secreted from yeast in the fermentation medium.

Starch-degrading enzymes can be those that are endo-amylases acting primarily on 1,4-linkages, and exo-amylases acting primarily on 1,4-linkages, debranching enzymes acting primarily on 1,6-linkages in starch, and cyclodextrin glycosyltransferases that degrade starch by catalysing mainly cyclization and disproportionate reactions.

Endoamylases (also known as glycogenases) cleave the 1,4-bonds in internal regions of the starch molecule. Alpha amylases of EC 3.2.1.1 include well known endoamylases that cause a rapid loss of viscosity of starch-containing compositions solution. Endoamylases can be divided into two categories of liquifying and saccharifying amylases according to degree of hydrolysis of substrate. Endoamylase degradation of starch can provide oligosaccharides of varying lengths.

Exoamylases act externally by cleaving chemical bonds from the non-reducing end of starch. The exoamlyases beta-amylases (EC 3.2.1.3) are able to cleave the 1,4-bonds in starch from the reducing end. Glucoamylases (EC 3.2.1.3) are able to cleave the 1,4-bonds in starch from the reducing end as well, but also cleave the 1,6-bonds. The use of exoamylases hence produce only low molecular weight products from starch, e.g. maltose and glucose, respectively (Wind, 1997).

Pullulanase (EC 3.2.1.41) and isoamylase (EC 3.2.1.68) are debranching enzymes that are specific for 1,6-bonds in starch. Some pullulanases are also able to cleave 1,4-glucosidic bonds. Cyclodextrin glycosyltransferases (CGTases, EC 2.4.1.19) produce cyclodextrins from starch, the rings which are composed of 6, 7 or 8 glucose units bound by—1,4-bonds, by catalyzing intra and intermolecular reaction of glycosyl transfer.

Any one or more of alpha-amylase, beta-amylases, glucoamylase, pullulanase, isoamylase, and cyclodextrin glycosyltransferases can be used to treat a starch containing composition to provide a fermentation medium according to the invention. In embodiments of the disclosure any one or more of these starch-degrading enzymes can be added externally to a starch- or starch product-containing composition, or can be secreted from a microbe in the fermentation medium to cause degradation of the starch. If secreted from a microbe, the microbe can be the engineered yeast having the heterologous sugar transporter, or can be secreted from a different microbe, whether it be a naturally-occurring microbe or a genetically-engineered microbe.

An exemplary process includes providing a fermentation medium that includes a fermentable carbohydrate composition having a partially hydrolyzed starch with a DE in the range of about 50 to about 70, and then fermenting the composition in the presence of an engineered yeast that secretes a glucoamylase. The glucoamylase in the fermentation media can efficiently digest the already partially hydrolyzed starch into degradation products including low molecular weight sugars such as glucose, which is typically the primary sugar in the treated composition. In the presence of higher levels of glucose the glucoamylase can promote reversion reactions and cause formation and increased concentrations of sugars such as isomaltose, maltulose, panose, and maltose. Increasing the DE in the feed material increases the concentration of free glucose entering the fermentation, which can lead to reversion reactions, such as glucose and fructose conversion to maltulose via glucoamylase.

The fermentation medium or fermentable carbohydrate composition, such as a partially hydrolyzed starch composition that is further enzymatically digested with an amylase, can be described in terms of the amount of one or more starch degradation products (glucose, maltulose, isomaltose, panose, maltose, etc.). The amount of a starch degradation product can be described as desired, such as in terms of the amount of the product present in the fermentation media, the amount of product as a percentage of the amount of the starting starch material, the amount of different degradation products in relation to one another, etc.

Sugars capable of being consumed and used by the yeast for fermentation can constitute the "fermentable carbohydrates" in the fermentation medium. The fermentable carbohydrates include glucose, maltose, isomaltose, maltulose, and panose, as well as longer oligomeric sugar molecules such as starch, maltodextrin, and amylose that can be broken down in the fermentation medium to mono- and disaccharides which can be consumed by the yeast.

In some modes of practice, the amount of glucose in the fermentation medium can be at least 10 g/L, at least 15 g/L, at least 20 g/L, at least 25 g/L, such as in the range of about 10 g/L to about 100 g/L. During fermentation a feed composition containing starch or a hydrolyzed starch product can be added to the fermentation media. If a starch-degrading enzyme is present in the fermentation medium, glucose can be generated by enzymatic action on the starch or hydrolyzed starch, and the amount of glucose available to the engineered yeast can be constantly replenished during fermentation to provide desired levels to support optimal growth of cells and bioproduct production. Preferably, under growth conditions, an amount of glucose is present that does not limit the growth of the cells, which can be referred to as a "non-growth limiting amount."

The fermentation media can also include amounts of low molecular weight non-glucose sugars that are derived from the enzymatic degradation of starch or starch hydrolysates. These low molecular weight non-glucose sugars can include disaccharides such as maltose, isomaltose, maltulose, panose, etc, which can be referred to as di- or tri-glucopyranosyl-based sugars.

Maltulose (4-α-D-glucopyranosyl-D-fructose) is a glycosylfructose disaccharide consisting of an α-D-glucopyranosyl residue joined to β-D-fructofuranose via a (1→4)-linkage.

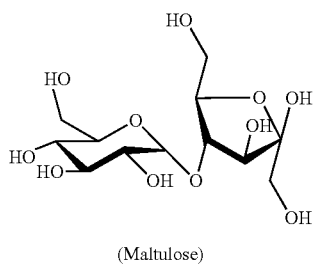

(Maltulose)

Maltulose can be formed by chemical isomerization of the reducing end glucose units during enzyme liquefaction of starch, and hydrolysis during subsequent saccharification with amyloglucosidase which forms maltulose as one of the products. Maltulose is resistant to hydrolysis by glucoamylase and α-amylases.

The ability of an engineered yeast of the disclosure to grow on maltulose can be demonstrated by replacing the carbon source (glucose) with a carbohydrate composition wherein maltulose is present in an amount of at least 97% (wt) in a synthetic yeast media, and determining whether the engineered yeast will grow in this media under standard yeast growth conditions. Engineered yeast can be cultured in this "synthetic medium" (6.7 g/L Yeast Nitrogen Base without amino acids, 1.9 g/L Synthetic Complete drop-out mix without uracil, 2.5 g/L maltulose at least 97% purity, 9.5 g/L MES buffer, adjusted to pH6.0 with 5M potassium hydroxide), at 30° C. with shaking 250 RPM under aerobic conditions. Under these conditions, the engineered yeast is considered to exhibit "growth" if the doubling time (1/rate) is not greater than about 50 hours (rate of 0.02 or greater)

Preferably the engineered yeast have a growth rate of about 0.05 or greater, about 0.07 or greater, about 0.10 or greater, about 0.12 or greater, about 0.14 or greater, about 0.15 or greater, about 0.16 or greater, about 0.17 or greater, about 0.18 or greater, about 0.19 or greater, about 0.20 or greater, such as in the range of about 0.10 to about 0.40, about 0.15 to about 0.35, or about 0.20 to about 0.30.

In embodiments of the disclosure, in the fermentation medium maltulose can be present at a concentration of at least 0.5 g/L, such as in the range of 0.5 g/L to 5 g/L, or 1.0 g/L to 5 g/L, or 1.25 g/L to 3 g/L. During the fermentation, the engineered yeast with the heterologous sugar transporter can utilize maltulose present in the medium and therefore reduce its accumulation in the medium. For example, during fermentation and with continuous addition of a starch product, the amount of maltulose can be kept below about 5 g/L, below about 4.5 g/L, below about 4 g/L, below about 3.5 g/L, below about 3.0 g/L, below about 2.5 g/L, below about 2.0 g/L, below about 1.5 g/L, or below about 1.0, by the ability of the engineered yeast to consume maltulose.

Isomaltose (O-α-D-glucopyranosyl-α[1-6]-α-D-glucopyranoside) is a disaccharide similar to maltose, but with a α-(1-6)-linkage instead of the α-(1-4)-linkage.

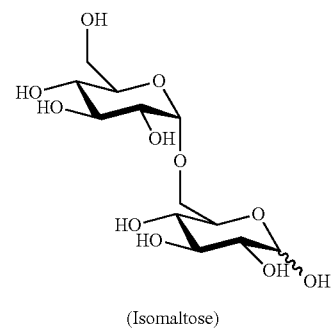

(Isomaltose)

Isomaltose can be formed by the repolymerization of glucose, and various yeast are unable to assimilate isomaltose or utilize it efficiently. However, in addition to being able to consume maltulose, the engineered yeast of the current disclosure are also able to beneficially consume isomaltose during a fermentation process.

In embodiments of the disclosure, in the fermentation medium isomaltose can be present at a concentration of at least 0.5 g/L, such as in the range of 0.5 g/L to 5 g/L, or 1.0 g/L to 5 g/L, or 1.25 g/L to 3 g/L. During the fermentation, the engineered yeast with the heterologous sugar transporter can utilize isomaltose present in the medium and therefore can prevent significant accumulation of isomaltose in the medium which would otherwise be detrimental to the fermentation process. For example, during fermentation and with continuous addition of a starch product, the amount of isomaltose can be kept below about 5 g/L, below about 4.5 g/L, below about 4 g/L, below about 3.5 g/L, below about 3.0 g/L, below about 2.5 g/L, below about 2.0 g/L, below about 1.5 g/L, or below about 1.0, by the ability of the engineered yeast to consume isomaltose.

Panose (O-α-D-glucopyranosyl-[1-6]-O-α-D-glucopyranosyl-[1-4]-α-glucopyranose) is a trisaccharide composed of three glucose units with α-(1-4) and α-(1-6)-linkages.

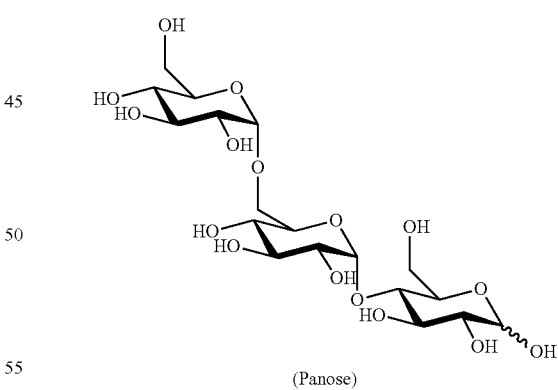

(Panose)

In addition to being able to consume maltulose, the engineered yeast of the current disclosure are also able to beneficially consume panose during a fermentation process.

In embodiments of the disclosure, in the fermentation medium panose can be present at a concentration of at least 0.5 g/L, such as in the range of 0.5 g/L to 5 g/L, or 1.0 g/L to 5 g/L, or 1.25 g/L to 3 g/L. During the fermentation, the engineered yeast with the heterologous sugar transporter can utilize panose present in the medium and therefore can prevent significant accumulation of panose in the medium which would otherwise be detrimental to the fermentation process. For example, during fermentation and with continuous addition of a starch product, the amount of panose can be kept below about 5 g/L, below about 4.5 g/L, below about 4 g/L, below about 3.5 g/L, below about 3.0 g/L, below about 2.5 g/L, below about 2.0 g/L, below about 1.5 g/L, or below about 1.0, by the ability of the engineered yeast to consume pannose.

Maltose (maltobiose, 4-O-α-D-glucopyranosyl-D-glucose) is a disaccharide formed from two units of glucose joined with an α(1→4) bond.

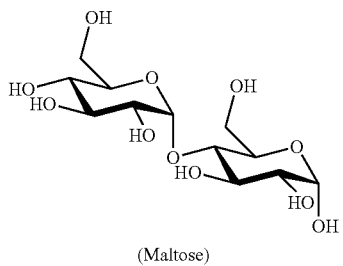

(Maltose)

In embodiments of the disclosure, in the fermentation medium maltose can be present at a concentration of at least 0.5 g/L, such as in the range of 0.5 g/L to 5 g/L, or 1.0 g/L to 5 g/L, or 1.25 g/L to 3 g/L. During the fermentation, the engineered yeast with the heterologous sugar transporter can utilize maltose present in the medium and therefore can prevent significant accumulation of maltose in the medium which would otherwise be detrimental to the fermentation process. For example, during fermentation and with continuous addition of a starch product, the amount of maltose can be kept below about 5 g/L, below about 4.5 g/L, below about 4 g/L, below about 3.5 g/L, below about 3.0 g/L, below about 2.5 g/L, below about 2.0 g/L, below about 1.5 g/L, or below about 1.0, by the ability of the engineered yeast to consume maltose.

The fermentation medium includes water and preferably includes nutrients, such as a nitrogen source (such as proteins), vitamins and salts. A buffering agent can also be present in the fermentation medium. Other components may also be present in the fermentation medium after a period of fermentation, such as fermentation products which can accumulate as the fermentation progresses, and other metabolites. Optionally, the fermentation medium can be buffered with a base such as calcium hydroxide or calcium carbonate, ammonia or ammonium hydroxide, sodium hydroxide, or potassium hydroxide in order to maintain a pH at which the organism functions well.

Embodiments of the disclosure provide an engineered yeast comprising a di- and tri-glucopyranosyl sugar transporter (also referred to herein as a "sugar transporter"), capable of transporting sugars such as maltulose, isomaltose, panose, and maltose into the cell. In embodiments of the disclosure, the engineered yeast includes an heterologous nucleic acid encoding a sugar transporter with an amino acid sequence having 90% or greater identity to SEQ ID NO:44, which is a previously unknown protein from the yeast. In a preferred embodiment, the engineered yeast express a sugar transporter with an amino acid sequence having has 91%, 92%, 93%, 94%, 95%, 96%, 97%, 98%, or 99% or greater identity to SEQ ID NO:44.

In some embodiments, the sugar transporter has one or more amino acid substitutions, deletions, or additions which cause the sequence to vary from SEQ ID NO:44 while retaining certain sequence features. That is, if the sugar transporter is modified, it is modified at one or more amino acid locations outside of regions that are conserved and/or important for sugar transporter activity. SEQ ID NO:44 can be compared to other sugar transporters to understand regions of identity, and areas of the sequence where substitutions, deletions, or additions would be permitted. Polypeptide sequence identity regions between SEQ ID NO:44 and other sugar transporters can be understood using sequence alignment tools as described herein.

The determination of "corresponding" amino acids from two or more sugar transporters can be determined by alignments of all or portions of their amino acid sequences. Sequence alignment and generation of sequence identity include global alignments and local alignments, which typically use computational approaches. In order to provide global alignment, global optimization forcing sequence alignment spanning the entire length of all query sequences is used. By comparison, in local alignment, shorter regions of similarity within long sequences are identified.

As used herein, an "equivalent position" means a position that is common to the two sequences (e.g., a SEQ ID NO:44 and a different sugar transporter sequence having the desired substitution(s)) that is based on an alignment of the amino acid sequences of one sugar transporters or as alignment of the three-dimensional structures. Thus either sequence alignment or structural alignment, or both, may be used to determine equivalence.

In some modes of practice, the BLAST algorithm is used to compare and determine sequence similarity or identity. In addition, the presence or significance of gaps in the sequence which can be assigned a weight or score can be determined. These algorithms can also be used for determining nucleotide sequence similarity or identity. Parameters for to determine relatedness are computed based on art known methods for calculating statistical similarity and the significance of the match determined. Gene products that are related are expected to have a high similarity, such as greater than 50% sequence identity. Exemplary parameters for determining relatedness of two or more sequences using the BLAST algorithm can be as follows.

Inspection of nucleic acid or amino acid sequences for two nucleic acids or two polypeptides will reveal sequence identity and similarities between the compared sequences. Sequence alignment and generation of sequence identity include global alignments and local alignments which are carried out using computational approaches. An alignment can be performed using BLAST (National Center for Biological Information (NCBI) Basic Local Alignment Search Tool) version 2.2.31 software with default parameters. Amino acid % sequence identity between amino acid sequences can be determined using standard protein BLAST with the following default parameters: Max target sequences: 100; Short queries: Automatically adjust parameters for short input sequences; Expect threshold: 10; Word size: 6; Max matches in a query range: 0; Matrix: BLOSUM62; Gap Costs: (Existence: 11, Extension: 1); Compositional adjustments: Conditional compositional score matrix adjustment; Filter: none selected; Mask: none selected. Nucleic acid % sequence identity between nucleic acid sequences can be determined using standard nucleotide BLAST with the following default parameters: Max target sequences: 100; Short queries: Automatically adjust parameters for short input sequences; Expect threshold: 10; Word size: 28; Max matches in a query range: 0; Match/Mismatch Scores: 1, −2; Gap costs: Linear; Filter: Low complexity regions; Mask: Mask for lookup table only. A sequence having an identity score of XX % (for example, 80%) with regard to a reference sequence using the NCBI BLAST version 2.2.31 algorithm with default parameters is considered to be at least XX % identical or, equivalently, have XX % sequence identity to the reference sequence.

Conserved domains can be identified using Blast alignments with well characterized proteins. Using this approach, one can identify which core conserved domains exist, such as the core Major Facilitator Superfamily (MFS) domain present in nearly all secondary transporters (cd06174). The core MFS domain resides between residues 111-550 in SEQ ID NO:44, Within the MFS domain lies residues within the translocation pore. Residues within the translocation pore could be altered such that transport is improved, decreased, or unaffected. Potential translocation pore substitutions in SEQ ID NO:44 could be introduced at any one or more of the following sites; 124, 127, 128, 129, 133, 134, 160, 163, 164, 167, 171, 172, 174, 175, 221, 222, 225, 226, 229, 230, 233, 245, 246, 249, 250, 256, 380, 383, 384, 387, 388, 390, 404, 408, 412, 415, 419, 476, 479, 480, 483, 499, 500, 503, 504, 507, 508, 511. As result, a transporter with less than 100% identity to SEQ ID NO:44 can be obtained.

A global alignment can be used to align sequences with significant identity to, for example, SEQ ID NO:44 in order to determine which corresponding amino acid position(s) in the target sequence (e.g., a sugar transporters ortholog) can be substituted with the one or more of the amino acid if a variant of SEQ ID NO:44 is used.

In other embodiments, the heterologous sugar transporter sequence optionally comprises additional sequence that is not present in the native sugar transporter polypeptide. The additional sequence can provide functionality to the sugar transporter that is not present in the native polypeptide. Additional functionalities include, for example, protease sites or binding sites for other proteins or materials.

An example of an additional sequence that may not be present in a native sugar transporter polypeptide, but that can be added, is a tag sequence. A tag sequence can be located at the C-terminus, the N-terminus, or both, of the sugar transporter sequence, and such proteins can be annotated as follows: [ST]-[$T_C$], etc., wherein "$T_C$" denotes one or more amino acids that provide the C-terminal tag sequence, or [$T_N$]-[ST], etc., wherein "$T_N$" denotes one or more amino acids that provide the N-terminal tag sequence. Exemplary peptide tags include up to 5, 10, 15, or 20 amino acids. The peptide tag can be useful for any one or more of a variety of purposes. For example, the tag can allow purification of the transporter from the media by the ability of a tag-binding member to specifically interact with the tag. The tag can also allow detection or identification of the protein using a tag-binding member with a detectable label. Exemplary short peptide tags are poly-Arg, FLAG, poly-His, c-myc, S, and Strep II. (See, for example, Terpe, K. (2003) Appl. Microbiol. Biotechnol. 60:523-533).

The engineered yeast can be prepared using one or more heterologous nucleic acids that encodes the sugar transporter, such as a transporter with an amino acid sequence having 90% or greater identity to SEQ ID NO:44. Exemplary nucleic acids include those such as SEQ ID NO:14 encoding SEQ ID NO:44, as well as those encoding amino acid sequences having between 90%-99% identity to SEQ ID NO:44 are contemplated.

In some embodiments the engineered yeast can have multiple copies of a nucleic acid encoding a heterologous sugar transporter. In these embodiments, the cell can be described in terms of the copy number of the nucleic acids that encode a heterologous sugar transporter. For example, the engineered yeast can have a heterologous sugar transporter nucleic acid copy number of two or more, such as a copy number in the range of two to twenty four. However, one of skill could engineer the yeast with more than twenty four copies of the heterologous sugar transporter nucleic acid using techniques known in the art. For example, the engineered yeast can have a heterologous sugar transporter nucleic acid copy number of two or more, such as a copy number in the range of two to twenty four, two to sixteen, or four to sixteen. For example, the engineered yeast can have a nucleic acid copy number of two, three, four, five, six, seven, eight, nine, ten, eleven, twelve, thirteen, fourteen, fifteen, or sixteen, seventeen, eighteen, nineteen, twenty, twenty one, twenty two, twenty three, or twenty four heterologous sugar transporter nucleic acids that are the same as one another, or different from one another, and which can encode the same heterologous sugar transporter polypeptide or different heterologous sugar transporter polypeptides.

If the yeast is engineered to include multiple copies of the heterologous sugar transporter gene, the copies can be placed in a tandem orientation at a nucleic acid site in the cell, such as integrated into a desired locus of a yeast chromosome as tandem repeats. Copies can also be placed in at multiple nucleic acid sites in the cell, such as integrated into multiple loci of a yeast chromosome(s).

Nucleic acids sequence(s) encoding the sugar transporter include sequence SEQ ID NO:44, as well as codon optimized sequences and codon variants of SEQ ID NO:44, as well as any regulatory sequence (e.g., terminator, promoter, etc.) and vector sequence (e.g., including a selection marker, integration marker, replication sequence, etc.) can, in some modes of practice, be prepared using known molecular techniques. General guidance for methods for preparing DNA constructs (e.g., for the DNA constructs including the gene encoding SEQ ID NO:44 can be found in Sambrook et al. Molecular Cloning, A Laboratory Manual, Cold Spring Harbor Laboratory Press, Cold Spring Harbor, N.Y., 1989; and Ausubel et al. Current Protocols in Molecular Biology, Greene Publishing and Wiley-Interscience, New York, N.Y., 1993.

PCR techniques can be used for preparing or modifying a sugar transporter nucleic acid sequence, such as to introduce one or more mutations in the sugar transporter nucleic acid sequence to provide a variant. PCR techniques are described in, for example, Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. The techniques may optionally include site-directed (or oligonucleotide-mediated) mutagenesis, PCR mutagenesis, and cassette mutagenesis of an earlier prepared DNA encoding a sugar transporter polypeptide.

Alternatively, nucleic acid molecules can be generated by custom gene synthesis providers such as IDT (Coralville, Iowa), DNA2.0 (Menlo Park, Calif.) or GeneArt (Life Technologies, Thermo Fisher Scientific).

An expression vector can be constructed to include the sugar transporter nucleic acid sequence operably linked to expression control sequences functional in the host organism. Expression vectors applicable for use in the host organisms include, for example, plasmids, episomes and artificial chromosomes. The vectors can include selection sequences or markers operable for stable integration into a host chromosome. Additionally, the vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art.

In some embodiments, a nucleic acid encoding a sugar transporter or any other polypeptide that is introduced into a host yeast can be codon optimized. A nucleic acid template that is used for expression of the sugar transporter can be the native DNA sequence that codes for the sugar transporter, or the template can be a codon-optimized version that is optimized for expression in a desired host cell. In this regard, a specific codon optimization scheme may be used. The use of preferred codons in the host organism may result in increased activity, for example as caused by improved expression of the gene. For example, codon optimized DNA constructs encoding SEQ ID NO:44, or a polypeptide that has about 90% or greater, about 95% or greater, about 97% or greater sequence identity to this sequences can be prepared and inserted into a desired host cell.

Databases that provide information on desired codon uses in particular host organisms are known in the art. In some embodiments, the sugar transporter nucleic acid is codon optimized for expression in an industrial yeast strain.

According to one embodiment of the disclosure, a DNA construct comprising a sugar transporter gene is operably linked to a promoter sequence, wherein the promoter sequence is functional in a host cell of choice. In some embodiments, the promoter shows transcriptional activity in a yeast host cell and may be derived from genes encoding proteins either homologous or heterologous to the host cell. In some embodiments the promoter sequence is a strong promoter selected from translational elongation factor promoter (pTEF), pyruvate decarboxylase (PDC) promoter, alcohol dehydrogenase (ADH1), glyceraldehyde-3-phosphate dehydrogenase promoter (pGPD/TDH3), and enolase (ENO) promoter. Other promoters that can be used to drive expression include the cytochrome c promoter (pCYC), and the phosphoglycerate kinase promoter (PGK). Optionally, an additional factor that controls expression such as an enhancer or the like may also be included on the vector.

The expression vector including the sugar transporter gene can also include any promoter and terminator sequence functional in the host cell. For example, the promoter sequence and the terminator sequence can be endogenous to the host cell, or the promoter sequence and the terminator sequence can be from an organism exogenous to the host cell, but yet still functional in the host cell.

The DNA construct may be introduced into a host cell using a vector. The vector may be any vector which when introduced into a host cell is stably maintained. In some embodiments, the vector is integrated into the host cell genome and is replicated. Vectors include cloning vectors, expression vectors, shuttle vectors, plasmids, phage particles, cassettes and the like. In some embodiments, the vector is an expression vector that comprises regulatory sequences operably linked to the sugar transporter coding sequence.

The DNA construct comprising the sugar transporter gene can further include a selectable marker, thereby facilitating the selection in a host cell. For example, the selectable marker can be for transformed yeast. Examples of yeast selectable marker include markers commonly used for selecting for transformed yeast cells. Auxotrophic markers can be used using a gene that controls an auxotrophy, meaning that the gene enables yeast to produce a nutrient required for the growth of the yeast. Examples of yeast genes that control auxotrophies include leucine auxotrophy (LEU2), histidine auxotrophy (HISS), uracil auxotrophy (URA3, URA5), and tryptophan auxotrophy (TRP1). MEL5, which encodes an alpha-galactosidase (melibiase) in yeast, can be used as a dominant selection marker to select for transformants of alpha-galactosidase negative yeast strains. Genetic modification of the yeast with one or more selective markers can allow the yeast to utilize certain substrates.

The DNA construct may be one which is integrated into the genome and replicated together with the chromosome(s) into which it has been integrated. For example, a yeast cell may be transformed with the DNA construct encoding the sugar transporter, and integrating the DNA construct, in one or more copies, in the host chromosome(s). This integration is generally considered to be an advantage, as the DNA sequence is more likely to be stably maintained. Integration of the DNA constructs into the host chromosome may be performed according to conventional methods, such as by homologous recombination or random integration.

In one mode of practice, one or more DNA construct(s) comprising the sugar transporter genes is integrated at a genetic locus, wherein the integration does not have a significant adverse effect on the health of the cell. For example, the integration can be at a locus of the genome that is not known to have any polypeptide coding sequence, or at a locus of the genome that has a gene that is not essential for function under desired growth conditions, such as under fermentation conditions using a starch product as the energy source. In *Saccharomyces cerevisiae*, a large amount of information is available about the essentiality of open reading frames (ORFs) in its genome. See, for example, sequence.stanford.edu/group/yeast_deletion_project/deletions3 available on the World Wide Web. This information can be used to as guidance for understanding the essentiality of genes in yeast strains, and engineering such strains accordingly. Given information known in the art, one of skill can choose one or more non-essential genes as targets for integrations of the one or more DNA construct(s) comprising the sugar transporter genes. Whether or not a gene is "essential" can be determined in growth conditions using rich media with glucose.

In some embodiments, in addition to the sugar transporter modification, the engineered yeast includes one or more additional genetic modifications. The one or more additional genetic modifications can affect other aspects of fermentation performance, such as starch degradation, and non-glucose sugar consumption.

In some embodiments the engineered yeast includes one or more genetic modifications, further to the sugar transporter modification, that promote consumption of a di- or tri-glucopyranosyl-based sugar, processing, or formation of a bioproduct using a di- or tri-glucopyranosyl-based sugar as a precursor. Such modifications may cause enzyme activity to be introduced into the cell, cause an increased amount of enzyme in the cell, and/or cause an increase in enzyme activity. For example, expression of a heterologous nucleic acid in a host that otherwise in a wild-type form does not have the nucleic acid can be referred to as expression that is introduced. If an enzyme is expressed in an amount greater than the amount of enzyme is expressed in the native host, the gene expression can be referred to as upregulated. Introduced or upregulated expression can be caused by a modification that is not present in the native host. If an enzyme, such as one in an altered form, exhibits activity greater than the activity of the enzyme in native form, the enzyme activity can be referred to as enhanced.

One or more types of genetic modifications can be used to cause introduced or upregulated expression, or enhanced activity. For example, the enhanced activity can be caused by the addition of or modifications to regulatory elements (promoters, terminators, etc.) that upregulate expression of the desired gene(s). The enhanced activity can also be caused by an increase in copy numbers of the desired gene(s). The enhanced activity can also be caused by one or more genetic modifications to nucleic acid sequences or proteins that may otherwise function to repress expression of the gene whose activity is desired to be enhanced.

As an example, upregulating the expression of a gene to provide a greater amount of enzyme in the cell can be performed by placing a gene under the control of a heterologous promoter that drives a greater level of expression than when the gene is driven by its native promoter. A heterologous promoter is one that is different than the native promoter of a particular gene. A gene under the control of a heterologous promoter can be a gene that is native to the host cell (i.e., an endogenous gene), or a gene that is non-native to the host.

The yeast cell can have a heterologous genetic modification causing the desired enzyme to have enhanced activity in the engineered yeast. Examples of heterologous modifications include, but are not limited to, the introduction of an exogenous gene into the yeast, or the modification of an endogenous gene and/or its surrounding genetic elements, such as expression regulatory elements. The heterologous modification can include one or more of the following: the use of a promoter that is different than the native promoter of the desired gene; the use of a terminator that is different than the native terminator of the desired gene; the introduction of the gene at a location in the genome that is different than its native location; the introduction of multiple copies of the desired gene.

The modifications can include changes to regulatory elements that either upregulate or down regulate expression of genes; increase in gene copy numbers, and deletions or mutations that eliminate expression, reduce expression, or increase expression or activity of a gene or gene product.

An additional genetic modification that can be included in the engineered yeast is the alteration or introduction of an enzyme activity that converts a low molecular weight non-glucose sugar to glucose. For example, one optional additional genetic modification affects or introduces isomaltase activity in the engineered yeast. Isomaltase can converting isomaltose to glucose by hydrolyzing the 1,6 ether linkage in isomaltose. An isomaltase may also exhibit cross activity for hydrolyzing the 1,4 ether linkages in maltose. The genetic modification can cause isomaltase activity to be introduced into the cell, cause an increased amount of isomaltase in the cell, and/or cause an increase in isomaltase activity.

In some embodiments further to the heterologous sugar transporter, the engineered cell includes a heterologous isomaltase gene, or an isomaltase gene under the control of a heterologous promoter that provides increased expression in the cell, or present in multiple copies in the cell. For example, an isomaltase (IMA) gene under the control of a heterologous promoter, such as a PDC promoter can be engineered into the yeast.

Examples of isomaltase genes that can be introduced into an engineered yeast include, but are not limited to *Saccharomyces cerevisiae* IMA1 (P53051), *Saccharomyces cerevisiae* IMA2 (Q08295), *Saccharomyces cerevisiae* IMA3 (P0CW40), *Saccharomyces cerevisiae* IMA4 (P0CW41), *Saccharomyces cerevisiae* IMA5 (P40884), *Bacillus subtilis* malL (O06994), *Bacillus cereus* malL (P21332), *Bacillus coagulans* malL (Q45101), *Bacillus* sp. malL (P29093), etc. Preferably the isomaltase gene encodes for a polypeptide having greater than 80%, 85%, 90%, 95%, 98% or 99% sequence identity with the amino acid sequence of accession number NP 011803.3 (*Saccharomyces cerevisiae* IMA1).

In some embodiments, the engineered yeast, further to the heterologous sugar transporter, includes a genetic modification that affects a starch-degrading polypeptide. For example, the genetic modification can be one that introduces a nucleic acid encoding a heterologous starch-degrading polypeptide into the yeast. The genetic modification may also be one that increases the amount of an endogenous or an exogenous (heterologous) starch-degrading polypeptide in the cell, such as by placing the gene under control of a strong promoter, or providing the gene in multiple copies in the cell, such as multiple copies of the gene integrated into the genome, or multiple copies present on a non-chromosomal construct (e.g., a plasmid).

In some embodiments the starch-degrading enzyme is a glucoamylase. Glucoamylases (E.C. 3.2.1.3) are amylolytic enzymes that hydrolyze 1,4-linked α-D-glucosyl residues successively from the nonreducing end of oligo- and polysaccharide chains with the release of D-glucose. Glucoamylases can also cleave α-1,6 bonds on amylopectin branching points. As used herein, the term "amylolytic activity" with reference to the heterologous glucoamylase pertains to these enzymatic mechanisms. A glucoamylase polypeptide can be a variant of a naturally occurring glucoamylase, or a portion of a naturally occurring glucoamylase (such as a glucoamylase that is truncated at its N-terminus, its C-terminus, or both), with the glucoamylase polypeptide retaining amylolytic activity.

Glucoamylases enzymes from various fungal and bacterial species also generally include a native "signal sequence." Generally, a signal sequence is a short amino acid stretch (typically in the range of 5-30 amino acids in length) that is located at the amino terminus of a newly synthesized protein. Most signal peptides include a basic N-terminal region (n-region), a central hydrophobic region (h-region) and a polar C-terminal region (c-region) (e.g., see von Heijne, G. (1986) Nucleic Acids Res. 14, 4683-4690). A signal sequence can target the protein to a certain part of the cell, or can target the protein for secretion from the cell. For example, it has been shown that the native N-terminal signal sequence of the *S. diastaticus* Glucoamylase STAI gene can target it to the endoplasmic reticulum of the secretory apparatus (for example, see Yamashita, I. et al., (1985) J. Bacteriol. 161, 567-573). Glucoamylase secretion signals can promote secretion of glucoamylase from the engineered yeast to promote the enzymatic breakdown of starch.

In some embodiments the engineered yeast include a nucleic acid encoding glucoamylase such as *Saccharomyces cerevisiae* STA1 (P04065); *Saccharomyces cerevisiae* STA2 (P29760); *Aspergillus awamori* GLAA (P69327); *Aspergillus oryzae* (strain ATCC 42149/RIB 40) glaA (P36914); *Rhizopus oryzae* amyB (NRRL 395, ABB77799.1); *Schwanniomyces occidentalis* GAM1 (P22861); *Aspergillus kawachii* gaI (P23176); *Aspergillus shirousami* glaA (P22832); *Candida albicans* (strain SC5314/ATCC MYA-2876) GAM1 (O74254); *Schizosaccharomyces pombe* meu17 (O60087); *Saccharomycopsis fibuligera* GLA1 (P26989); *Saccharomycopsis fibuligera* GLU1 (P08017.1); or *Saccharomycopsis fibuligera* Glm (CAC83969).

In one embodiment, the engineered yeast further includes at least one glucoamylase polypeptide that has at least 90% identity to the Glm glucoamylase from the yeast strain *Saccharomycopsis fibuligera* IFO 0111. Hostinova et al. (Archives of Biochemistry and Biophysics, 411:189-195, 2003) describes the nucleotide sequence of the glucoamylase gene Glm in the yeast strain *Saccharomycopsis fibuligera* IFO 0111. According to Hostinova et al., the *Saccharomycopsis fibuligera* Glm gene is transcribed into a 1.7 kb RNA transcript that codes for a 515 amino acid protein. In the 515 amino acid-long polypeptide chain 26 N-terminal amino acid residues constitute the signal peptide and subsequent 489 amino acid residues constitute the mature protein. Mature Glm, which lacks the signal sequence and is 489 amino acids long, has a predicted molecular weight of 54,590 Da in deglycosylated form. U.S. Patent Application Ser. No. 62/139,312 (filed Mar. 27, 2015) describes engineered yeast strains including a multiple copies of heterologous *Saccharomycopsis fibuligera* Glm gene.

In some aspects the engineered yeast has tolerance to a higher amount of a bioderived product, such as ethanol, in the fermentation media. In some embodiments, the engineered yeast is an "industrial yeast" which refers to any yeasts used conventionally in ethanol fermentation. Examples include sake yeasts, shochu yeasts, wine yeasts, beer yeasts, baker's yeasts, and the like. Sake yeasts demonstrate high ethanol fermentability and high ethanol resistance and genetic stability. Typically, industrial yeast have high ethanol resistance and preferably are viable at ethanol concentrations of 10% or greater.

In exemplary embodiments, the host cell is *S. cerevisiae*. Some *S. cerevisiae* have high tolerance to ethanol. Various strains of ethanol tolerant yeast are commercially available, such as RED STAR™ and ETHANOL RED™ yeast (Fermentis/Lesaffre, USA), FALI™ (Fleischmann's Yeast, USA), SUPERSTART™ and THERMOSACC™ yeast (Ethanol Technology, Wis., USA), BIOFERM™ AFT and XR™ (NABC—North American Bioproducts Corporation, GA, USA), GERT STRAND™ (Gert Strand AB, Sweden), and FERMIOL™ (DSM Specialties).

Industrial yeasts are typically prototrophic and therefore do not have an auxotrophic marker suitable for selecting for a transformant. If the host cell does not have the genetic background that would otherwise facilitate selection or retention of the sugar transporter gene within the cell upon transformation, the host cell can be engineered to introduce one or more genetic mutation(s) to establish use of a marker gene in association with and to maintain the sugar transporter gene in the cell. For example, a commercially available ethanol tolerant yeast cell can be genetically modified prior to introducing the sugar transporter gene in the cell.

A marker for a different auxotrophy can be provided by disrupting the gene that controls the auxotrophy. In one mode of practice, an ethanol tolerant strain of yeast is engineered to disrupt copies of one or more genes that control auxotrophies, such as LYS2, LEU2, HIS3, URA3, URA5, and TRP1. In the case of providing uracil auxotrophy, for example, a normal ura3 gene of an ethanol tolerant yeast can be replaced with an ura3$^-$ fragment obtained from a uracil auxotrophic mutant (for example, a *Saccharomyces cerevisiae* MT-8 strain) to disrupt the normal URA3 gene. In the case of a URA3-disrupted strain, the presence/absence of a marker can be easily identified or selected by taking advantage of the fact that a URA3 gene-disrupted strain is able to grow in a medium containing 5-fluoroorotic acid (5-FOA) while a normal URA3 strain (wild-type yeast or usual industrial yeast) is not able to grow. In the case of a LYS2 gene-disrupted strain, the presence/absence of a marker can be easily identified or selected by taking advantage of the fact that a LYS2-disrupted strain is able to grow in a medium containing α-aminoadipic acid while a normal LYS2 strain (wild-type yeast or usual industrial yeast) is not able to grow. Methods for disrupting an auxotrophy-controlling gene and for selectively separating auxotrophy-controlling gene mutants may be used depending on the auxotrophy employed. Alternatively, one can employ dominant selection markers, such as the amdS from *Aspergillus nidulans* (U.S. Pat. No. 5,876,988), which allows for growth on acetamide as the sole nitrogen source; or ARO4-OFP, which allows for growth in the presence of fluorophenylalanine (Fukuda et. al.). These markers can be used repeatedly using the recyclable cre-loxP system, or alternatively can be used to create auxotrophic strains that allow additional markers to be utilized (U.S. Pat. No. 4,959,317).

In some embodiments the heterologous sugar transporter is introduced into a yeast that does not have a native (endogenous) isomaltose sugar transporter. For example, the yeast can be one that has no gene having any significant identity (e.g., greater than 90%) to *Saccharomyces cerevisiae* MAL11 (P53048). Experiments associated with the current disclosure have also discovered that some ethanol tolerant yeast strains do not have a native isomaltose transporter.

After the yeast has been engineered to provide a desired genetic background for introduction of the sugar transporter gene, one or more gene construct(s) is introduced into a cell to integrate into the genome, or to be stably maintained and allow for expression. Methods for introducing a gene construct into a host cell include transformation, transduction, transfection, co-transfection, electroporation. In particular, yeast transformation can be carried out using the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein.

The transformation of exogenous nucleic acid sequences including the sugar transporter gene can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of the introduced nucleic acid sequences or their corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The engineered yeast strains expressing a heterologous sugar transporter, optionally with one or more other genetic modifications, can be used in a fermentation process to make a product. The fermentation product (also referred to herein as "bioproduct") can be any product that can be prepared by enzymatic degradation of a starch material by the glucoamylase, and formation of glucose and non-glucose sugars, and use of these sugars by the engineered yeast of the disclosure by fermentation. In embodiments, the fermentation product is selected from the group consisting of: amino acids, organic acids, alcohols, diols, polyols, fatty acids, monacyl glycerides, diacyl glycerides, triacyl glycerides, sweeteners, sophorolipids, and mixtures thereof. In a preferred embodiment, a fermentation method of the disclosure produces ethanol as the bioproduct. Other exemplary bioproducts that are organic acids or amino acids include lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, and acetic acid and derivatives thereof and salts thereof.

The engineered yeast are cultured under conditions so that fermentation can occur. Although conditions can vary depending on the particular organism and desired fermentation product, typical conditions include a temperature of about 20° C. or greater, and more typically in the range of about 30° C. to about 50° C. During fermentation the reaction mixture can be mixed or agitated. In some modes of practice, the mixing or agitation can occur by the mechanical action of sparging gas to the fermentation broth. Alternatively direct mechanical agitation such as by an impellor or by other means can be used during fermentation.

In some cases fermentation is carried out in industrial capacity fermenters in order to achieve commercial scale economic benefits and control. In an embodiment, the fermentation is carried out in a fermenter that has a capacity of about 5,000 gallons or more. In another embodiment, the process is carried out in fermentation broth quantities of at least 25,000 gallons. In yet another embodiment, a batch process is carried out in to produce batches of at least 25,000 gallons of final fermentation broth. In a continuous process, vessels of at least 200,000 gallons can be used. In some modes of practice, the fermentation is carried out as a single batch until completion.

The pH of the fermentation media can be adjusted to provide optimal conditions for sugar transporter activity, cell growth, and fermentation activity to provide a desired product, such as ethanol. For example, pH of the solution can be adjusted to in the range of 3 to 5.5. In one mode of practice, the pH of the fermentation media is in the range of 4 to 4.5.

In other modes of practice, the fermentation is carried out as a fed batch fermentation process. In this mode of practice, a first portion of a total amount of starch material to be fermented is added to the fermentation media as a substrate for fermentation. Additional starch material is added in one or more portions to provide more substrate for the engineered yeast in the media. The addition of starch can be regulated and the formation of glucose can be monitored to provide efficient fermentation.

In some modes of practice, the fermentation is carried out in a continuous mode of operation. In this mode, multiple fermenters operate in series in which a starch material is supplied in the first fermenter, which is fed to second fermenter and so on until the starch hydrolysate is converted to ethanol. Continuous operation can be operated using between 2-7 fermenters.

In some modes of practice, a portion of the total amount of starch material such as partially hydrolyzed starch is added to the fermentation broth using a variable rate addition system. Examples of such systems include a variable speed pump or a metering valve (such as a throttle valve) operably connected to a pump, which pump or valve can be utilized to vary the amount of starch material introduced into the fermentation broth over time. In some modes of practice, during the addition of a portion of the starch material, glucose concentration is monitored by a real-time monitoring system.

Real-time monitoring systems include systems that directly monitor glucose concentration and systems that indirectly monitor glucose concentration. Examples of real-time monitoring systems that typically directly monitor glucose concentration include systems based on infrared (IR) spectroscopy, near-infrared (NIR) spectroscopy systems, Fourier transform infrared (FTIR) systems, systems based on refractive index, automated enzyme based measurement systems such as a YSI 2950 Biochemistry Analyzer sold by YSI Life Sciences systems, high performance liquid chromatography (HPLC) based systems, gas chromatography (GC) based systems, and other real-time monitoring systems known to one of skill in the art. Additionally real-time monitoring systems that indirectly monitor/measure the glucose concentration of a fermentation process can be developed by determining the typical carbon distribution in a particular fermentation process and correlating the glucose concentration present in the fermentation broth to another parameter exhibited by the fermentation, such as, for example, a correlation of the glucose level present in the fermentation broth with a measurement of the carbon dioxide evolution rate and the amount of carbon dioxide present in an off-gas stream from the fermentation vessel. The carbon dioxide can be readily measured through use of a mass spectrometer or other suitable instrumental technique for measuring the components of the off-gas stream. In a preferred embodiment, the glucose concentration is monitored by a real-time monitoring system using infrared spectroscopy. In another one embodiment, the glucose concentration is monitored by a real-time monitoring system using near-infrared spectroscopy. The real time monitoring systems interface with equipment that controls the introduction of starch material into the fermentation medium to modulate the formation of glucose to a desired concentration in the fermentation medium.

Various analytic techniques can be used to identify and quantify mono- and disaccharides that are present in the fermentation medium. As a general matter, Techniques such as size exclusion chromatography, ligand conversion in which mono- and disaccharides may form complexes with metal counterions, partition (normal-phase) in which certain mono- and disaccharides have a tendency to partition in stationary phases (or aqueous phases), anion exchange in which certain mono- and disaccharides have a tendency to exchange anions, borate complex anion exchange certain mono- and disaccharides have a tendency to complex with borate to exchange anions, can be used. In one mode of analysis, samples of the fermentation medium can be taken and analyzed for metabolite concentrations by HPLC with refractive index and UPLC with ELSD detection As noted above, the present fermentation process uses a genetically modified yeast expressing the heterologous sugar transporter, and optionally including other genetic modifications. The engineered yeast in the fermentation media can be present along with starch degrading enzymes that are added to the fermentation medium, or released from a yeast in the fermentation medium, such as the engineered yeast. These starch degrading enzymes are therefore directly exposed to the medium conditions and affect the carbohydrate composition in the fermentation media. In the fermentation media the glucoamylase can cause hydrolysis and release of D-glucose from the non-reducing ends of the starch or related oligo- and polysaccharide molecules by cleaving alpha-(1,4) and alpha-(1,6) glucosidic bonds. Low molecular weight non-glucose sugars, such as maltulose, isomaltose, and pannose can also be formed in the fermentation medium.

Methods of the disclosure may be described in terms of concentrations of compounds in the fermentation medium at two or more different times during fermentation, and the difference between such concentrations. For example, the concentration of sugar can be measured at a first time point at the beginning of fermentation, and then at a later, second time point during the fermentation process. The period of time between the first and second time points can define a fermentation period. In embodiments, the fermentation period is about 30 hours or greater, about 40 hours or greater, about 50 hours or greater, or about 60 hours or greater, such as a period of time in the range of about 40 to about 120 hours, or 50 to about 110 hours.

For purposes of illustrating aspects of the disclosure, the concentrations of sugars can be described relative to a control fermentation condition. One control fermentation condition is fermenting using a yeast that does not have a heterologous sugar transporter. The control yeast can be one that is genetically identical to the engineered yeast, with the exception that it lacks the gene that encodes the heterologous sugar transporter. Strain 1-9 is an example of a control yeast that lacks a heterologous sugar transporter, and strain 1-8 is an example of a yeast that expresses a heterologous sugar transporter, but has the same genetic background as strain 1-9.

The advantage of using yeast of the current disclosure can be understood by the ability of the engineered yeast to reduce the concentration of oligo sugars that may accumulate during fermentation. In a fermentation method the engineered yeast with heterologous sugar transporter can be present in a fermentation medium at a first time point (e.g., $T_0$) along with glucose and amounts of oligo sugars, such as maltulose, isomaltose, maltose, and panose, such as in the range of about 0.5 g/L to about 5 g/L (i.e., a first concentration of oligo sugars). At the first time point $T_0$ the fermentation medium may have little (e.g., less than 10 g/L, or less than 5 g/L) or no bioproduct such as ethanol. A fermentation medium with the same carbohydrate content but with a control yeast that does not express heterologous sugar transporter can be used for comparative purposes. Fermentation can be run under identical conditions using the engineered yeast with heterologous sugar transporter and control yeast, such as by continuous addition of a feed that includes a partially hydrolyzed starch composition. During a period of fermentation the yeast consume glucose and generate the bioproduct such as ethanol which accumulates in the fermentation medium. During the course of fermentation, oligo sugars can be introduced along with the partially hydrolyzed starch feed, and/or can be formed in the fermentation medium, such as by reverse conversion of glucose to glucose oligomers by glucoamylases. The engineered yeast with heterologous sugar transporter provides for consumption of the oligo sugars so their concentrations are lower after a period of fermentation (i.e., second concentrations at a second time point) as compared to the control yeast.

Ability of the engineered yeast can be reflected in or more ways, such as the concentration of an oligo sugar at the end of the fermentation period, the percent reduction in amount of oligo sugar as compared to a control yeast, and/or the amount of oligo sugar at the end of fermentation as compared to the amount at the beginning of fermentation.

For example, using a control yeast and over a fermentation period, the amount of maltulose can increase from a first concentration to a second concentration. Under the same conditions the accumulation of maltulose using the yeast that expresses a heterologous sugar transporter is not as great as in the control fermentation, with maltulose accumulating to an amount that is less than in amount formed in the control fermentation. For example, using yeast that express a heterologous sugar transporter the amount of maltulose at the second time point can be less than about 90%, less than about 85%, less than about 80%, or less than about 75% than the amount of maltulose at the second time point in the control fermentation, such as 50-85% of the amount of maltulose at the second time point in the control fermentation.

Maltulose levels may also be expressed relative to the amount of maltulose present at the beginning of fermentation. For example, using yeast that expresses a heterologous sugar transporter, the amount of maltulose at the second time point can be not greater than four times the concentration at the first time point, not greater than three times the concentration at the first time point, or not greater than is two times the concentration at the first time point.

The concentration of maltulose at the second time point may be expressed as an absolute value. For example, at the second time point in the fermentation medium maltulose can be present in an amount not greater than 1.5 g/L, in an amount not greater than 1.4 g/L, or in an amount not greater than 1.3 g/L.

Fermentation benefits provided by the engineered yeast that expresses a heterologous sugar transporter can also be understood in view of the yeast's ability to reduce the amounts of other oligo sugars such as isomaltose, maltose, and panose after a period of fermentation.

For example, using yeast that express a heterologous sugar transporter the amount of isomaltose at the second time point can be less than about 75%, less than about 50%, less than about 30%, or less than about 20% than the amount of maltulose at the second time point in the control fermentation, such as 15-75% of the amount of maltulose at the second time point in the control fermentation.

The amounts of other disaccharides at various time points during fermentation can be described. For example, the amount of isomaltose at a second time point can be expressed relative to the amount of isomaltose present at the beginning of fermentation. For example, using yeast that expresses a heterologous sugar transporter, the amount of isomaltose at the second time point can be less than the amount at the first time point, less than 75% of the amount at the first time point, or less than 50% the amount at the first time point.

The concentration of isomaltose at the second time point may also be expressed as an absolute value. For example, at the second time point in the fermentation medium isomaltose can be present in an amount not greater than 1.0 g/L, an amount not greater than 0.75 g/L, or an amount not greater than 0.5 g/L.

As another example, using yeast that express a heterologous sugar transporter the amount of maltose at the second time point can be less than about 75%, less than about 50%, less than about 35%, or less than about 25% of the amount of maltose at the second time point in the control fermentation, such as 20-75% of the amount of maltose at the second time point in the control fermentation.

Maltose levels may also be expressed relative to the amount of maltose present at the beginning of fermentation. For example, using yeast that expresses a heterologous sugar transporter, the amount of maltose at the second time point can be less than the amount at the first time point, less than 75% of the amount at the first time point, or less than 55% the amount at the first time point.

The concentration of maltose at the second time point may also simply be as an absolute value. For example, at the second time point in the fermentation medium maltose can be present in an amount not greater than 1.5 g/L, an amount not greater than 1.25 g/L, or an amount not greater than 1.0 g/L.

As another example, using yeast that express a heterologous sugar transporter the amount of panose at the second time point can be less than about 75%, less than about 50%, less than about 40%, or less than about 30% of the amount of panose at the second time point in the control fermentation, such as 25-75% of the amount of panose at the second time point in the control fermentation.

Panose levels may also be expressed relative to the amount of panose present at the beginning of fermentation. For example, using yeast that expresses a heterologous sugar transporter, the amount of panose at the second time point can be less than the amount at the first time point, less than 85% of the amount at the first time point, or less than 75% the amount at the first time point.

The concentration of panose at the second time point may also be expressed as an absolute value. For example, at the second time point in the fermentation medium panose can be present in an amount not greater than 1.0 g/L, an amount not greater than 0.85 g/L, or an amount not greater than 0.75 g/L. Methods of the disclosure may be described in terms of a rate at which a type of sugar is consumed during fermentation. The rate of consumption of glucose, which is typically the primary sugar in the treated composition, as well as other sugars including isomaltose, maltulose, panose, and maltose, can be described.

The "consumption rate of a substrate", such as maltulose, is defined using the following equation:

$$\frac{\text{total substrate consumed}}{\text{batch time} \times \text{volume at end of fermentation}}$$

That is, the substrate consumed divided by the product of batch time and the fermentation volume at the end of fermentation. The "consumption rate of a substrate" is commonly expressed in grams per liter per hour (g/(L-h)). The "total substrate consumed" is defined as the "total substrate added" minus the "residual substrate". It is expressed in units of grams (g)

The "total substrate added" is the mass of substrate present in the fermentation medium at the time of inoculation in addition to the mass of any additional substrate added or formed (for example, the formation of glucose or a non-glucose sugar due to hydrolysis of starch prior to the end of fermentation. The "total substrate added" is commonly expressed in units of grams (g).

The "residual substrate" is the mass of substrate present in the broth at the end of fermentation. The "residual substrate" is commonly expressed in units of grams (g). In this way, one can calculate a "maltulose consumption rate" or "consumption rate of maltulose". Other exemplary consumption rates can include "glucose consumption rate" or "sugar consumption rate". In some embodiments the fermentation method provides a fermentation method wherein Ethanol is produced at a rate of at least 5 g/L*h during peak fermentation and, glucose is consumed at a rate in the range of 1 g/L*hr to 25 g/L*hr, or more specifically, in the range of 5 g/L*hr to 10 g/L*hr.

In some embodiments the fermentation method provides a fermentation method wherein isomaltose is consumed at a rate in the range of 0.005 g/L*hr to 1.0 g/L*hr, or more specifically, in the range of 0.01 g/L*hr to 0.05 g/L*hr.

In some embodiments the fermentation method provides a fermentation method wherein maltulose is consumed at a rate in the range of 0.005 g/L*hr to 0.1 g/L*hr, or more specifically, in the range of 0.01 g/L*hr to 0.05 g/L*hr.

In some embodiments the fermentation method provides a fermentation method wherein panose is consumed at a rate in the range of 0.005 g/L*hr to 0.1 g/L*hr, or more specifically, in the range of 0.01 g/L*hr to 0.05 g/L*hr.

In some embodiments the fermentation method provides a fermentation method wherein maltose is consumed at a rate in the range of 0.005 g/L*hr to 0.1 g/L*hr, or more specifically, in the range of 0.01 g/L*hr to 0.05 g/L*hr.

In some embodiments, the disclosure provides a method for producing ethanol by fermentation, wherein the ethanol is present in the fermentation media at a concentration of 80 g/L or greater. In the method, a liquid media comprising a starch material and an engineered yeast having a heterologous sugar transporter is fermented. Fermentation can provide an ethanol concentration of about 80 g/L or greater in the liquid media, such as in the range of about 90 g/L to about 140 g/L, in the range of about 90 g/L to about 140 g/L, in the range of about 100 g/L to about 140 g/L, or in the range of about 110 g/L to about 140 g/L.

In embodiments of the disclosure, after a desired period of fermentation the fermentation medium has an ethanol concentration of about 80 g/L or greater in the liquid media, and a maltulose concentration of below about 5 g/L, below about 4.5 g/L, below about 4 g/L, below about 3.5 g/L, below about 3.0 g/L, below about 2.5 g/L, below about 2.0 g/L, below about 1.5 g/L, or below about 1.0.

In embodiments of the disclosure, after a desired period of fermentation the fermentation medium has an ethanol concentration of about 80 g/L or greater in the liquid media, and a isomaltose concentration of below about 5 g/L, below about 4.5 g/L, below about 4 g/L, below about 3.5 g/L, below about 3.0 g/L, below about 2.5 g/L, below about 2.0 g/L, below about 1.5 g/L, or below about 1.0.

In embodiments of the disclosure, after a desired period of fermentation the fermentation medium has an ethanol concentration of about 80 g/L or greater in the liquid media, and a panose concentration of below about 5 g/L, below about 4.5 g/L, below about 4 g/L, below about 3.5 g/L, below about 3.0 g/L, below about 2.5 g/L, below about 2.0 g/L, below about 1.5 g/L, or below about 1.0.

The engineered yeast of the current disclosure can also be described in terms of the engineered yeast's growth rate. The growth rate of yeast can be defined by L=log(numbers) where numbers is the number of yeast cells formed per unit volume (mL), versus T (time). In embodiments of the disclosure, the genetically modified yeast comprising a heterologous sugar transporter is capable of promoting uptake and fermentation of maltulose, wherein the cell is capable of growing in a liquid medium having the maltulose at a rate that is greater than 0.02.

In some modes of practice, the fermentation product can be recovered from the fermentation broth. The manner of accomplishing this will depend on the particular product. However, in some modes of practice, the organism is separated from the liquid phase, typically via a filtration step or centrifugation step, and the product recovered via, for example, distillation, extraction, crystallization, membrane separation, osmosis, reverse osmosis, or other suitable technique.

The fermentation product may be first treated with one or more agents a treatment system. The treated fermentation product can then be sent to a distillation system. In the distillation system, the fermentation product can be distilled and dehydrated into ethanol. In some embodiments, the components removed from the fermentation media include water, soluble components, oil and unfermented solids. Some of these components can be used for other purposed, such as for an animal feed product. Other co-products, for example, syrup can be recovered from the stillage.

Backset is the remaining fermentation broth following the removal of a bioproduct, such as alcohol, during the distillation process. Scrubber water is the liquid collected from a scrubber. Definitions of common terms of the disclosure can be found in *The Alcohol Textbook*, 4$^{th}$ Edition. 1995.

The present disclosure also provides a method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a composition as described herein.

In one aspect, the present invention relates to a fermentation method that produces ethanol while producing lower amounts of acetaldehyde that other fermentation processes. Acetaldehyde is an undesirable fermentation byproduct that is typically emitted in the offgas of a fermentation process. It has been surprisingly found that some embodiments of the genetically engineered yeast described herein produce significantly less acetaldehyde than other yeast strains while producing similar or even greater amounts of ethanol.

In another aspect, the present invention relates to certain fermentation parameter ranges or values that result in reduced acetaldehyde production during fermentation. In some embodiments, these fermentation parameter ranges can be used in a fermentation process utilizing any of the genetically engineered yeasts described herein. In some embodiments, these fermentation parameter ranges can be used in a fermentation process utilizing any commercially relevant *S. cerevisiae* yeast, for example but not limited to ETHANOL RED™ yeast or TRANSFERM™ yeast. The fermentation parameters associated with reduced acetaldehyde production include the DE of the partially hydrolyzed starch in the fermentation medium, the glucose concentration of the fermentation medium, and/or the GA activity of the fermentation process. It is contemplated that setting and/or maintaining these parameters during fermentation at the values or within the ranges described herein can result in lower amounts of acetaldehyde being produced compared to current commercial ethanol fermentation processes. Further, the reduced acetaldehyde effect can be greater when using the genetically engineered yeasts of the present invention compared to other yeasts.

In some embodiments, the DE of the partially hydrolyzed starch used in the fermentation methods described herein is less than 20 after inoculation. In some such embodiments, the DE is less than 20 within 1 h, 2 h, 3 h, 4 h, or 5 h of inoculation. In some embodiments, the DE of the partially hydrolyzed starch used in the fermentation methods described herein is less than 25, less than 30, less than 35, less than 40, less than 45, or less than 50 within 5 h after inoculation.

In some embodiments, the glucose concentration during the fermentation is less than about 80 g/L. In some embodiments, the glucose concentration does not exceed 80 g/L for at least the initial portion of the fermentation, for example within 1 h, 2 h, 3 h, 4 h, or 5 h of inoculation. In some embodiments, the glucose concentration of the medium does not exceed 80, 75, 70, 65, 60, 55, 50, 45, or 40 g/L during fermentation and the total amount of acetaldehyde produced during the fermentation is reduced compared to a fermentation process using a yeast and with a glucose concentration exceeding 80, 95, 90, 95, 100, or 105 g/L. In some such embodiments, the glucose concentration of the medium does not exceed 70 g/L during fermentation and the total amount of acetaldehyde produced during the fermentation is reduced compared to a fermentation process using a yeast and with a glucose concentration exceeding 80, 95, 90, 95, 100, or 105 g/L.

In some embodiments, the GA activity in the fermentation medium during fermentation is lower compared to other ethanol fermentation processes. In some embodiments, the GA activity is less than 0.8 times, 0.75 times, 0.7 times, 0.65 times, 0.6 times, 0.55 times, or 0.5 times a standard GA activity, referred to as "1×GA activity." "1×GA activity" means the minimum enzyme dose added at inoculation that will produce 135 g/L glucose via hydrolysis of starch at 9 h after inoculation, plus or minus 5%. In some embodiments, the GA activity is in the range of 0.675 to 0.8 times the 1×GA activity.

The above parameter ranges, either alone or in combination, can reduce the total amount of acetaldehyde produced in the fermentation by 25, 30, 35, 40, 45, 50, 55, 60, 65, 70, 75, 80, 85, 90 or 95% compared to other fermentation processes, for example a process with a glucose concentration exceeding 90 g/L within 10 hours or less of inoculation. In some embodiments, to compare the amounts of acetaldehyde produced in two different fermentation processes it is useful to measure the total amount of acetaldehyde produced at a given carbon dioxide evolution rate (CER). As would be understood by a person skilled in the art, comparing fermentation processes at the same or similar CER can be used instead of time to normalize the progression of the fermentation process for comparison purposes. The carbon dioxide evolution rate (CER) is determined according to methods known in the art. The CER is based on the flow rates of all gases supplied to the fermentation, the flow rates of all gases leaving the fermentation, the relative $CO_2$ concentrations of all such gas streams, and the volume of the fermentation medium. The CER is measured in units of mmol $L^{-1}$ $h^{-1}$.

Example #1. *Saccharomyces cerevisiae* Base Strain Construction

Strain 1 is transformed with SEQ ID NO 1. SEQ ID NO 1 contains the following elements: i) an expression cassette for a mutant version of a 3-deoxy-D-arabino-heptulosonate-7-phosphate (DAHP) synthase gene from *Saccharomyces cerevisiae* (ARO4-OFP) corresponding to nucleotides 479-2647; ii) loxP sequence corresponding to nucleotides 445-478 and 2648-2681, and iii) flanking DNA for targeted chromosomal integration into integration locus A where nucleotides 1-436 correspond to the integration locus A 5' flanking region and nucleotides 2691-3182 correspond to the integration locus A 3' flanking region. Transformants are selected on synthetic complete media containing 3.5 g/L of p-fluorophenylalanine, and 1 g/L L-tyrosine (ScD-PFP). Resulting transformants are streaked for single colony isolation on ScD-PFP. A single colony is selected. Correct integration of SEQ ID NO: 1 into one allele of locus A is verified by PCR in the single colony. A PCR verified isolate is designated Strain 1-1.

Strain 1-1 is transformed with SEQ ID NO 2. SEQ ID NO 2 contains the following elements: i) a codon optimized expression cassette for a acetamidase (amdS) gene from *Aspergillus nidulans* corresponding to nucleotides 638-2284 with a TEF1 promoter corresponding to nucleotides 2285-2740 and a TEF1 terminator corresponding to nucleotides 478-637; ii) loxP sequence corresponding to nucleotides 444-477 and 2741-2774, and iii) flanking DNA for targeted chromosomal integration into integration locus A where nucleotides 1-435 correspond to the integration locus A 5' flanking region and nucleotides 2783-3275 correspond to the integration locus A 3' flanking region. Transformants are selected on Yeast Nitrogen Base (without ammonium sulfate or amino acids) containing 80 mg/L uracil and 1 g/L acetamide as the sole nitrogen source. Resulting transformants are streaked for single colony isolation on Yeast Nitrogen Base (without ammonium sulfate or amino acids) containing 80 mg/L uracil and 1 g/L acetamide as the sole nitrogen source. A single colony is selected. Correct integration of SEQ ID NO 2 into the second allele of locus A is verified by PCR in the single colony. A PCR verified isolate is designated Strain 1-2.

Strain 1-2 is co-transformed with SEQ ID NO 3 and SEQ ID NO 4. SEQ ID NO 3 contains the following elements: i) an open reading frame for a cre recombinase from P1 bacteriophage corresponding to nucleotides 53-1084, and ii) flanking DNA homologous to SEQ ID NO 4 corresponding to nucleotides 1-47 and 1086-1132. SEQ ID NO 4 contains the following elements: i) a 2μ origin of replication corresponding to nucleotides 2195-3350; ii) a URA3 selectable marker from *Saccharomyces cerevisiae* corresponding to nucleotides 3785-4901; and iii) flanking DNA containing a PGK promoter corresponding to nucleotides 5791-6376 and CYC1 terminator corresponding to nucleotides 10-199 from *Saccharomyces cerevisiae*. For the remaining part of SEQ ID NO 4, a pUC origin of replication corresponds to nucleotides 386-1053; and an ampicillin resistance gene corresponds to nucleotides 1204-2061. Transformants are selected on synthetic dropout media lacking uracil (ScD-Ura). Resulting transformants are streaked for single colony isolation on YPD. A single colony is selected. The isolated colony is screened for growth on ScD-PFP and Yeast Nitrogen Base (without ammonium sulfate or amino acids) containing 80 mg/L uracil and 1 g/L acetamide as the sole nitrogen source. Loss of the ARO4-OFP and amdS genes is verified by PCR. The PCR verified isolate is struck to ScD-Ura to verify loss of the replicating plasmid. The PCR verified isolate is designated Strain 1-3.

Example #2. Over-Expressing the Native Isomaltase in Strain 1-3 to Create Strain 1-4

Strain 1-3 was transformed with SEQ ID NO 5 and SEQ ID NO 6. SEQ ID NO 5 contains 5' homology to the integration locus B, an expression cassette for the native IMA1, and part of the expression cassette for the amdS marker. SEQ ID NO 6 contains part of the amdS selection marker, and 3' homology to integration locus B. Transformants were selected on YNB+acetamide. Resulting transformants were struck to YPD for single colony isolation. A single colony is selected. Presence of the integration is confirmed by PCR. A single colony is designated Strain 1-4.

Example #3. Measuring Isomaltase Activity in Strain 1-4

Strain 1 and Strain 1-4 are grown overnight at 30° C. and 250 RPM in 50 mls of YPD 100 g/L glucose supplemented with 40 mg/L uracil contained in a standard baffled 250 ml shake flask. The entire flask was spun down at 4000 RPM for 10 minutes, and the supernatant discarded. The pellet was washed with 10 mls of ice-cold 100 mM potassium phosphate pH 7.0, before storage at −80° C. Prior to the assay, each pellet was re-suspended in 1 ml of ice-cold 100 mM potassium phosphate pH 7.0 and transferred to a 2.0 ml screw cap tube containing 0.5 ml volume of ~500 micron sterile glass beads. After two successive 1-minute rounds in a bead mill, with 1-minute on ice in between, the debris was pelleted at 14,000 RPM for 10 minutes at 4° C. The resulting supernatant was used for enzyme analysis, using a two-step protocol in 96-well microtiter plates. The first reaction contained 10 μl cell free extract (CFE), 10 μl 100 mM isomaltose, and 80 μl of 100 mM potassium phosphate pH 7.0. After 30 minutes incubation at 30° C., 20 μl of the first reaction is added to 180 μl of HXK/G6PDH master mix (Sigma Catalog number G3293). A standard curve using samples with known glucose concentrations is used to calculate the amount of isomaltose consumed in the samples. Protein concentration was determined using the Advanced Protein Assay (Cytoskeleton Inc., Catalog number ADV01-A), A unit is defined as the amount of enzyme that catalyzes the conversion of 1 micro mole of substrate per minute.

The results in FIG. 1 show that Strain 1-4 has higher isomaltase activity compared to Strain 1.

Example #4. Transformation of Strain 1-3 with Potential Isomaltose Transporters

Figure 2:
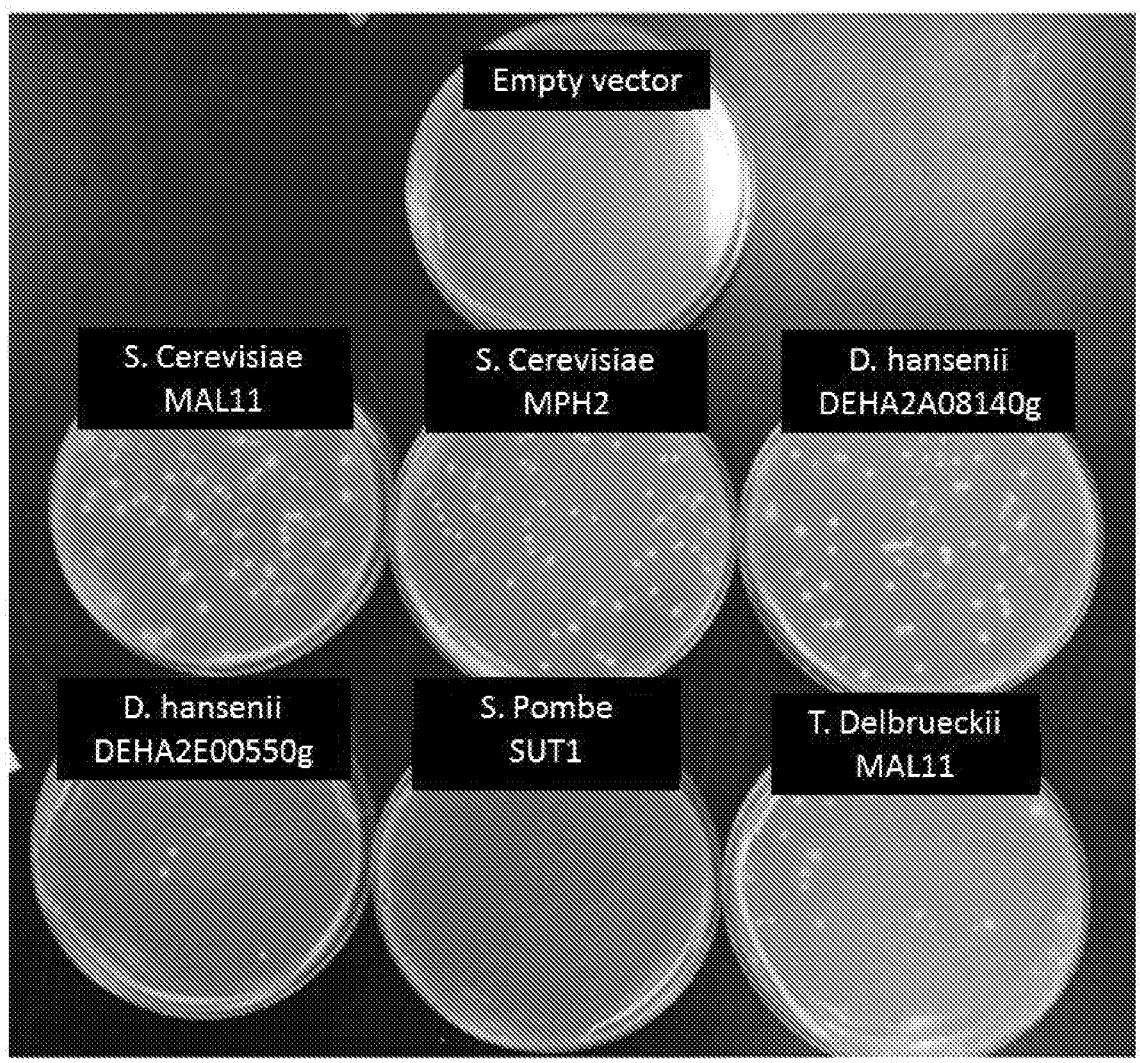
FIG. 2 is a picture of yeast grown on isomaltose selection plates.

Strain 1-3 is transformed with SEQ ID NO. 7 through 12 individually combined with SEQ ID NO. 13 (Table 1). SEQ ID NO 7 through 12 contain open reading frames for potential isomaltose transporters, as well as a small overhangs to facilitate homologous recombination with SEQ ID NO 13. SEQ ID NO 13 contains 1) a CYC1 terminator corresponding to nucleotides 4-227 bp, 2) a centromere to allow for stable replication (CEN6) corresponding to nucleotides 2485-3003 bp, and 3) an expression cassette for an orotidine-5'-phosphate decarboxylase (URA3) corresponding to nucleotides 3262-4359 bp), and 4) a ADH1 promoter corresponding to nucleotides 5090-5835 bp. SEQ ID NO 13 also includes an ampicillin resistance gene corresponding to nucleotides 1496-2352 bp. Transformants are selected on either ScD-Ura or Sc-Ura containing 10 g/L isomaltose (TCI # I0231). Roughly 500-1000 transformants are obtained on ScD-Ura selection after 3 days at 30° C. for each transformation (not shown). Variable numbers of transformants are obtained on Sc-Ura 10 g/L isomaltose after 7 days at 30° C., shown in FIG. 2.

The results shown in Table 1 indicate that the ScMAL11, ScMPH2, DhMAL11 (DEHA2A08140 g), DhMAL11 (DEHA2E00550 g) and TdMAL11 are functional in Strain 1-3 and are capable of transporting isomaltose, whereas the SpSUT1 and the empty vector failed to produce any visible colonies capable of growth on isomaltose.

TABLE 1

| SEQ ID # | Source | Accession # | Growth on Isomaltose |
|---|---|---|---|
| 7 | *Saccharomyces cerevisiae* MAL11 | NP_011805.3 | Positive |
| 8 | *Saccharomyces cerevisiae* MPH2 | NP_010034.1 | Positive |
| 9 | *Debaromyces hansenii* DEHA2A08140g | XP_456684.2 | Positive |

TABLE 1-continued

| SEQ ID # | Source | Accession # | Growth on Isomaltose |
|---|---|---|---|
| 10 | Debaromyces hansenii DEHA2E00550g | XP_459351.2 | Positive |
| 11 | Schizosaccharomyces pombe SUT1 | CAB16264.1 | Negative |
| 12 | Torulaspora delbrueckii MAL11 | AAQ75121.1 | Positive |
| 13 | Empty vector | na | Negative |

Example #5. Transformation of Strain 1-5 with Additional Transporters

Strain 1-5 was obtained from the Invitrogen Yeast Gene Deletion Library (Catalog number 95401.H2, record number 7294). Strain 1-5 is transformed with SEQ ID NO 14-29 individually combined with SEQ ID NO 13. SEQ ID NO 14-29 contain the full open reading frames of each individual transporter described in Table 2, codon optimized for Saccharomyces cerevisiae, with 5' and 3' homology to enable recombination with SEQ ID NO 13. SEQ ID NO 14-29 are obtained from an ERGO database. Transformants are selected on either ScD-Ura or Sc-Ura containing 10 g/L isomaltose (Tokyo Chemical Company catalog number 10231). The transformation was successful for each transformation on ScD-Ura selection after 3 days at 30° C. Several of the transformations were successful on Sc-Ura 10 g/L isomaltose after 7 days at 30° C., shown in FIG. 3.

Figure 3:
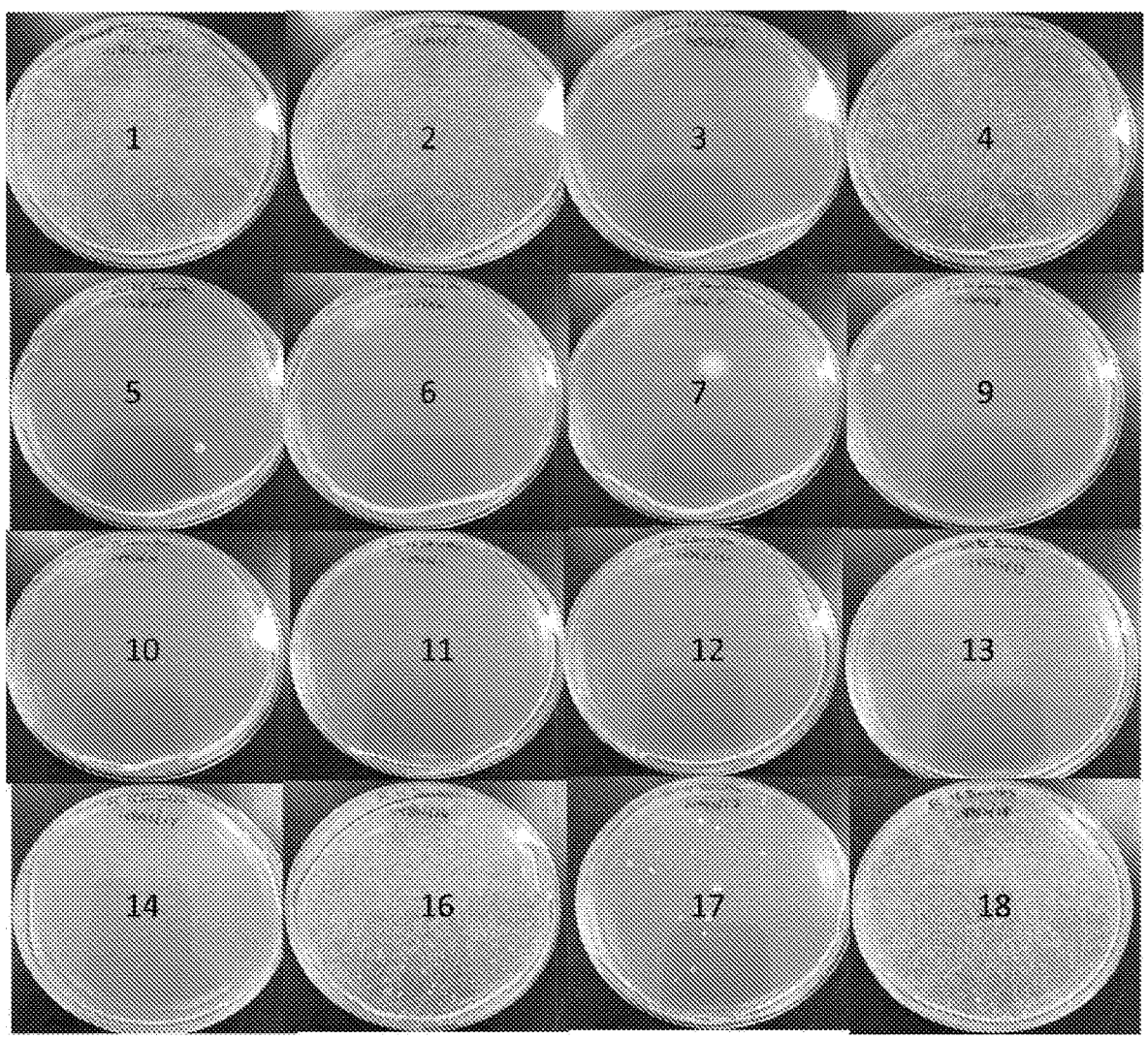
FIG. 3 is a picture of yeast grown on isomaltose selection plates.

The results in FIG. 3 show the SmMAL11-1, SmMAL11-2, SpMAL11, and the three ScMAL11 variants complemented the null phenotype (albeit the ScMAL11-CBS7690 produced far few transformants).

TABLE 2

Description of transporters described in Example 5

| SEQ ID # | Plate # in FIG. 3 | Source | Accession number | Growth on isomaltose |
|---|---|---|---|---|
| 14 | 1 | Saccharomyces mikatae 1 | NA | Positive |
| 15 | 2 | Saccharomyces mikatae 2 | NA | Positive |
| 16 | 3 | Saccharomyces cerevisiae RM11-1a | EDV11818.1 | Negative |
| 17 | 4 | Saccharomyces paradoxus | NA | Positive |
| 18 | 5 | Kluyveromyces lactis | XP 451541.1 | Negative |
| 19 | 6 | Pichia stipitis CBS 6054 | XP_001382383.1 | Negative |
| 20 | 7 | Pichia stipitis CBS 6054 | XP_001385456.1 | Negative |
| 21 | 9 | Pichia stipitis CBS 6054 | XP_001385693.1 | Negative |
| 22 | 10 | Hansenula polymorpha NCYC 495 leu1.1 | AAX92669.1 | Negative |
| 23 | 11 | Candida albicans SC5314 | XP_722051.1 | Negative |
| 24 | 12 | Candida dubliniensis CD36 | XP_002420747.1 | Negative |
| 25 | 13 | Aspergillus oryzae RIB40 | NA | Negative |
| 26 | 14 | Aspergillus fumigatus Af293 | NA | Negative |
| 27 | 16 | Saccharomyces cerevisiae ZTW | AJR80312.1 | Positive |
| 28 | 17 | Saccharomyces cerevisiae MAL11 (CBS 7690) | NA | Positive |
| 29 | 18 | Saccharomyces cerevisiae MAL11 (FostersO) | AAY99642.1 | Positive |

Example #6. Construction of Strains Containing Heterologous Transporters Harbored on Stable Replicating Plasmids Strain 1-3 is transformed with SEQ ID NO 13 and SEQ ID NO 14. Transformants are selected on ScD-Ura. Resulting transformants are streaked for single colony isolation on ScD-Ura. A single colony is saved as Strain 1-6.

Strain 1-3 is transformed with SEQ ID NO 30. SEQ ID NO 30 contains the following elements: i) URA3 expression cassette corresponding to nucleotides 195 to 1292, ii) a centromere to allow for stable replication (CEN6) corresponding to nucleotides 4305 to 4823. For the remaining part of SEQ ID NO 30, a pUC origin of replication corresponds to nucleotides 2495 to 3168; and an ampicillin resistance gene corresponds to nucleotides 3316 to 4173.

Transformants are selected on ScD-Ura. Resulting transformants are streaked for single colony isolation on ScD-Ura. A single colony is saved as Strain 1-7.

Strain 1-4 is transformed with SEQ ID NO 13 and SEQ ID NO 14. Transformants are selected on ScD-Ura. Resulting transformants are streaked for single colony isolation on ScD-Ura. A single colony is saved as Strain 1-8.

Strain 1-4 is transformed with SEQ ID NO 30. Transformants are selected on ScD-Ura. Resulting transformants are streaked for single colony isolation on ScD-Ura. A single colony is saved as Strain 1-9.

Example #7. 2 L Fed Batch Fermentations with 95DE Feedstock Comparing Strain 1-8 and Strain 1-9 to Strain 1

Seed flasks were started in 500 mL baffled flasks with 100 mL of ScD-Ura media. The flasks were inoculated with a single colony from a ScD-Ura plate, and incubated for 20-24 hours at 30° C. and 250 rpm. Two separate fermentation media stocks were made. The first media stock consisted of 278 mls of 95DE (95% hydrolyzed starch), 456 mls sterilized Light Steep Water, 1.9 g of Urea, which was added to a sterilized 2 L Benchtop Biostat B through a diptube in the head plate. This was inoculated to an initial pitch of 0.2 $OD_{600}$ (0.06 g/l cell dry weight) from the seed flask. The second media stock consisted of 1000 mls of 95DE and 100 g of glucose, of which 750 mls was removed and added at a variable rate after inoculation until exhausted (before 66 hour time point). At 16 hours, 2 g/L isomaltose was spiked into the fermentation using a 100 g/L stock solution. Temperature was controlled at 30° C., the broth was stirred at an agitation of 100-150 rpm, and air was sparged into the media at 0.38 slpm. Once these set points had been reached the Dissolved Oxygen (DO) probe was calibrated and the % DO of the fermentation was monitored. The pH of the fermentation was also monitored but not controlled. $CO_2$ production, $O_2$ consumption, and ethanol evaporation were also monitored in the off gas. Samples are taken and analyzed for metabolite concentrations in the broth during fermentation by HPLC with refractive index and UPLC with ELSD detection.

Figure 4:
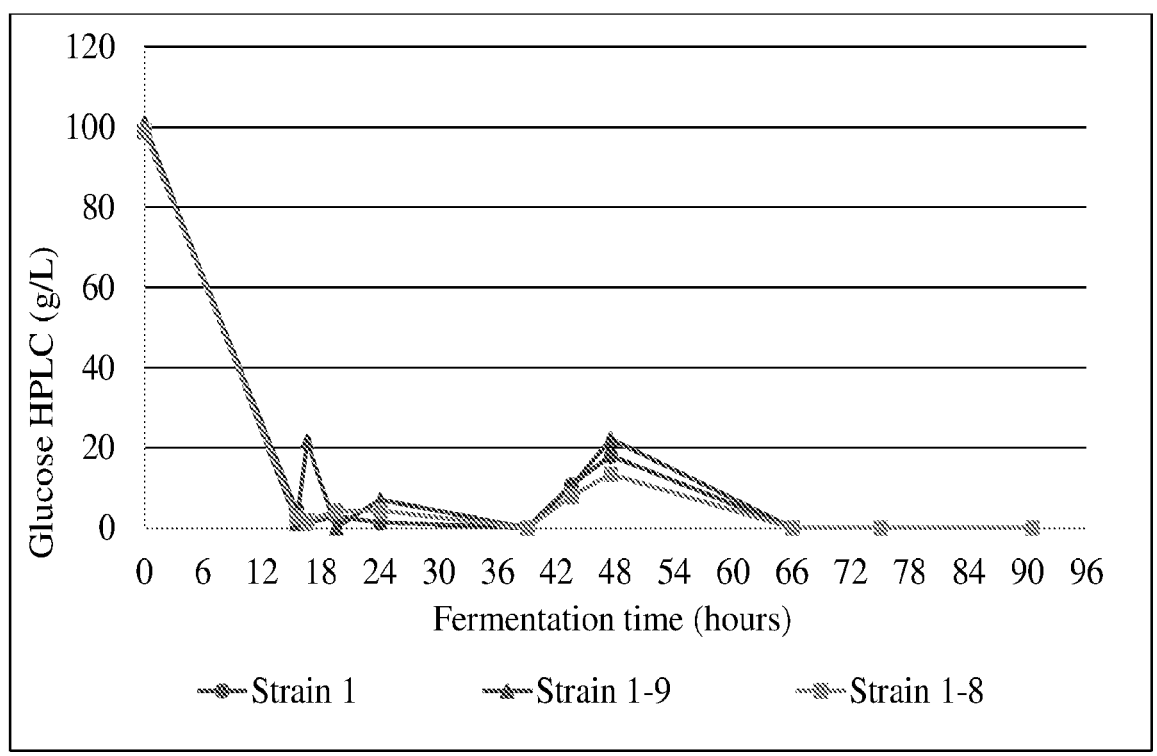
FIG. 4 is a graph showing glucose consumption over time in 2 L fed batch fermentations with 95DE feedstocks using Strain 1, 1-8, and 1-9.
Figure 5:
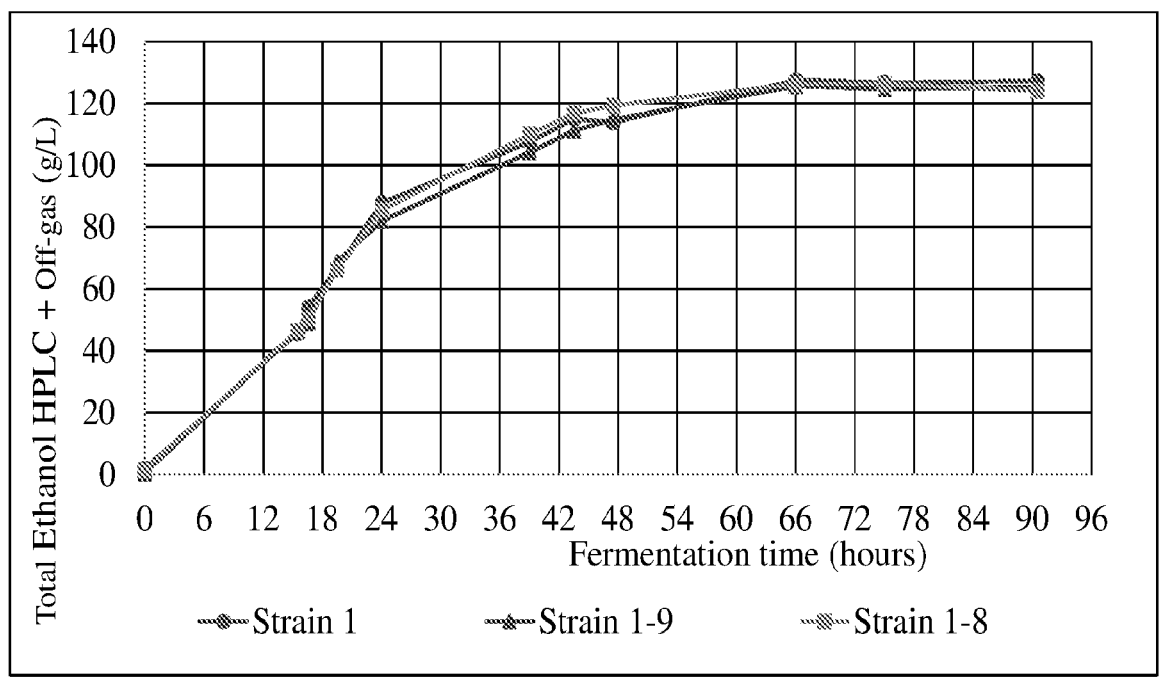
FIG. 5 is a graph showing ethanol production over time in 2 L fed batch fermentations with 95DE feedstocks using Strains 1, 1-8, and 1-9.
Figure 6:
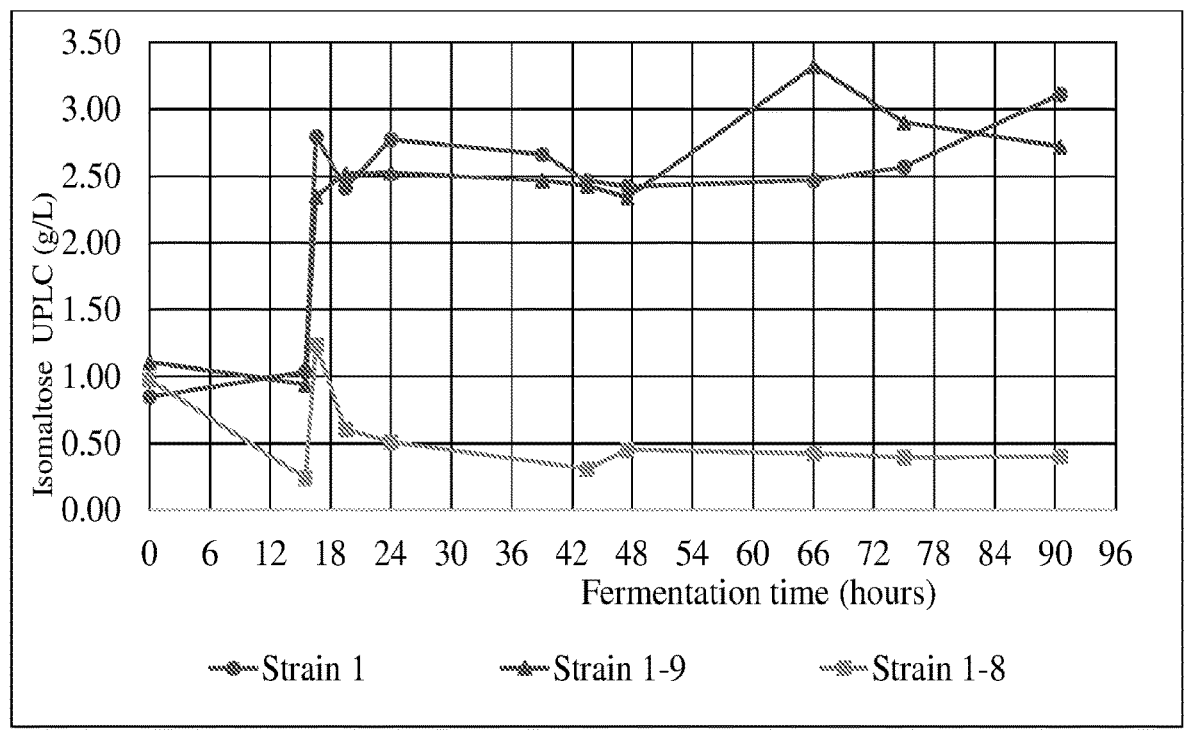
FIG. 6 is a graph showing isomaltose consumption over time in 2 L fed batch fermentations with 95DE feedstock using Strain 1, 1-8, and 1-9.
Figure 7:
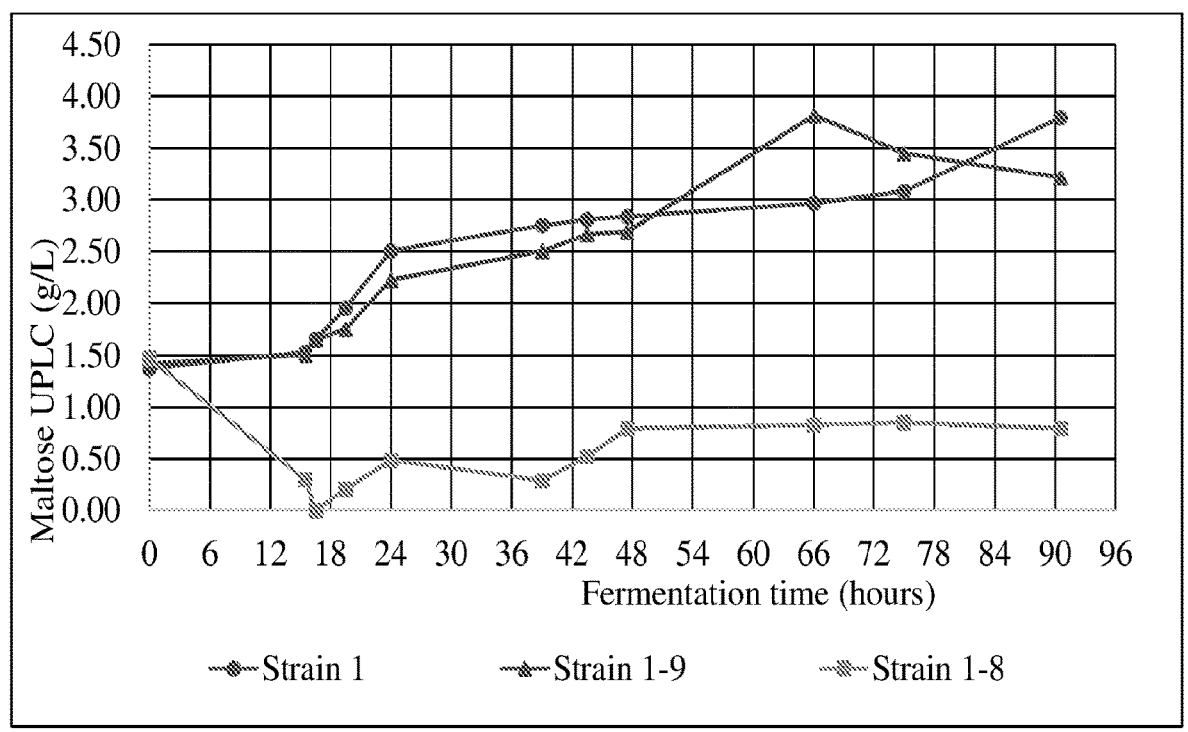
FIG. 7 is a graph showing maltose consumption over time in 2 L fed batch fermentations with 95DE feedstock using Strain 1, 1-8, and 1-9.
Figure 8:
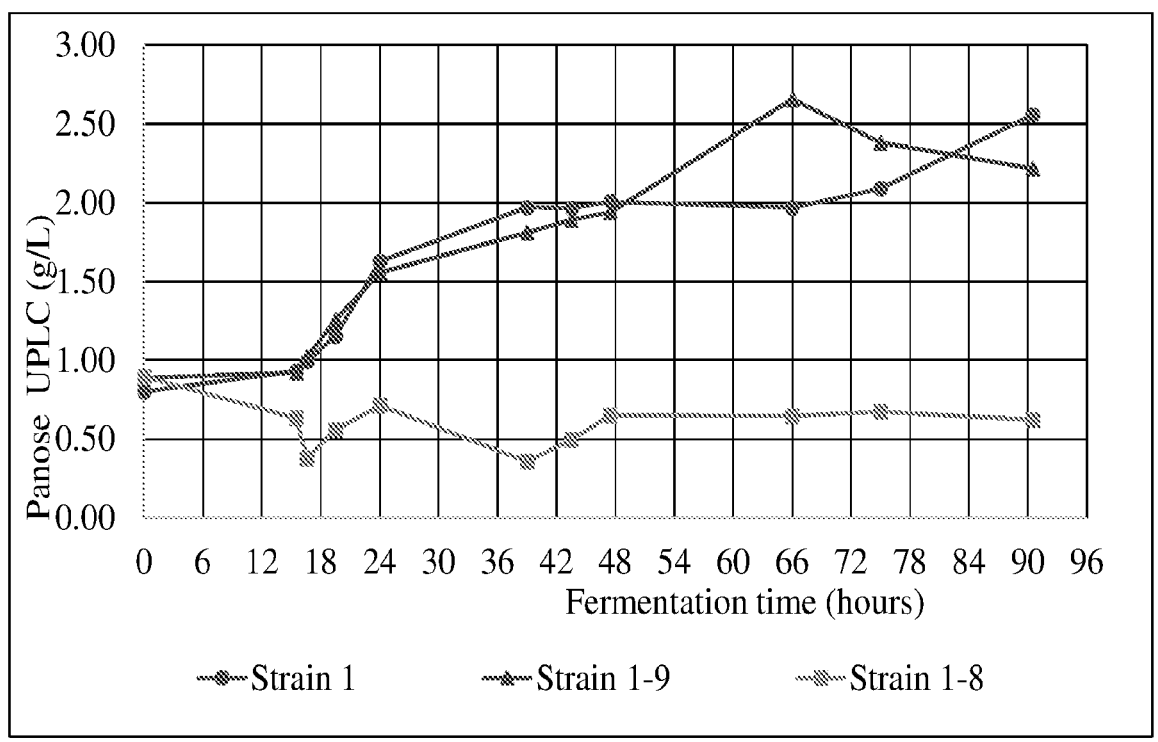
FIG. 8 is a graph showing panose consumption over time in 2 L fed batch fermentations with 95DE feedstock using Strain 1, 1-8, and 1-9.
Figure 9:
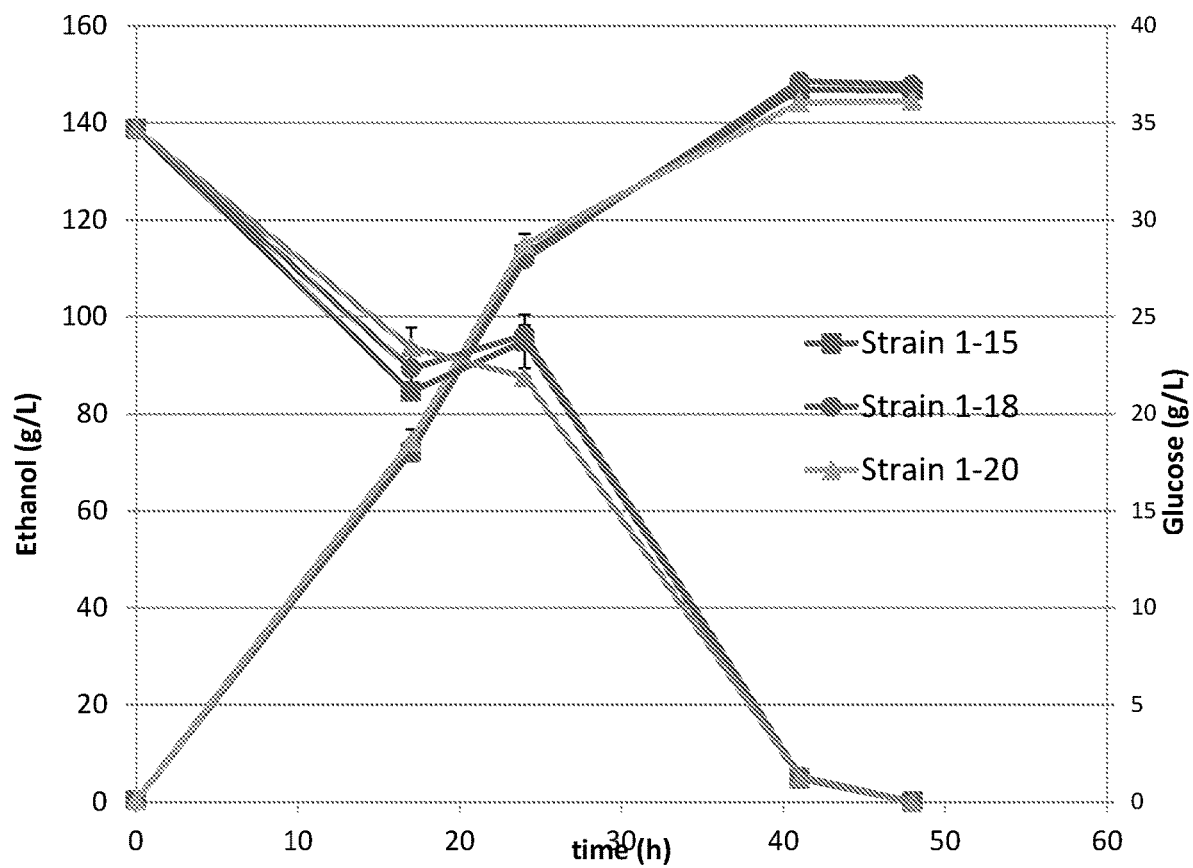
FIG. 9 is a graph showing glucose consumption and ethanol production in simultaneous saccharification and fermentation (SSF) shake flasks.

The results clearly show that the Strain 1-8 is capable of reducing the three primary oligo sugars in 95DE: isomaltose (FIG. 6), maltose (FIG. 7), and panose (FIG. 8) relative to the control Strain 1-9 and the original Wild Type Strain 1. Ethanol production and glucose consumption was similar between the strains (FIG. 4 and FIG. 5).

TABLE 3

Summary results for 2 L fed batch fermentations with 95DE feedstock

| ID | Strain 1 | Strain 1-9 | Strain 1-8 |
|---|---|---|---|
| Fermentation time (h) | 66 | 66 | 66 |
| Max EtOH titer (g/L) | 127.45 | 125.56 | 126.21 |
| Rate (g/L/h) | 1.90 | 1.89 | 1.89 |
| Residual isomaltose (g/L) | 2.46 | 3.32 | 0.42 |
| Residual maltose (g/L) | 2.96 | 3.82 | 0.83 |
| Residual panose (g/L) | 1.97 | 2.65 | 0.65 |

Example #8. Generation of a Strain Containing Two Heterologous Copies of ScIMA1 and SmMAL11-1 Integrated into the Genome of Strain 1-3

Strain 1-3 was transformed with SEQ ID NO 31. SEQ ID NO 31 contains 5' homology to locus C, an expression cassette for the ScIMA1, an expression cassette for the URA3 marker, an expression cassette for the SmMAL11-1, and 3' homology to integration locus C. Transformants are selected on ScD-Ura. Resulting transformants are streaked for single colony isolation on ScD-Ura. A single colony is selected. Presence of the integration at locus C is verified by PCR. The PCR verified isolate is saved as Strain 1-10. Strain 1-10 was transformed with SEQ ID NO 32. SEQ ID NO 32 contains 5' homology to integration locus C, an expression cassette for the ScIMA1, an expression cassette for the *Aspergillus nidulans* acetamidase gene (amdS), an expression cassette for the SmMAL11-1, and 3' homology to locus C. Transformants were selected on Yeast Nitrogen Base (without ammonium sulfate or amino acids) containing 1 g/L acetamide as the sole nitrogen source. Resulting transformants were streaked for single colony isolation on Yeast Nitrogen Base (without ammonium sulfate or amino acids) containing 1 g/L acetamide as the sole nitrogen source. A single colony was selected. Correct integration of SEQ ID NO 32 at the remaining allele of locus C was verified by PCR. The PCR verified isolate was designated Strain 1-11.

Example #9. Transformation of Strain 1-3 to Create a Comparison Yeast to Strain 1-11, which Lacks the ScIMA1 and SmMAL11-1 Over-Expression Strain 1-3 was transformed with SEQ ID NO 33. SEQ ID NO 33 contains 5' homology to the integration locus C, an expression cassette for GFP (green fluorescent protein), an expression cassette for the native URA3, and 3' homology to locus C. Transformants are selected on ScD-Ura. Resulting transformants are streaked for single colony isolation on ScD-Ura. A single colony is selected. Presence of the integration at locus C is verified by PCR. The PCR verified isolate is saved as Strain 1-12.

Strain 1-12 is transformed with SEQ ID NO 34. SEQ ID NO 34 contains 5' homology to integration locus C, an expression cassette for GFP, an expression cassette for the *Aspergillus nidulans* acetamidase gene (amdS), and 3' homology to locus C. Transformants were selected on Yeast Nitrogen Base (without ammonium sulfate or amino acids) containing 1 g/L acetamide as the sole nitrogen source. Resulting transformants were streaked for single colony isolation on Yeast Nitrogen Base (without ammonium sulfate or amino acids) containing 1 g/L acetamide as the sole nitrogen source. A single colony was selected. Correct integration of SEQ ID NO 34 at the remaining allele of locus C was verified by PCR. The PCR verified isolate was designated Strain 1-13. Strain 1-13 is used to study the effect caused by deletion of the gene at locus C in the absence of the ScIMA1 and SmMAL11-1.

Example 10. Generation of a Strain Containing Four Copies of the *Saccharomycopsis fibuligera* Glucoamylase Strain 1-3 was co-transformed with SEQ ID NO: 35 and SEQ ID NO:36. SEQ ID NO: 35 contains the following elements: i) DNA homologous to the 5' region of the native CYB2 gene; and ii) an expression cassette for a unique codon optimized variant of the *Saccharomycopsis fibuligera* glucoamylase, under control of the TDH3 promoter and CYC1 terminator; and iii) the URA3 promoter as well as a portion of the URA3 gene. SEQ ID NO: 36 contains the following elements: i) a portion of the URA3 gene and terminator; and ii) an expression cassette for a unique codon optimized variant of the *Saccharomycopsis fibuligera* glucoamylase, under control of the PGK promoter and RPL3 terminator; and iii) DNA homologous to the 3' region of the native CYB2 gene. Transformants were selected on ScD-Ura. Resulting transformants were streaked for single colony isolation on ScD-Ura. A single colony was selected. Correct integration of SEQ ID NO: 35 and SEQ ID NO: 36 at one allele of CYB2 was verified by PCR. The PCR verified isolate was designated Strain 1-14.

Strain 1-14 was co-transformed with SEQ ID NO: 37 and SEQ ID NO: 38. SEQ ID NO: 37 contains the following elements: i) DNA homologous to the 5' region of integration locus B; and ii) an expression cassette for a unique codon optimized variant of the *Saccharomycopsis fibuligera* glucoamylase, under control of the TDH3 promoter and CYC1 terminator; and iii) the TEF1 promoter and a portion of the *Aspergillus nidulans* acetamidase gene (amdS). SEQ ID NO:38 contains the following elements: i) a portion of the *Aspergillus nidulans* acetamidase gene (amdS) and ADH1 terminator; and ii) an expression cassette for a unique codon optimized variant of the *Saccharomycopsis fibuligera* glucoamylase, under control of the PGK promoter and RPL3 terminator; and iii) DNA homologous to the 3' region of integration locus B. Transformants were selected on Yeast Nitrogen Base (without ammonium sulfate or amino acids) containing 80 mg/L uracil and 1 g/L acetamide as the sole nitrogen source. Resulting transformants were streaked for single colony isolation on Yeast Nitrogen Base (without ammonium sulfate or amino acids) containing 80 mg/L uracil and 1 g/L acetamide as the sole nitrogen source. A single colony was selected. Correct integration of SEQ ID NO:37 and SEQ ID NO:38 at the remaining allele of integration locus B was verified by PCR. The PCR verified isolate was designated Strain 1-15.

Strain 1-15 was transformed with SEQ ID NO:39. SEQ ID NO: 39 contains the following elements: i) an expression cassette for a mutant version of a 3-deoxy-D-arabino-heptulosonate-7-phosphate (DAHP) synthase gene from *Saccharomyces cerevisiae* (ARO4-OFP); 2) an expression cassette for a cre recombinase from P1 bacteriophage; 3) an expression cassette containing the native URA3, and 4) the *Saccharomyces cerevisiae* CEN6 centromere. Transformants were selected on synthetic complete media containing 3.5 g/L of p-fluorophenylalanine, and 1 g/L L-tyrosine (ScD-PFP). Resulting transformants were streaked for single colony isolation on ScD-PFP. A single colony was selected.

Loss of the URA3 and amdS genes are verified by PCR. The PCR verified isolate was designated Strain 1-16.

Example #11. Transformation of Strain 1-16 with Two Copies of the *Saccharomyces cerevisiae* IMA1 and Two Copies of the *Saccharomyces mikatae* MAL11-1

Strain 1-16 was transformed with SEQ ID NO 31. SEQ ID NO 31 contains 5' homology to integration locus C, an expression cassette for the ScIMA1, an expression cassette for the URA3 marker, an expression cassette for the SmMAL11-1, and 3' homology to integration locus C locus. Transformants are selected on ScD-Ura. Resulting transformants are streaked for single colony isolation on ScD-Ura. A single colony is selected. Presence of the integration at locus C is verified by PCR. The PCR verified isolate is saved as Strain 1-17.

Strain 1-17 was transformed with SEQ ID NO: 32. SEQ ID NO 32 contains 5' homology to integration locus C, an expression cassette for the ScIMA1, an expression cassette for the *Aspergillus nidulans* acetamidase gene (amdS), an expression cassette for the SmMAL11-1, and 3' homology to the integration locus C. Transformants were selected on Yeast Nitrogen Base (without ammonium sulfate or amino acids) containing 1 g/L acetamide as the sole nitrogen source. Resulting transformants were streaked for single colony isolation on Yeast Nitrogen Base (without ammonium sulfate or amino acids) containing 1 g/L acetamide as the sole nitrogen source. A single colony was selected. Correct integration of SEQ ID NO:32 at the remaining allele of locus C was verified by PCR. The PCR verified isolate was designated Strain 1-18.

Example #12. Transformation of Strain 1-16 to Create a Comparison Yeast to Strain 1-18 which Lacks the ScIMA1 and SmMAL11-1 Over-Expression Strain 1-16 is grown overnight and transformed with SEQ ID NO 40. SEQ ID NO 40 contains 5' homology to integration locus C, an expression cassette for URA3, and 3' homology to locus C. Transformants are selected on ScD-Ura agar plates. Resulting transformants are streaked for single colony isolation on YPD. A single colony is selected. Presence of the integration is confirmed by PCR. The PCR verified isolate is designated Strain 1-19.

Strain 1-19 was transformed with SEQ ID NO 41. SEQ ID NO 41 contains 5' homology to integration locus C, homology to the upstream region of URA3, an expression cassette for the *Aspergillus nidulans* acetamidase gene (amdS), homology to the downstream region of URA3 and 3' homology to integration C locus. Transformants were selected on Yeast Nitrogen Base (without ammonium sulfate or amino acids) agar plates containing 1 g/L acetamide as the sole nitrogen source. Resulting transformants were streaked for single colony isolation on Yeast Nitrogen Base (without ammonium sulfate or amino acids) containing 1 g/L acetamide as the sole nitrogen source. A single colony was selected. Correct integration of SEQ ID NO: 41 at the remaining allele of locus C was verified by PCR. The PCR verified isolate was designated Strain 1-20. Strain 1-20 is used to study the effect caused by deletion of the gene at locus C in the absence of the ScIMA1 and SmMAL11 but in the presence of the *Saccharomycopsis fibuligera* glucoamylase.

Strain 1-19 was transformed with SEQ ID NO 42. SEQ ID NO 42 contains 5' homology to integration locus C, an expression cassette for the *Aspergillus nidulans* acetamidase gene (amdS), and 3' homology to integration C locus. Transformants were selected on Yeast Nitrogen Base (without ammonium sulfate or amino acids) agar plates containing 1 g/L acetamide as the sole nitrogen source. Resulting transformants were streaked for single colony isolation on Yeast Nitrogen Base (without ammonium sulfate or amino acids) containing 1 g/L acetamide as the sole nitrogen source. A single colony was selected. Correct integration of SEQ ID NO: 42 at the remaining allele of locus C was verified by PCR. The PCR verified isolate was designated Strain 1-21. Strain 1-21 is used to study the effect caused by deletion of the gene at locus C in the absence of the ScIMA1 and SmMAL11 but in the presence of the *Saccharomycopsis fibuligera* glucoamylase.

Example #13. Simultaneous Saccharification and Fermentation (SSF) in Shake Flasks for Strains Over-Expressing the Sf GA, ScIMA1, and the SmMAL11-1

Strain 1-15, 1-18 and 1-20 were struck to a YPD plate and incubated at 30° C. until single colonies are visible (1-2 days). Cells from the YPD plate are scraped into sterile shake flask medium and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1-0.3 Immediately prior to inoculating, 50 mL of shake flask medium is added to a 250 mL non-baffled shake flask (Corning 4995-250) fitted with a screw cap containing a gas-permeable seal (corning 1395-45LTMC) The shake flask medium consists of 625 g partially hydrolyzed corn starch, 150 g filtered light steep water, 150 g water, 25 g glucose, and 1 g urea. Duplicate flasks for each strain are incubated at 30° C. with shaking in an orbital shake at 100 rpm for 48 hours. Samples are taken and analyzed for metabolite concentrations in the broth during fermentation by HPLC with refractive index and UPLC with ELSD detection.

Figure 10:
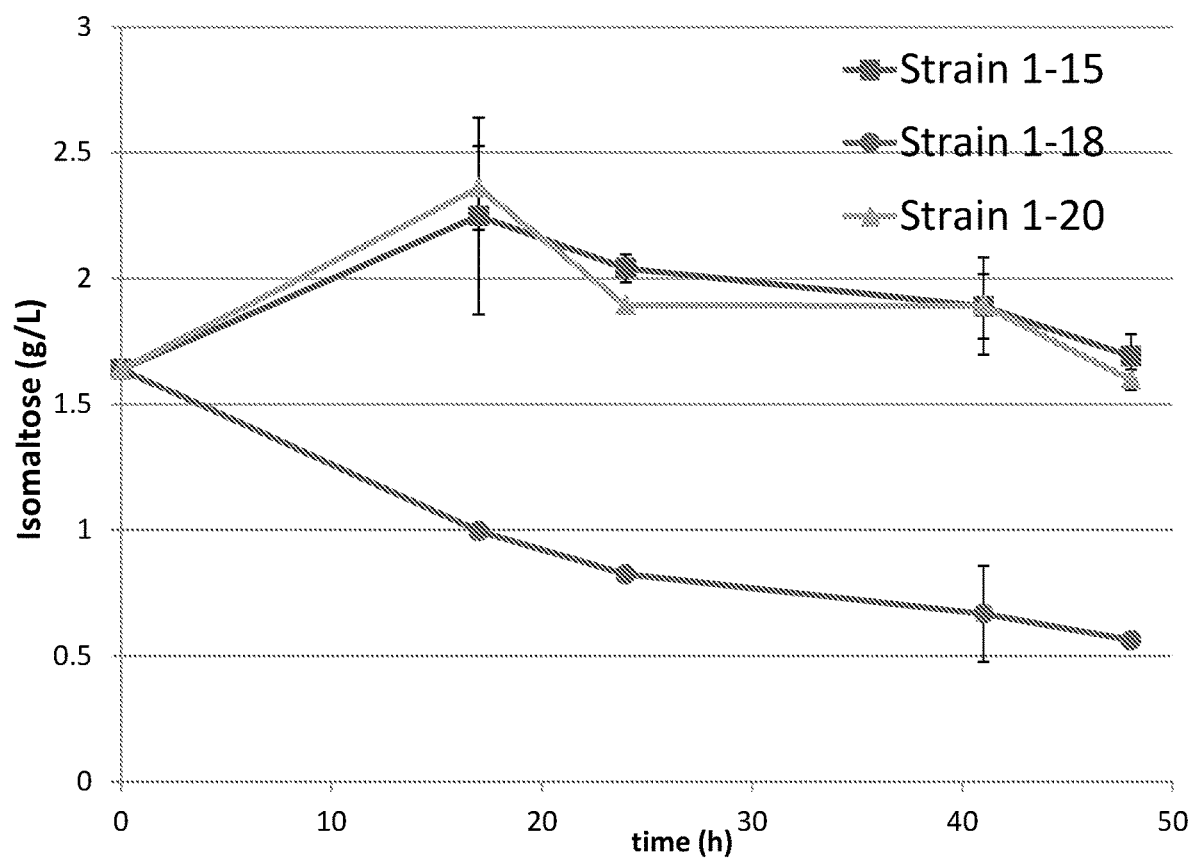
FIG. 10 is a graph showing isomaltose consumption over time in SSF shake flasks using Strains 1-15, 1-18, and 1-20.
Figure 11:
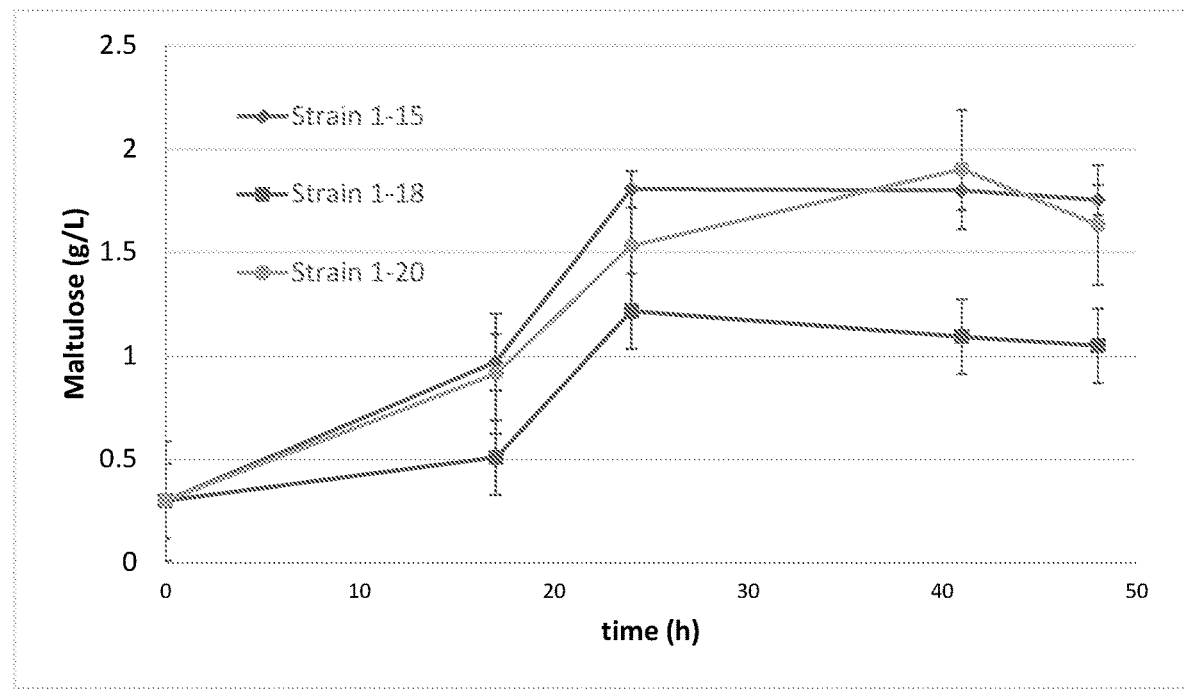
FIG. 11 is a graph showing maltulose consumption over time in SSF shake flasks using Strains 1-15, 1-18, and 1-20.
Figure 12:
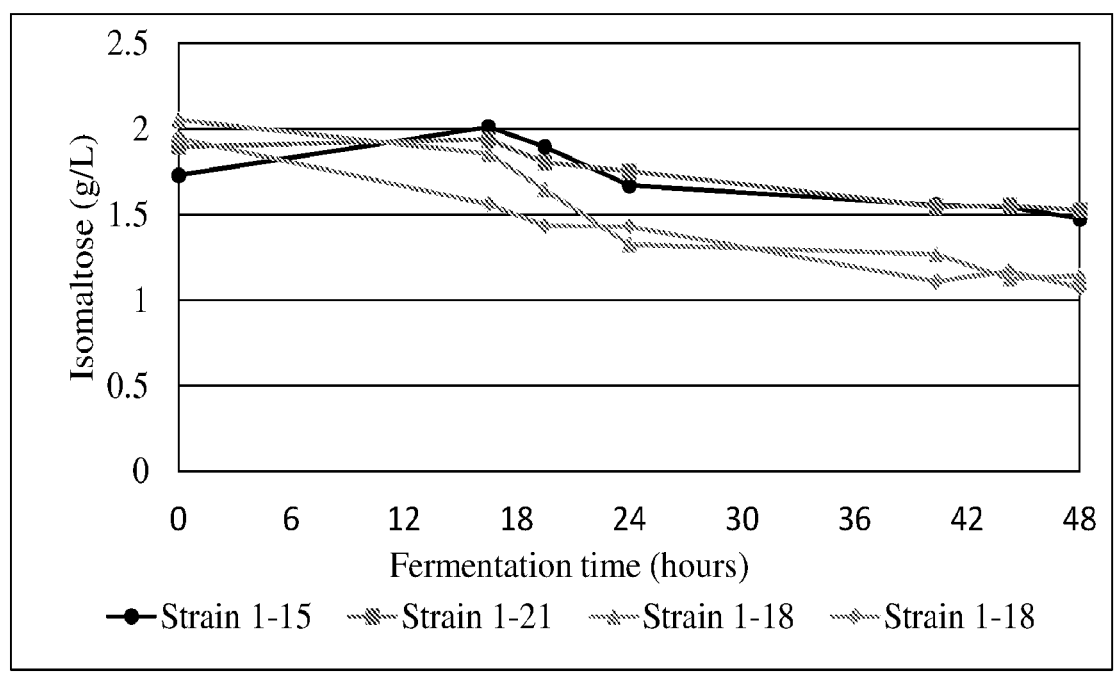
FIG. 12 is a graph showing isomaltose consumption over time using SSF in 2 L Benchtop Biostat B fermentors for Strain 1-15, 1-18, and 1-21.
Figure 13:
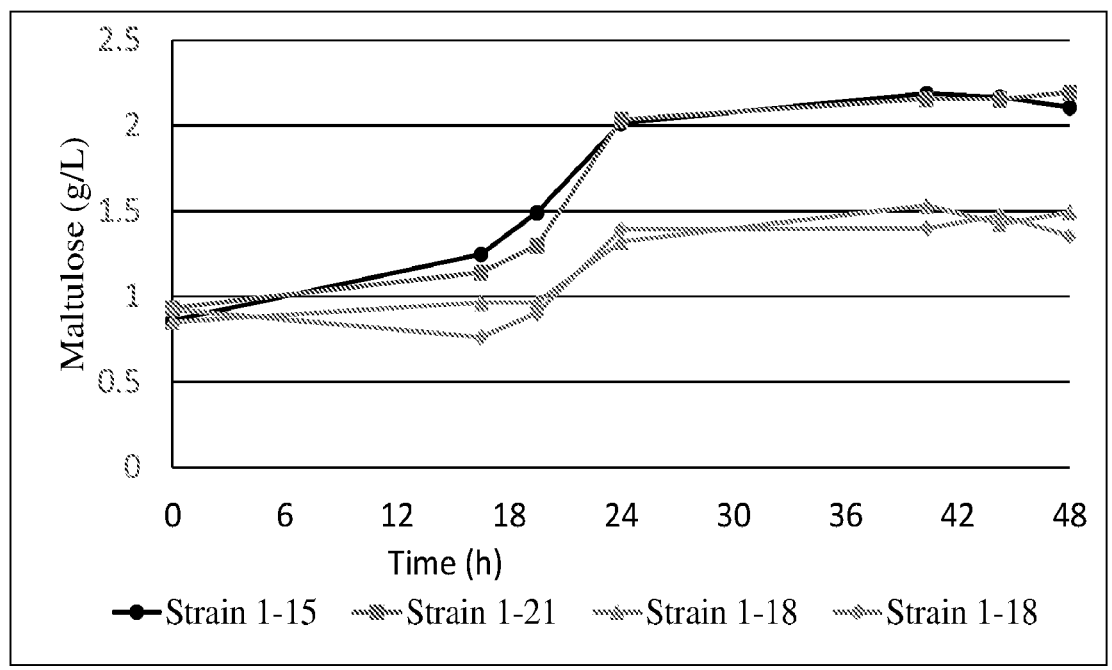
FIG. 13 is a graph showing maltulose consumption over time using SSF in 2 L Benchtop Biostat B fermentors for Strain 1-15, 1-18, and 1-21.
Figure 14:
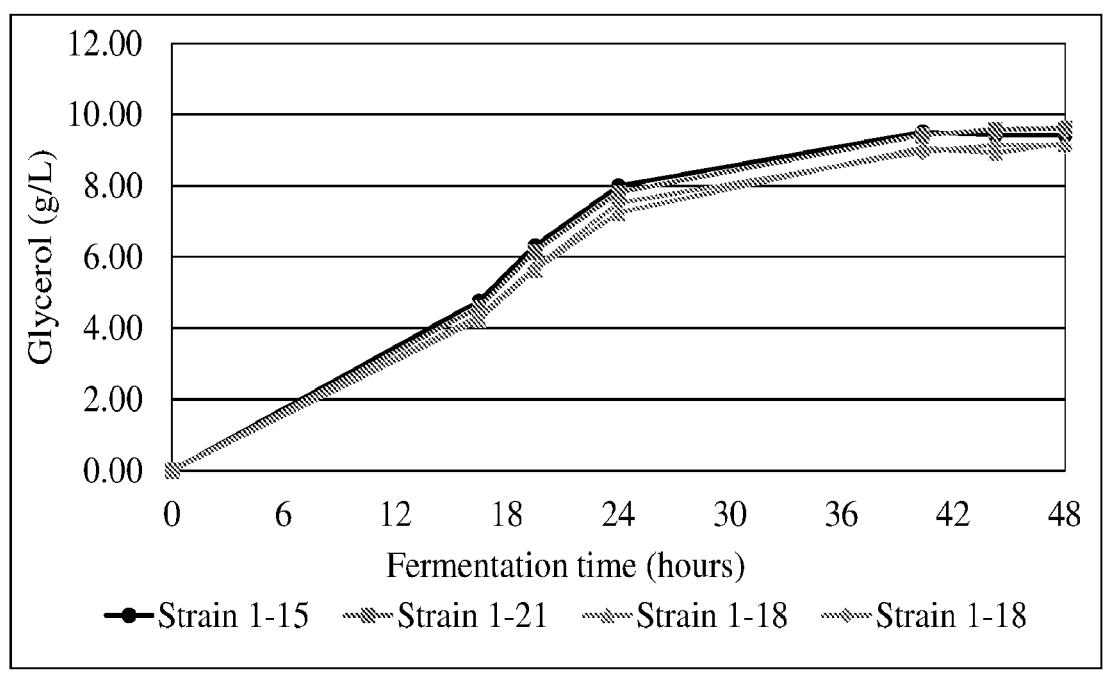
FIG. 14 is a graph showing glycerol over time for Strains 1-15, 1-18, and 1-21 in 2 L Benchtop Biostat B SSF fermentations.

The results shown in FIGS. 10 and 11 demonstrate the improved isomaltose and maltulose consumption in strain 1-18.

Example #14. Simultaneous Saccharification and Fermentation in 2 L Benchtop Biostat B Fermentors for Strain 1-15, 1-18 and 1-21

Seed flasks for strains 1-15, 1-18 and 1-21 containing 50 mL of Yeast Mold Broth in a 250 mL baffled shake flask were inoculated from a fresh YPD plate to an approximate $OD_{600}$ of 0.2. The shake flasks were incubated for ~22 hours at 30° C. and agitated at 250 rpm. Inoculum volume was calculated to target an initial pitch of 0.2 $OD_{600}$ (0.06 g/l cell dry weight). Duplicate fermentors were inoculated with Strain 1-18. Media preparation took place in a sterile hood and was mixed in a previously sterilized container prior to transfer into the individual fermentors. To prepare the media, the Liquefact material was added followed by the 95DE (95% hydrolyzed starch), Light Steep Water (LSW), and Backset (BS). Target a final volume of roughly 1.5 L of media per fermenter (Table 4). Urea was dissolved in a small amount of sterile water prior to adding to the inoculum. A 100 g/l isomaltose solution was prepared in sterile water and added to each fermentor to increase the starting isomaltose concentration by 1 g/l isomaltose (TCI #I0231). Due to variability in the feedstocks, exact amounts of each material are variable. Media was pumped into the sterile vessel through a diptube in the head plate. Each fermentor was inoculated with roughly 25 mls from the overnight seed culture through a port in the headplate The temperature was controlled at 30° C., the broth was stirred at an agitation of 175 rpm, and air was sparged into the media at 0.38 slpm. Once these set points had been reached the Dissolved Oxygen (DO) probe was calibrated and the % DO of the fermentation was monitored. The pH of the fermentation was also monitored but not controlled. $CO_2$ production, $O_2$ consumption, and ethanol evaporation were also monitored in the off gas. Samples are taken and analyzed for metabolite concentrations in the broth during fermentation by HPLC with refractive index and UPLC with ELSD detection.

TABLE 4

Per Fermenter Media Recipe

| Components | Per fermenter |
| --- | --- |
| Liquifact (mL) | 851 |
| 95DE (95% hydrolyzed starch) (mL) | 300 |
| LSW (mL) | 337 |
| BS (mL) | 12 |
| Urea (g) | 0.32 |
| Isomaltose (g) | 1.5 |
| total | 1500 |

TABLE 5

Summary results for SSF in 2 L Benchtop Biostat B fermentors for Strain strains 1-15, 1-18 and 1-21

| ID | Strain 1-15 | Strain 1-21 | Strain 1-18 Replicate 1 | Strain 1-18 Replicate 2 |
| --- | --- | --- | --- | --- |
| Fermentation time (h) | 48 | 48 | 48 | 48 |
| Max EtOH titer (g/L) | 152.18 | 153.71 | 156.38 | 156.34 |
| EtOH production rate (g/L/h) | 3.14 | 3.18 | 3.23 | 3.25 |
| Residual Isomaltose (g/L) | 1.47 | 1.52 | 1.14 | 1.07 |
| Residual Maltulose (g/L) | 2.11 | 2.19 | 1.49 | 1.35 |
| Final Glycerol titer (g/L) | 9.51 | 9.61 | 9.18 | 9.13 |

Example #15. Recycling the Selectable Markers in Strain 1-18 and Restoring Integration Locus A to Wild Type Strain 1-18 was transformed with SEQ ID NO:39. Transformants were selected on synthetic complete media containing 3.5 g/L of p-fluorophenylalanine, and 1 g/L L-tyrosine (ScD-PFP). Resulting transformants were streaked for single colony isolation on ScD-PFP. A single colony was selected. Loss of the URA3 and amdS genes at integration locus C are verified by PCR. The PCR verified isolate was designated Strain 1-22.

Strain 1-22 was transformed with SEQ ID NO:43. SEQ ID NO:43 contains the follow element, a expression cassette for the native URA3, with 5' and 3' homology to the disrupted URA3 locus in Strain 1-22. Transformants were selected on ScD-ura. Resulting transformants were streaked for single colony isolate on ScD-ura. A single colony was selected. The PCR verified isolate was designated Strain 1-23.

Example #16. SSF Fermentation in 4 L Fermentors for Strain 1-23 and Strain 1

Seed flasks containing 50 mL of Yeast Mold Broth in a 250 mL baffled shake flask were inoculated from a fresh YPD plate to a starting $OD_{600}$ of approximately 0.2. The shake flasks were incubated for 22 hours at 30° C. and agitated at 250 rpm. Inoculum volume was calculated to target an initial pitch of 0.2 $OD_{600}$ (0.06 g/l cell dry weight). Fermentations were run using New Brunswick Bioflo 310 fermentation units. The 4 L fermentations were run at 30° C. with the agitation set at 100 rpm and the sparged air set at 0.25 volumes of air per volume of medium (VVM). The fermentation media components are listed in Table 6. Free amino nitrogen (FAN) levels were targeted at 600 ppm (500 ppm from raw light steep water and 100 ppm from urea). $CO_2$ production and $O_2$ consumption were also monitored in the off gas. Samples are taken and analyzed for metabolite concentrations in the broth during fermentation by HPLC with refractive index or ELSD detection. $CO_2$ production, 02 consumption, and ethanol evaporation were also monitored in the off gas. In addition, gas bag samples were taken at identical CER levels to measure volatile organic compounds. Duplicate fermentations were conducted for each strain. 1.17 ml of commercial glucoamylase (Dupont Distillase) was added to Strain 1 fermentations. Samples are taken and analyzed for metabolite concentrations in the broth during fermentation by HPLC with refractive index and UPLC with ELSD detection.

Figure 15:
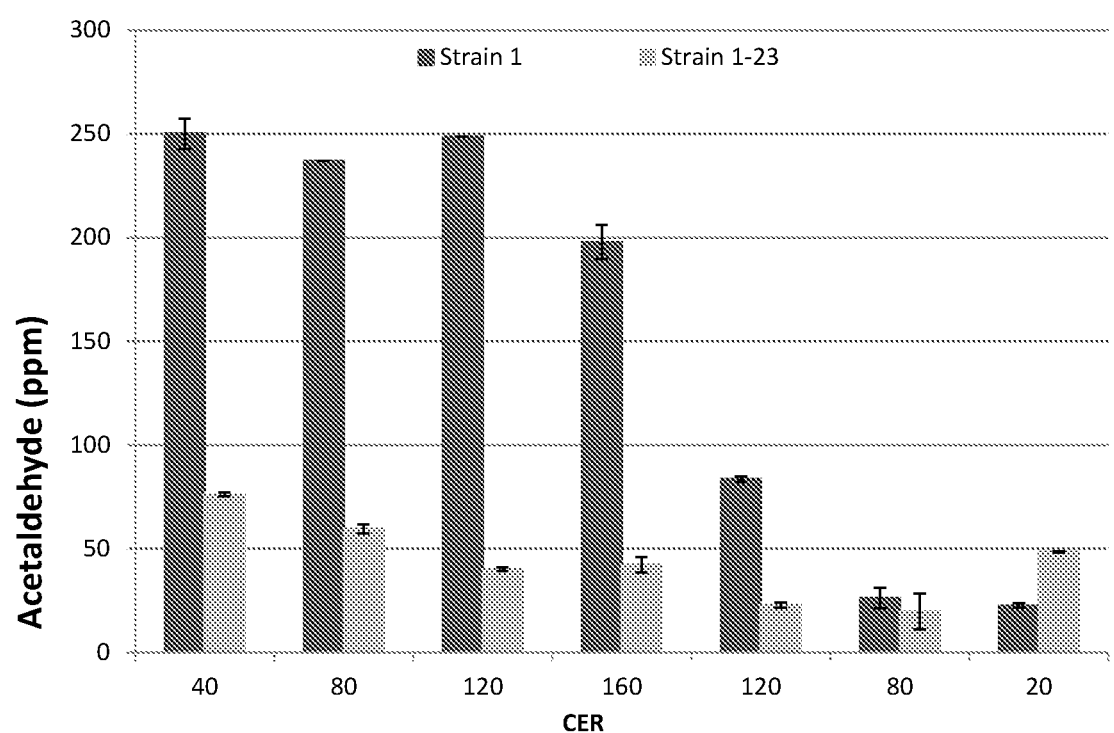
FIG. 15 is a graph showing acetaldehyde production from SSF offgas for Strains 1 and 1-23.

The result in Table 8 show that Strain 1-23 is capable of reducing maltose, isomaltose, maltulose, maltotriose, and panose relative to a strain without the genetic modifications. The results in FIG. 15 also show that Strain 1-23 produces less acetaldehyde than Strain 1. FIG. 15 shows ppm acetaldehyde in the offgas plotted against CER (carbon dioxide evolution rate) at successive phases of a fermentation. CER provides a normalized metric for comparing different strains in similar phases of a fermentation. Finally, the results shown in Table 7 show that Strain 1-23 is capable of producing ethanol at a higher yield than Strain 1.

TABLE 6

Fermentation media composition

| Batch SSF Medium | L | Kg |
| --- | --- | --- |
| Glucose (683 g/L) | 0.293 | 0.367 |
| Liquifact | 1.919 | 2.215 |
| LSW | 0.912 | 0.959 |
| Backset | 0.776 | 0.798 |
| Distillase (Strain 1 only) | 0.001 | |
| Inoculum | 0.049 | |
| Urea | 0.05 | 0.050 |
| Total | 4.000 | |

TABLE 7

Summary of data

| | Strain 1 Replicate 1 | Strain 1 Replicate 2 | Strain 1-23 Replicate 1 | Strain 1-23 Replicate 2 |
| --- | --- | --- | --- | --- |
| Fermentation time (hours) | 45 | 45 | 45 | 45 |
| EtOH titer (g/L) | 104.3 | 104.0 | 108.3 | 107.3 |

TABLE 7-continued

Summary of data

|  | Strain 1 Replicate 1 | Strain 1 Replicate 2 | Strain 1-23 Replicate 1 | Strain 1-23 Replicate 2 |
|---|---|---|---|---|
| EtOH production rate (g/L*h) | 3.1 | 3.2 | 3.4 | 3.4 |

TABLE 8

Metabolite levels at end of fermentation (g/L)

|  | Glycerol | Glucose | Maltulose | Maltose | Trehalose | Isomaltose | Maltotriose | Panose |
|---|---|---|---|---|---|---|---|---|
| Strain 1 | 12.8713 | 0.3591 | 1.9687 | 1.0138 | 1.6361 | 1.0386 | 0.3883 | 0.2095 |
| Strain 1 | 12.9851 | 0.3495 | 2.0136 | 0.7197 | 1.6145 | 1.0569 | 0.3958 | 0.3144 |
| Strain 1-23 | 10.9701 | 0.1796 | 0.5198 | 0.208 | 1.9531 | 0.3613 | 0.253 | 0.1721 |
| Strain 1-23 | 10.8937 | 0.1929 | 0.5138 | 0.2252 | 1.9534 | 0.3279 | 0.1928 | 0.1808 |

Example #17 Specific Aerobic Growth Rates

Specific aerobic growth rates were determined for several of the strains described above. Synthetic media containing 6.7 g/L Yeast Nitrogen Base without amino acids, 1.9 g/L Synthetic Complete drop-out mix without uracil, 2.5 g/L maltulose, 9.5 g/L MES buffer, adjusted to pH6.0 with 5M potassium hydroxide, was used. Overnight 15 ml falcon snap cap tubes containing 4 mls of media were inoculated to a starting $OD_{600}$ of 0.5 and placed in a 30° C. shaking incubator with an agitation of 250 RPM. After 16 hours, the $OD_{600}$ was measured and the cells diluted to an $OD_{600}$ of 0.05 in 25 mls fresh media, contained in a 125 ml baffled shake flask, incubated in a 30° C. shaking incubator with an agitation of 250 RPM. The $OD_{600}$ was monitored for four hours. The growth rate is reported as the exponential of a trend line fitted to the $OD_{600}$ data plotted on a logarithmic scale, using a minimum of four sample points.

As Table 9 shows, the growth rate on maltulose is significantly higher in strains containing the SmMAL11-1 transporter.

TABLE 9

Growth rates on maltulose

| Strain | Growth rate |
|---|---|
| 1 | <0.01 |
| 1-13 | <0.01 |
| 1-11 | 0.27 |
| 1-15 | <0.01 |
| 1-21 | <0.01 |
| 1-18 | 0.28 |
| 1-23 | 0.25 |
| 1-6 | 0.22 |
| 1-7 | <0.01 |
| 1-8 | 0.20 |
| 1-9 | <0.01 |

TABLE 10

SEQ ID NO listing

| | |
|---|---|
| SEQ ID NO 1 | 2-436 bp: 5' homology to integration locus A<br>445-478 bp: loxP |
| | 479-2647 bp: ARO4-OFP expression cassette<br>2648-2681 bp: loxP<br>2690-3180 bp: 3' homology to integration locus A |
| SEQ ID NO 2 | 2-435 bp: 5' homology to integration locus A<br>445-478 bp: loxP<br>478-637 bp: TEF1 terminator<br>638-2284 bp: *Aspergillus nidulans* amdS<br>2285-2740 bp: TEF1 promoter<br>2741-2774 bp: loxP<br>2777-3274 bp: 3' homology to integration locus A |
| SEQ ID NO 3 | 1-47 bp: homology to SEQ ID NO 4<br>53-1084 bp: cre recombinase ORF<br>1086-1132 bp: homology to SEQ ID NO 4 |
| SEQ ID NO 4 | 10-199 bp: CYC1 terminator<br>386-1053 bp: pUC origin of replication<br>1204-2061 bp: ampicillin resistance gene<br>2195-3350 bp: 2 micron origin of replication<br>3785-4901 bp: URA3 expression cassette |
| SEQ ID NO 5 | 1-70 bp: 5' homology to integration locus B<br>119-711 bp: PGK promoter<br>712-2481 bp: ScIMA1 gene<br>2490-2745 bp: GAL10 terminator<br>2774-2807 bp: loxP<br>2834-3289 bp: TEF1 promoter<br>3290-3916 bp: *Aspergillus nidulans* amdS (partial) |
| SEQ ID NO 6 | 1-1498 bp: *Aspergillus nidulans* amdS (partial)<br>1499-1658 bp: TEF1 terminator<br>1659-1692 bp: loxP<br>1784-1856 bp: 3' homology to integration locus B |
| SEQ ID NO 7 | 1-39 bp: Homology to SEQ ID 13<br>40-1889 bp: ScMAL11 gene<br>1890-1928 bp: Homology to SEQ ID 13 |
| SEQ ID NO 8 | 1-39 bp: Homology to SEQ ID 13<br>40-1869 bp: ScMPH2 gene<br>1870-1907 bp: Homology to SEQ ID 13 |
| SEQ ID NO 9 | 1-39 bp: Homology to SEQ ID 13<br>40-1779 bp: DhMAL11-1 gene<br>1780-1815 bp: Homology to SEQ ID 13 |
| SEQ ID NO 10 | 1-39 bp: Homology to SEQ ID 13<br>40-1788 bp: DhMAL11-2 gene |

TABLE 10-continued

SEQ ID NO listing

| | |
|---|---|
| | 1789-1825 bp: Homology to SEQ ID 13 |
| SEQ ID NO 11 | 1-39 bp: Homology to SEQ ID 13<br>40-1698 bp: SpSUT1 gene<br>1699-1734 bp: Homology to SEQ ID 13 |
| SEQ ID NO 12 | 1-39 bp: Homology to SEQ ID 13<br>40-1922 bp: TdMAL11 gene<br>1923-1962 bp: Homology to SEQ ID 13 |
| SEQ ID NO 13 | 4-227 bp: CYC1 terminator<br>1496-2352 bp: Ampicillin resistance gene<br>2485-3003 bp: *Saccharomyces cerevisiae* CEN6 centromere<br>3262-3477 bp: *Saccharomyces cerevisiae* URA3 promoter<br>3478-4278 bp: *Saccharomyces cerevisiae* URA3 gene<br>4279-4359 bp: *Saccharomyces cerevisiae* URA3 terminator<br>5090-5835 bp: ADH1 promoter |
| SEQ ID NO 14 | SEQ ID NO 14<br>1-39 bp: 5' Homology to SEQ ID NO 13<br>40-1893: *Saccharomyces mikatae* MAL11-1 gene<br>1894-1961: 3' Homology to SEQ ID NO 13 |
| SEQ ID NO 15 | 1-39 bp: 5' Homology to SEQ ID NO 13<br>40-1887 bp: *Saccharomyces mikatae* MAL11-2 gene<br>1888-1955 bp: 3' Homology to SEQ ID NO 13 |
| SEQ ID NO 16 | 1-39 bp: 5' Homology to SEQ ID NO 13<br>40-1884 bp: *Saccharomyces cerevisiae* RM11-1a MAL11 gene<br>1885-1952 bp: 3' homology to SEQ ID NO 13 |
| SEQ ID NO 17 | 1-39 bp: 5' Homology to SEQ ID NO 13<br>40-1887 bp: *Saccharomyces paradoxus* MAL11 gene<br>1888-1955 bp: 3' Homology to SEQ ID NO 13 |
| SEQ ID NO 18 | 1-39 bp: 5' Homology to SEQ ID NO 13<br>40-1770 bp: *Kluyveromyces lactic* MAL11 gene<br>1771-1838 bp: 3' Homology to SEQ ID NO 13 |
| SEQ ID NO 19 | 1-39 bp: 5' Homology to SEQ ID NO 13<br>40-1785 bp: *Pichia Stipitis* MAL11 gene<br>1786-1853 bp: 3' Homology to SEQ ID NO 13 |
| SEQ ID NO 20 | 1-39 bp: 5' Homology to SEQ ID NO 13<br>40-1791 bp: *Pichia Stipitis* MAL11 gene<br>1792-1859 bp: 3' Homology to SEQ ID NO 13 |
| SEQ ID NO 21 | 1-39 bp: 5' Homology to SEQ ID NO 13<br>40-1785 bp: *Pichia stipitis* MAL11 gene<br>1786-1853 bp: 3' Homology to SEQ ID NO 13 |
| SEQ ID NO 22 | 1-39 bp: 5' Homology to SEQ ID NO 13<br>40-1608 bp: *Hansenula polymorpha* MAL11 gene<br>1609-1676 bp: 3' Homology to SEQ ID NO 13 |
| SEQ ID NO 23 | 1-39 bp: 5' Homology to SEQ ID NO 13<br>40-1806 bp: *Candida albicans* MAL11 gene<br>1807-1874 bp: 3' Homology to SEQ ID NO 13 |
| SEQ ID NO 24 | 1-39 bp: 5' Homology to SEQ ID NO 13<br>40-1803 bp: *Candida dubliniensis* MAL11 gene<br>1804-1871 bp: 3' Homology to SEQ ID NO 13 |
| SEQ ID NO 25 | 1-39 bp: 5' Homology to SEQ ID NO 13<br>40-1659 bp: *Aspergillus oryzae* MAL11 gene<br>1660-1727 bp: 3' Homology to SEQ ID NO 13 |
| SEQ ID NO 26 | 1-39 bp: 5' Homology to SEQ ID NO 13<br>40-1686 bp: *Aspergillus fumigatus* MAL11 gene<br>1687-1754 bp: 3' Homology to SEQ ID NO 11 |
| SEQ ID NO 27 | 1-39 bp: 5' Homology to SEQ ID NO 13<br>40-1890 bp: *Saccharomyces cerevisiae* ZTW MAL11 gene<br>1891-1958 bp: 3' Homology to SEQ ID NO 13 |
| SEQ ID NO 28 | 1-39 bp: 5' Homology to SEQ ID NO 13<br>40-1785 bp: *Saccharomyces cerevisiae* CBS7690 MAL11 gene<br>1786-1853 bp: 3' Homology to SEQ ID NO 13 |
| SEQ ID NO 29 | 1-39 bp: 5' Homology to SEQ ID NO 13<br>40-1611 bp: *Saccharomyces cerevisiae* FostersO MAL11 gene<br>1612-1679 bp: 3' Homology to SEQ ID NO 13<br>411-1211 bp: URA3 gene |
| SEQ ID NO 30 | 1584-2156 bp: lacZ gene<br>3316-4173 bp: Ampicillin resisitance gene<br>4305-4823 bp: CEN6 centromere |
| SEQ ID NO 31 | 1-303 bp: 5' Homology to integration locus C<br>309-901 bp: *Saccharomyces cerevisiae* PGK promoter<br>902-2671 bp: *Saccharomyces cerevisiae* IMA1 gene<br>2680-2935 bp: *Saccharomyces cerevisiae* GAL10 terminator<br>2978-3011 bp: loxP<br>3012-4641 bp: *Saccharomyces cerevisiae* URA3 expression cassette<br>4642-4675 bp: loxP<br>4690-5435 bp: *Saccharomyces cerevisiae* ADH1 promoter<br>5436-7289 bp: *Saccharomyces mikatae* MAL11-1 gene<br>7298-7521 bp: *Saccharomyces cerevisiae* CYC1 terminator<br>7554-8086 bp: 3' Homology to integration locus C |
| SEQ ID NO 32 | 1-303 bp: 5' Homology to integration locus C<br>309-901 bp: *Saccharomyces cerevisiae* PGK promoter<br>902-2671 bp: *Saccharomyces cerevisiae* IMA1 gene<br>2680-2935 bp: *Saccharomyces cerevisiae* GAL10 terminator<br>2985-3018 bp: loxP<br>3178-3019 bp: *Saccharomyces cerevisiae* TEF1 terminator<br>3179-4825 bp: *Aspergillus nidulans* amdS gene<br>4826-5281 bp: *Saccharomyces cerevisiae* TEF1 promoter<br>5282-5315 bp: loxP<br>5324-5547 bp: *Saccharomyces cerevisiae* CYC1 terminator<br>5556-7409 bp: *Saccharomyces mikatae* MAL11-1 gene<br>7410-8149 bp: *Saccharomyces cerevisiae* ADH1 promoter<br>8154-8685 bp: 3' Homology to integration locus C |
| SEQ ID NO 33 | 1-70 bp: 5' Homology to integration locus C<br>161-753 bp: *Saccharomyces cerevisiae* PGK promoter<br>757-1461 bp: Dasher GFP gene<br>1486-1678 bp: *Saccharomyces cerevisiae* |

TABLE 10-continued

SEQ ID NO listing

| | |
|---|---|
| | CYC1 terminator |
| | 1801-1834 bp: loxP |
| | 1835-3229 bp: *Issatchenkia orientalis* URA3 expression cassette |
| | 3230-3263 bp: loxP |
| | 3356-3426 bp: 3' Homology to integration locus C |
| SEQ ID NO 34 | 1-70 bp: 5' Homology to integration locus C |
| | 119-711 bp: *Saccharomyces cerevisiae* PGK promoter |
| | 715-1419 bp: Dasher GFP gene |
| | 1444-1636 bp: *Saccharomyces cerevisiae* CYC1 terminator |
| | 1711-1744 bp: loxP |
| | 1745-2200 bp: *Saccharomyces cerevisiae* TEF1 promoter |
| | 2201-3847 bp: *Aspergillus nidulans* amdS gene |
| | 3848-4007 bp: *Saccharomyces cerevisiae* TEF1 terminator |
| | 4008-4041 bp: loxP |
| | 4135-4205 bp: 3' Homology to integration locus C |
| SEQ ID NO 35 | 2-1003 bp: 5' Homology to integration locus B |
| | 1010-1691 bp: *Saccharomyces cerevisiae* TDH3 promoter |
| | 1698-3245 bp: *Saccharomycopsis fibuligera* glucoamylase gene |
| | 3254-3477 bp: *Saccharomyces cerevisiae* CYC1 terminator |
| | 3486-3519 bp: loxP |
| | 3520-4026 bp: *Saccharomyces cerevisiae* URA3 promoter |
| | 4027-4630 bp: *Saccharomyces cerevisiae* URA3 gene (partial) |
| SEQ ID NO 36 | 7-606 bp: *Saccharomyces cerevisiae* URA3 gene (partial) |
| | 607-927 bp: *Saccharomyces cerevisiae* URA3 terminator |
| | 928-961 bp: loxP |
| | 968-1554 bp: *Saccharomyces cerevisiae* PGK promoter |
| | 1561-3108 bp: *Saccharomycopsis fibuligera* glucoamylase gene |
| | 3117-3354 bp: *Saccharomyces cerevisiae* RPL3 terminator |
| | 3363-4362 bp: 3' Homology to integration locus B |
| SEQ ID NO 37 | 2-1003 bp: 5' Homology to integration locus B |
| | 1010-1691 bp: *Saccharomyces cerevisiae* TDH3 promoter |
| | 1698-3245 bp: *Saccharomycopsis fibuligera* glucoamylase gene |
| | 3254-3477 bp: *Saccharomyces cerevisiae* CYC1 terminator |
| | 3486-3519 bp: loxP |
| | 3520-3975 bp: *Saccharomyces cerevisiae* TEF1 promoter |
| | 3976-5015 bp: *Aspergillus nidulans* amdS gene (partial) |
| SEQ ID NO 38 | 7-1032 bp: *Aspergillus nidulans* amdS (partial) |
| | 1033-1335 bp: *Saccharomyces cerevisiae* ADH1 terminator |
| | 1336-1369 bp: loxP |
| | 1376-1962 bp: *Saccharomyces cerevisiae* PGK promoter |
| | 1969-3516 bp: *Saccharomycopsis fibuligera* glucoamylase gene |
| | 3525-3762 bp: *Saccharomyces cerevisiae* RPL3 terminator |
| | 3771-4770 bp: 3' Homology to integration locus B |
| SEQ ID NO 39 | 1-511 bp: *Saccharomyces cerevisiae* TEF1 promoter |
| | 517-1629 bp: *Saccharomyces cerevisiae* ARO4-OFP |
| | 2070-2675 bp: *Saccharomyces cerevisiae* PGK promoter |
| | 2682-3713 bp: cre recombinase gene |
| | 3724-3913 bp: *Saccharomyces cerevisiae* CYC1 terminator |
| | 4620-4700 bp: *Saccharomyces cerevisiae* URA3 terminator |
| | 4702-5501 bp: *Saccharomyces cerevisiae* URA3 gene |
| | 5502-5717 bp: *Saccharomyces cerevisiae* URA3 promoter |
| | 6626-7483 bp: Ampicillin resistance gene |
| SEQ ID NO 40 | 1-70 bp: 5' Homology to integration locus C |
| | 157-663 bp: upstream region of *Saccharomyces cerevisiae* URA3 |
| | 664-1467 bp: *Saccharomyces cerevisiae* URA3 gene |
| | 1468-1788 bp: downstream region of *Saccharomyces cerevisiae* URA3 |
| | 1928-1997 bp: 3' Homology to integration locus C |
| SEQ ID NO 41 | 1-70 bp: 5' Homology to integration locus C |
| | 111-554 bp: upstream region of *Saccharomyces cerevisiae* URA3 |
| | 553-586 bp: loxP |
| | 587-746 bp: *Saccharomyces cerevisiae* TEF1 terminator |
| | 737-2393 bp: *Aspergillus nidulans* amdS gene |
| | 2394-2849 bp: *Saccharomyces cerevisiae* TEF1 promoter |
| | 2850-2883 bp: loxP |
| | 2886-3383 bp: downstream region of *Saccharomyces cerevisiae* URA3 |
| | 3407-3476 bp: 3' Homology to integration locus C |
| SEQ ID NO 42 | 1-70 bp: 5' Homology to integration locus C |
| | 168-201 bp: loxP |
| | 202-361 bp: *Saccharomyces cerevisiae* TEF1 terminator |
| | 362-2008 bp: *Aspergillus nidulans* amdS gene |
| | 2009-2464 bp: *Saccharomcyes cerevisiae* TEF1 promoter |
| | 2465-2498 bp: loxP |
| | 2593-2662 bp: 3' Homology to integration locus C |
| SEQ ID NO 43 | 45-551 bp: upstream region of *Saccharomyces cerevisiae* URA3 |
| | 552-1355 bp: *Saccharomyces cerevisiae* URA3 gene |
| | 1356-1676 bp: downstream region of *Saccharomyces cerevisiae* URA3 |
| SEQ ID NO 44 | SmMAL11 amino acid sequence |
| SEQ ID NO 45 | *Saccharomycopsis fibuligera* glucoamylase sequence |

Example #18 SSF Fermentation Varying GA Dose for Strain 1 and Strain 1-23

Seed flasks containing 50 mL of Yeast Mold Broth in a 250 mL baffled shake flask are inoculated from a glycerol stock. The shake flasks are incubated for 16 hours at 30° C. and agitated at 250 rpm. Inoculum volume is calculated to target an initial pitch of 0.03 $OD_{600}$. Fermentations are run using eight 2 L Biostat B fermentation units. The 1.5 L fermentations are run at 30° C. with the agitation set at 175 rpm and the sparged air set at 0.25 volumes of air per volume of medium (VVM). The fermentation media components are listed in Table 11. Free amino nitrogen (FAN) levels are targeted at 600 ppm (500 ppm from light steep water and 100 ppm from urea). Samples are taken and analyzed for metabolite concentrations in the broth during fermentation by HPLC with refractive index. $CO_2$ production, $O_2$ consumption, and ethanol evaporation are monitored in the off gas. In addition, gas bag samples are taken at three equivalent CER levels to measure volatile organic compounds (between 8 and 15 hours after inoculation). Duplicate fermentations are conducted for each strain and each condition. Three levels of commercial glucoamylase (DuPont Distillase) are added to Strain 1 fermentations (see Table 12 below). One Glucoamylase Unit (GAU) is the amount of enzyme that will liberate one gram of reducing sugars calculated as glucose per hour from soluble starch substrate under the conditions of the GAU assay.

Definition of the GAU assay: 1) add 50 ul of enzyme (or dilutions thereof) to 50 ul of 1% starch solution (0.5 g Sigma soluble starch dissolved in 50 mls of near boiling water, then pH adjust with 1 ml of 3M NaOAc, pH 5. Incubate desired time (between 15 minutes and 1 hour) at 30 C. Perform this step in a PCR plate. 2) Add 100 ul of DNS reagent (dissolve 1 g of DNS in 50 mls water, add 30 g sodium potassium tartrate, then add 20 mls of 2N NaOH, bring up volume to 100 mls). Incubate plate at 99 C in PCR machine for 10 minutes. Cool to room temp. 3) Transfer 100 ul to fresh 96-well flat bottom and read abs at 540 nm. Prepare a standard curve of glucose concentrations of 0 to 2.5 g/L to generate a regression line to calculate your actual glucoamylase activity. One Glucoamylase Unit (GAU) is the amount of enzyme that will liberate one gram of glucose per liter per hour from soluble starch.

Figure 16:
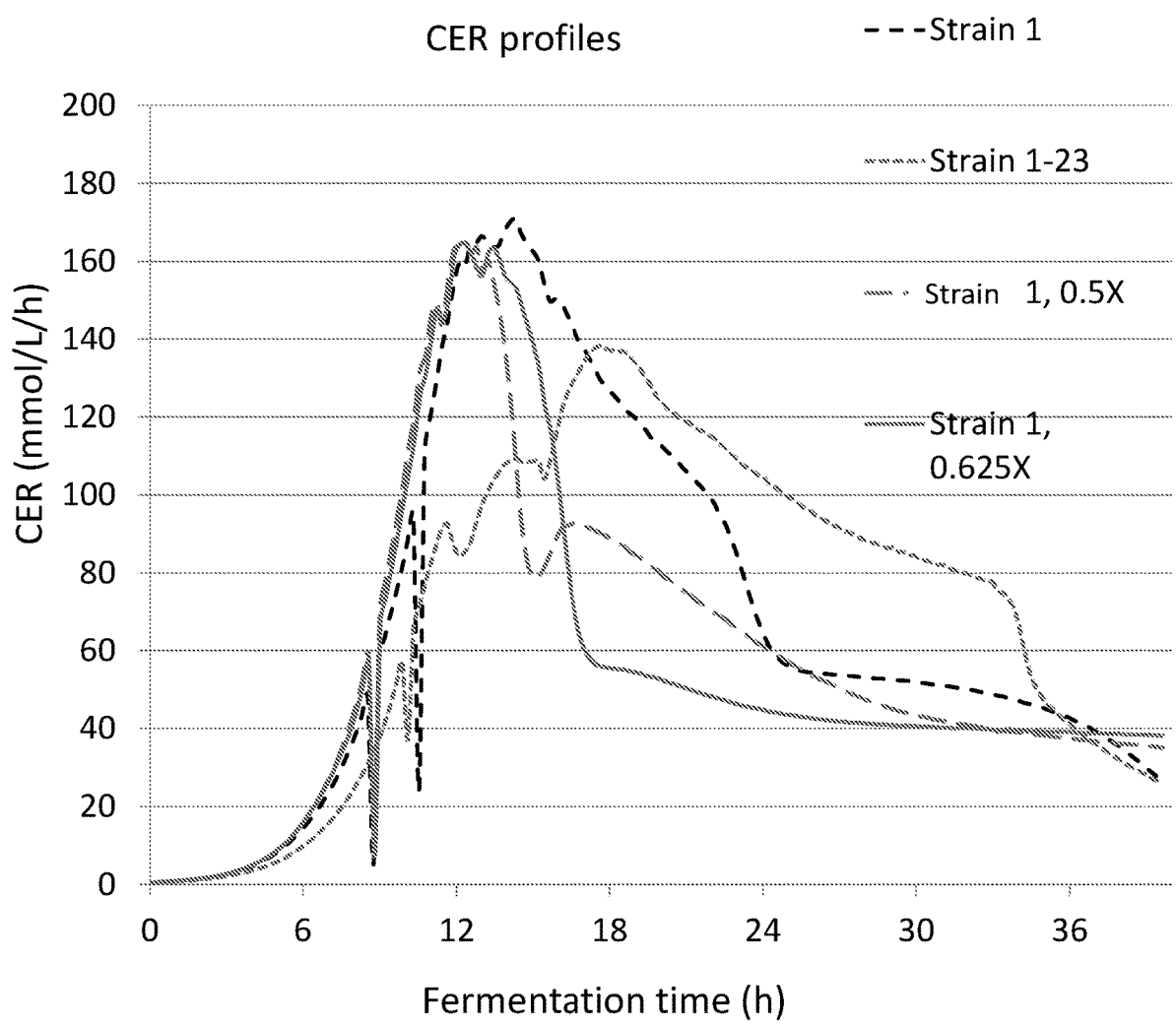
FIG. 16 is a graph showing CER profiles for Strains 1 and 1-23 in a SSF process (one replicate shown for each strain in each condition).
Figure 17:
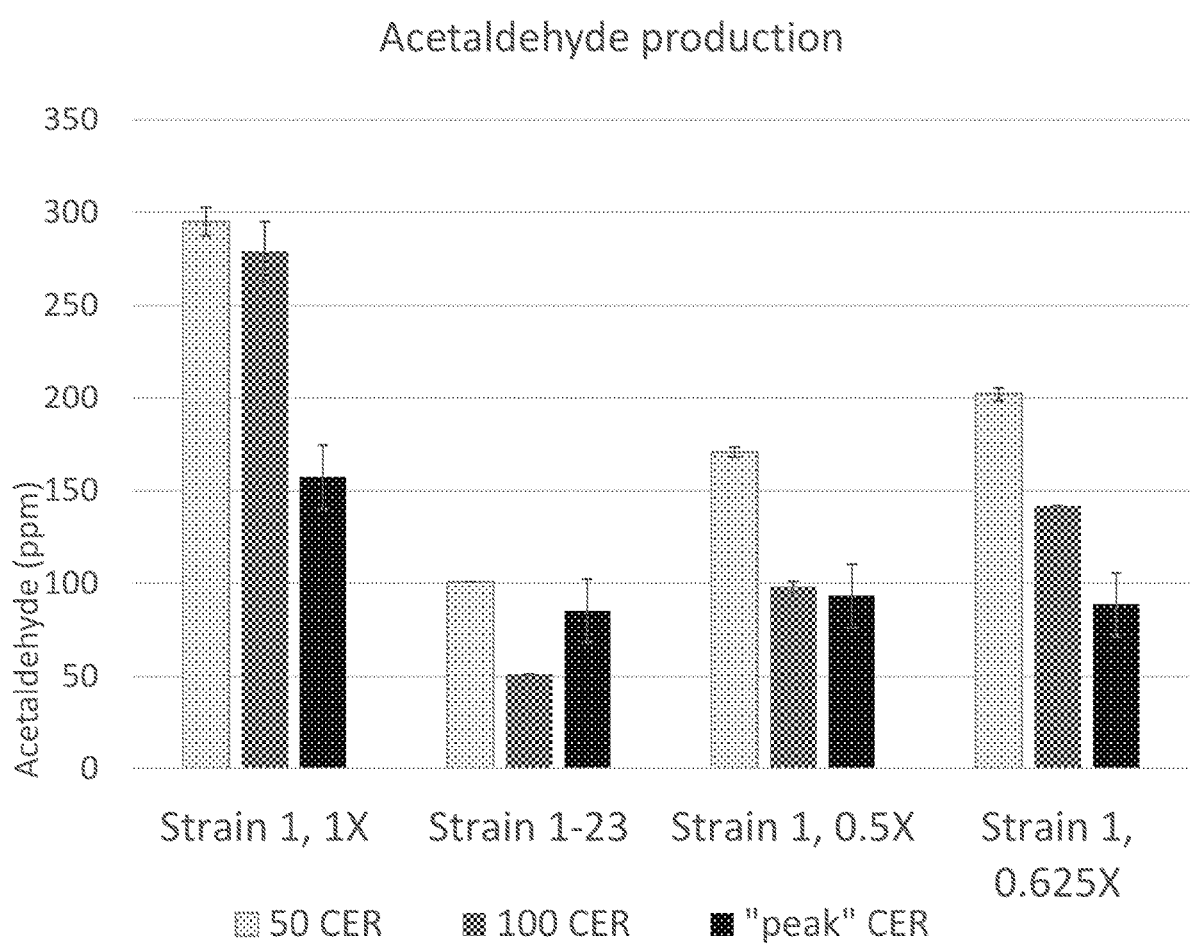
FIG. 17 is a graph showing acetaldehyde production at two different CER levels leading up to peak CER for Strains 1 and 1-23 in a SSF process.
Figure 18:
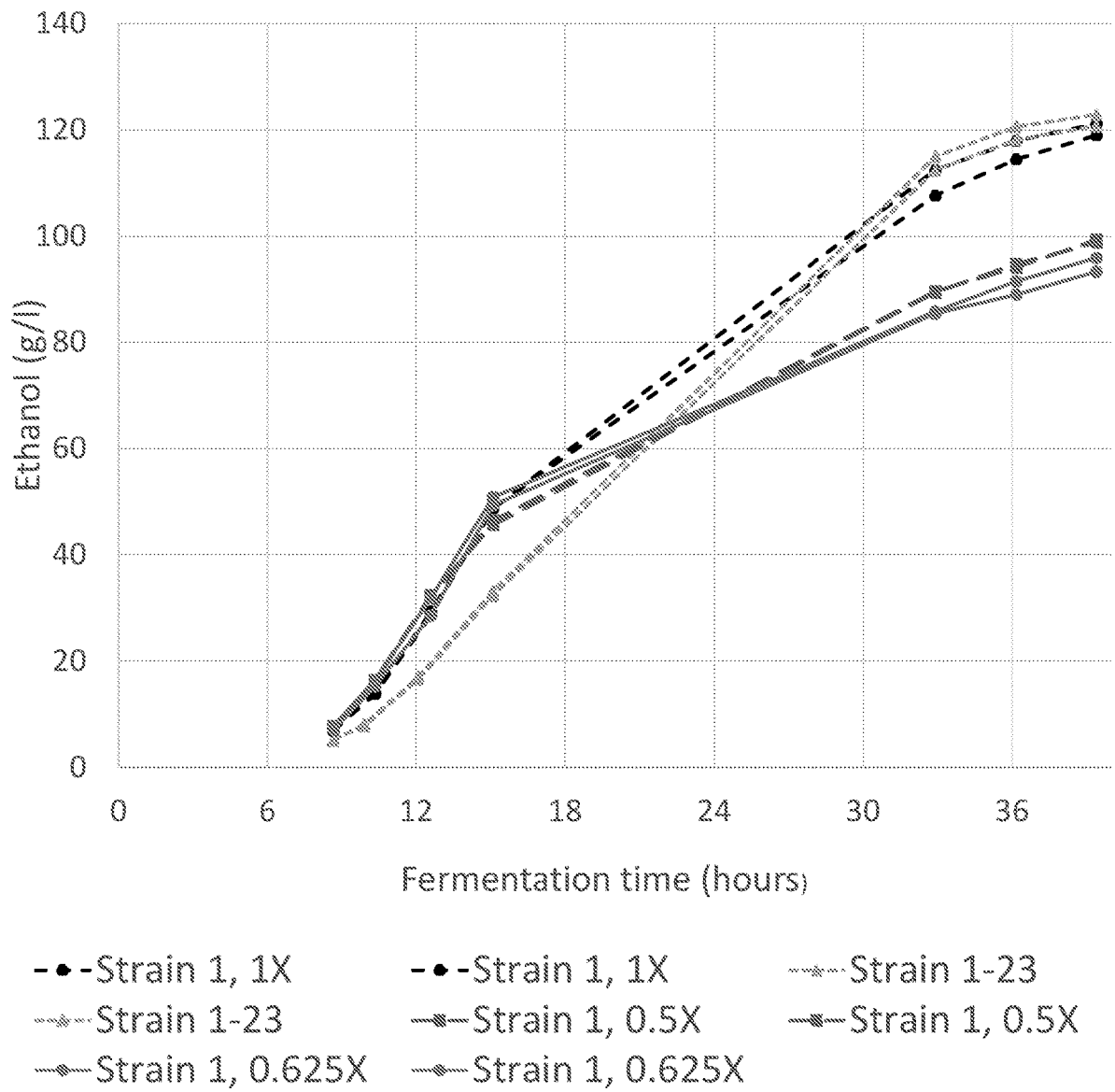
FIG. 18 is a graph showing Ethanol production versus time for Strains 1 and 1-23 in a SSF process.
Figure 19:
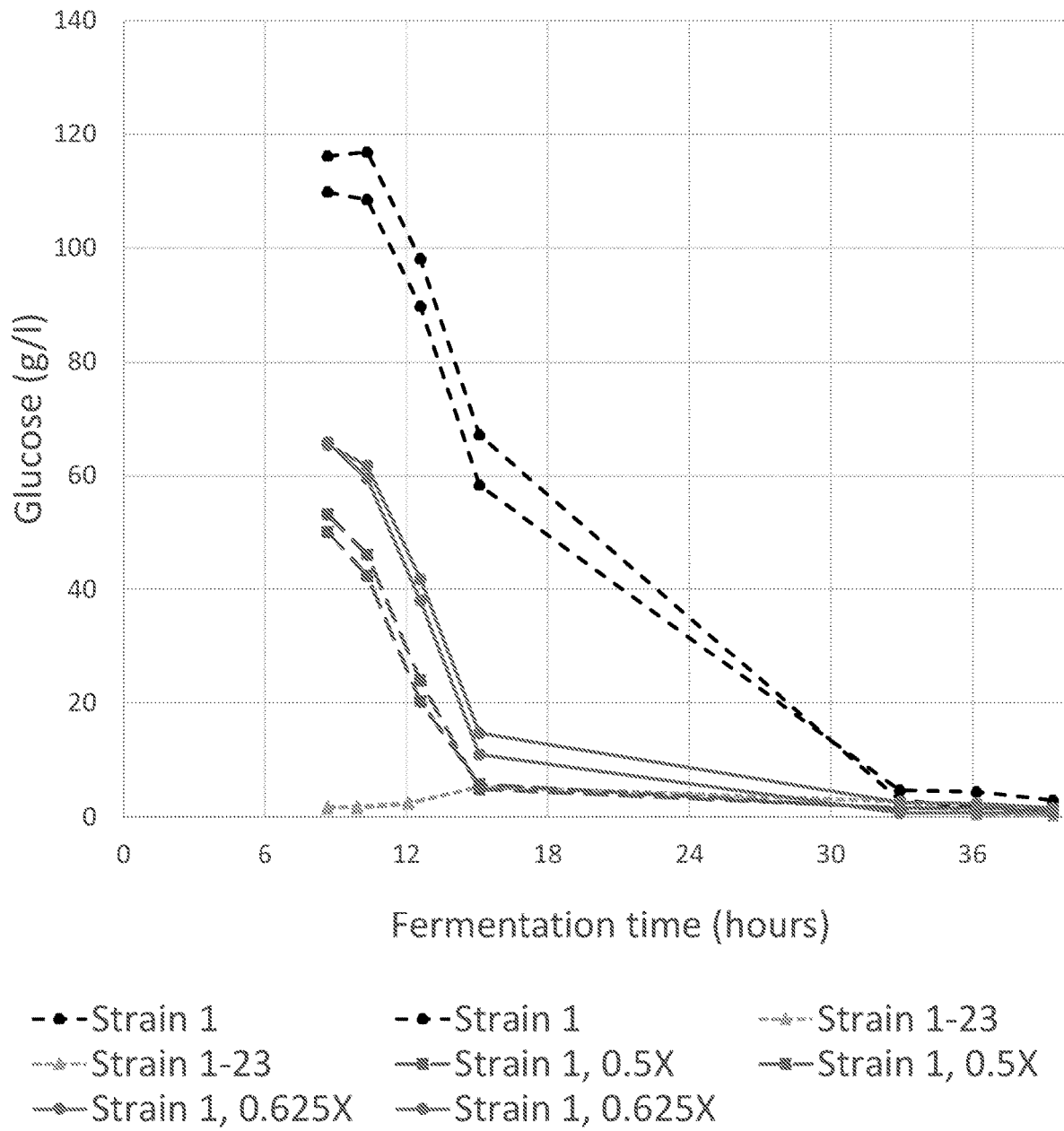
FIG. 19 is a graph showing glucose levels versus time for Strains 1 and 1-23 in a SSF process.

FIG. 16 shows the CER profiles during the fermentation for one replicate for each condition. Three gas bag samples were collected and analyzed, two prior to the peak CER, and one at peak CER. FIG. 17 shows reduced acetaldehyde in the off gas at all three time points for Strain 1-23 compared to Strain 1. Also, reducing the GA dose in Strain 1 can also reduce the acetaldehyde in the off-gas. FIGS. 18 and 19 show the ethanol and glucose profiles. Strain 1 has equivalent ethanol production rates up to 15 hours, at which point the fermentation becomes glucose limited for Strain 1 fermentations with 0.5× and 0.625×GA dose. Strain 1 with 0.5× and 0.625×GA dose fail to finish the fermentation within the allotted time.

TABLE 11

Fermentation Media Recipe

| Component | Stock concentration | Final concentration in media | Units | mL of volume per fermentor | grams per fermentor | Sterilization |
|---|---|---|---|---|---|---|
| Liquefact | 420 | 300 | g/l sugar | 1071.4 | | None |
| LSW | 2400 | 500 | ppm FAN | 312.5 | | 30 min 121 C. |
| Urea | solid | 0.215 | g/L | | 0.323 | None |
| Water | | Balance | ml/L | 115.7 | | 30 min 121 C. |
| Total | | | | 1500 | | |

TABLE 12

Distillase Dose

| Strain | Distillase Dose | Volume of GA added per fermentor (μL) | GAU |
|---|---|---|---|
| Strain 1 | 1X | 600 | 53.3 |
| Strain 1 | 1X | 600 | 53.3 |
| Strain 1-23 | 0 | 0 | 0 |
| Strain 1-23 | 0 | 0 | 0 |
| Strain 1 | 0.5X | 300 | 26.6 |
| Strain 1 | 0.5X | 300 | 26.6 |
| Strain 1 | 0.625X | 375 | 33.3 |
| Strain 1 | 0.625X | 375 | 33.3 |

What is claimed is:

1. A fermentation method comprising:
   providing a fermentation medium comprising a hydrolyzed starch composition comprising maltulose and an engineered yeast comprising a gene encoding a heterologous di- or tri-glucopyranosyl sugar transporter polypeptide with an amino acid sequence at least 90% identical to SEQ ID NO:44, wherein maltulose is present at a first concentration of 0.5 g/L or greater at a first time point; and
   fermenting the fermentable carbohydrate composition in the medium over a period of time to a second time point wherein maltulose is present in the medium at a second concentration, and the second concentration is less than a concentration of maltulose obtained using an otherwise identical yeast that does not have the heterologous sugar transporter at the second time point under the same fermentation conditions.

2. The fermentation method of claim 1 wherein the maltulose is present in the medium at the at the first time point a concentration in the range of 0.5 g/L to 5 g/L.

3. The fermentation method of claim 1 wherein the genetically modified yeast is prepared from a yeast that does not have a sugar transporter with 90% or greater identity to Sc MAL11 (SEQ ID NO:7), a functional isomaltose transporter, or from a yeast that has no ability to grow on maltulose.

4. The fermentation method of claim 1 which provides an ethanol concentration of 80 g/L or greater in the liquid medium at the second time point.

5. The fermentation method of claim 1 wherein genetically modified yeast further comprises a heterologous isomaltase, or an endogenous isomaltase expressed at levels higher than in an unmodified yeast.

6. The fermentation method of claim 5 wherein the endogenous isomaltase is under the control of a heterologous promoter, present in multiple copies in the engineered yeast, or both.

7. The fermentation method of claim 1 wherein the genetically modified yeast further comprises a gene encoding a heterologous glucoamylase selected from the group consisting of *Saccharomycopsis fibuligera* glucoamylase, *Aspergillus niger* glucoamylase, *Trichoderma reesei* glucoamylase, *Trametes* cingulate glucoamylase, *Penicillium oxalicum* glucoamylase, *Rhizopus oryzae* glucoamylase, *Aspergillus awamori* glucoamylase, and *Talaromyces emersonii* glucoamylase.

8. The fermentation method of claim 1 wherein the genetically modified yeast further comprises a gene encoding a heterologous glucoamylase which has 90% or greater sequence identity to SEQ ID NO:45 (Sf Glm).

9. The fermentation method of claim 1 wherein the genetically modified yeast further comprises a gene encoding a heterologous glucoamylase comprising a heterologous secretion sequence.

10. A genetically modified yeast comprising a gene encoding a heterologous di- or tri-glucopyranosyl sugar transporter polypeptide with an amino acid sequence at least 90% identical to SEQ ID NO:44, wherein the yeast is capable of growing at a rate of 0.02 or greater on synthetic media comprising a carbohydrate composition wherein maltulose is present in an amount of at least 97% (wt) in the carbohydrate composition, grown under standard conditions.

11. The genetically modified yeast of claim 10 wherein the heterologous di- or tri-glucopyranosyl sugar transporter polypeptide has is at least 95%, identical to SEQ ID NO:44.

12. The genetically modified yeast of claim 10, wherein the heterologous di- or tri-glucopyranosyl sugar transporter polypeptide comprises SEQ ID NO:44.

13. The genetically modified yeast of claim 10 prepared from a yeast that does not have a sugar transporter with 90% or greater identity to Sc MAL11 (SEQ ID NO: 7), a functional isomaltose transporter, or from a yeast that has no ability to grow on maltulose.

14. The genetically modified yeast of claim 10 further comprising a gene encoding a heterologous glucoamylase selected from the group consisting of *Saccharomycopsis fibuligera* glucoamylase, *Aspergillus niger* glucoamylase, *Trichoderma reesei* glucoamylase, *Trametes* cingulate glucoamylase, *Penicillium oxalicum* glucoamylase, *Rhizopus oryzae* glucoamylase, *Aspergillus awamori* glucoamylase, and *Talaromyces emersonii* glucoamylase.

15. The genetically modified yeast of claim 10 further comprising a heterologous gene encoding a glucoamylase wherein the heterologous glucoamylase has 90% or greater sequence identity to SEQ ID NO:45 (Sf Glm).

16. The genetically modified yeast of claim 14 wherein the heterologous glucoamylase comprises a heterologous secretion sequence.

17. The genetically modified yeast of claim 10, wherein the yeast is capable of growing in media having greater than 80 g/L ethanol.

* * * * *

UNITED STATES PATENT AND TRADEMARK OFFICE
CERTIFICATE OF CORRECTION

| | | |
|---|---|---|
| PATENT NO. | : 12,180,529 B2 | Page 1 of 2 |
| APPLICATION NO. | : 16/062771 | |
| DATED | : December 31, 2024 | |
| INVENTOR(S) | : Christopher K. Miller et al. | |

It is certified that error appears in the above-identified patent and that said Letters Patent is hereby corrected as shown below:

On the Title Page

In Column 1, page 2, Item (56) Line 3 delete "Mlla-Garcia" and insert -- Villa-Garcia --, therefor.
In Column 1, page 2, Item (56) Line 13 delete "W" and insert -- A1 --, therefor.
In Column 1, page 2, Item (56) Line 17 delete "W" and insert -- A1 --, therefor.
In Column 1, page 2, Item (56) Line 9 delete "b-Ketoacyl" and insert -- β-ketoacyl --, therefor.
In Column 2, page 2, Item (56) Line 4 delete "a-Factor-directed" and insert -- α-Factor-directed --, therefor.
In Column 2, page 2, Item (56) Line 17 delete "vol. 65" and insert -- vol. 65, --, therefor.
In Column 2, page 2, Item (56) Line 19 delete "*Year: 2015)." and insert -- (Year: 2015). --, therefor.
In Column 2, page 2, Item (56) Line 29 delete "Sep. 1987 vol. 169 No. 9." and insert -- Sep. 1987, vol. 169, No. 9. --, therefor.
In Column 2, page 3, Item (56) Line 33 delete "al." and insert -- al., --, therefor.
In Column 2, page 3, Item (56) Line 40 delete "al." and insert -- al., --, therefor.

In the Specification

In Column 7, Line 11 delete "an" and insert -- a --, therefor.
In Column 9, Line 38 delete ")" and insert -- ). --, therefor.
In Column 11, Line 58 delete "an" and insert -- a --, therefor.
In Column 18, Line 3 delete "(006994)," and insert -- (O06994), --, therefor.
In Column 18, Line 64 delete "(074254);" and insert -- (O74254); --, therefor.
In Column 18, Line 65 delete "(060087);" and insert -- (O60087); --, therefor.
In Column 22, Line 50 delete "detection" and insert -- detection. --, therefor.
In Column 25, Line 46 delete "(g)" and insert -- (g). --, therefor.
In Column 31, Line 28 delete "10231)." and insert -- I0231). --, therefor.
In Column 36, Line 35 delete ")" and insert -- ). --, therefor.
In Column 37, Line 63 delete "a" and insert -- an --, therefor.
In Column 38, Line 21 delete "02" and insert -- $O_2$ --, therefor.

Signed and Sealed this
Sixth Day of May, 2025

Coke Morgan Stewart
*Acting Director of the United States Patent and Trademark Office*

In the Claims

In Column 225, Claim 11, Line 3 delete "has".